(12) United States Patent
Dolle et al.

(10) Patent No.: US 7,297,796 B2
(45) Date of Patent: Nov. 20, 2007

(54) SULFAMOYL BENZAMIDE DERIVATIVES AND METHODS OF THEIR USE

(75) Inventors: Roland E. Dolle, King of Prussia, PA (US); Karin Worm, East Windsor, NJ (US); Q. Jean Zhou, Malvern, PA (US)

(73) Assignee: Adolor Corporation, Exton, PA (US)

( * ) Notice: Subject to any disclaimer, the term of this patent is extended or adjusted under 35 U.S.C. 154(b) by 0 days.

(21) Appl. No.: 11/251,160

(22) Filed: Oct. 13, 2005

(65) Prior Publication Data
US 2006/0079557 A1 Apr. 13, 2006

Related U.S. Application Data

(60) Provisional application No. 60/618,387, filed on Oct. 13, 2004.

(51) Int. Cl.
C07D 211/06 (2006.01)
(52) U.S. Cl. .................. 546/205; 546/86; 546/317; 514/602; 514/319
(58) Field of Classification Search ............. 546/205, 546/86, 317; 516/317; 514/602, 319
See application file for complete search history.

(56) References Cited

U.S. PATENT DOCUMENTS

| 3,565,920 A | * | 2/1971 | Werner | 549/494 |
| 6,228,808 B1 | | 5/2001 | Kehne et al. | 504/239 |

FOREIGN PATENT DOCUMENTS

| EP | 0 659 748 B1 | | 7/2000 |
| GB | 1328169 | * | 8/1973 |
| GB | 2 295 616 A | | 6/1996 |
| WO | WO 03/087061 A1 | | 10/2003 |
| WO | WO 2004/017920 A3 | | 3/2004 |
| WO | WO 2004/018414 A2 | | 3/2004 |

OTHER PUBLICATIONS

Kushner et al., Anticonvulsants. N-Benzylamides, J. Org. Chem.; 1951; 16(8); 1283-1288.*
Bhargava, H.N., et al., "Effect of nitric oxide synthases inhibition on tolerance to the analgesic action of D-Pen$^2$, D-Pen$^5$ enkephalin and morphine in the mouse," *Neuropeptides*, 1996, 30(3), 219-223.
Bilsky, E.J., et al., "Effects of naloxone and D-Phe-Cys-Tyr-D-Trp-Arg-Thr-Pen-Thr-NH$_2$ and the protein kinase inhibitors H7 and H8 on acute morphine dependence and antinociceptive tolerance in mice," *J. Pharmacol. Exp. Ther.*, 1996, 277(1), 484-490.
Cheng, Y.-C., et al., "Relationship between the inhibition constant ($K_i$) and the concentration of inhibitor which causes 50 percent inhibition ($I_{50}$) of an enzymatic reaction," *Biochem. Pharmacol.*, 1973, 22, 3099-3108.
Compton, D.R., et al., "Cannabinoid behaviors: specific versus nonspecific actions," *Marijuana: An International Research Report*, 1987, 7, 213-218.
DeLean, A.P., et al., "Simultaneous analysis of families of sigmoidal curves: application to bioassay, radioligand assay, and physiological dose-response curves," *Am. J. Physiol.*, 1978, 235, E97-E102.
Dixon, W.J., "Efficient analysis of experimental observations," *Ann. Rev. Pharmacol. Toxicol.*, 1980, 20, 441-462.
Dourish, C.T., et al., "Enhancement of morphine analgesia and prevention of morphine tolerance in the rat by the cholecystokinin antagonist L-364,718," *Eur. J. Pharmacol.*, 1988, 147, 469-472.
Duan, J., et al., "Trifluoromethylation of organic halides with methyl halodifluoroacetates—a process via difluorocarbene and trifluoromethide intermediates," *J. of Fluorine Chemistry*, 1993, 61, 279-284.
Gill, E.W., et al., "Brain levels of $\Delta^1$-tetrahydrocannabinol and its metabolites in mice-correlation with behaviour, and the effect of the metabolic inhibitors SKF 525A and piperonyl butoxide," *Biochem. Pharmacol.*, 1972, 21, 2237-2248.
Gill, E.W., et al., "Preliminary experiments on the chemistry and pharmacology of cannabis," *Nature*, 1970, 228, 134-136.
Greene, T.W., et al., :Protection for the hydroxyl group, including 1,2- and 1,3-diols, *Protective Groups in Organic Synthesis*, 3$^{rd}$ Ed., Wiley & Sons, 1991, Chapter 2, 10-123.
Howlett, A.C., et al., "International union of pharmacology. XXVII.. Classification of cannabinoid receptors," *Pharmacological Reviews*, 2002, 54(2), 161-202.
Idris, A.I., et al., "Regulation of bone mass, bone loss and osteoclast activity by cannabinoid receptors," *Nature Medicine*, 2005, 11(7), 774-779.
Iwamura, H., et al., "In vitro and in vivo pharmacological characterization of JTE-907, a novel selective ligand for cannabinoid $CB_2$ receptor," *J. Pharm. Exp. Ther.*, 2001, 296(2), 420-425.
Jain, K.K., "A guide to drug evaluation for chronic pain," *Emerging Drugs*, 2000, 5(2), 241-257.
Kim, S.H., et al., "An experimental model for peripheral neuropathy produced by segmental spinal nerve ligation in the rat," *Pain*, 1992, 50, 355-363.

(Continued)

*Primary Examiner*—Johann Richter
*Assistant Examiner*—Chukwuma Nwaonicha
(74) *Attorney, Agent, or Firm*—Woodcock Washburn LLP

(57) ABSTRACT

Novel sulfamoyl benzamide compounds, pharmaceutical compositions containing the sulfamoyl benzamide compounds, and methods of their pharmaceutical use are disclosed. In certain embodiments, the sulfamoyl benzamide compounds are agonists and/or modulating ligands of cannabinoid receptors and may be useful, inter alia, for treating and/or preventing pain, gastrointestinal disorders, inflammation, auto-immune diseases, ischemic conditions, immune-related disorders, hypertension, neurological disorders, and neurodegenerative diseases, for providing cardioprotection against ischemic and reperfusion effects, for inducing apoptosis in malignant cells, for inhibiting mechanical hyperalgesia associated with nerve injury, and as an appetite stimulant.

135 Claims, No Drawings

OTHER PUBLICATIONS

LaBuda, C.J., et al., "Enhanced formalin nociceptive responses following L5 nerve ligation in the rat reveals neuropathy-induced inflammatory hyperalgesia," *Pain*, 2001, 94, 59-63.

LaBuda, C.J., et al., "Morphine and gabapentin decrease mechanical hyperalgesia and escape/avoidance behavior in a rat model of neuropathic pain," *Neurosci. Letts.*, 2000, 290, 137-140.

LaBuda, C.J., et al., "A behavioral test paradigm to measure the aversive quality of inflammatory and neuropathic pain in rats," *Exp. Neurol.*, 2000, 163, 490-494.

Lavey, B.J., et al., "Triaryl bis-sulfones as a new class of cannabinoid CB2 receptor inhibitors: identification of a lead and initial SAR studies," *Bioorg. & Med. Chem. Lett*, 2005, 15, 783-786.

Lunn, C.A., et al., "Triaryl bis-sulfones as a new class of cannabinoid CB2 receptor inhibitors: identification of a lead and initial biological characterization," ICRS 15th Annual Symposium of the Cannabinoids, Clearwater Beach, FL, Jun. 24-27, 2005, p. 3.

Malan, T.P., Jr., et al., "CB$_2$ cannabinoid receptor agonists: pain relief without psychoactive effects?," *Curr. Opin. Pharm.*, 2003, 3, 62-67.

Mao, M.J., et al., "Oral administration of dextromethorphan prevents the development of morphine tolerance and dependence in rats," *Pain*, 1996, 67, 361-368.

Mechoulam, R., "Cannabinoids as therapeutic agents," *CRC Press*, Boca Raton, FL, 1986, 1-19.

Nichols, M.L., et al., "Enhancement of the antiallodynic and antinociceptive efficacy of spinal morphine by antisera to dynorphin A (1-13) or MK-801 in a nerve-ligation model of peripheral neuropathy," *Pain*, 1997, 69, 317-322.

Parolaro, D., "Presence and functional regulations of cannabinoid receptors in immune cells," *Life Sci.*, 1999, 65(6/7), 637-644.

Pertwee, R.B., "Pharmacology of cannabinoid receptor ligands," *Current Medicinal Chem.*, 1999, 6, 635-664.

Pertwee, R.G., "The ring test: a quantitative method for assessing the 'cataleptic', effect of cannabis in mice," *Br. J. Pharmacology*, 1972, 46, 753-763.

Pertwee, R.G., "Cannabinoid receptors and pain," *Prog. in Neurobiol.*, 2001, 63, 569-611.

Rice, A.S., "Cannabinoids and pain," *Curr. Opin. Investig. Drugs*, 2001, 2(3), 399-414.

Rinaldi-Carmona, M., et al., "SR 144528, the first potent and selective antagonist of the CB2 cannabinoid receptor," *J. of Pharmacology & Experimental Therapeutics*, 1998, 284(2), 644-650.

Yang, C., et al., "Palladium-catalyzed cyanation of aryl bromides promoted by low-level organotin compounds," *Organic Letts.*, 2004, 6(17), 2837-2840.

\* cited by examiner

SULFAMOYL BENZAMIDE DERIVATIVES AND METHODS OF THEIR USE

CROSS REFERENCE TO RELATED APPLICATION

This application claims the benefit of U.S. Provisional Application Ser. No. 60/618,387, filed Oct. 13, 2004, the disclosure of which is incorporated herein by reference in its entirety.

FIELD OF THE INVENTION

This invention relates to novel sulfamoyl benzamide compounds, pharmaceutical compositions containing such compounds, and the use thereof. More particularly, the present invention relates to novel sulfamoyl benzamide compounds that may affect the cannabinoid receptor system and thus may be useful, inter alia, as agonists or antagonists of cannabinoid receptors.

BACKGROUND OF THE INVENTION

*Cannabis sativa* preparations have long been known as therapeutic agents to treat various diseases (Mechoulam, R., "Cannabinoids as Therapeutic Agents" CRC Press, Boca Raton, Fla. 1-19, 1986). The native active constituent, $\Delta^9$-tetrahydrocannabinol ($\Delta^9$-THC), is prescribed today, under the generic name dronabinol, as an anti-emetic and for enhancement of appetite, mainly in AIDS patients. However, separation between the clinically undesirable psychotropic effects and the therapeutically desirable effects on the peripheral nervous systems, the cardiovascular system, the immune and endocrine system is problematic. The discovery of two cannabinoid receptors, CB1 and CB2, has helped to elucidate the diverse cannabinoid effects.

The CB1 receptor has been cloned from rat, mouse, and human tissues and exhibits 97-99% amino acid sequence identity across species. The CB2 receptor exhibits 48% homology with the CB1 receptor (A. C. Howlett et al. *Pharmacological Reviews* 2002, 54, 161-202). The structures of both receptors are consistent with seven transmembrane G-protein coupled receptors. In addition, both receptors exert their effect by negative regulation of adenylyl cyclase activity through pertussis toxin-sensitive GTP-binding proteins. They were also shown to activate the mitogen activated protein kinase (MAPK) in certain cell types (Parolaro, D., *Life Sci.* 1999, 65, 637-44).

The CB1 receptor is expressed mainly in the CNS and to a lesser extent in other tissues including, for example, gastrointestinal tissues, immune cells, reproductive organs, heart, lung, urinary bladder and adrenal gland. The CB2 receptor is expressed mostly in peripheral tissue associated with immune functions including, for example, macrophages, B, T cells and mast cells, as well as in peripheral nerve terminals (Pertwee, R. G., *Prog. Neurobiol.* 2001, 63, 569-611). The central distribution pattern of CB1 receptors accounts for several unwanted pharmacological properties of cannabinoids, such as impaired cognition and memory, altered control of motor function, and psychotropic and other neurobehavioral effects. CB1 receptors are also found on pain pathways in brain, spinal cord and at the peripheral terminals of primary sensory neurons (A. S. Rice, *Curr. Opin. Investig. Drugs* 2001 2(3), 399-414).

CB1 knockout mice have been shown to be unresponsive to cannabinoids in behavioral assays providing molecular evidence that the psychotropic effects, including sedation, hallucinations and antinociception are manifested through the activation of the CB1 receptor, present primarily in the CNS. Analysis of the CB2 knockout mouse has corroborated the evidence for the function of CB2 receptors in modulating the immune system. The CB2 receptor does not affect immune cell development and differentiation as determined by FACS analysis of cells from the spleen, lymph node and thymus from CB2 knockout mice. Further studies in these mice have shown that the immunosuppressive effects of $\Delta^9$-THC are mediated by the CB2 receptor.

Cannabinoid receptor agonists, such as CP55,940 and WIN 55,212-2, produce potent antinociception with equivalent efficacy to morphine in animal models of acute pain, persistent inflammatory pain and neuropathic pain. They also induce a number of unwanted CNS side effects. Furthermore, the known cannabinoid receptor agonists are in general highly lipophilic and insoluble in water. There is thus a need for cannabinoid receptor agonists with improved properties for the use as therapeutic agents.

Known CB1 cannabinoid receptor agonists produce a characteristic profile of in vivo effects in mice, including suppression of spontaneous activity, antinociception, hypothermia, and catalepsy. Measurement of these four properties, commonly referred to as the tetrad test, has played a key role in establishing the structure-activity relation of cannabinoids and cannabimemetics acting at CB1 receptors. Catalepsy in mice is indicative of CB1 activation and predictive of cannabinoid psychoactivity. Pertwee showed a correlation between catalepsy in the ring test in mice and the previously validated dog static ataxia model (R. G. Pertwee, *Br. J. Pharmacology* 1972, 46, 753-763). Therefore, catalepsy in mice is viewed as excellent predictor of CNS effects in humans (D. R. Compton, *Marijuana: An International Research Report* 7, 213-218, 1987; E. W. Gill and G. Jones, *Biochem. Pharmacol.* 21, 2237-2248, 1972; E. W. Gill et al. *Nature* 228, 134-136, 1970).

Efforts have been made to separate therapeutic effects from undesirable CNS side effects by increasing the selectivity for the CB2 receptor, thereby leading to efforts to design compounds with selectivity for the CB2 receptor over the CB1 receptor. These compounds would be predicted to lack side effects even if they penetrate the CNS because they would not activate the CB1 receptors in the CNS (Malan, T. Philip, Jr. et al. "CB2 cannabinoid receptor agonists: pain relief without psychoactive effects?" *Curr Op. Pharm.* 2003, 3(1), 62-67; WO2004/017920).

Recent studies have identified CB2 selective inverse agonists with antiedema effects in vivo (Iwamura et al., *J. Pharm. Exp. Ther.* 2001, 420-425; Lavey et al. *Bioorg. Med. Chem. Lett.* 2005, 783-786), suggesting an involvement of CB2 selective inverse agonists in inflammatory processes and the pharmacological efficacy of CB2 inverse agonists by themselves.

Lunn, et al. (ICRS 15th Annual Symposium of the Cannabinoids, Clearwater Beach, Fla., Jun. 24-27, 2005) have reported that CB2 receptor-selective inverse agonists are capable of altering cellular chemotaxis mediated by either cannabinoids or chemokines, both in vivo and in vitro. They have reported that administration of these compounds can decrease allergic eosinophilia in animal models for asthma.

Other research has shown that pharmacological antagonists of CB1 and CB2 receptors prevented ovariectomy-induced bone loss in vivo and caused osteoclast inhibition in vitro by promoting osteoclast apoptosis and inhibiting production of several osteoclast survival factors. These studies show that the CB1 receptor has a role in the regulation of bone mass and ovariectomy-induced bone loss and that CB1- and CB2-selective cannabinoid receptor antagonists are a new class of osteoclast inhibitors that may be of value in the treatment of osteoporosis and other bone diseases (A. I Idris, et al., *Nature Medicine,* 2005,11(7), 774-79).

There is considerable interest in developing new cannabimimetic compounds possessing preferentially high affinity for the CB2 receptor. Such compounds that preferentially stimulate the CB2 receptor, directly or indirectly, may provide clinically useful effects without unwanted effects on the subject's central nervous system and can offer a rational therapeutic approach to a variety of disease states. The present invention is directed to these and other important ends.

SUMMARY OF THE INVENTION

Accordingly, the present invention is directed, in part, to novel sulfamoyl benzamide compounds which may be modulators, agonists, inverse agonists, and/or antagonists of cannabinoid receptors and which thus may be useful, inter alia, for the treatment of diseases or disorders which are associated with the cannabinoid receptor system.

Specifically, in one embodiment, the present invention relates to compounds of formula I:

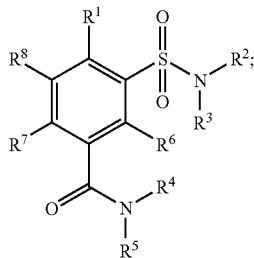

I wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

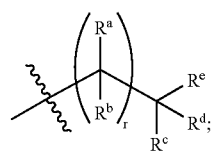

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;
$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;

provided that:
at least two of $R^c$, $R^d$, and $R^e$ are other than H; and
when $R^1$, $R^6$, $R^7$, and $R^8$ are each H, then $R^d$ and $R^e$ taken together form a bicycloalkyl or tricycloalkyl ring;
or a pharmaceutically acceptable salt thereof.

In another embodiment, the present invention is directed compounds of formula I':

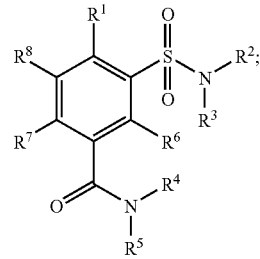

I' wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

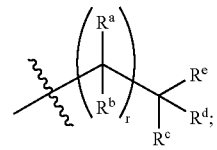

$R^a$, $R^b$, and $R^c$ are each independently H or alkyl;
$R^d$ and $R^e$ taken together with the carbon atom to which they are attached form a carbocyclic ring;
$R^6$, $R^7$, and $R^8$ are each independently H, F, Cl, Br, or alkyl;
$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;

provided that:
(1) when $R^d$ and $R^e$ taken together with the carbon atom to which they are attached form a monocyclic carbocyclic ring, then $R^c$ is alkyl; and
(2) when $R^5$ is:

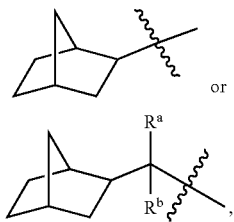

then $R^2$ and $R^3$ are taken together with the nitrogen atom to which they are attached to form a 3- to 8-membered heterocycloalkyl ring;

or a pharmaceutically acceptable salt thereof

The present invention is also directed, in part, to compounds of formula III:

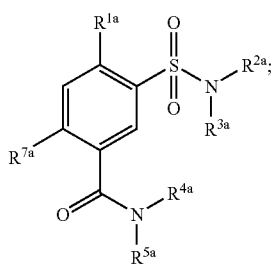

wherein:
$R^{1a}$ is F or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H or chloro;
provided that:
the compound of formula III is other than N-benzyl-4-bromo-3-(morpholine-4-sulfonyl)-benzamide, N-benzyl-4-bromo-3-(piperidine-1-sulfonyl)-benzamide, N-benzyl-4-fluoro-N-methyl-3-(piperidine-1-sulfonyl)-benzamide, or N-benzyl-4-fluoro-N-methyl-3-(morpholine-4-sulfonyl)-benzamide;
or a pharmaceutically acceptable salt thereof.

The present invention is also directed, in part, to compounds of formula IV:

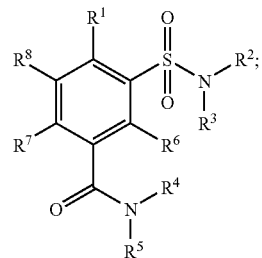

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

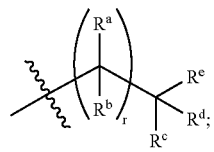

each $R^a$, $R^b$, and $R^c$, is independently H or alkyl;
$R^d$ and $R^e$ taken together with the carbon atom to which they are attached form a carbocyclic ring; or $R^c$, $R^d$, and $R^e$, taken together with the carbon atom to which they are attached, form a bicycloalkyl or tricycloalkyl ring;
$R^6$, $R^7$, and $R^8$ are each independently H, F, Cl, Br, or alkyl;
$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;
provided that:
(1) when $R^d$ and $R^e$ taken together with the carbon atom to which they are attached form a monocyclic carbocyclic ring, then $R^c$ is alkyl;
(2) when $R^5$ is:

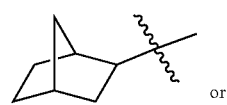

-continued

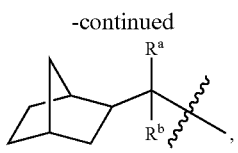

then R² and R³ are taken together with the nitrogen atom to which they are attached to form a 3- to 8-membered heterocycloalkyl ring;

(3) when R¹ is H or Cl, R² and R³ are each independently cyclohexyl, 1,5-dimethyl-2-phenyl-1,2-dihydro-pyrazol-3-on-4-yl, or substituted or unsubstituted alkyl, substituted or unsubstituted benzyl, or substituted or unsubstituted phenyl, or R² and R³ taken together with the nitrogen atom to which they are attached form a 3- to 8-membered heterocycloalkyl ring, wherein 1 of the heterocycloalkyl ring carbon atoms may be optionally replaced by —O— or —N(R⁹)—, R⁶, R⁸, and R$^b$ are H, and R⁷ is H or chloro, then R⁵ is other than 1-adamantyl, adamant-1-ylmethyl, or adamant-1-yleth-1-yl; and (4) the compound of formula IV is other than N-(2-adamantan-1-yl-ethyl)-2,4-dichloro-5-dimethylsulfamoyl-benzamide, N-(2-adamantan-1-yl-ethyl)-3-(morpholine-4-sulfonyl)-benzamide, N-adamantan-1-yl-4-methyl-3-(piperidine-1-sulfonyl)-benzamide, N-(1-adamantan-1-yl-ethyl)-4-methyl-3-(piperidine-1-sulfonyl)-benzamide, N-adamantan-1-ylmethyl-3-(ethyl-phenyl-sulfamoyl)-4-methyl-benzamide, N-adamantan-1-yl-4-bromo-3-(morpholine-4-sulfonyl)-benzamide, N-(1-adamantan-1-yl-ethyl)-4-fluoro-3-(morpholine-4-sulfonyl)-benzamide, 2,4-dichloro-N-(3,5-dimethyl-adamantan-1-yl)-5-dimethylsulfamoyl-benzamide, or N-cycloheptyl-4-methyl-3-(morpholinosulfonyl)benzamide;

or a pharmaceutically acceptable salt thereof.

In some embodiments, the invention is directed to compounds selected from the group consisting of:
4-bromo-N-(2,2-dimethylpropyl)-3-(piperidine-1-sulfonyl)-benzamide;
3-(N-benzyl-N-methylsulfamoyl)-4-bromo-N-(2,2-dimethylpropyl)-benzamide;
3-(N-benzyl-N-methylsulfamoyl)-4-bromo-N-isobutyl-benzamide;
4-chloro-N-(2,2-dimethylpropyl)-3-(piperidine-1-sulfonyl)-benzamide;
N-(2,2-dimethylpropyl)-4-methyl-3-(piperidine-1-sulfonyl)-benzamide;
4-bromo-N-(2,2-dimethylpropyl)-3-(pyrrolidine-1-sulfonyl)-benzamide; and a pharmaceutically acceptable salt thereof.

In some other embodiments, the invention is directed to compounds selected from the group consisting of:
N-(2,2-dimethylpropyl)-4-methyl-3-(morpholine-4-sulfonyl)-benzamide;
4-methyl-3-(morpholine-4-sulfonyl)-N-(1-morpholin-4-ylbutan-2-yl)-benzamide;
3-(1,3-dihydroisoindole-2-sulfonyl)-N-(2,2-dimethylpropyl)-4-methylbenzamide;
3-(1,3-dihydroisoindole-2-sulfonyl)-4-methyl-N-(1-morpholin-4-ylbutan-2-yl)-benzamide;
4-methyl-3-(morpholinosulfonyl)-N(3,3,5-trimethylcyclohexyl)-benzamide;
N-(3,3-dimethylbutan-2-yl)-4-methyl-3-(morpholinosulfonyl)-benzamide;
N-(4-hydroxy-3,3-dimethylbutan-2-yl)-4-methyl-3-(morpholinosulfonyl)-benzamide;
N,N-diisopropyl-4-methyl-3-(morpholinosulfonyl)-benzamide;
4-bromo-3-(morpholine-4-sulfonyl)-N-(2,2-dimethylbutan-2-yl)-benzamide;
4-bromo-3-(pyrrolidine-1-sulfonyl)-N-(2,2-dimethylbutan-2-yl)-benzamide;
4-bromo-3-(N,N-dimethylsulfamoyl-N-(2,2-dimethylbutan-2-yl)-benzamide;
4-(3-methoxyprop-1-ynyl)-3-(morpholinosulfonyl)-N-(1,3,3-trimethylbicyclo[2.2.1]heptan-2-yl)benzamide
4-(3-methoxyprop-1-ynyl)-3-(morpholinosulfonyl)-N-((1S,4R)-1,3,3-trimethylbicyclo[2.2.1]heptan-2-yl)benzamide and a pharmaceutically acceptable salt thereof.

In other embodiments, the invention is directed to pharmaceutical compositions comprising a pharmaceutically acceptable carrier; and a compound of formula I:

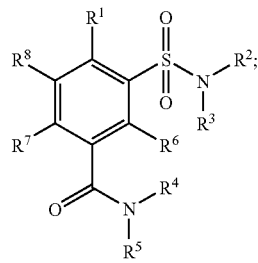

wherein:
R¹ is H, alkyl, cycloalkyl, cycloalkylalkyl, aryl, aralkyl, heterocycloalkyl, heterocycloalkylalkyl, heteroaryl, heteroaralkyl, F, Cl, or Br;
R² and R³ are each independently H, alkyl, cycloalkyl, cycloalkylalkyl, aryl, aralkyl, heterocycloalkyl, heterocycloalkylalkyl, heteroaryl, or heteroaralkyl, provided that at least one of R² and R³ is other than H; or R² and R³ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R⁹)—, —N(R¹⁰)—C(=O)—, or —C(=O)—N(R¹⁰)— groups;
R⁴ is H or alkyl;
R⁵ is:

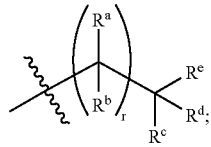

each R$^a$, R$^b$, R$^c$, R$^d$, and R$^e$ is independently H or alkyl; or R$^d$ and R$^e$ taken together with the carbon atom to which they are attached form a carbocyclic ring;
R⁶, R⁷, and R⁸ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:

at least two of $R^c$, $R^d$, and $R^e$ are other than H; and when $R^1$, $R^6$, $R^7$, and $R^8$ are each H, then $R^d$ and $R^e$ taken together form a bicycloalkyl or tricycloalkyl ring;

or a pharmaceutically acceptable salt thereof.

In certain embodiments, the invention is directed to pharmaceutical compositions, comprising:

a pharmaceutically acceptable carrier; and a compound of formula Ia:

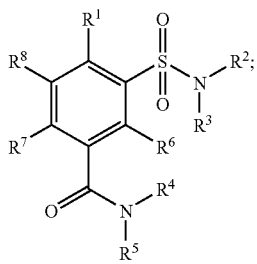

Ia wherein:

$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

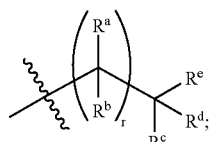

each $R^a$, $R^b$, $R^c$, $R^d$, and $R^e$ are each independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:

(1) when $R^d$ and $R^e$ taken together with the carbon atom to which they are attached form a monocyclic carbocyclic ring, then $R^c$ is alkyl or the monocyclic carbocyclic ring is an alkylcycloalkyl ring;

(2) at least two of $R^c$, $R^d$, and $R^e$ are other than H; and (3) when $R^1$ is methyl or bromo, $R^2$, $R^4$, $R^6$, $R^7$, and $R^8$ are each H, and $R^3$ is methyl, then $R^5$ is other than but-2-yl, pent-2-yl, hex-2-yl, hept-2-yl, 1,1,1-dimethyleth-1-yl, 1-dimethylprop-1-yl, 1,1-dimethylbut-1-yl, or 1,1-dimethylpent-1-yl;

or a pharmaceutically acceptable salt thereof.

In other embodiments, the invention is directed to pharmaceutical compositions comprising a pharmaceutically acceptable carrier; and a compound of formula III:

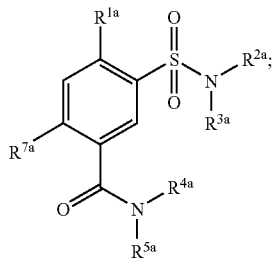

III wherein:

$R^{1a}$ is F, Cl, or Br;

$R^{2a}$ is methyl;

$R^{3a}$ is benzyl; or $R^{2a}$ and $R^{3a}$ when taken together with the nitrogen atom to which they are attached, form a morpholine, piperidine or pyrrolidine ring;

$R^{4a}$ is H or methyl;

$R^{5a}$ is benzyl, 3-methoxybenzyl, or pyrid-3-yl methyl; and $R^{7a}$ is H, F, Cl, or Br;

or a pharmaceutically acceptable salt thereof.

In other embodiments, the present invention is directed to pharmaceutical compositions, comprising:

a pharmaceutically acceptable carrier; and a compound of formula VI:

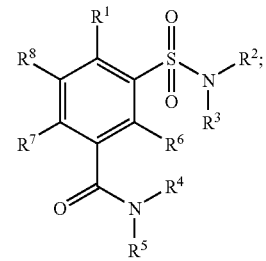

VI wherein:

$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

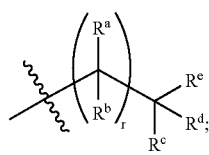

each $R^a$, $R^b$, $R^c$, $R^d$, and $R^e$ is independently H or alkyl; or $R^d$ and $R^e$ taken together with the carbon atom to which they are attached form a carbocyclic ring; or $R^c$, $R^d$, and $R^e$, taken together with the carbon atom to which they are attached, form a bicycloalkyl or tricycloalkyl ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:

(1) when $R^d$ and $R^e$ taken together with the carbon atom to which they are attached form a monocyclic carbocyclic ring, then $R^c$ is alkyl or the monocyclic carbocyclic ring is an alkylcycloalkyl ring;

(2) at least two of $R^c$, $R^d$, and $R^e$ are other than H; and (3) when $R^1$ is methyl or bromo, $R^2$, $R^4$, $R^6$, $R^7$, and $R^8$ are each H, and $R^3$ is methyl, then $R^5$ is other than but-2-yl, pent-2-yl, hex-2-yl, hept-2-yl, 1,1,1-dimethyleth-1-yl, 1-dimethylprop-1-yl, 1,1-dimethylbut-1-yl, or 1,1-dimethylpent-1-yl;

or a pharmaceutically acceptable salt thereof.

In other embodiments, the invention is directed to methods of binding cannabinoid receptors in a patient in need thereof, comprising the step of administering to the patient in need thereof, an effective amount of a compound of formula I:

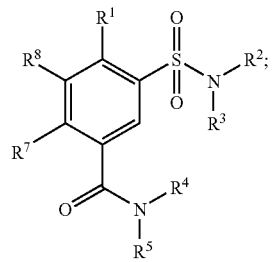

wherein:

$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

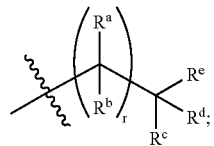

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:

at least two of $R^c$, $R^d$, and $R^e$ are other than H; and when $R^1$, $R^6$, $R^7$, and $R^8$ are each H, then $R^d$ and $R^e$ taken together form a bicycloalkyl or tricycloalkyl ring;

or a pharmaceutically acceptable salt thereof.

In other embodiments, the invention is directed to methods of binding cannabinoid receptors in a patient in need thereof, comprising the step of administering to the patient in need thereof, an effective amount of a compound of formula Ia:

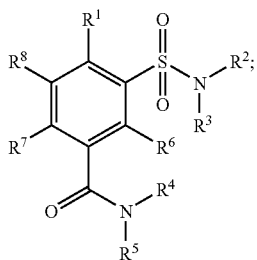

Ia wherein:
  R¹ is H, alkyl, cycloalkyl, cycloalkylalkyl, aryl, aralkyl, heterocycloalkyl, heterocycloalkylalkyl, heteroaryl, heteroaralkyl, F, Cl, or Br;
  R² and R³ are each independently H, alkyl, cycloalkyl, cycloalkylalkyl, aryl, aralkyl, heterocycloalkyl, heterocycloalkylalkyl, heteroaryl, or heteroaralkyl, provided that at least one of R² and R³ is other than H; or R² and R³ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R⁹)—, —N(R¹⁰)—C(=O)—, or —C(=O)—N(R¹⁰)—;
  R⁴ is H or alkyl;
  R⁵ is:

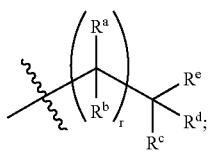

each $R^a$, $R^b$, $R^c$, $R^d$, and $R^e$ is independently H or alkyl; or $R^d$ and $R^e$ taken together with the carbon atom to which they are attached form a carbocyclic ring;
  R⁶, R⁷, and R⁸ are each independently H, F, Cl, Br, or alkyl;
  R⁹ is H, alkyl, aryl, —C(=O)—R¹¹, —C(=O)—OR¹¹, —[C(R¹¹)(R¹¹)]ₛ—C(=O)—OR¹¹, —SO₂R¹¹, or —C(=O)N(R¹¹)R¹¹;
  R¹⁰ is H, alkyl, or aryl;
  each R¹¹ is independently H or alkyl;
  r is 0, 1, 2, or 3; and
  s is 1, 2, 3, or 4;

provided that:
  (1) when $R^d$ and $R^e$ taken together with the carbon atom to which they are attached form a monocyclic carbocyclic ring, then $R^c$ is alkyl or the monocyclic carbocyclic ring is an alkylcycloalkyl ring; and
  (2) at least two of $R^c$, $R^d$, and $R^e$ are other than H;
  or a pharmaceutically acceptable salt thereof.

In other embodiments, the invention is directed to methods of binding cannabinoid receptors in a patient in need thereof, comprising the step of administering to the patient in need thereof, an effective amount of a compound of formula III:

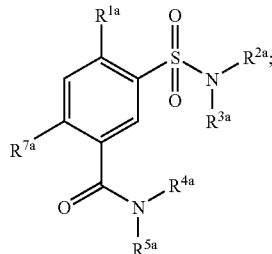

III wherein:
  $R^{1a}$ is F, Cl, or Br;
  $R^{2a}$ is methyl;
  $R^{3a}$ is benzyl; or $R^{2a}$ and $R^{3a}$ when taken together with the nitrogen atom to which they are attached, form a morpholine, piperidine or pyrrolidine ring;
  $R^{4a}$ is H or methyl;
  $R^{5a}$ is benzyl, 3-methoxybenzyl, or pyrid-3-yl methyl; and
  $R^{7a}$ is H, F, Cl, or Br;
  or a pharmaceutically acceptable salt thereof.

In other embodiments, the invention is directed to methods of binding cannabinoid receptors in a patient in need thereof, comprising the step of administering to the patient in need thereof, an effective amount of a compound of formula VI:

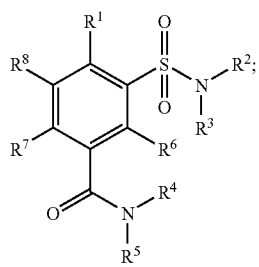

VI wherein:
  R¹ is H, alkyl, cycloalkyl, cycloalkylalkyl, aryl, aralkyl, heterocycloalkyl, heterocycloalkylalkyl, heteroaryl, heteroaralkyl, F, Cl, or Br;
  R² and R³ are each independently H, alkyl, cycloalkyl, cycloalkylalkyl, aryl, aralkyl, heterocycloalkyl, heterocycloalkylalkyl, heteroaryl, or heteroaralkyl, provided that at least one of R² and R³ is other than H; or R² and R³ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R⁹)—, —N(R¹⁰)—C(=O)—, or —C(=O)—N(R¹⁰)—;

$R^4$ is H or alkyl;
$R^5$ is:

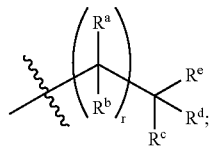

each $R^a$, $R^b$, $R^c$, $R^d$, and $R^e$ is independently H or alkyl; or $R^d$ and $R^e$ taken together with the carbon atom to which they are attached form a carbocyclic ring; or $R^c$, $R^d$, and $R^e$, taken together with the carbon atom to which they are attached, form a bicycloalkyl or tricycloalkyl ring;

$R^6$, $R^7$, and $R^8$ are each independently H, F, Cl, Br, or alkyl;

$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:
(1) when $R^d$ and $R^e$ taken together with the carbon atom to which they are attached form a monocyclic carbocyclic ring, then $R^c$ is alkyl or the monocyclic carbocyclic ring is an alkylcycloalkyl ring; and
(2) at least two of $R^c$, $R^d$, and $R^e$ are other than H;

or a pharmaceutically acceptable salt thereof.

In certain embodiments, the present invention is directed to methods of treating a gastrointestinal disorder, comprising the step of administering to the patient in need thereof, an effective amount of a compound of formula I:

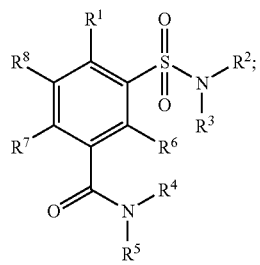

I wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;
$R^5$ is:

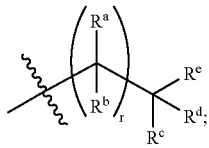

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:
at least two of $R^c$, $R^d$, and $R^e$ are other than H;
when $R^1$, $R^6$, $R^7$, and $R^9$ are each H, then $R^d$ and $R^e$ taken together form a bicycloalkyl or tricycloalkyl ring; and
the compound of formula I is not:

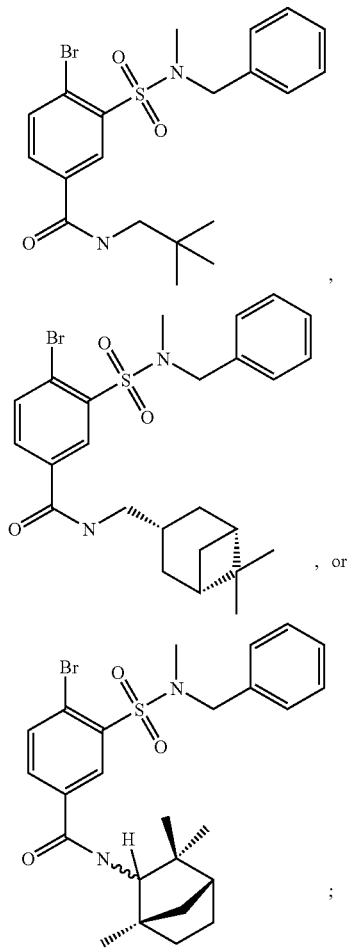

or a pharmaceutically acceptable salt thereof.

In certain embodiments, the present invention is directed to methods of treating a gastrointestinal disorder, comprising the step of administering to the patient in need thereof, an effective amount of a compound of formula III:

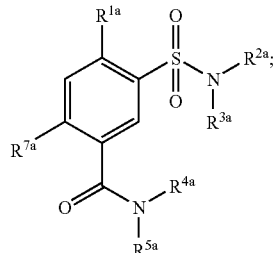

wherein:
$R^{1a}$ is F, Cl, or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl, or Br;
or a pharmaceutically acceptable salt thereof.

In some embodiments, the present invention is directed to methods of treating inflammation, comprising the step of administering to the patient in need thereof, an effective amount of a compound of formula I:

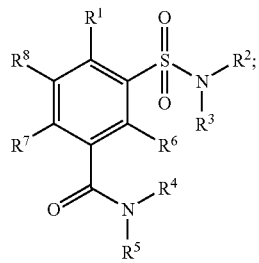

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

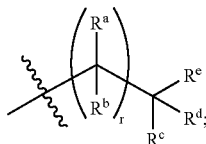

each $R^a$, $R^b$, $R^c$, $R^d$, and $R^e$ is independently H or alkyl; or $R^d$ and $R^e$ taken together with the carbon atom to which they are attached form a carbocyclic ring;
$R^6$, $R^7$, and $R^8$ are each independently H, F, Cl, Br, or alkyl;
$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —SO$_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;
provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

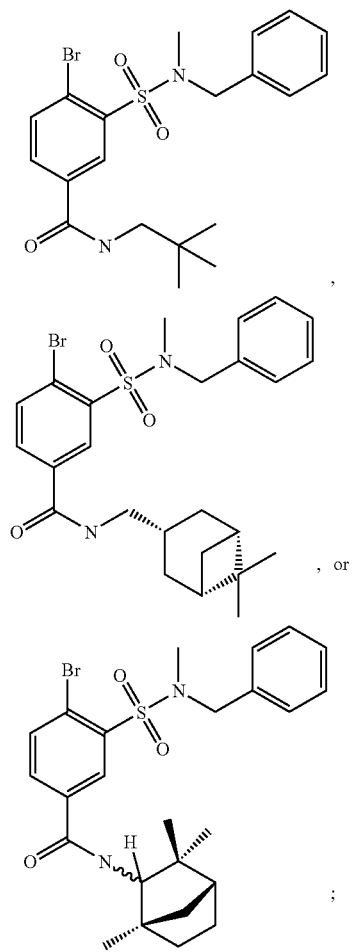

or a pharmaceutically acceptable salt thereof.

In some embodiments, the present invention is directed to methods of treating inflammation, comprising the step of administering to the patient in need thereof, an effective amount of a compound of formula III:

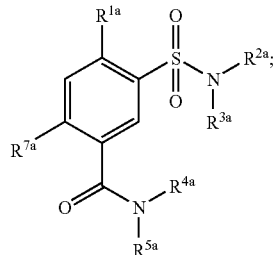

wherein:
$R^{1a}$ is F, Cl, or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl, or Br;
or a pharmaceutically acceptable salt thereof.

In certain embodiments, the present invention is directed to methods of treating auto immune diseases, comprising the step of administering to the patient in need thereof, an effective amount of a compound of formula I:

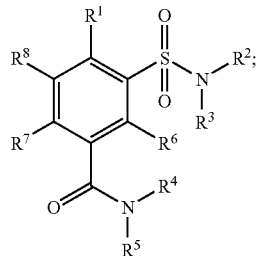

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

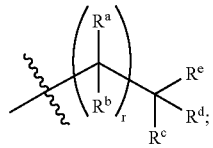

each $R^a$, $R^b$, $R^c$, $R^d$, and $R^e$ is independently H or alkyl; or $R^d$ and $R^e$ taken together with the carbon atom to which they are attached form a carbocyclic ring;
$R^6$, $R^7$, and $R^8$ are each independently H, F, Cl, Br, or alkyl;
$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;
provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

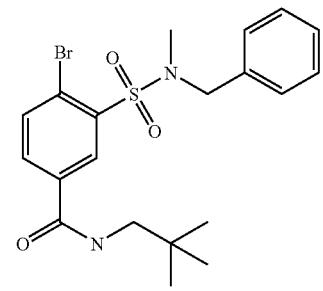

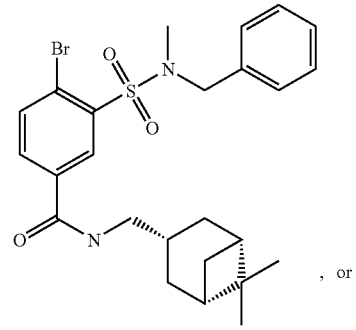

, or

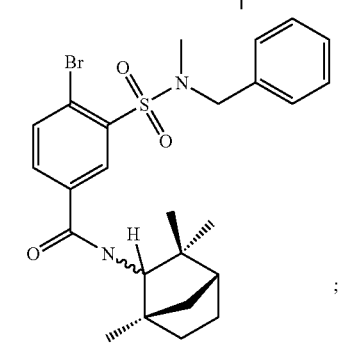

;

or a pharmaceutically acceptable salt thereof.

In certain embodiments, the present invention is directed to methods of treating auto immune diseases, comprising the step of administering to the patient in need thereof, an effective amount of a compound of formula III:

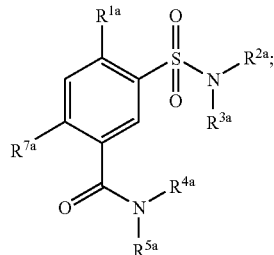

III wherein:
- $R^{1a}$ is F, Cl, or Br;
- $R^{2a}$ is methyl;
- $R^{3a}$ is benzyl; or $R^{2a}$ and $R^{3a}$ when taken together with the nitrogen atom to which they are attached, form a morpholine, piperidine or pyrrolidine ring;
- $R^{4a}$ is H or methyl;
- $R^{5a}$ is benzyl, 3-methoxybenzyl, or pyrid-3-yl methyl; and
- $R^{7a}$ is H, F, Cl, or Br;

or or a pharmaceutically acceptable salt thereof.

In some embodiments, the present invention is directed to methods of inhibiting mechanical hyperalgesia associated with nerve injury, comprising the step of administering to the patient in need thereof, an effective amount of a compound of formula I:

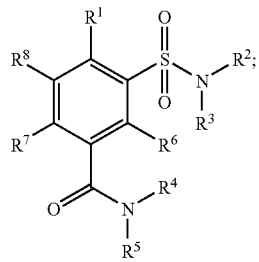

I wherein:
- $R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
- $R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
- $R^4$ is H or alkyl;
- $R^5$ is:

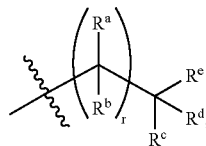

- each $R^a$, $R^b$, $R^c$, $R^d$, and $R^e$ is independently H or alkyl; or $R^d$ and $R^e$ taken together with the carbon atom to which they are attached form a carbocyclic ring;
- $R^6$, $R^7$, and $R^8$ are each independently H, F, Cl, Br, or alkyl;
- $R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;
- $R^{10}$ is H, alkyl, or aryl;
- each $R^{11}$ is independently H or alkyl;
- r is 0, 1, 2, or 3; and
- s is 1, 2, 3, or 4;

provided that:
- at least two of $R^c$, $R^d$, and $R^e$ are other than H;
- when $R^1$, $R^6$, $R^7$, and $R^8$ are each H, then $R^d$ and $R^e$ taken together form a bicycloalkyl or tricycloalkyl ring; and the compound of formula I is not:

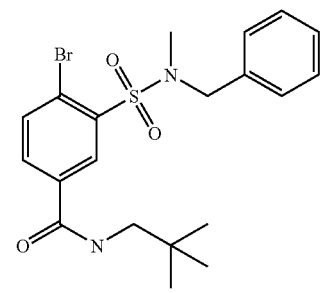

,

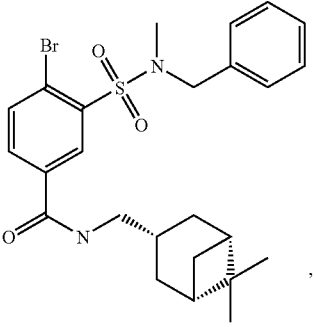

, or

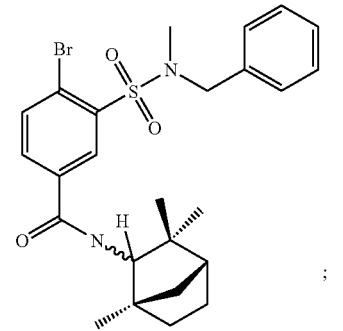

;

or a pharmaceutically acceptable salt thereof.

In some embodiments, the present invention is directed to methods of inhibiting mechanical hyperalgesia associated with nerve injury, comprising the step of administering to the patient in need thereof, an effective amount of a compound of formula III:

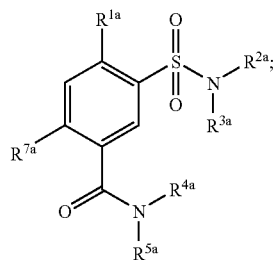

III wherein:
$R^{1a}$ is F, Cl, or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl, or Br;
or a pharmaceutically acceptable salt thereof.

In some embodiments, the present invention is directed to methods of treating an immune related disorder, comprising the step of administering to the patient in need thereof, an effective amount of a compound of formula I:

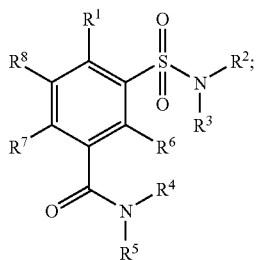

I wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

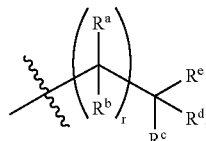

each $R^a$, $R^b$, $R^c$, $R^d$, and $R^e$ is independently H or alkyl; or $R^d$ and $R^e$ taken together with the carbon atom to which they are attached form a carbocyclic ring;
$R^6$, $R^7$, and $R^8$ are each independently H, F, Cl, Br, or alkyl;
$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;

provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

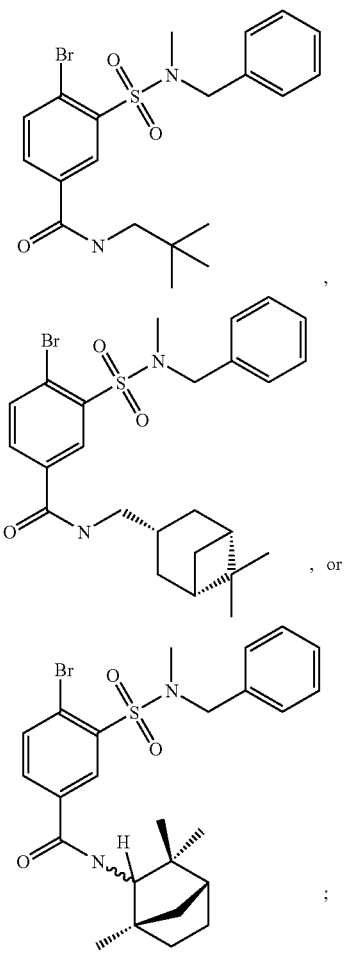

or a pharmaceutically acceptable salt thereof.

In some embodiments, the present invention is directed to methods of treating an immune related disorder, comprising the step of administering to the patient in need thereof, an effective amount of a compound of formula III:

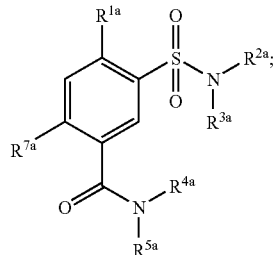

wherein:
$R^{1a}$ is F, Cl, or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl, or Br;
or a pharmaceutically acceptable salt thereof.

In certain embodiments, the present invention is directed to methods of treating pain, comprising the step of administering to the patient in need thereof, an effective amount of a compound of formula I:

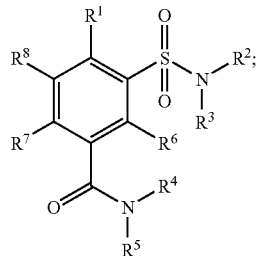

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

each $R^a$, $R^b$, $R^c$, $R^d$, and $R^e$ is independently H or alkyl; or $R^d$ and $R^e$ taken together with the carbon atom to which they are attached form a carbocyclic ring;
$R^6$, $R^7$, and $R^8$ are each independently H, F, Cl, Br, or alkyl;
$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;
provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

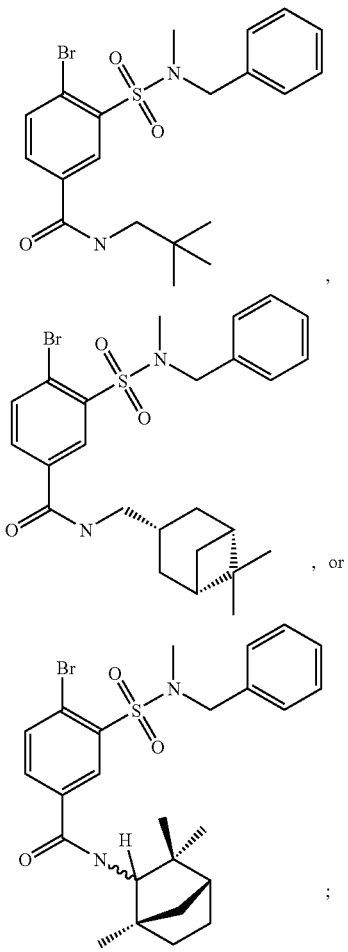

or a pharmaceutically acceptable salt thereof.

In certain embodiments, the present invention is directed to methods of treating pain, comprising the step of administering to the patient in need thereof, an effective amount of a compound of formula III:

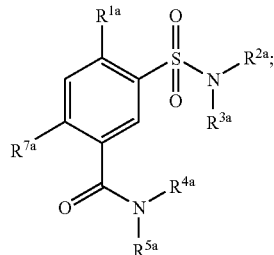

wherein:
R$^{1a}$ is F, Cl, or Br;
R$^{2a}$ is methyl;
R$^{3a}$ is benzyl; or R$^{2a}$ and R$^{3a}$ when taken together with the nitrogen atom to which they are attached, form a morpholine, piperidine or pyrrolidine ring;
R$^{4a}$ is H or methyl;
R$^{5a}$ is benzyl, 3-methoxybenzyl, or pyrid-3-yl methyl; and
R$^{7a}$ is H, F, Cl, or Br;

or a pharmaceutically acceptable salt thereof.

In some embodiments, the present invention is directed to methods of treating hypertension, comprising the step of administering to the patient in need thereof, an effective amount of a compound of formula I:

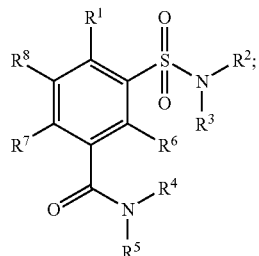

wherein:
R$^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;
R$^4$ is H or alkyl;
R$^5$ is:

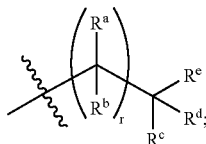

each R$^a$, R$^b$, R$^c$, R$^d$, and R$^e$ is independently H or alkyl; or R$^d$ and R$^e$ taken together with the carbon atom to which they are attached form a carbocyclic ring;
R$^6$, R$^7$, and R$^8$ are each independently H, F, Cl, Br, or alkyl;
R$^9$ is H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;
R$^{10}$ is H, alkyl, or aryl;
each R$^{11}$ is independently H or alkyl;
r is 0, 1, 2, or 3; and
s is 1, 2, 3, or 4;

provided that:
at least two of R$^c$, R$^d$, and R$^e$ are other than H;
when R$^1$, R$^6$, R$^7$, and R$^8$ are each H, then R$^d$ and R$^e$ taken together form a bicycloalkyl or tricycloalkyl ring; and the compound of formula I is not:

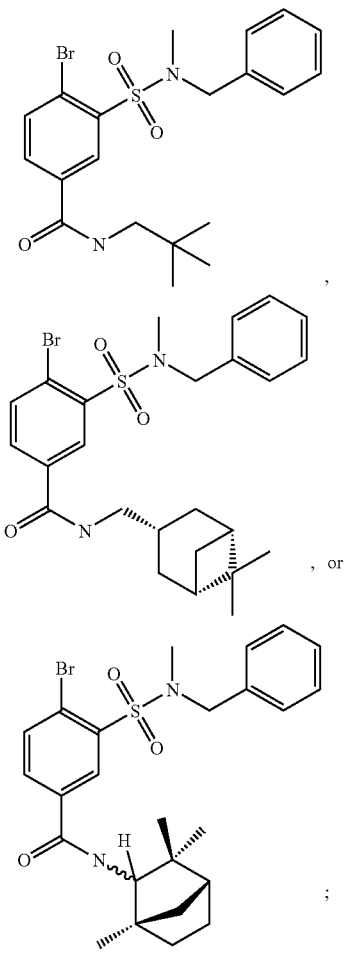

or a pharmaceutically acceptable salt thereof.

In some embodiments, the present invention is directed to methods of treating hypertension, comprising the step of administering to the patient in need thereof, an effective amount of a compound of formula III:

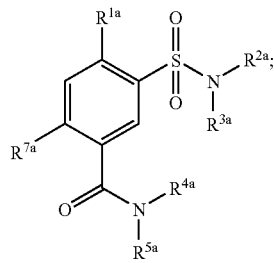

III wherein:
R$^{1a}$ is F, Cl, or Br;
R$^{2a}$ is methyl;
R$^{3a}$ is benzyl; or R$^{2a}$ and R$^{3a}$ when taken together with the nitrogen atom to which they are attached, form a morpholine, piperidine or pyrrolidine ring;
R$^{4a}$ is H or methyl;
R$^{5a}$ is benzyl, 3-methoxybenzyl, or pyrid-3-yl methyl; and
R$^{7a}$ is H, F, Cl, or Br;
or a pharmaceutically acceptable salt thereof.

In other embodiments, the present invention is directed to methods of providing cardioprotection against ischemic and reperfusion effects, comprising the step of administering to the patient in need thereof, an effective amount of a compound of formula I:

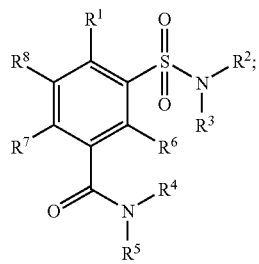

I wherein:
R$^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;
R$^4$ is H or alkyl;
R$^5$ is:

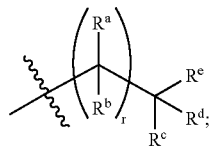

each R$^a$, R$^b$, R$^c$, R$^d$, and R$^e$ is independently H or alkyl; or R$^d$ and R$^e$ taken together with the carbon atom to which they are attached form a carbocyclic ring;
R$^6$, R$^7$, and R$^8$ are each independently H, F, Cl, Br, or alkyl;
R$^9$ is H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;
R$^{10}$ is H, alkyl, or aryl;
each R$^{11}$ is independently H or alkyl;
r is 0, 1, 2, or 3; and
s is 1, 2, 3, or 4;

provided that:
at least two of R$^c$, R$^d$, and R$^e$ are other than H;
when R$^1$, R$^6$, R$^7$, and R$^8$ are each H, then R$^d$ and R$^e$ taken together form a bicycloalkyl or tricycloalkyl ring; and
the compound of formula I is not:

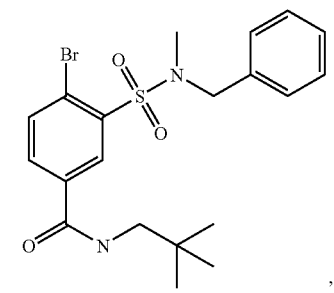

,

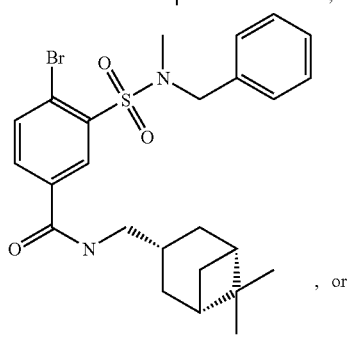

, or

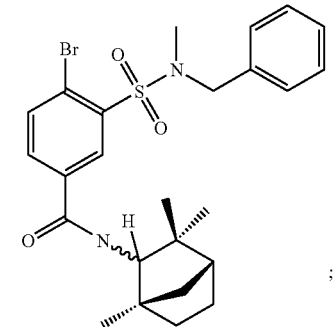

;

or a pharmaceutically acceptable salt thereof.

In other embodiments, the present invention is directed to methods of providing cardioprotection against ischemic and reperfusion effects, comprising the step of administering to the patient in need thereof, an effective amount of a compound of formula III:

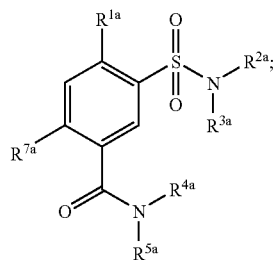

III wherein:
- $R^{1a}$ is F, Cl, or Br;
- $R^{2a}$ is methyl;
- $R^{3a}$ is benzyl; or $R^{2a}$ and $R^{3a}$ when taken together with the nitrogen atom to which they are attached, form a morpholine, piperidine or pyrrolidine ring;
- $R^{4a}$ is H or methyl;
- $R^{5a}$ is benzyl, 3-methoxybenzyl, or pyrid-3-yl methyl; and
- $R^{7a}$ is H, F, Cl, or Br;

or a pharmaceutically acceptable salt thereof.

In some embodiments, the present invention is directed to methods of treating neurodegenerative diseases, comprising the step of administering to the patient in need thereof, an effective amount of a compound of formula I:

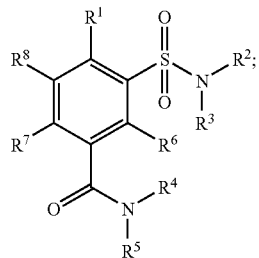

I wherein:
- $R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
- $R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
- $R^4$ is H or alkyl;
- $R^5$ is:

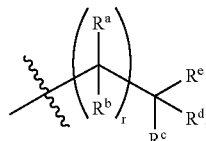

- each $R^a$, $R^b$, $R^c$, $R^d$, and $R^e$ is independently H or alkyl; or $R^d$ and $R^e$ taken together with the carbon atom to which they are attached form a carbocyclic ring;
- $R^6$, $R^7$, and $R^8$ are each independently H, F, Cl, Br, or alkyl;
- $R^9$ is H, alkyl, aryl, —C(=O)—$R^{11}$, —C(=O)—$OR^{11}$, —[C($R^{11}$)($R^{11}$)]$_s$—C(=O)—$OR^{11}$, —SO$_2$$R^{11}$, or —C(=O)N($R^{11}$)$R^{11}$;
- $R^{10}$ is H, alkyl, or aryl;
- each $R^{11}$ is independently H or alkyl;
- r is 0, 1, 2, or 3; and
- s is 1, 2, 3, or 4;

provided that:
- at least two of $R^c$, $R^d$, and $R^e$ are other than H;
- when $R^1$, $R^6$, $R^7$, and $R^8$ are each H, then $R^d$ and $R^e$ taken together form a bicycloalkyl or tricycloalkyl ring; and
- the compound of formula I is not:

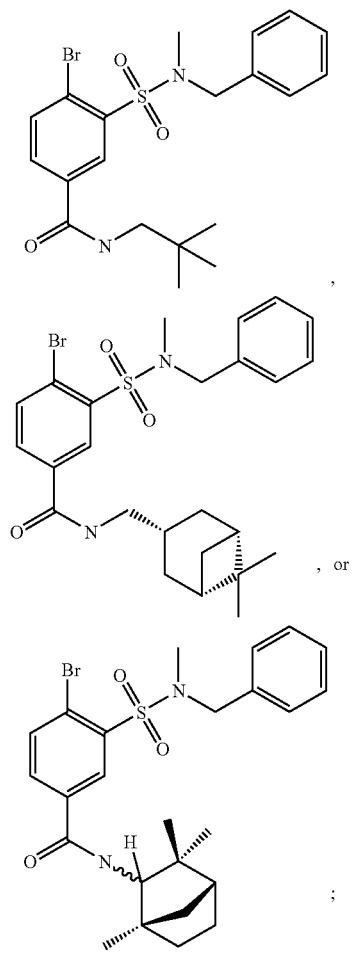

or a pharmaceutically acceptable salt thereof.

In some embodiments, the present invention is directed to methods of treating neurodegenerative diseases, comprising the step of administering to the patient in need thereof, an effective amount of a compound of formula III:

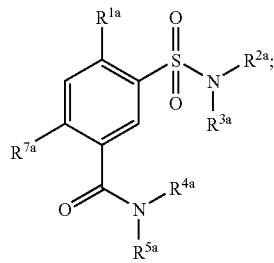

III wherein:
$R^{1a}$ is F, Cl, or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl, or Br;
or a pharmaceutically acceptable salt thereof.

In other embodiments, the present invention is directed to methods of treating neurological disorders comprising the step of administering to the patient in need thereof, an effective amount of a compound of formula I:

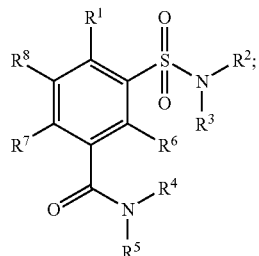

I wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

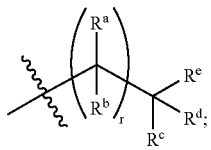

each $R^a$, $R^b$, $R^c$, $R^d$, and $R^e$ is independently H or alkyl; or $R^d$ and $R^e$ taken together with the carbon atom to which they are attached form a carbocyclic ring;
$R^6$, $R^7$, and $R^8$ are each independently H, F, Cl, Br, or alkyl;
$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;

provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

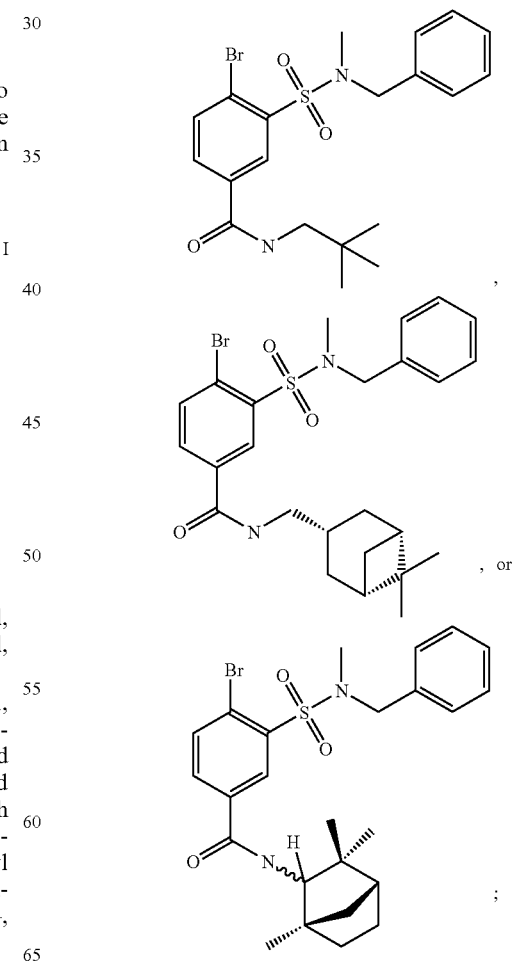

or a pharmaceutically acceptable salt thereof.

In other embodiments, the present invention is directed to methods of treating neurological disorders comprising the step of administering to the patient in need thereof, an effective amount of a compound of formula III:

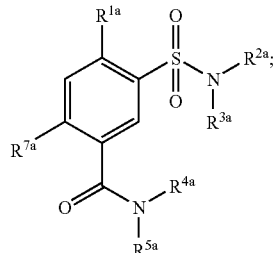

III wherein:
$R^{1a}$ is F, Cl, or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl, or Br;
or a pharmaceutically acceptable salt thereof.

In other embodiments, the present invention is directed to methods for modulating appetite, comprising the step of administering to a patient in need thereof, an effective amount of a compound of formula I:

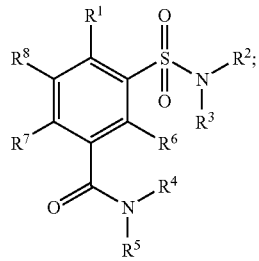

I wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

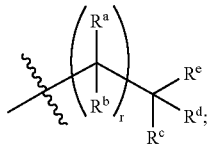

each $R^a$, $R^b$, $R^c$, $R^d$, and $R^e$ is independently H or alkyl; or $R^d$ and $R^e$ taken together with the carbon atom to which they are attached form a carbocyclic ring;
$R^6$, $R^7$, and $R^8$ are each independently H, F, Cl, Br, or alkyl;
$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —SO$_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;

provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

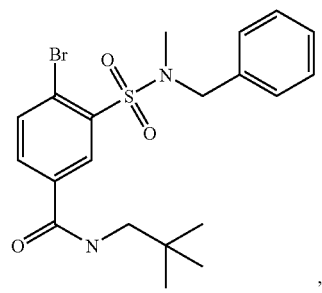

,

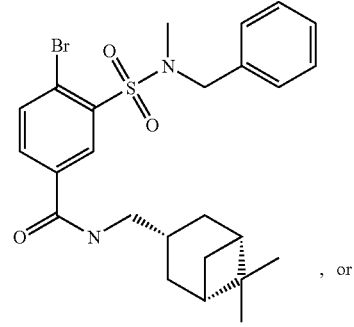

, or

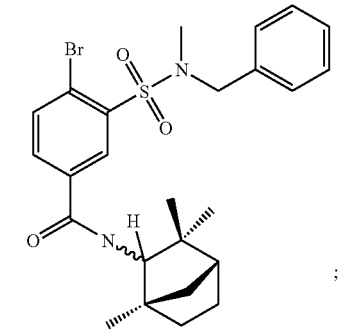

;

or a pharmaceutically acceptable salt thereof.

In other embodiments, the present invention is directed to methods for modulating appetite, comprising the step of administering to a patient in need thereof, an effective amount of a compound of formula III:

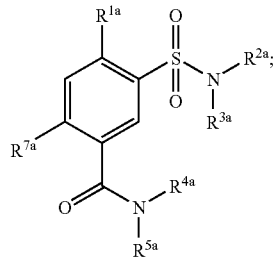

III wherein:
$R^{1a}$ is F, Cl, or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl, or Br;
or a pharmaceutically acceptable salt thereof.

In other embodiments, the present invention is directed to methods of inducing apoptosis in malignant cells comprising the step of contacting said cells with an effective amount of a compound of formula I:

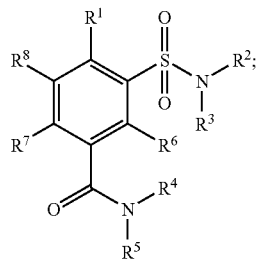

I wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

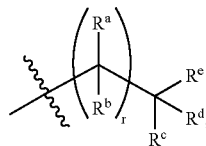

each $R^a$, $R^b$, $R^c$, $R^d$, and $R^e$ is independently H or alkyl; or $R^d$ and $R^e$ taken together with the carbon atom to which they are attached form a carbocyclic ring;
$R^6$, $R^7$, and $R^8$ are each independently H, F, Cl, Br, or alkyl;
$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;

provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

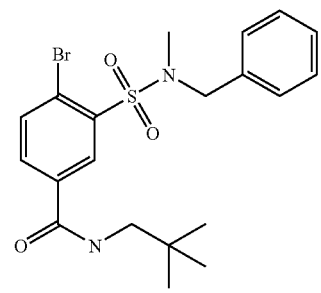

,

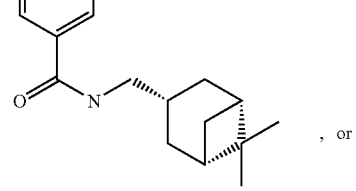

, or

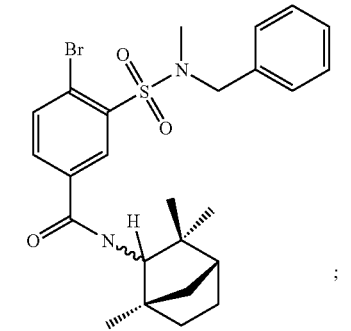

;

or a pharmaceutically acceptable salt thereof.

In other embodiments, the present invention is directed to methods of inducing apoptosis in malignant cells comprising the step of contacting said cells with an effective amount of a compound of formula III:

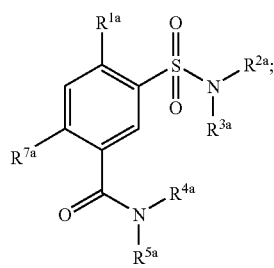

wherein:
$R^{1a}$ is F, Cl, or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl, or Br;

or a pharmaceutically acceptable salt thereof.

DETAILED DESCRIPTION OF ILLUSTRATIVE EMBODIMENTS

As employed above and throughout the disclosure, the following terms, unless otherwise indicated, shall be understood to have the following meanings.

As used herein, "alkyl" refers to an optionally substituted, saturated straight, or branched, hydrocarbon having from about 1 to about 10 carbon atoms (and all combinations and subcombinations of ranges and specific numbers of carbon atoms therein), preferably with from about 1 to about 6, more preferably 1 to about 3 carbon atoms. Alkyl groups can be optionally substituted. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, "alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

As used herein, "alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

As used herein, "alkoxy" and "alkoxyl" refer to an optionally substituted alkyl-O— group wherein alkyl is as previously defined. IN some preferred embodiments, the alkyl moieties of the alkoxy have from about 1 to about 4, more preferably from about 1 to about 3, carbon atoms. Exemplary alkoxy and alkoxyl groups include methoxy, ethoxy, n-propoxy, i-propoxy, n-butoxy, and heptoxy.

As used herein, "aryl" and "aromatic" each refer to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "aralkyl" refers to an optionally substituted moiety composed of an alkyl radical bearing an aryl substituent and having from about 6 to about 50 carbon atoms (and all combinations and subcombinations of ranges and specific numbers of carbon atoms therein), with from about 6 to about 10 carbon atoms being preferred. Non-limiting examples include, for example, benzyl, diphenylmethyl, triphenylmethyl, phenylethyl, and diphenylethyl.

As used herein, "heteroaryl" refers to an optionally substituted aryl ring system wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members (and all combinations and subcombinations of ranges and specific numbers of carbon and heteroatom ring members) are preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached via a carbon or a heteroatom to the rest of the molecule.

As used herein, "cycloalkyl" or "carbocyclic ring" each refers to an optionally substituted, mono-, di-, tri-, or other multicyclic alicyclic ring system having from about 3 to about 20 carbon atoms (and all combinations and subcombinations of ranges and specific numbers of carbon atoms therein). In some preferred embodiments, the cycloalkyl groups have from about 3 to about 8 carbon atoms. Multiring structures may be bridged or fused ring structures, wherein the additional groups fused or bridged to the cycloalkyl ring may include optionally substituted cycloalkyl, aryl, heterocycloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

As used herein, "bicycloalkyl" refers to an optionally substituted, alicyclic group having two bridged rings in its structure and having from about 7 to about 20 carbon atoms (and all combinations and subcombinations of ranges and specific numbers of carbon atoms therein), with from about 7 to about 15 carbon atoms being preferred. Exemplary bicycloalkyl-ring structures include, but are not limited to, norbornyl, bornyl, [2.2.2]-bicyclooctyl, cis-pinanyl, trans-pinanyl, camphanyl, iso-bornyl, and fenchyl.

As used herein, "tricycloalkyl" refers to an optionally substituted, alicyclic group having three bridged rings in its structure and having from about 7 to about 20 carbon atoms (and all combinations and subcombinations of ranges and specific numbers of carbon atoms therein), with from about 7 to about 15 carbon atoms being preferred. Exemplary tricycloalkyl ring structures include, but are not limited to, tricyclo[5.1.2.0$^{2,6}$]decane, 1,7,7-trimethyl tricyclo[2.2.1.0$^{2,6}$]heptane, alpha-santalol, patchouli alcohol, alpha-cedrene, and longifolene.

As used herein, "alkylcycloalkyl" refers to an optionally substituted ring system comprising a cycloalkyl group having one or more alkyl substituents, wherein cycloalkyl and alkyl are each as previously defined. Exemplary alkylcycloalkyl groups include, for example, 2-methylcyclohexyl, 3,3-dimethylcyclopentyl, trans-2,3-dimethylcyclooctyl, and 4-methyldecahydronaphthalenyl.

As used herein, "cycloalkylalkyl" refers to an optionally substituted ring system composed of an alkyl radical having one or more cycloalkyl substituents, wherein cycloalkyl and alkyl are as previously defined. In some preferred embodiments, the alkyl moieties of the cycloalkylalkyl groups have from about 1 to about 3 carbon atoms. Exemplary cycloalkylalkyl groups include, but are not limited to, cyclohexylmethyl, 4-[4-methyldecahydronaphthalenyl]-pentyl, 3-[trans-2,3-dimethylcyclooctyl]-propyl, and cyclopentylethyl.

As used herein, "heteroaralkyl" and "heteroarylalkyl" each refers to an optionally substituted ring system composed of a heteroaryl substituted alkyl radical where heteroaryl and alkyl are as previously defined. Non-limiting examples include, for example, 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, the term "heterocycloalkyl" and "heterocyclic ring" each refers to an optionally substituted ring system composed of a cycloalkyl radical wherein in at least one of the rings, one or more of the carbon atom ring members is independently replaced by a heteroatom group selected from the group consisting of O, S, N, and NH, wherein cycloalkyl is as previously defined. Heterocycloalkyl ring systems having a total of from about 5 to about 14 carbon atom ring members and heteroatom ring members (and all combinations and subcombinations of ranges and specific numbers of carbon and heteroatom ring members) are preferred. In other preferred embodiments, the heterocyclic groups may be fused to one or more aromatic rings. In certain preferred embodiments, heterocycloalkyl moieties are attached via a ring carbon atom to the rest of the molecule. Exemplary heterocycloalkyl groups include, but are not limited to, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, thiazolidinyl, piperazinyl, 2-oxo-morpholinyl, morpholinyl, 2-oxo-piperidinyl, piperadinyl, decahydroquinolyl, octahydrochromenyl, octahydro-cyclopenta[c]pyranyl, 1,2,3,4,-tetrahydroquinolyl, 1,2,3,4-tetrahydroquinazolinyl, octahydro-[2]pyridinyl, decahydro-cycloocta[c]furanyl, 1,2,3,4-tetrahydroisoquinolyl, 2-oxo-imidazolidinyl, and imidazolidinyl. In some embodiments, two moieties attached to a heteroatom may be taken together to form a heterocycloalkyl ring, such as when $R^2$ and $R^3$, taken together with the nitrogen atom to which they are attached, form a heterocycloalkyl ring. In certain of these embodiments, 1 or 2 of the heterocycloalkyl ring carbon atoms may be replaced by other moieties which contain either one (—O—, —S—, —N($R^9$)—) or two (—N($R^{10}$)—C(=O)—, or —C(=O)—N($R^{10}$)—) ring replacement atoms. When a moiety containing one ring replacement atom replaces a ring carbon atom, the resultant ring, after replacement of a ring atom by the moiety, will contain the same number of ring atoms as the ring before ring atom replacement. When a moiety containing two ring replacement atoms replaces a ring carbon atom, the resultant ring after replacement will contain one more ring atom than the ring prior to replacement by the moiety. For example, when a piperidine ring has one of its ring carbon atoms replaced by —N($R^{10}$)—C(=O)—, the resultant ring is a 7-membered ring containing 2 ring nitrogen atoms and the carbon of a carbonyl group in addition to 4 other carbon ring atoms ($CH_2$ groups) from the original piperidine ring.

As used herein, "heterocycloalkylalkyl" refers to an optionally substituted ring system composed of an alkyl radical having one or more heterocycloalkyl substituents, wherein heterocycloalkyl and alkyl are as previously defined. In some preferred embodiments, the alkyl moieties of the heterocycloalkylalkyl groups have from about 1 to about 3 carbon atoms. Exemplary heterocycloalkyl groups include, but are not limited to, azepanylmethyl, tetrahydrofuranylethyl, hexahydropyrimidinylisobutyl, tetrahydrothienylpropyl, piperidinyl-2,2-dimethylethyl, pyrrolidinylmethyl, isoxazolidinylethyl, isothiazolidinylpropyl, pyrazolidinylmethyl, oxazolidinylbutyl, thiazolidinylisopropyl, piperazinylmethyl, 2-oxo-morpholinylmethyl, morpholinylethyl, 2-oxo-piperidinylethyl, piperadinylmethyl, decahydroquinolylethyl, octahydrochromenylpropyl, octahydro-cyclopenta[c]pyranylbutyl, 1,2,3,4,-tetrahydroquinolylethyl, 1,2,3,4-tetrahydroquinazolinylmethyl, octahydro-[2]pyridinylethyl, decahydro-cycloocta[c]furanylmethyl, 1,2,3,4-tetrahydroisoquinolylmethyl, 2-oxo-imidazolidinylethyl, and imidazolidinylmethyl.

As used herein, the term "spiroalkyl" refers to an optionally substituted alkylene diradical, both ends of which are bonded to the same carbon atom of the parent group to form a spirocyclic group. The spirocyclic group, as herein defined, has 3 to 20 ring atoms, preferably with 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7]dodecane.

As used herein, "halo" and "halogen" each refers to a fluoro, chloro, bromo, or iodo moiety with fluoro, chloro, or bromo moieties being preferred.

As used herein, "perfluorinated", when used in conjunction with "alkyl" refers to an alkyl group wherein the hydrogen atoms attached to the terminal carbon of the alkyl chain are replaced by fluorine atoms, more preferably the hydrogen atoms attached to the terminal carbon and one or more of the remaining hydrogen atoms attached to the alkyl chain are replaced by fluorine atoms, with all hydrogen atoms attached to the alkyl chain being replaced by fluorine atoms being most preferred, and wherein alkyl is as previously defined.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), oxo (=O), nitro (—$NO_2$), cyano (—CN), amino (—$NH_2$), —N-substituted amino (—NHR"), -N,N-disubstituted amino (—N(R")R"), carboxy (—COOH), —O—C(=O)R", —C(=O)R", —OR", —C(=O)OR", —NHC(=O)R", aminocarbonyl (—C(=O)$NH_2$), —N-substituted aminocarbonyl (—C(=O)NHR"), -N,N-disubstituted aminocarbonyl (—C(=O)N(R")R"), thiol, thiolato (—SR"), sulfonic acid (—$SO_3$H), phosphonic acid (—$PO_3$H), —P(=O)(OR")OR", S(=O)R", —S(=$O)_2$R", —S(=$O)_2NH_2$, —S(=O)$_2$ NHR", —S(=$O)_2$NR"R", —NHS(=$O)_2$R", —NR"S(=$O)_2$R", —$CF_3$, —$CF_2CF_3$, —NHC(=O)NHR", —NHC(=O)NR"R", —NR"C(=O) NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, or when two R" groups are attached to the same nitrogen atom within a substituent, as herein above defined, R" and R" can be taken together with the nitrogen atom to which they are attached to form a 3- to 8-membered heterocycloalkyl ring, wherein one or two of the heterocycloalkyl ring carbon atoms independently may be optionally replaced by —O—, —S—, —SO, —SO$_2$—, —NH—, —N(alkyl)-, —N(acyl)-, —N(aryl)-, or —N(aroyl)-groups, for example.

As used herein, "cannabinoid" refers to any one of a group of naturally occurring compounds of related structure that may be isolable from Cannabis sativa, more commonly known as marijuana, and structurally modified derivatives thereof. Cannabinoids include for example, compounds such as $\Delta^9$-tetrahydrocannabinol, $\Delta^8$-tetrahydrocannabinol, cannabichromene, cannabicyclol, cannabidiol, cannabielsoin, cannabigerol, cannabinol, cannabitriol, nabilone, and nantradol, and numerous structural variants. Typically cannabinoids are lipophilic in terms of their solubility.

As used herein, "cannabimimetic" refers to any of a group of endogenous or exogenous receptor ligands that bind one or more of the receptors bound by cannabinoids and mimic one or more behaviors of cannabinoids while so bound. Examples of endogenous cannabimimetics (also referred to as "endocannabinoids") produced in mammalian tissues include, for example, arachidonoylethanolamide (anandamide), 2-arachidonoyl glycerol, 1(3)-arachidonoyl glycerol, and palmitoylethanolamide. Examples of exogenous cannabimimetics include, for example WIN 55,212-2, CP 55,940, HU-210, and the like. Other examples of exogenous cannbimimetics may be found in publications such as R. B. Pertwee, "Pharmacology of Cannabinoid Receptor Ligands", Current Medicinal Chemistry, 1999, 6, 635-664, and A. C. Howlett, et al. "International Union of Pharmacology. XXVII. Classification of Cannabinoid Receptors", Pharmacological Reviews, 2002, 54(2), 161-202, the disclosures of which are each hereby incorporated herein by reference, in their entireties.

As used herein, the term "antagonist" refers to a compound that binds to a receptor to form a complex that preferably does not elicit any response, in the same manner as an unoccupied receptor, and does not alter the equilibrium between inactive and active receptor.

As used herein, "agonist" refers to a ligand that produces a conformational change in the receptor and alters the equilibrium of the receptor's active and inactive states, which in turn induces a series of events, resulting in a measurable biological response. Agonists include, for example, conventional agonists, which exhibit positive receptor activity, and inverse agonists, which exhibit a negative intrinsic activity.

As used herein, "side effect" refers to a consequence other than the one(s) for which an agent or measure is used, as the adverse effects produced by a drug, especially on a tissue or organ system other then the one sought to be benefited by its administration. In the case, for example, of cannabinoids, the term "side effect" may refer to such conditions as, for example, psychotropic effects, such as confusion, anxiety, panic, distortion of perception, fantasizing, sedation, inner unrest, irritability and insomnia, sweating, rhinorrhoea, loose stools, hiccups, dry mouth, tachycardia, ataxia, dizziness, orthostatic hypotension, and anorexia.

As used herein, "effective amount" refers to an amount of a compound as described herein that may be therapeutically effective to inhibit, prevent or treat the symptoms of particular disease, disorder or side effect. Such diseases, disorders and side effects include, but are not limited to, those pathological conditions associated with the binding of cannabinoid receptors (for example, in connection with the treatment and/or prevention of pain), wherein the treatment or prevention comprises, for example, agonizing the activity thereof by contacting cells, tissues or receptors with compounds of the present invention. Thus, for example, the term "effective amount," when used in connection with cannabinoids, for example, for the treatment of pain, refers to the treatment and/or prevention of the painful condition. The term "effective amount", when used in connection with the present cannabinoid receptor agonist compounds, refers to the treatment, reduction and/or prevention of side effects typically associated with cannabinoids including, for example, such side effects as those hereinabove mentioned.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "in combination with", "combination therapy" and "combination products" refer, in certain embodiments, to the concurrent administration to a patient of cannabinoids and the compounds of the present invention. When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "hydrate" refers to a compound of the present invention which is associated with water in the molecular form, i.e., in which the H—OH bond is not split, and may be represented, for example, by the formula R.H$_2$O, where R is a compound of the invention. A given compound may form more than one hydrate including, for example, monohydrates (R.H$_2$O) or polyhydrates (R.nH$_2$O wherein n is an integer >1) including, for example, dihydrates (R.2H$_2$O), trihydrates (R.3H$_2$O), and the like, or hemihydrates, such as, for example, R.n$_{/2}$H$_2$O, R.n$_{/3}$H$_2$O, R.n$_{/4}$H$_2$O and the like wherein n is an integer.

As used herein, "solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer >1) including, for example, disolvates (R.2(solvent)), trisolvates (R.3(solvent)), and the like, or hemisolvates, such as, for example, R.n$_{/2}$(solvent), R.n$_{/3}$(solvent), R.n$_{/4}$(solvent) and the like wherein n is an integer. Solvents herein include mixed solvents, for example, methanol/water, and as such, the solvates may incorporate one or more solvents within the solvate.

As used herein, "acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

As used herein, "patient" refers to animals, including mammals, preferably humans.

As used herein, "prodrug" refers to compounds specifically designed to maximize the amount of active species that reaches the desired site of reaction, which are of themselves typically inactive or minimally active for the activity desired, but through biotransformation are converted into biologically active metabolites.

As used herein, the term "stereoisomers" refers to compounds that have identical chemical constitution, but differ as regards the arrangement of the atoms or groups in space.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

Asymmetric carbon atoms may be introduced into the molecule depending on the structure of the moiety $R^5$ when $R^a$ and $R^b$ are non-identical or when $R^c$, $R^d$, and $R^e$ are non-identical. For example, when $R^a$ is hydrogen and $R^b$ is other than H, the carbon atom to which $R^a$ is attached is asymmetric.

The term "treatment" as used herein includes preventative (e.g., prophylactic), curative or palliative treatment and "treating" as used herein also includes preventative, curative and palliative treatment.

As used herein, the term "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation for Chronic Pain"; *Emerging Drugs*, 5(2), 241-257(2000)). Non-limiting examples of pain include nociceptive pain, inflammatory pain, visceral pain, somatic pain, neuropathic pain, AIDS pain, cancer pain, phantom pain, and psychogenic pain, and pain resulting from hyperalgesia, pain caused by rheumatoid arthritis, migraine, allodynia, and the like.

Other asymmetric centers are contemplated in the present invention. Asymmetric centers are, by convention, present in $R^5$ moieties structure such as those shown below at the ring carbon atoms identified with an asterisk (*). As such, these classes of compounds can exist as

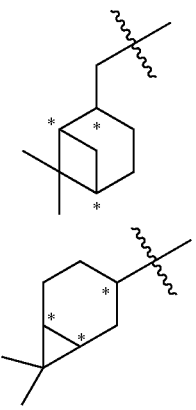

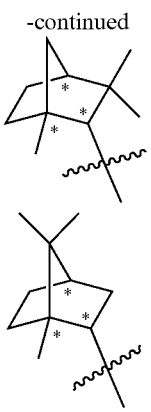

the individual "R" or "S" stereoisomers at each or any of these asymmetric centers, alone or in combination with any other asymmetric centers so formed in the compound to provide single enantiomers, any of the possible racemic mixtures of isomers or diastereomeric mixtures thereof, and all are contemplated as within the scope of the present invention.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

Accordingly, the present invention is directed, in part, to a new class of cannabinoid receptor modulator compounds, preferably phenyl compounds, which are highly useful in connection with the binding of cannabinoid receptors. Compounds binding cannabinoid receptors may act as agonists, inverse agonists, and/or antagonists toward the cannabinoid receptors. In situations where a cannabimimetic compound or ligand agonizes one or more cannabinoid receptors, the resultant binding is believed to trigger an event or series of events in the cell that results in a change in the cell's activity, its gene regulation, or the signals that it sends to neighboring cells, similar to that of a cannabinoid. Thus, in some embodiments, compounds of the invention may serve as preventatives or treatments of diseases or disorders in which cannabinoid receptors are implicated. In situations where a cannabimimetic compound or ligand antagonizes one or more cannabinoid receptors, the resultant binding typically occurs comparatively to a greater extent relative to that of the endogenous cannabinoid, but does not trigger one or more of the events of signal transduction. Compounds acting as inverse agonists are believed to bind more strongly to the inactive form of the receptor, thereby inhibiting the normal regulatory functions of the receptor and its endogenous regulatory ligands. Compounds with either inverse agonist or antagonist properties are highly useful, for example, in connection with the study of functions of cannabinoid receptors, which may result, for example, in the development of new cannabimimetic agonist compounds, such as those, for example, reported in Rinaldi-Carmona, M. et al., *Journal of Pharmacology and Experimental Therapeutics*, 1998, 284(2), 644-650, the disclosure of which is hereby incorporated herein by reference, in its entirety.

In one embodiment, the present invention is directed to compounds of formula I:

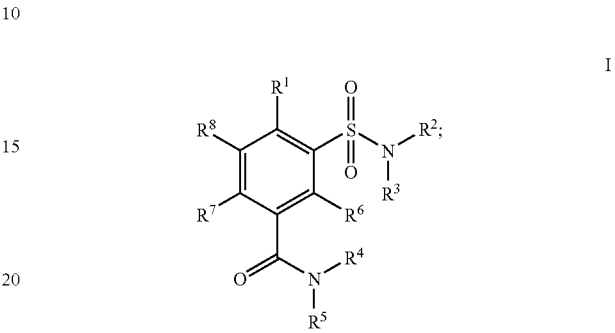

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

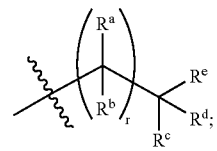

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:
at least two of $R^c$, $R^d$, and $R^e$ are other than H; and
when $R^1$, $R^6$, $R^7$, and $R^8$ are each H, then $R^d$ and $R^e$ taken together form a bicycloalkyl or tricycloalkyl ring;

or a pharmaceutically acceptable salt thereof.

In another embodiment, the present invention is directed to compounds of formula I':

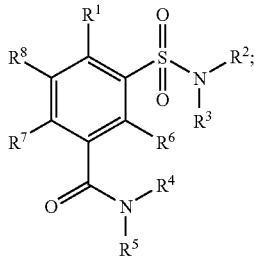

wherein:
- $R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
- $R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
- $R^4$ is H or alkyl;
- $R^5$ is:

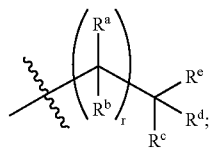

- $R^a$, $R^b$, and $R^c$ are each independently H or alkyl;
- $R^d$ and $R^e$ taken together with the carbon atom to which they are attached form a carbocyclic ring;
- $R^6$, $R^7$, and $R^8$ are each independently H, F, Cl, Br, or alkyl;
- $R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;
- $R^{10}$ is H, alkyl, or aryl;
- each $R^{11}$ is independently H or alkyl;
- r is 0, 1, 2, or 3; and
- s is 1, 2, 3, or 4;

provided that:
(1) when $R^d$ and $R^e$ taken together with the carbon atom to which they are attached form a monocyclic carbocyclic ring, then $R^c$ is alkyl; and
(2) when $R^5$ is:

 or

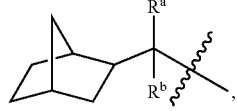, then $R^2$ and $R^3$ are taken together with the nitrogen atom to which they are attached to form a 3- to 8-membered heterocycloalkyl ring;

or a pharmaceutically acceptable salt thereof.

In certain preferred embodiments of formula I and/or I' compounds, $R^1$ is H, alkyl, F, Cl, or Br, more preferably alkyl, F, Cl, or Br. In embodiments where $R^1$ is alkyl, it is preferably $C_{1-6}$ alkyl, more preferably $C_{1-3}$ alkyl, more preferably still methyl or isopropyl. In embodiments where $R^1$ is aryl, it is preferably phenyl. In embodiments where $R^1$ is F, Cl, or Br, Cl or Br is more preferred, yet still more preferred Br.

In other embodiments of formula I and/or I' compounds, $R^1$ is heterocycloalkyl or heteroaryl. When $R^1$ is heterocycloalkyl or heteroaryl, the attachment of the heterocycloalkyl or heteroaryl to the rest of the formula I compound is at a ring carbon atom of the heterocycloalkyl or heteroaryl moiety.

In some preferred embodiments of formula I and/or I' compounds, $R^2$ and $R^3$ are each independently alkyl, cycloalkyl, cycloalkylalkyl, aryl, aralkyl, heterocycloalkyl, heterocycloalkylalkyl, heteroaryl, or heteroaralkyl, more preferably cycloalkyl, cycloalkylalkyl, aryl, aralkyl, heterocycloalkyl, heterocycloalkylalkyl, heteroaryl, or heteroaralkyl, more preferably still alkyl or aralkyl. In embodiments where $R^2$ or $R^3$ is alkyl, it is independently preferably $C_{1-6}$ alkyl, more preferably $C_{1-3}$ alkyl, more preferably still methyl. In embodiments where $R^2$ or $R^3$ is aralkyl, it is preferably benzyl. In certain preferred embodiments, one of $R^2$ and $R^3$ is alkyl, preferably $C_{1-6}$ alkyl, more preferably $C_{1-3}$ alkyl, with methyl being still more preferred. In other preferred embodiments, at least one of $R^2$ and $R^3$ is other than alkyl, more preferably at least one of $R^2$ and $R^3$ is aralkyl, yet more preferably benzyl.

In other preferred embodiments of formula I and/or I' compounds, $R^2$ and $R^3$ when taken together with the nitrogen atom to which they are attached, form a 3- to 8-membered, more preferably 5- to 6-membered, heterocycloalkyl ring, wherein one or two, more preferably one, of the heterocycloalkyl ring carbon atoms independently is each optionally replaced by —O—, —S—, —N($R^9$)—, —N($R^{10}$)—C(=O)—, or —C(=O)—N($R^{10}$)—, more preferably by —O—, —S—, or —N($R^9$)—, more preferably still by —O— or —N($R^9$)— groups. In certain other preferred embodiments, when $R^2$ and $R^3$ taken together with the nitrogen atom to which they are attached form a 5- to 6-membered heterocycloalkyl ring, the heterocycloalkyl ring is piperidine, morpholine, piperazine, or pyrrolidine, each optionally substituted.

In other preferred embodiments, when $R^2$ and $R^3$, taken together with the nitrogen atom to which they are attached, form a 3- to 8-membered heterocycloalkyl ring, the heterocycloalkyl ring is optionally substituted with at least one substituent selected from the group consisting of alkyl, alkoxyl, halo, N,N-dialkylaminocarbonyl, alkoxycarbonyl, and hydroxyl. More preferably the heterocycloalkyl ring formed is selected from the group consisting of morpholin-4-yl, pyrrolidin-1-yl, 1,3-dihydroisoindol-2-yl, 3,4-dihydro- 2H-quinolin-1-yl, octahydroquinolin-1-yl, 2,6-dimethyl-morpholin-1-yl, 3,5-dimethylpiperidin-1-yl, 2-methylpiperidin-1-yl, 4-hydroxypiperidin-1-yl, 3-N,N-diethylaminocarbonylpiperidin-1-yl, 3-fluoropiperidin-1-yl, 3-hydroxypyrrolidin-1-yl, 3-ethoxycarbonylpiperidin-1-yl, or 3-N,N-diethylaminocarbonylpyrrolidin-1-yl.

In other preferred embodiments of formula I and/or I' compounds, $R^4$ is H or $C_{1-6}$ alkyl. More preferably, in embodiments where $R^4$ is alkyl, it is preferably $C_{1-3}$ alkyl, yet more preferably methyl.

In some preferred embodiments of formula I and/or I' compounds, each $R^a$, $R^b$, $R^c$, $R^d$, and $R^e$ is independently H or $C_{1-6}$ alkyl. In embodiments where any of $R^a$, $R^b$, $R^c$, $R^d$, and $R^e$ is independently $C_{1-6}$ alkyl, it is preferably $C_{1-3}$ alkyl, with methyl being even more preferred. In certain embodiments, $R^a$ and $R^b$ are each H. In other embodiments, one of $R^a$ and $R^b$ is H and the other is H or alkyl. In some preferred embodiments, $R^d$ and $R^e$ are each alkyl. In other preferred embodiments, $R^c$ is alkyl, more preferably $C_{1-6}$ alkyl, with $C_{1-3}$ alkyl being even more preferred.

In certain preferred embodiments of formula I and/or I' compounds, $R^d$ and $R^e$ taken together with the carbon atom to which they are attached form a carbocyclic ring having from about 3 to about 15, more preferably 3 to about 12, yet more preferably 3 to about 10, carbon atoms wherein the carbocyclic ring is optionally further substituted, more preferably further substituted, with 1-5, more preferably 1-3 groups, independently selected from alkyl, hydroxyl, and alkoxyl, more preferably alkyl, wherein each said alkyl group or alkyl moiety of alkoxyl group is more preferably $C_{1-4}$ alkyl, yet more preferably $C_{1-3}$ alkyl, even more preferably methyl.

In certain preferred embodiments of formula I and/or I' compounds, $R^1$ and $R^e$ taken together with the carbon atom to which they are attached form a monocyclic carbocyclic ring.

In some preferred embodiments or formula I and/or I' compounds, $R^d$ and $R^e$, taken together with the carbon atom to which they are attached, form a 3- to 12-membered carbocyclic ring, wherein the carbocyclic ring is substituted with 0-5 groups each independently selected from $C_{1-4}$ alkyl and $C_{1-4}$ alkoxyl.

In certain other preferred embodiments of formula I and/or I' compounds, $R^d$ and $R^e$ taken together with the carbon atom to which they are attached form a bicycloalkyl or tricycloalkyl, more preferably bicycloalkyl, optionally substituted with 1-3 alkyl groups. Yet more preferably, the bicycloalkyl or tricycloalkyl group is:

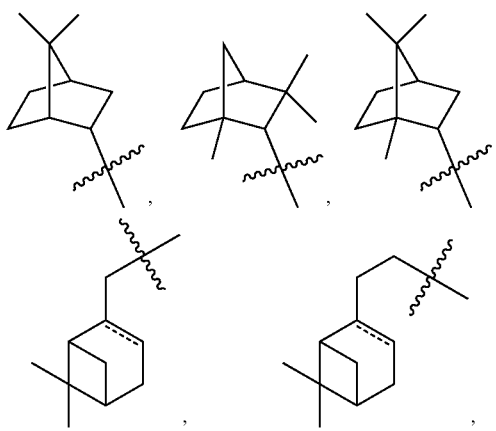

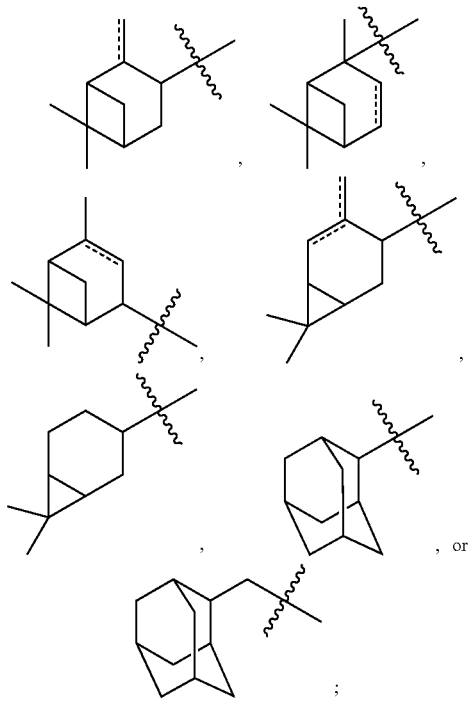

or an enantiomeric or diastereomeric form thereof;

wherein:

------ represents a single or double bond between the two bonded carbon atom termini.

In some preferred embodiments of formula I and/or I' compounds, $R^6$ and $R^7$ are each independently H, F, Cl, or Br, more preferably, H or Cl, still more preferably H. In embodiments where $R^1$ is alkyl, it is preferably $C_{1-6}$ alkyl, more preferably $C_{1-3}$ alkyl, more preferably still methyl. In other embodiments where $R^1$ is alkyl, it is preferably substituted with one or more fluorine atoms, more preferably perfluorinated.

In other preferred embodiments of formula I and/or I' compounds, $R^8$ is H or alkyl. In embodiments where $R^8$ is alkyl, it is preferably $C_{1-6}$ alkyl, more preferably $C_{1-3}$ alkyl, still more preferably methyl. In other embodiments where $R^8$ is alkyl, alkyl is preferably substituted with one to seven fluorine atoms, more preferably mono-, di- or tri-fluoromethyl, still more preferably trifluoromethyl. In other preferred embodiments, $R^8$ is H.

In certain preferred embodiments of formula I and/or I' compounds, $R^9$ is H, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$.

In some embodiments of formula I and/or I' compounds where any $R^{11}$ is independently alkyl, it is preferably independently, $C_{1-6}$ alkyl, more preferably, independently methyl, ethyl, or tert-butyl.

In other preferred embodiments of formula I and/or I' compounds, r is 0, 1, or 2, more preferably 0 or 1.

In certain preferred embodiments of formula I and/or I' compounds, s is 1, 2, 3, or 4; more preferably 1, 2, or 3, even more preferably 1 or 2, still more preferably 1.

In some preferred embodiments, the formula I and/or I' compound is:

4-bromo-N-(2,2-dimethyl-propyl)-3-(piperidine-1-sulfonyl)-benzamide;
4-chloro-3-(piperidine-1-sulfonyl)-N-(1,3,3-trimethyl-bicyclo-[2.2.1]hept-2-yl)-benzamide;
3-(benzyl-methyl-sulfamoyl)-4-bromo-N-(2,2-dimethylpropyl)-benzamide;
4-bromo-N-(6,6-dimethyl-bicyclo-[3.1.1]hept-2-yl-methyl)-3-(piperidine-1-sulfonyl)-benzamide;
3-(benzyl-methyl-sulfamoyl)-4-bromo-N-(6,6-dimethyl-bicyclo-[3.1.1]hept-2-yl-methyl)-benzamide;
3-(benzyl-methyl-sulfamoyl)-4-bromo-N-isobutyl-benzamide;
4-bromo-3-(piperidine-1-sulfonyl)-N-(1,3,3-tri-methylbicyclo[2.2.1]hept-2-yl)-benzamide;
4-isopropyl-3-(piperidine-1-sulfonyl)-N-(1,3,3-trimethyl-bicyclo-[2.2.1]-hept-2-yl)-benzamide;
3-(piperidine-1-sulfonyl)-N,S-(1,3,3-trimethyl-bicyclo-[2.2.1]hept-2-yl)-benzamide;
3-(piperidine-1-sulfonyl)-N,R-(1,3,3-trimethylbicyclo-[2.2.1]hept-2-yl)-benzamide;
3-(benzyl-methyl-sulfamoyl)-4-bromo-N-(1,3,3-trimethylbicyclo[2.2.1]hept-2-yl)-benzamide;
4-[2-methyl-5-(1,3,3-trimethylbicyclo-[2.2.1]hept-2-yl-carbamoyl)-benzenesulfonyl]-pipera-zine-1-carboxylic acid tert-butyl ester;
4-methyl-3-(morpholine-4-sulfonyl)-N,S-(1,3,3-trimethyl-bicyclo[2.2.1]-hept-2-yl)-benzamide;
4-methyl-3-(morpholine-4-sulfonyl)-N,R-(1,3,3-trimethyl-bicyclo[2.2.1]-hept-2-yl)-benzamide;
2-(piperidine-1-sulfonyl)-biphenyl-4-carboxylic acid (1,3,3-trimethyl-bicyclo-[2.2.1]hept-2-yl)-amide;
{4-[2-methyl-5-(1,3,3-trimethyl-bicyclo-[2.2.1]hept-2-yl-carbamoyl)-benzene-sulfonyl]-pipera-zin-1-yl}-acetic acid methyl ester;
4-[2-methyl-5-(1,3,3-trimethyl-bicyclo-[2.2.1]hept-2yl-carbamoyl)-benzenesulfonyl]-piperazine-1-carboxylic acid ethylamide;
3-(4-methanesulfonyl-piperazine-1-sulfonyl)-4-methyl-N-(1,3,3-tri-methyl-bicyclo-[2.2.1]-hept-2-yl)-benzamide;

or a pharmaceutically acceptable salt thereof.

In some more preferred embodiments, the formula I and/or I' compound is:
4-chloro-3-(piperidine-1-sulfonyl)-N-(1,3,3-trimethylbicyclo-[2.2.1]hept-2-yl)-benzamide;
3-(benzyl-methyl-sulfamoyl)-4-bromo-N-(6,6-dimethylbicyclo-[3.1.1]hept-2-yl-methyl)-benzamide;
4-bromo-3-(piperidine-1-sulfonyl)-N-(1,3,3-trimethylbicyclo[2.2.1]hept-2-yl)-benzamide;
4-isopropyl-3-(piperidine-1-sulfonyl)-N-(1,3,3-trimethylbicyclo-[2.2.1]-hept-2-yl)-benzamide;
4-methyl-3-(piperidine-1-sulfonyl)-N,R-(1,3,3-trimethylbicyclo-[2.2.1]-hept-2-yl)-benzamide;
3-(piperidine-1-sulfonyl)-N-(1,3,3-trimethylbicyclo-[2.2.1]hept-2-yl)-benzamide;
3-(benzyl-methyl-sulfamoyl)-4-bromo-N-(1,3,3-trimethylbicyclo[2.2.1]hept-2-yl)-benzamide;
4-methyl-3-(morpholine-4-sulfonyl)-N,S-(1,3,3-trimethylbicyclo[2.2.1]-hept-2-yl)-benzamide;
4-methyl-3-(morpholine-4-sulfonyl)-N,R-(1,3,3-trimethylbicyclo[2.2.1]-hept-2-yl)-benzamide;
2-(piperidine-1-sulfonyl)-biphenyl-4-carboxylic acid (1,3,3-trimethyl-bicyclo-[2.2.1]hept-2-yl)-amide;

or a pharmaceutically acceptable salt thereof.

In some even more preferred embodiments, the formula I and/or I' compound is:
4-chloro-3-(piperidine-1-sulfonyl)-N-(1,3,3-trimethylbicyclo-[2.2.1]hept-2-yl)-benzamide;
3-(benzyl-methyl-sulfamoyl)-4-bromo-N-(6,6-dimethylbicyclo-[3.1.1]hept-2-yl-methyl)-benzamide;
4-bromo-3-(piperidine-1-sulfonyl)-N-(1,3,3-trimethylbicyclo[2.2.1]hept-2-yl)-benzamide;
3-(benzyl-methyl-sulfamoyl)-4-bromo-N-(1,3,3-trimethyl-bicyclo[2.2.1]hept-2-yl)-benzamide;
4-methyl-3-(morpholine-4-sulfonyl)-N,S-(1,3,3-trimethyl-bicyclo[2.2.1]-hept-2-yl)-benzamide;

or a pharmaceutically acceptable salt thereof.

In some preferred embodiments of formula I and/or I' compounds, the compound has the following formula II:

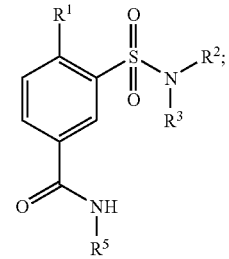

wherein:
R$^1$ is H, alkyl, aryl, F, Cl, or Br;
R$^2$ and R$^3$ are each independently alkyl or aralkyl, or R$^2$ and R$^3$, when taken together with the nitrogen atom to which they are attached, form a 5- or 6-membered heterocycloalkyl ring, wherein one of the carbon atoms of the heterocycloalkyl ring is optionally replaced by an —O— or —N(R$^9$)— group; and
R$^9$ is —C(=O)—O-alkyl, —CH$_2$—C(=O)—O-alkyl, —SO$_2$-alkyl, or —C(=O)N(H)-alkyl;

or a pharmaceutically acceptable salt thereof.

In certain preferred embodiments of formula II compounds where R$^1$ is alkyl, it is preferably C$_{1-6}$ alkyl, more preferably C$_{1-3}$ alkyl, even more preferably methyl or isopropyl. In certain other preferred embodiments of formula II compounds where R$^1$ is aryl, it is preferably phenyl.

In other preferred embodiments of formula II compounds, R$^2$ and R$^3$ are each independently alkyl, more preferably C$_{1-6}$ alkyl, more preferably C$_{1-3}$ alkyl, still more preferably methyl, or aralkyl, more preferably C$_{1-3}$ alkaryl, more preferably still phenethyl or benzyl, yet more preferably benzyl. In certain other preferred embodiments, R$^2$ and R$^3$, when taken together with the nitrogen atom to which they are attached, form a 5- or 6-membered heterocycloalkyl ring, wherein one of the carbon atoms of the heterocycloalkyl ring may be, more preferably is, optionally replaced by an —O— or —N(R$^9$)— group, more preferably replaced by —O—.

In certain other preferred embodiments of formula II compounds, R$^d$ and R$^e$ taken together with the carbon atom to which they are attached form a carbocyclic, more preferably bicycloalkyl or tricycloalkyl, even more preferably bicycloalkyl ring, optionally substituted with 1-3 alkyl groups. Yet more preferably, the bicycloalkyl or tricycloalkyl group is:

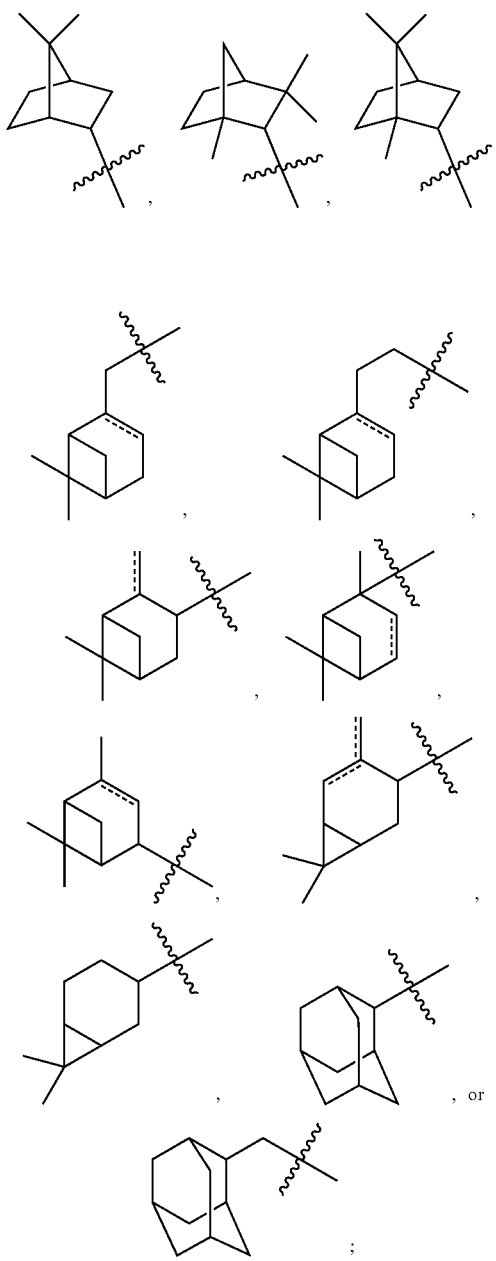

or an enantiomeric or diastereomeric form thereof;

wherein:

- - - - - represents a single or double bond between the two bonded carbon atom termini.

In some preferred embodiments of formula II compounds, wherein $R^9$ is —C(=O)—O-alkyl, —CH$_2$—C(=O)—O-alkyl, —SO$_2$-alkyl, or —C(=O)N(H)-alkyl, the alkyl is preferably $C_{1-6}$ alkyl, more preferably $C_{1-3}$ alkyl, with methyl and ethyl being still more preferred.

In other preferred embodiments of formula II compounds, $R^a$, $R^b$, and $R^c$ are each H.

In other embodiments, the present invention is directed to compounds of formula III:

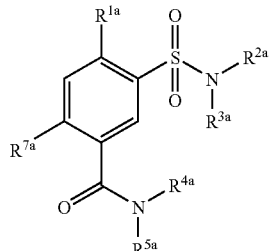

wherein:
$R^{1a}$ is F or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H or chloro;

provided that:
the compound of formula III is other than N-benzyl-4-bromo-3-(morpholine-4-sulfonyl)-benzamide, N-benzyl-4-bromo-3-(piperidine-1-sulfonyl)-benzamide, N-benzyl-4-fluoro-N-methyl-3-(piperidine-1-sulfonyl)-benzamide, or N-benzyl-4-fluoro-N-methyl-3-(morpholine-4-sulfonyl)-benzamide;
or a pharmaceutically acceptable salt thereof.

In certain preferred embodiments of formula III compounds, $R^{1a}$ is Br.

In other preferred embodiments of formula III compounds, $R^{2a}$ and $R^{3a}$ when taken together with the nitrogen atom to which they are attached, form a morpholine or piperidine ring.

In certain other preferred embodiments of formula III compounds, $R^{5a}$ is benzyl.

In some preferred embodiments of formula III compounds, $R^{7a}$ is H. In other preferred embodiments, when $R^{1a}$ is F, then $R^{7a}$ is chloro.

In some preferred embodiments of formula III compounds, the compound is selected from the group consisting of:
N-benzyl-2-chloro-4-fluoro-5-(morpholine-4-sulfonyl)-benzamide;
3-(N-benzyl-N-methylsulfamoyl)-4-bromo-N-pyridin-3-yl-methyl-benzamide;
4-bromo-N-(3-methoxybenzyl)-3-(piperidine-1-sulfonyl)-benzamide;
4-bromo-N-(3-methoxybenzyl)-3-(pyrrolidine-1-sulfonyl)-benzamide;
N-benzyl-4-bromo-3-(pyrrolidine-1-sulfonyl)-benzamide;
N-benzyl-4-bromo-N-methyl-3-(morpholine-4-sulfonyl)-benzamide; and a pharmaceutically acceptable salt thereof; more preferably N-benzyl-2-chloro-4-fluoro-5-(morpholine-4-sulfonyl)-benzamide; or a pharmaceutically acceptable salt thereof.

In other embodiments, the present invention is directed to compounds of formula IV:

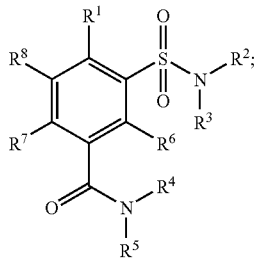

wherein:
- R¹ is H, alkyl, cycloalkyl, cycloalkylalkyl, aryl, aralkyl, heterocycloalkyl, heterocycloalkylalkyl, heteroaryl, heteroaralkyl, F, Cl, or Br;
- $R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
- $R^4$ is H or alkyl;
- $R^5$ is:

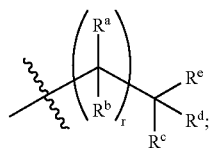

each $R^a$, $R^b$, and $R^c$, is independently H or alkyl;
$R^d$ and $R^e$ taken together with the carbon atom to which they are attached form a carbocyclic ring; or $R^c$, $R^d$, and $R^e$, taken together with the carbon atom to which they are attached, form a bicycloalkyl or tricycloalkyl ring;
$R^6$, $R^7$, and $R^8$ are each independently H, F, Cl, Br, or alkyl;
$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;
$R^{10}$ is H, alkyl, or aryl;
each $R^{11}$ is independently H or alkyl;
r is 0, 1, 2, or 3; and
s is 1, 2, 3, or 4;

provided that:
(1) when $R^d$ and $R^e$ taken together with the carbon atom to which they are attached form a monocyclic carbocyclic ring, then $R^c$ is alkyl;

(2) when $R^5$ is:

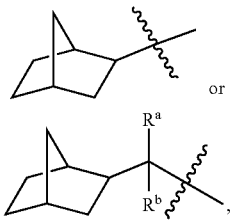

then $R^2$ and $R^3$ are taken together with the nitrogen atom to which they are attached to form a 3- to 8-membered heterocycloalkyl ring;

(3) when $R^1$ is H or Cl, $R^2$ and $R^3$ are each independently cyclohexyl, 1,5-dimethyl-2-phenyl-1,2-dihydro-pyrazol-3-on-4-yl, or substituted or unsubstituted alkyl, substituted or unsubstituted benzyl, or substituted or unsubstituted phenyl, or $R^2$ and $R^3$ taken together with the nitrogen atom to which they are attached form a 3- to 8-membered heterocycloalkyl ring, wherein 1 of the heterocycloalkyl ring carbon atoms may be optionally replaced by —O— or —N($R^9$)—, $R^6$, $R^8$, and $R^b$ are H, and $R^7$ is H or chloro, then $R^5$ is other than 1-adamantyl, adamant-1-ylmethyl, or adamant-1-yleth-1-yl; and (4) the compound of formula IV is other than N-(2-adamantan-1-yl-ethyl)-2,4-dichloro-5-dimethylsulfamoyl-benzamide, N-(2-adamantan-1-yl-ethyl)-3-(morpholine-4-sulfonyl)-benzamide, N-adamantan-1-yl-4-methyl-3-(piperidine-1-sulfonyl)-benzamide, N-(1-adamantan-1-yl-ethyl)-4-methyl-3-(piperidine-1-sulfonyl)-benzamide, N-adamantan-1-ylmethyl-3-(ethyl-phenyl-sulfamoyl)-4-methyl-benzamide, N-adamantan-1-yl-4-bromo-3-(morpholine-4-sulfonyl)-benzamide, N-(1-adamantan-1-yl-ethyl)-4-fluoro-3-(morpholine-4-sulfonyl)-benzamide, 2,4-dichloro-N-(3,5-dimethyl-adamantan-1-yl)-5-dimethylsulfamoyl-benzamide, or N-cycloheptyl-4-methyl-3-(morpholinosulfonyl)benzamide;

or a pharmaceutically acceptable salt thereof.

In some preferred embodiments of formula IV compounds, each $R^a$, $R^b$, and $R^c$ is independently H or $C_{1-6}$ alkyl. In embodiments where any of $R^a$, $R^b$, and $R^c$ is independently $C_{1-6}$ alkyl, it is preferably $C_{1-3}$ alkyl, with methyl being even more preferred. In certain embodiments, $R^a$ and $R^b$ are each H. In other embodiments, one of $R^a$ and $R^b$ is H and the other is H or alkyl. In other preferred embodiments, $R^c$ is alkyl, more preferably $C_{1-6}$ alkyl, with $C_{1-3}$ alkyl being even more preferred.

In some preferred embodiments of formula IV compounds, $R^c$, $R^d$, and $R^e$, taken together with the carbon atom to which they are attached, form a bicycloalkyl or tricycloalkyl ring, yet more preferably adamant-1-yl. More preferably, the bicycloalkyl or tricycloalkyl ring is substituted with 1-3 groups selected independently from alkyl, alkoxyl, or hydroxyl, more preferably alkyl, wherein each said alkyl group or alkyl moiety of alkoxyl group is more preferably $C_{1-3}$ alkyl, yet more preferably methyl.

In certain preferred embodiments, the formula IV compounds have the formula V:

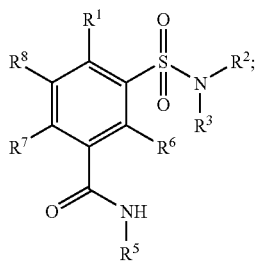

wherein:
R¹ is H, alkyl, F, or Br;
R² and R³ are each independently alkyl or aralkyl, or R² and R³, when taken together with the nitrogen atom to which they are attached, form a 5- or 6-membered heterocycloalkyl ring, wherein one of the ring carbon atoms may be optionally replaced by —O— or —N(R⁹)—;
R⁷ is H, Cl, or alkyl;
R⁸ is H or alkyl; and
R⁹ is H, alkyl, —C(=O)—O-alkyl, —CH₂—C(=O)—O-alkyl, —SO₂-alkyl, or —C(=O)N(H)-alkyl.

In other preferred embodiments of formula IV compounds, R¹, R², R³, R⁴, Rᵈ, Rᵉ, R⁶, R⁷, R⁸, R⁹, R¹⁰, R¹¹, r, and s are as described hereinabove for compounds of formula I.

In certain preferred embodiments, the formula IV compounds are selected from the group consisting of:
N-adamantan-2-yl-4-methyl-3-(morpholine-4-sulfonyl)-benzamide;
N-(1-adamantan-1-ylethyl)-4-methyl-3-(morpholine-4-sulfonyl)-benzamide;
4-methyl-3-(morpholine-4-sulfonyl)-N-(1,7,7-trimethylbicyclo[2.2.1]-hept-2-yl)-benzamide;
N-bicyclo-[2.2.1]hept-2-yl-4-methyl-3-(morpholine-4-sulfonyl)-benzamide;
N-[1-(3-hydroxy-adamantan-1-yl)-ethyl]-4-methyl-3-(morpholine-4-sulfonyl)-benzamide;
4-methyl-3-(1,3-dihydroisoindole-2-sulfonyl)-N-(1,3,3-trimethylbicyclo-[2.2.1]-hept-2-yl)-benzamide;
N-bicyclo-[2.2.1]hept-2-yl-3-(1,3-dihydroisoindole-2-sulfonyl)-4-methylbenzamide;
3-(1,3-dihydroisoindole-2-sulfonyl)-4-methyl-N-(1,7,7-trimethylbicyclo-[2.2.1]hept-2-yl)-benzamide;
3-(1,3-dihydroisoindole-2-sulfonyl)-N-[1-(3-hydroxyadamantan-1-yl)-ethyl]-4-methylbenzamide;
N-adamantan-2-yl-3-(3,4-dihydro-2H-quinoline-1-sulfonyl)-4,5-dimethylbenzamide;
N-(1-adamantan-1-ylethyl)-3-(3,4-dihydro-2H-quinoline-1-sulfonyl)-4,5-dimethylbenzamide;
3-(3,4-dihydroquinolin-1(2H)-ylsulfonyl)-4,5-dimethyl-N-(1,3,3-trimethylbicyclo-[2.2.1]-heptan-2-yl)-benzamide;
N-adamantan-2-yl-3,4-dimethyl-5-(octahydroquinoline-1-sulfonyl)-benzamide;
N-(1-adamantan-1-ylethyl)-3,4-dimethyl-5-(octahydroquinoline-1-sulfonyl)-benzamide;
3,4-dimethyl-5-(octahydroquinolin-1(2H)-ylsulfonyl)-N-(1,3,3-trimethylbicyclo-[2.2.1]heptan-2-yl)benzamide;
N-adamantan-2-yl-3-(2,6-dimethylmorpholine-4-sulfonyl)-4-methylbenzamide;
N-(1-adamantan-1-ylethyl)-3-(2,6-dimethylmorpholine-4-sulfonyl)-4-methylbenzamide;
3-(2,6-dimethylmorpholinosulfonyl)-4-methyl-N-(1,3,3-trimethylbicylo-[2.2.1]heptan-2-yl)-benzamide;
N-adamantan-2-yl-3-(2,6-dimethylmorpholine-4-sulfonyl)-4,5-dimethylbenzamide;
N-(1-adamantan-1-ylethyl)-3-(2,6-dimethylmorpholine-4-sulfonyl)-4,5-dimethylbenzamide;
3-(2,6-dimethylmorpholinosulfonyl)-4,5-dimethyl-N-(1,3,3-trimethylbicyclo-[2.2.1]heptan-2-yl)-benzamide;
N-adamantan-2-yl-5-(N-benzyl-N-methylsulfamoyl)-2-chloro-4-fluoro-benzamide;
N-(1-adamantan-1-ylethyl)-5-(N-benzyl-N-methylsulfamoyl)-2-chloro-4-fluorobenzamide;
5-(N-benzyl-N-methylsulfamoyl)-2-chloro-4-fluoro-N-(1,3,3-trimethylbicyclo[2.2.1]-heptan-2-yl)benzamide;
3,4-dimethyl-5-(morpholinosulfonyl)-N-(1,3,3-trimethylbicyclo-[2.2.1]heptan-2-yl)-benzamide;
N-((6,6-dimethylbicyclo-[3.1.1]-heptan-2-yl)methyl)-3,4-dimethyl-5-(morpholinosulfonyl)-benzamide;
N-(1-adamantan-1-ylethyl)-5-(morpholinosulfonyl)-4,5-dimethylbenzamide;
3-(N-benzyl-N-methyl-sulfamoyl)-4,5-dimethyl-N-(1,3,3-trimethylbicyclo-[2.2.1]-heptan-2-yl)benzamide;
3-(N-benzyl-N-methyl-sulfamoyl)-N-((6,6-dimethylbicyclo-[3.1.1]-heptan-2-yl)methyl)-4,5-dimethylbenzamide;
N-(1-adamantan-1-ylethyl)-5-(N-benzyl-N-methyl-sulfamoyl)-4,5-dimethylbenzamide;
1-(2,3-dimethyl-5-(1,3,3-trimethylbicyclo-[2.2.1]heptan-2-ylcarbamoyl)-phenylsulfonyl)-N,N-diethylpiperidine-3-carboxamide;
3-(azetidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)benzamide;
3-(4-hydroxypiperidin-1-ylsulfonyl)-4-methyl-N-(1,3,3-trimethylbicyclo-[2.2.1]-heptan-2-yl)-benzamide;
N,N-diethyl-1-(2-methyl-5-(1,3,3-trimethylbicylo-[2.2.1]heptan-2-ylcarbamoyl)-phenylsulfonyl)-piperidine-3-carboxamide;
3-(N-(2-methoxyethyl)-N-methylsulfamoyl)-4-methyl-N-(1,3,3-trimethylbicyclo-[2.2.1]heptan-2-yl)-benzamide;
N,N-diethyl-1-(2-methyl-5-(1,3,3-trimethylbicyclo-[2.2.1]heptan-2-ylcarbamoyl)-phenylsulfonyl)-pyrrolidine-3-carboxamide;
N-(1-adamantan-1-ylmethyl)-5-(morpholinosulfonyl)-2-chloro-4-fluorobenzamide;
4-methyl-3-(morpholinosulfonyl)-N-(2,6,6-trimethylbicyclo-[3.1.1]-heptan-3-yl)-benzamide;
4-methyl-3-(morpholinosulfonyl)-N-(2,6,6-trimethylbicyclo-[3.1.1]heptan-3-yl)-benzamide;
4-ethyl-3-(morpholine-4-sulfonyl)-N-(1,3,3-trimethylbicyclo[2.2.1]hept-2-yl)-benzamide;
4-isopropyl-3-(morpholine-4-sulfonyl)-N-(1,3,3-trimethylbicyclo[2.2.1]hept-2-yl)-benzamide;
4-propyl-3-(morpholine-4-sulfonyl)-N-(1,3,3-trimethylbicyclo[2.2.1]hept-2-yl)-benzamide;
4-(3-methoxypropyl)-3-(morpholine-4-sulfonyl)-N-(1,3,3-trimethylbicyclo-[2.2.1]hept-2-yl)-benzamide;
5-methyl-3-(morpholine-4-sulfonyl)-N-(1,3,3-trimethylbicyclo[2.2.1]hept-2-yl)-benzamide;
4,6-dimethyl-3-(morpholine-4-sulfonyl)-N-(1,3,3-trimethylbicyclo-[2.2.1]hept-2-yl)-benzamide;
3-(N,N-dimethylsulfamoyl-4-bromo-N-(1,3,3-trimethylbicyclo-[2.2.1]-hept-2-yl)-benzamide;
4-bromo-3-(N-methylsulfamoyl)-N-(1,3,3-trimethylbicyclo-[2.2.1]-hept-2-yl)-benzamide;

4-bromo-3-(N-phenylsulfamoyl)-N-(1,3,3-trimethylbicyclo-[2.2.1]-hept-2-yl)-benzamide;
4-bromo-3-(morpholinosulfonyl)-N-(1,3,3-trimethylbicyclo-[2.2.1]-heptan-2-yl)-benzamide;
4-bromo-3-(3-fluoropiperidin-1-ylsulfonyl)-N-(1,3,3-trimethylbicyclo-[2.2.1]heptan-2-yl)-benzamide;
4-bromo-3-(pyrrolidin-1-ylsulfonyl)-N-(1,3,3-trimethylbicyclo-[2.2.1]-heptan-2-yl)-benzamide;
4-bromo-3-(3,5-dimethylpiperidin-1-ylsulfonyl)-N-(1,3,3-trimethylbicyclo-[2.2.1]heptan-2-yl)-benzamide;
4-bromo-3-(2,6-dimethylmorpholinosulfonyl)-N-(1,3,3-trimethylbicyclo-[2.2.1]heptan-2-yl)-benzamide;
ethyl 1-(2-bromo-5-(1,3,3-trimethylbicyclo-[2.2.1]heptan-2-yl-carbamoyl)-phenylsulfonyl)-piperidine-3-carboxylate;
4-bromo-N-((6,6-dimethylbicyclo-[3.1.1]-heptan-2-yl)methyl)-3-(N-((6,6-dimethylbicyclo[3.1.1]heptan-3-yl)methyl)sulfamoyl)-benzamide;
2-chloro-4-fluoro-5-(morpholinosulfonyl)-N-(1,3,3-trimethylbicyclo-[2.2.1]heptan-2-yl)-benzamide;
N-(1-adamantan-1-ylethyl)-5-(morpholinosulfonyl)-2-chloro-4-fluorobenzamide; and a pharmaceutically acceptable salt thereof.

More preferably, the formula IV compounds are selected from the group consisting of:
N-adamantan-2-yl-4-methyl-3-(morpholine-4-sulfonyl)-benzamide;
N-(1-adamantan-1-ylethyl)-4-methyl-3-(morpholine-4-sulfonyl)-benzamide;
4-methyl-3-(morpholine-4-sulfonyl)-N-((1S,4R)-1,7,7-trimethylbicyclo[2.2.1]-hept-2-yl)-benzamide;
N-(R)-bicyclo-[2.2.1]hept-2-yl-4-methyl-3-(morpholine-4-sulfonyl)-benzamide;
N-[1-(3-hydroxy-adamantan-1-yl)-ethyl]-4-methyl-3-(morpholine-4-sulfonyl)-benzamide;
4-methyl-3-(1,3-dihydroisoindole-2-sulfonyl)-N,S-(1,3,3-trimethylbicyclo-[2.2.1]-hept-2-yl)-benzamide;
N-(R)-bicyclo-[2.2.1]hept-2-yl-3-(1,3-dihydroisoindole-2-sulfonyl)-4-methylbenzamide;
3-(1,3-dihydroisoindole-2-sulfonyl)-4-methyl-N-((1S,4R)-1,7,7-trimethylbicyclo-[2.2.1]hept-2-yl)-benzamide;
3-(1,3-dihydroisoindole-2-sulfonyl)-N-[1-(3-hydroxyadamantan-1-yl)-ethyl]-4-methylbenzamide;
N-adamantan-2-yl-3-(3,4-dihydro-2H-quinoline-1-sulfonyl)-4,5-dimethylbenzamide;
N-(1-adamantan-1-ylethyl)-3-(3,4-dihydro-2H-quinoline-1-sulfonyl)-4,5-dimethylbenzamide;
3-(3,4-dihydroquinolin-1(2H)-ylsulfonyl)-4,5-dimethyl-N-((1S,4R)-1,3,3-trimethylbicyclo-[2.2.1]-heptan-2-yl)-benzamide;
N-adamantan-2-yl-3,4-dimethyl-5-(octahydroquinoline-1-sulfonyl)-benzamide;
N-(1-adamantan-1-ylethyl)-3,4-dimethyl-5-(octahydroquinoline-1-sulfonyl)-benzamide;
3,4-dimethyl-5-(octahydroquinolin-1(2H)-ylsulfonyl)-N-((1S,4R)-1,3,3-trimethylbicyclo-[2.2.1]heptan-2-yl)benzamide;
N-adamantan-2-yl-3-(2,6-dimethylmorpholine-4-sulfonyl)-4-methylbenzamide;
N-(1-adamantan-1-ylethyl)-3-(2,6-dimethylmorpholine-4-sulfonyl)-4-methylbenzamide;
3-(2,6-dimethylmorpholinosulfonyl)-4-methyl-N-((1S,4R)-1,3,3-trimethylbicylo-[2.2.1]heptan-2-yl)-benzamide;
N-adamantan-2-yl-3-(2,6-dimethylmorpholine-4-sulfonyl)-4,5-dimethylbenzamide;
N-(1-adamantan-1-ylethyl)-3-(2,6-dimethylmorpholine-4-sulfonyl)-4,5-dimethylbenzamide;
3-(2,6-dimethylmorpholinosulfonyl)-4,5-dimethyl-N-((1S,4R)-1,3,3-trimethylbicyclo-[2.2.1]heptan-2-yl)-benzamide;
N-adamantan-2-yl-5-(N-benzyl-N-methylsulfamoyl)-2-chloro-4-fluoro-benzamide;
N-(1-adamantan-1-ylethyl)-5-(N-benzyl-N-methylsulfamoyl)-2-chloro-4-fluorobenzamide;
5-(N-benzyl-N-methylsulfamoyl)-2-chloro-4-fluoro-N-((1S,4R)-1,3,3-trimethylbicyclo[2.2.1]-heptan-2-yl)benzamide;
3,4-dimethyl-5-(morpholinosulfonyl)-N-((1S,4R)-1,3,3-trimethylbicyclo-[2.2.1]heptan-2-yl)-benzamide;
N-(((1S,2R,5S)-6,6-dimethylbicyclo-[3.1.1]-heptan-2-yl)methyl)-3,4-dimethyl-5-(morpholinosulfonyl)-benzamide;
N-(1-adamantan-1-ylethyl)-5-(morpholinosulfonyl)-4,5-dimethylbenzamide;
3-(N-benzyl-N-methyl-sulfamoyl)-4,5-dimethyl-N-((1S,4R)-1,3,3-trimethylbicyclo-[2.2.1]-heptan-2-yl)benzamide;
3-(N-benzyl-N-methyl-sulfamoyl)-N-(((1S,2R,5S)-6,6-dimethylbicyclo-[3.1.1]-heptan-2-yl)methyl)-4,5-dimethylbenzamide;
N-(1-adamantan-1-ylethyl)-5-(N-benzyl-N-methyl-sulfamoyl)-4,5-dimethylbenzamide;
1-(2,3-dimethyl-5-((1S,4R)-1,3,3-trimethylbicyclo-[2.2.1]heptan-2-ylcarbamoyl)-phenylsulfonyl)-N,N-diethylpiperidine-3-carboxamide;
3-(azetidin-1-ylsulfonyl)-4-methyl-N-((1S,4R)-1,3,3-trimethylbicyclo-[2.2.1]-heptan-2-yl)-benzamide;
3-((S)-3-hydroxypyrrolidin-1-ylsulfonyl)-4-methyl-N-((1S,4R)-1,3,3-trimethylbicyclo-[2.2.1]-heptan-2-yl)-benzamide;
3-((R)-3-hydroxypyrrolidin-1-ylsulfonyl)-4-methyl-N-((1S,4R)-1,3,3-trimethylbicyclo-[2.2.1]-heptan-2-yl)benzamide;
3-(4-hydroxypiperidin-1-ylsulfonyl)-4-methyl-N-((1S,4R)-1,3,3-trimethylbicyclo-[2.2.1]-heptan-2-yl)-benzamide;
N,N-diethyl-1-(2-methyl-5-((1S,4R)-1,3,3-trimethylbicylo-[2.2.1]heptan-2-ylcarbamoyl)-phenylsulfonyl)-piperidine-3-carboxamide;
3-(N-(2-methoxyethyl)-N-methylsulfamoyl)-4-methyl-N-((1S,4R)-1,3,3-trimethylbicyclo-[2.2.1]heptan-2-yl)-benzamide;
N,N-diethyl-1-(2-methyl-5-((1S,4R)-1,3,3-trimethylbicyclo-[2.2.1]heptan-2-ylcarbamoyl)-phenylsulfonyl)-pyrrolidine-3-carboxamide;
N-(1-adamantan-1-ylmethyl)-5-(morpholinosulfonyl)-2-chloro-4-fluorobenzamide;
4-methyl-3-(morpholinosulfonyl)-N-((1R,2R,3R,5S)-2,6,6-trimethylbicyclo-[3.1.1]-heptan-3-yl)-benzamide;
4-methyl-3-(morpholinosulfonyl)-N-((1S,2S,3S,5R)-2,6,6-trimethylbicyclo-[3.1.1]heptan-3-yl)-benzamide;
4-ethyl-3-(morpholine-4-sulfonyl)-N-((1S,4R)-1,3,3-trimethylbicylo[2.2.1]hept-2-yl)-benzamide;
4-isopropyl-3-(morpholine-4-sulfonyl)-N-((1S,4R)-1,3,3-trimethylbicylo[2.2.1]hept-2-yl)-benzamide;
4-propyl-3-(morpholine-4-sulfonyl)-N-((1S,4R)-1,3,3-trimethylbicylo[2.2.1]hept-2-yl)-benzamide;
4-(3-methoxypropyl)-3-(morpholine-4-sulfonyl)-N-((1S,4R)-1,3,3-trimethylbicyclo-[2.2.1]hept-2-yl)-benzamide;
5-methyl-3-(morpholine-4-sulfonyl)-N-((1S,4R)-1,3,3-trimethylbicyclo[2.2.1]-hept-2-yl)-benzamide;
4,6-dimethyl-3-(morpholine-4-sulfonyl)-N-((1S,4R)-1,3,3-trimethylbicyclo-[2.2.1]hept-2-yl)-benzamide;

3-(N,N-dimethylsulfamoyl-4-bromo-N-((1S,4R)-1,3,3-trimethylbicyclo-[2.2.1]-hept-2-yl)-benzamide;
4-bromo-3-(N-methylsulfamoyl)-N-((1S,4R)-1,3,3-trimethylbicyclo-[2.2.1]-hept-2-yl)-benzamide;
4-bromo-3-(N-phenylsulfamoyl)-N-((1S,4R)-1,3,3-trimethylbicyclo-[2.2.1]-hept-2-yl)-benzamide;
4-bromo-3-(morpholinosulfonyl)-N-((1S,4R)-1,3,3-trimethylbicyclo-[2.2.1]-heptan-2-yl)-benzamide;
4-bromo-3-(3-fluoropiperidin-1-ylsulfonyl)-N-((1S,4R)-1,3,3-trimethylbicyclo-[2.2.1]heptan-2-yl)-benzamide;
4-bromo-3-(pyrrolidin-1-ylsulfonyl)-N-((1S,4R)-1,3,3-trimethylbicyclo-[2.2.1]-hept-2-yl)-benzamide;
4-bromo-3-(3,5-dimethylpiperidin-1-ylsulfonyl)-N-((1S,4R)-1,3,3-trimethylbicyclo-[2.2.1]heptan-2-yl)-benzamide;
4-bromo-3-(2,6-dimethylmorpholinosulfonyl)-N-((1S,4R)-1,3,3-trimethylbicyclo-[2.2.1]heptan-2-yl)-benzamide;
ethyl 1-(2-bromo-5-((1S,4R)-1,3,3-trimethylbicyclo-[2.2.1]heptan-2-yl-carbamoyl)-phenylsulfonyl)-piperidine-3-carboxylate;
4-bromo-N-(((1S,2R,5S)-6,6-dimethylbicyclo-[3.1.1]-heptan-2-yl)methyl)-3-(N-(((1R,3S,5S)-6,6-dimethylbicyclo[3.1.1]heptan-3-yl)methyl)sulfamoyl)-benzamide;
2-chloro-4-fluoro-5-(morpholinosulfonyl)-N-((1S,4R)-1,3,3-trimethylbicyclo-[2.2.1]heptan-2-yl)-benzamide;
N-(1-adamantan-1-ylethyl)-5-(morpholinosulfonyl)-2-chloro-4-fluorobenzamide; and a pharmaceutically acceptable salt thereof.

Still more preferably the formula IV compounds are selected from the group consisting of:
3,4-dimethyl-5-(morpholinosulfonyl)-N-(1,3,3-trimethylbicyclo-[2.2.1]heptan-2-yl)-benzamide;
3-(azetidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)-benzamide;
4-(3-methoxypropyl)-3-(morpholine-4-sulfonyl)-N-(1,3,3-trimethylbicyclo-[2.2.1]hept-2-yl)-benzamide;
5-methyl-3-(morpholine-4-sulfonyl)-N-(1,3,3-trimethylbicyclo[2.2.1]-hept-2-yl)-benzamide;
N-(1-adamantan-1-yl-ethyl)-4-methyl-3-(morpholine-4-sulfonyl)-benzamide;
4-methyl-3-(morpholine-4-sulfonyl)-N-(1,7,7-trimethylbicyclo-[2.2.1]-hept-2-yl)-benzamide;
N-((6,6-dimethylbicyclo-[3.1.1]-heptan-2-yl)methyl)-3,4-dimethyl-5-(morpholino-sulfonyl)-benzamide;
4-propyl-3-(morpholine-4-sulfonyl)-N-(1,3,3-trimethylbicyclo-[2.2.1]-hept-2-yl)-benzamide;
4-bromo-3-(3-fluoropiperidin-1-ylsulfonyl)-N-(1,3,3-trimethylbicyclo-[2.2.1]-heptan-2-yl)-benzamide; and a pharmaceutically acceptable salt thereof.

Yet more preferably, the formula IV compounds are selected from the group consisting of:
3,4-dimethyl-5-(morpholinosulfonyl)-N-((1S,4R)-1,3,3-trimethylbicyclo-[2.2.1]heptan-2-yl)-benzamide;
3-(azetidin-1-ylsulfonyl)-4-methyl-N-((1S,4R)-1,3,3-trimethylbicyclo-[2.2.1]-heptan-2-yl)-benzamide;
3-((S)-3-hydroxypyrrolidin-1-ylsulfonyl)-4-methyl-N-((1S,4R)-1,3,3-trimethylbicyclo-[2.2.1]-heptan-2-yl)-benzamide;
4-(3-methoxypropyl)-3-(morpholine-4-sulfonyl)-N-((1S,4R)-1,3,3-trimethylbicyclo-[2.2.1]hept-2-yl)-benzamide;
5-methyl-3-(morpholine-4-sulfonyl)-N-((1S,4R)-1,3,3-trimethylbicyclo[2.2.1]-hept-2-yl)-benzamide;
N-(1-adamantan-1-yl-ethyl)-4-methyl-3-(morpholine-4-sulfonyl)-benzamide;
4-methyl-3-(morpholine-4-sulfonyl)-N-((1S,4R)-1,7,7-trimethylbicyclo-[2.2.1]-hept-2-yl)-benzamide;
N-(((1S,2R,5S)-6,6-dimethylbicyclo-[3.1.1]-heptan-2-yl)methyl)-3,4-dimethyl-5-(morpholino-sulfonyl)-benzamide;
4-propyl-3-(morpholine-4-sulfonyl)-N,S-(1,3,3-trimethylbicyclo-[2.2.1]-hept-2-yl)-benzamide;
4-bromo-3-(3-fluoropiperidin-1-ylsulfonyl)-N-((1S,4R)-1,3,3-trimethylbicyclo-[2.2.1]-heptan-2-yl)-benzamide; and a pharmaceutically acceptable salt thereof.

Even more preferably, the formula IV compounds are selected from the group consisting of:
3,4-dimethyl-5-(morpholinosulfonyl)-N-(1,3,3-trimethylbicyclo-[2.2.1]heptan-2-yl)-benzamide;
3-(3-hydroxypyrrolidin-1-ylsulfonyl)-4-methyl-N-(1,3,3-trimethylbicyclo-[2.2.1]-heptan-2-yl)-benzamide;
N-(1-adamantan-1-yl-ethyl)-4-methyl-3-(morpholine-4-sulfonyl)-benzamide;
4-methyl-3-(morpholine-4-sulfonyl)-N-(1,7,7-trimethylbicyclo-[2.2.1]-hept-2-yl)-benzamide;
4-(3-methoxypropyl)-3-(morpholine-4-sulfonyl)-N-(1,3,3-trimethylbicyclo-[2.2.1]hept-2-yl)-benzamide; and a pharmaceutically acceptable salt thereof.

Most preferably, the formula IV compounds are selected from the group consisting of:
3,4-dimethyl-5-(morpholinosulfonyl)-N-((1S,4R)-1,3,3-trimethylbicyclo-[2.2.1]heptan-2-yl)-benzamide;
3-((S)-3-hydroxypyrrolidin-1-ylsulfonyl)-4-methyl-N-((1S,4R)-1,3,3-trimethylbicyclo-[2.2.1]-heptan-2-yl)-benzamide;
N-(1-adamantan-1-yl-ethyl)-4-methyl-3-(morpholine-4-sulfonyl)-benzamide;
4-methyl-3-(morpholine-4-sulfonyl)-N-((1S,4R)-1,7,7-trimethylbicyclo-[2.2.1]-hept-2-yl)-benzamide;
4-(3-methoxypropyl)-3-(morpholine-4-sulfonyl)-N-((1S,4R)-1,3,3-trimethylbicyclo-[2.2.1]hept-2-yl)-benzamide; and a pharmaceutically acceptable salt thereof.

The compounds employed in the methods of the present invention may exist in prodrug form. As used herein, "prodrug" is intended to include any covalently bonded carriers which release the active parent drug, for example, as a compound as described herein in vivo when such prodrug is administered to a mammalian subject. Since prodrugs are known to enhance numerous desirable qualities of pharmaceuticals (e.g., solubility, bioavailability, manufacturing, etc.) the compounds employed in the present methods and compositions may, if desired, be delivered in prodrug form. Thus, the present invention contemplates prodrugs. Prodrugs of the compounds employed in the present invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxy groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl groups. Preferred hydroxyl protecting groups include the benzyl and the tertiary-butyldimethylsilyl groups. Other preferred protecting groups that may be employed in accordance with the present invention may be described in Greene, T. W. and Wuts, P. G. M., *Protective Groups in Organic Synthesis* 3d. Ed., Wiley & Sons, 1991.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosure of which is hereby incorporated herein by reference, in its entirety.

Although the compounds of the present invention may be administered as the pure chemicals, it is preferable to present the active ingredient as a pharmaceutical composition. The invention thus further provides pharmaceutical compositions comprising one or more of the cannabinoid receptor modulator compounds of the present invention, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

In accordance with certain embodiments of the present invention, the compositions of the invention may further comprise at least one cannabinoid. A variety of cannabinoids are available that may be suitable for use in the present methods and compositions. Generally speaking, it is only necessary that the cannabinoid provide the desired effect (for example, pain alleviation), and be capable of being incorporated into the present combination products and methods (discussed in detail below). In preferred embodiments, the present methods and compositions may involve a cannabinoid that is selected from $\Delta^9$-tetrahydrocannabinol and cannabidiol, and mixtures thereof.

Alternatively, in accordance with certain embodiments of the present invention, the compositions of the invention may further comprise at least one opioid. A wide variety of opioids are available that may be suitable for use in the present methods and compositions. Generally speaking, it is only necessary that the opioid provide the desired effect (for example, pain alleviation), and be capable of being incorporated into the present combination products and methods (discussed in detail below). In preferred embodiments, the present methods and compositions may involve an opioid that is selected from alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil and/or tramadol. More preferably, the opioid is selected from morphine, codeine, oxycodone, hydrocodone, dihydrocodeine, propoxyphene, fentanyl, tramadol, and mixtures thereof.

While not intending to be bound by any theory or theories of operation, it is contemplated that opioid side effects, such as constipation, vomiting, and nausea, may result from undesirable interaction of the opioid with peripheral opioid receptors, such as peripheral μ receptors. According to one aspect of the present invention, administration of the compounds of the invention, preferably the compounds, as described herein, or a pharmaceutically acceptable salt thereof, may block interaction of the opioid compounds with the peripheral receptors, thereby preventing and/or inhibiting the side effects, while preferably not interfering with the therapeutic effect of the opioid in the CNS.

The opioid component of the present methods and compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference,* 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J., et al., *Pain,* 1996, 67, 361), L-364,718 and other CCK antagonists (Dourish, C. T., et al., *Eur. J. Pharmacol.,* 1988, 147, 469), NOS inhibitors (Bhargava, H. N., et al., *Neuropeptides,* 1996, 30, 219), PKC inhibitors (Bilsky, E. J., et al., *J. Pharmacol. Exp. Ther.,* 1996, 277, 484), and dynorphin antagonists or antisera (Nichols, M. L., et al., *Pain,* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Alternatively, in accordance with certain other embodiments of the present invention, the compositions of the invention may further comprise at least one analgesic, such as for example, COX2 inhibitors, aspirin, acetaminophen, ibuprofen, naproxen, and the like, and mixtures thereof. Generally speaking, it is only necessary that the analgesic provide the desired effect (for example, pain alleviation), and be capable of being incorporated into the present combination products and methods (discussed in detail below).

Alternatively, in accordance with still other embodiments of the present invention, the compositions of the invention may further comprise at least one therapeutic agent selected from the group consisting of anti-seizure agents, such as for example, carbamazepine, gabapentin, lamotrigine, and phenyloin, anti-depressants such as, for example, amitryptiline, NMDA receptor antagonists, ion channel antagonists, nicotinic receptor agonists, and antiParkinson's agents, such as for example, Deprenyl, Amantadine, Levodopa, and Carbidopa. Generally speaking, it is only necessary that the anti seizure agent, anti-depressant, NMDA receptor antagonist, ion channel antagonist, nicotinic receptor agonist, or anti-Parkinson's agent provide the desired effect (for example, inhibition of seizures, alleviation of depression, and the like), and be capable of being incorporated into the present combination products and methods (discussed in detail below).

The compounds of the invention may be administered in an effective amount by any of the conventional techniques well-established in the medical field. The compounds employed in the methods of the present invention including, for example, the compounds as described herein may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages. Although the proper dosage of the products of this invention will be readily ascertainable by one skilled in the art, once armed with the present disclosure, by way of general guidance, for example, typically a daily dosage of the compound of the invention, preferably a compound as described herein, may range from about 0.001 to about 100 milligrams of the compound of the invention, preferably a compound as described herein, (and all combinations and subcombinations of ranges and specific dosage amounts therein), per kilogram of patient body weight. Preferably, the daily dosage may be about 0.01 to about 10 milligrams of the compound of the invention, preferably a compound as described herein per kilogram of patient body weight. Even more preferably, the daily dosage may be about 0.1 milligrams of the compound of the invention, preferably a compound as described herein per kilogram of patient body weight. With regard to a typical dosage form of this type, such as a tablet, the compounds of the invention, preferably a compound as described herein, generally may be present in an amount of about 0.1 to about 4 milligrams.

The combination products of this invention, such as pharmaceutical compositions comprising cannabinoids and/or opioids in combination with the compounds described herein may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the cannabinoid and/or opioid compounds and the compounds described herein may be administered at the same time (that is, together), or in any order. When not administered at the same time, preferably the administration of a cannabinoid and/or opioid and the compounds as described herein occurs less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the cannabinoids and/or opioids and the compounds as described herein are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where a cannabinoid and/or opioid compound is combined with the compounds as described herein, for example, typically a daily dosage may range from about 0.01 to about 100 milligrams of the cannabinoid and/or opioid (and all combinations and subcombinations of ranges therein) and about 0.001 to about 100 milligrams of the compounds as described herein (and all combinations and subcombinations of ranges therein), per kilogram of patient body weight. Preferably, the a daily dosage may be about 0.1 to about 10 milligrams of the cannabinoid and/or opioid and about 0.01 to about 10 milligrams of the compounds as described herein per kilogram of patient body weight. Even more preferably, the daily dosage may be about 1.0 milligrams of the cannabinoid and/or opioid and about 0.1 milligrams of the compounds as described herein per kilogram of patient body weight. With regard to a typical dosage form of this type of combination product, such as a tablet, the cannabinoid compounds (e.g. $\Delta^9$-tetrahydrocannabinol or cannabidiol) and/or the opioid compounds (e.g., morphine) and generally may be present in an amount of about 15 to about 200 milligrams, and the compounds as described herein in an amount of about 0.1 to about 4 milligrams.

Particularly when provided as a single dosage form, the potential exists for a chemical interaction between the combined active ingredients (for example, a cannabinoid and the compounds as described herein). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

Pharmaceutical kits useful in, for example, the treatment of pain, which comprise a therapeutically effective amount of a cannabinoid and/or opioid along with a therapeutically effective amount of a sulfamoyl benzamide compound of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The opioid or cannabinoid compound and the compound as described herein may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The compounds of the present invention may be used in methods to bind cannabinoid receptors, more preferably CB1 or CB2 cannabinoid receptors, still more preferably CB2 receptors. Such binding may be accomplished by contacting the receptor with an effective amount of the compound of the invention. The cannabinoid receptors may be located in the central nervous system or located peripherally to the central nervous system or in both locations. Preferably, the contacting step conducted in an aqueous medium, preferably at physiologically relevant ionic strength, pH, and the like.

Thus, in certain preferred embodiments, the invention is directed to pharmaceutical compositions comprising a pharmaceutically acceptable carrier; and a compound of formula I:

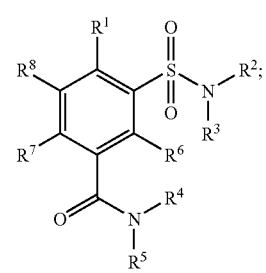

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

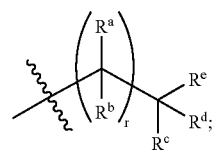

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

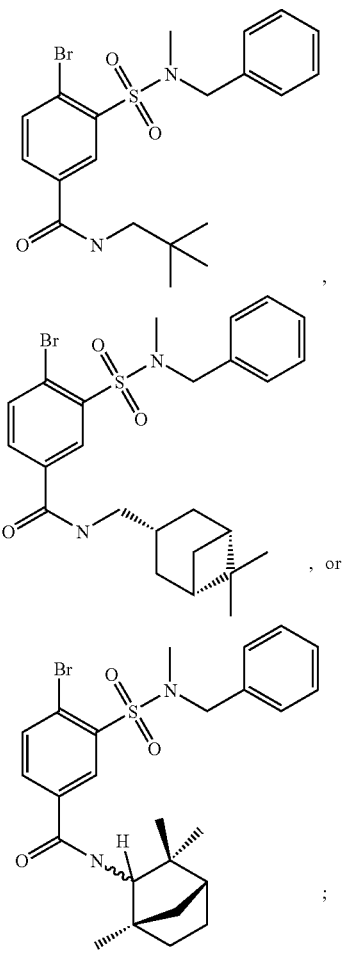

or a pharmaceutically acceptable salt thereof.

In other embodiments, the invention is directed to pharmaceutical compositions comprising a pharmaceutically acceptable carrier; and a compound of formula Ia:

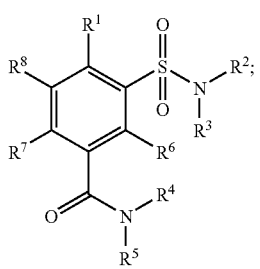

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;
$R^5$ is:

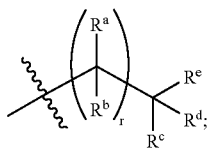

each $R^a$, $R^b$, $R^c$, $R^d$, and $R^e$ are each independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;
each $R^{11}$ is independently H or alkyl;
r is 0, 1, 2, or 3; and
s is 1, 2, 3, or 4;

provided that:
(1) when $R^d$ and $R^e$ taken together with the carbon atom to which they are attached form a monocyclic carbocyclic ring, then $R^c$ is alkyl or the monocyclic carbocyclic ring is an alkylcycloalkyl ring;
(2) at least two of $R^c$, $R^d$, and $R^e$ are other than H; and
(3) when $R^1$ is methyl or bromo, $R^2$, $R^4$, $R^6$, $R^7$, and $R^8$ are each H, and $R^3$ is methyl, then $R^5$ is other than but-2-yl, pent-2-yl, hex-2-yl, hept-2-yl, 1,1,1-dimethyleth-1-yl, 1-dimethylprop-1-yl, 1,1-dimethylbut-1-yl, or 1,1-dimethylpent-1-yl;

or a pharmaceutically acceptable salt thereof.

In certain preferred embodiments, the compound of formula Ia is other than:

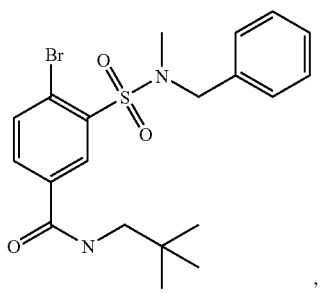

-continued

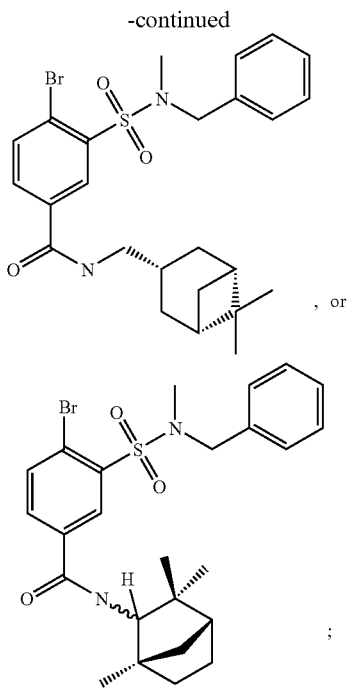

In other preferred embodiments of formula Ia compounds, $R^1$, $R^2$, $R^3$, $R^4$, $R^a$, $R^b$, $R^c$, $R^d$, $R^e$, $R^6$, $R^7$, $R^8$, $R^9$, $R^{10}$, $R^{11}$, r, and s are as described hereinabove for compounds of formula I.

In other preferred embodiments of pharmaceutical compositions, the compound formula Ia is selected from the group consisting of:
4-bromo-N-(2,2-dimethyl-propyl)-3-(piperidine-1-sulfonyl)-benzamide;
4-chloro-3-(piperidine-1-sulfonyl)-N-(1,3,3-trimethyl-bicyclo[2.2.1]hept-2-yl)-benzamide;
3-(N-benzyl-N-methylsulfamoyl)-4-bromo-N-(2,2-dimethylpropyl)-benzamide;
4-bromo-N-(6,6-dimethyl-bicyclo[3.1.1]hept-2-yl-methyl)-3-(piperidine-1-sulfonyl)-benzamide;
3-(N-benzyl-N-methylsulfamoyl)-4-bromo-N-(6,6-dimethyl-bicyclo[3.1.1]hept-2-yl-methyl)-benzamide;
3-(N-benzyl-N-methylsulfamoyl)-4-bromo-N-isobutyl-benzamide;
4-bromo-3-(piperidine-1-sulfonyl)-N-(1,3,3-tri-methylbicyclo[2.2.1]hept-2-yl)-benzamide;
4-isopropyl-3-(piperidine-1-sulfonyl)-N-(1,3,3-trimethyl-bicyclo[2.2.1]-hept-2-yl)-benzamide;
3-(piperidine-1-sulfonyl)-N,S-(1,3,3-trimethyl-bicyclo[2.2.1]hept-2-yl)-benzamide;
3-(piperidine-1-sulfonyl)-N,R-(1,3,3-trimethylbicyclo[2.2.1]hept-2-yl)-benzamide;
3-(N-benzyl-N-methylsulfamoyl)-4-bromo-N-(1,3,3-trimethyl-bicyclo[2.2.1]hept-2-yl)-benzamide;
4-[2-methyl-5-(1,3,3-trimethyl-bicyclo[2.2.1]hept-2-yl-carbamoyl)-benzenesulfonyl]-piperazine-1-carboxylic acid tert-butyl ester;
4-methyl-3-(morpholine-4-sulfonyl)-N,S-(1,3,3-trimethyl-bicyclo[2.2.1]-hept-2-yl)-benzamide;
4-methyl-3-(morpholine-4-sulfonyl)-N,R-(1,3,3-trimethyl-bicyclo[2.2.1]-hept-2-yl)-benzamide;
2-(piperidine-1-sulfonyl)-biphenyl-4-carboxylic acid (1,3,3-trimethyl-bicyclo[2.2.1]hept-2-yl)-amide;
{4-[2-methyl-5-(1,3,3-trimethyl-bicyclo[2.2.1]hept-2-yl-carbamoyl)-benzene-sulfonyl]-piperazin-1-yl}-acetic acid methyl ester;
4-[2-methyl-5-(1,3,3-trimethyl-bicyclo[2.2.1]hept-2yl-carbamoyl)-benzenesulfonyl]-piperazine-1-carboxylic acid ethylamide;
4-chloro-N-(2,2-dimethylpropyl)-3-(piperidine-1-sulfonyl)-benzamide;
N-(2,2-dimethyl-propyl)-4-methyl-3-(piperidine-1-sulfonyl)-benzamide;
4-bromo-N-(2,2-dimethylpropyl)-3-(pyrrolidine-1-sulfonyl)-benzamide;
4-methyl-3-(piperidine-1-sulfonyl)-N-(1,3,3-trimethyl-bicyclo[2.2.1]hept-2-yl)-benzamide;
3-(4-acetyl-piperazine-1-sulfonyl)-4-bromo-N-(1,3,3-trimethyl-bicyclo[2.2.1]-hept-2-yl)-benzamide;
4-methyl-3-(piperazine-1-sulfonyl)-N-(1,3,3-trimethylbicyclo[2.2.1]hept-2-yl)-benzamide;
3-(4-methanesulfonyl-piperazine-1-sulfonyl)-4-methyl-N-(1,3,3-tri-methyl-bicyclo[2.2.1]-hept-2-yl)-benzamide; and a pharmaceutically acceptable salt thereof.

In other embodiments, the invention is directed to pharmaceutical compositions comprising a pharmaceutically acceptable carrier; and a compound of formula III:

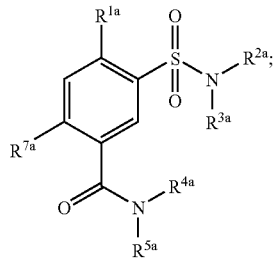

wherein:
$R^{1a}$ is F, Cl or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl or Br;
or a pharmaceutically acceptable salt thereof.

In other preferred embodiments of pharmaceutical compositions, the compound of formula III is selected from the group consisting of:
N-benzyl-4-bromo-3-(morpholine-4-sulfonyl)-benzamide;
N-benzyl-2-chloro-4-fluoro-5-(morpholine-4-sulfonyl)-benzamide;
3-(N-benzyl-N-methylsulfamoyl)-4-bromo-N-pyridin-3-yl-methylbenzamide;
4-bromo-N-(3-methoxybenzyl)-3-(piperidine-1'-sulfonyl)-benzamide;
4-bromo-N-(3-methoxybenzyl)-3-(pyrrolidine-1-sulfonyl)-benzamide;
N-benzyl-4-bromo-3-(pyrrolidine-1-sulfonyl)-benzamide;
N-benzyl-4-bromo-3-(piperidine-1-sulfonyl)-benzamide,
N-benzyl-4-bromo-N-methyl-3-(morpholine-4-sulfonyl)-benzamide; and a pharmaceutically acceptable salt thereof.

In certain other embodiments, the present invention is directed to pharmaceutical compositions, comprising:

a pharmaceutically acceptable carrier; and a compound of formula VI:

VI wherein:
R$^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;
R$^4$ is H or alkyl;
R$^5$ is:

each R$^a$, R$^b$, R$^c$, R$^d$, and R$^e$ is independently H or alkyl; or R$^d$ and R$^e$ taken together with the carbon atom to which they are attached form a carbocyclic ring; or R$^c$, R$^d$, and R$^e$, taken together with the carbon atom to which they are attached, form a bicycloalkyl or tricycloalkyl ring;
R$^6$, R$^7$, and R$^8$ are each independently H, F, Cl, Br, or alkyl;
R$^9$ is H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;
R$^{10}$ is H, alkyl, or aryl;
each R$^{11}$ is independently H or alkyl;
r is 0, 1, 2, or 3; and
s is 1, 2, 3, or 4;
provided that:
(1) when R$^d$ and R$^e$ taken together with the carbon atom to which they are attached form a monocyclic carbocyclic ring, then R$^c$ is alkyl or the monocyclic carbocyclic ring is an alkylcycloalkyl ring;
(2) at least two of R$^c$, R$^d$, and R$^e$ are other than H; and
(3) when R$^1$ is methyl or bromo, R$^2$, R$^4$, R$^6$, R$^7$, and R$^8$ are each H, and R$^3$ is methyl, then R$^5$ is other than but-2-yl, pent-2-yl, hex-2-yl, hept-2-yl, 1,1,1-dimethyleth-1-yl, 1-dimethylprop-1-yl, 1,1-dimethylbut-1-yl, or 1,1-dimethylpent-1-yl;

or a pharmaceutically acceptable salt thereof.

In some preferred embodiments of formula IV compounds, each R$^a$, R$^b$, and R$^c$ is independently H or C$_{1-6}$ alkyl. In embodiments where any of R$^a$, R$^b$, and R$^c$ is independently C$_{1-6}$ alkyl, it is preferably C$_{1-3}$ alkyl, with methyl being even more preferred. In certain embodiments, R$^a$ and R$^b$ are each H. In other embodiments, one of R$^a$ and R$^b$ is H and the other is H or alkyl. In other preferred embodiments, R$^c$ is alkyl, more preferably C$_{1-6}$alkyl, with C$_{1-3}$alkyl being even more preferred.

In some preferred embodiments of formula VI compounds, R$^c$, R$^d$, and R$^e$, taken together with the carbon atom to which they are attached, form a bicycloalkyl or tricycloalkyl ring, yet more preferably adamant-1-yl. More preferably, the bicycloalkyl or tricycloalkyl ring is substituted with 1-3 groups selected independently from alkyl, alkoxyl, or hydroxyl, more preferably alkyl, wherein each said alkyl group or alkyl moiety of alkoxyl group is more preferably C$_{1-3}$ alkyl, yet more preferably methyl.

In other preferred embodiments of formula VI compounds, R$^1$, R$^2$, R$^3$, R$^4$, R$^a$, R$^b$, R$^c$, R$^d$, R$^e$, R$^6$, R$^7$, R$^8$, R$^9$, R$^{10}$, R$^{11}$, r, and s are as described hereinabove for compounds of formula I.

In certain preferred embodiments of pharmaceutical compositions, the formula VI compounds are selected from the group consisting of:
N-adamantan-2-yl-4-methyl-3-(morpholine-4-sulfonyl)-benzamide;
N-(1-adamantan-1-ylethyl)-4-methyl-3-(morpholine-4-sulfonyl)-benzamide;
4-methyl-3-(morpholine-4-sulfonyl)-N-(1,7,7-trimethylbicyclo[2.2.1]-hept-2-yl)-benzamide;
N-bicyclo-[2.2.1]hept-2-yl-4-methyl-3-(morpholine-4-sulfonyl)-benzamide;
N-[1-(3-hydroxy-adamantan-1-yl)-ethyl]-4-methyl-3-(morpholine-4-sulfonyl)-benzamide;
N-(2,2-dimethylpropyl)-4-methyl-3-(morpholine-4-sulfonyl)-benzamide;
4-methyl-3-(morpholine-4-sulfonyl)-N-(1-morpholin-4-ylbutan-2-yl)-benzamide;
4-methyl-3-(1,3-dihydroisoindole-2-sulfonyl)-N-(1,3,3-trimethylbicyclo-[2.2.1]-hept-2-yl)-benzamide;
N-bicyclo-[2.2.1]hept-2-yl-3-(1,3-dihydroisoindole-2-sulfonyl)-4-methylbenzamide;
3-(1,3-dihydroisoindole-2-sulfonyl)-4-methyl-N-(1,7,7-trimethylbicyclo-[2.2.1]hept-2-yl)-benzamide;
3-(1,3-dihydroisoindole-2-sulfonyl)-N-(2,2-dimethylpropyl)-4-methylbenzamide;
3-(1,3-dihydroisoindole-2-sulfonyl)-N-[1-(3-hydroxyadamantan-1-yl)-ethyl]-4-methylbenzamide;
3-(1,3-dihydroisoindole-2-sulfonyl)-4-methyl-N-(1-morpholin-4-ylbutan-2-yl)-benzamide;
N-adamantan-2-yl-3-(3,4-dihydro-2H-quinoline-1-sulfonyl)-4,5-dimethylbenzamide;
N-(1-adamantan-1-ylethyl)-3-(3,4-dihydro-2H-quinoline-1-sulfonyl)-4,5-dimethylbenzamide;
3-(3,4-dihydroquinolin-1(2H)-ylsulfonyl)-4,5-dimethyl-N-(1,3,3-trimethylbicyclo-[2.2.1]-heptan-2-yl)-benzamide;
N-adamantan-2-yl-3,4-dimethyl-5-(octahydroquinoline-1-sulfonyl)-benzamide;

N-(1-adamantan-1-ylethyl)-3,4-dimethyl-5-(octahydro-quinoline-1-sulfonyl)-benzamide;
3,4-dimethyl-5-(octahydroquinolin-1(2H)-ylsulfonyl)-N-(1,3,3-trimethylbicyclo-[2.2.1]heptan-2-yl)benzamide;
N-adamantan-2-yl-3-(2,6-dimethylmorpholine-4-sulfonyl)-4-methylbenzamide;
N-(1-adamantan-1-ylethyl)-3-(2,6-dimethylmorpholine-4-sulfonyl)-4-methylbenzamide;
3-(2,6-dimethylmorpholinosulfonyl)-4-methyl-N-(1,3,3-trimethylbicylo-[2.2.1]heptan-2-yl)-benzamide;
N-adamantan-2-yl-3-(2,6-dimethylmorpholine-4-sulfonyl)-4,5-dimethylbenzamide;
N-(1-adamantan-1-ylethyl)-3-(2,6-dimethylmorpholine-4-sulfonyl)-4,5-dimethylbenzamide;
3-(2,6-dimethylmorpholinosulfonyl)-4,5-dimethyl-N-(1,3,3-trimethylbicyclo-[2.2.1]heptan-2-yl)-benzamide;
N-adamantan-2-yl-5-(N-benzyl-N-methylsulfamoyl)-2-chloro-4-fluoro-benzamide;
N-(1-adamantan-1-ylethyl)-5-(N-benzyl-N-methylsulfamoyl)-2-chloro-4-fluorobenzamide;
5-(N-benzyl-N-methylsulfamoyl)-2-chloro-4-fluoro-N-(1,3,3-trimethylbicyclo[2.2.1]-heptan-2-yl)benzamide;
3,4-dimethyl-5-(morpholinosulfonyl)-N-(1,3,3-trimethylbicyclo-[2.2.1]heptan-2-yl)-benzamide;
N-((6,6-dimethylbicyclo-[3.1.1]-heptan-2-yl)methyl)-3,4-dimethyl-5-(morpholinosulfonyl)-benzamide;
N-(1-adamantan-1-ylethyl)-5-(morpholinosulfonyl)-4,5-dimethylbenzamide;
3-(N-benzyl-N-methyl-sulfamoyl)-4,5-dimethyl-N-(1,3,3-trimethylbicyclo-[2.2.1]-heptan-2-yl)benzamide;
3-(N-benzyl-N-methyl-sulfamoyl)-N-((6,6-dimethylbicyclo-[3.1.1]-heptan-2-yl)methyl)-4,5-dimethylbenzamide;
N-(1-adamantan-1-ylethyl)-5-(N-benzyl-N-methyl-sulfamoyl)-4,5-dimethylbenzamide;
1-(2,3-dimethyl-5-(1,3,3-trimethylbicyclo-[2.2.1]heptan-2-ylcarbamoyl)-phenylsulfonyl)-N,N-diethylpiperidine-3-carboxamide;
3-(azetidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)benzamide;
3-(4-hydroxypiperidin-1-ylsulfonyl)-4-methyl-N-(1,3,3-trimethylbicyclo-[2.2.1]-heptan-2-yl)-benzamide;
N,N-diethyl-1-(2-methyl-5-(1,3,3-trimethylbicylo-[2.2.1]heptan-2-ylcarbamoyl)-phenylsulfonyl)-piperidine-3-carboxamide;
3-(N-(2-methoxyethyl)-N-methylsulfamoyl)-4-methyl-N-(1,3,3-trimethylbicyclo-[2.2.1]heptan-2-yl)-benzamide;
N,N-diethyl-1-(2-methyl-5-(1,3,3-trimethylbicyclo-[2.2.1]heptan-2-ylcarbamoyl)-phenylsulfonyl)-pyrrolidine-3-carboxamide;
N-(1-adamantan-1-ylmethyl)-5-(morpholinosulfonyl)-2-chloro-4-fluorobenzamide;
4-methyl-3-(morpholinosulfonyl)-N(3,3,5-trimethylcyclohexyl)-benzamide;
4-methyl-3-(morpholinosulfonyl)-N-(2,6,6-trimethylbicyclo-[3.1.1]-heptan-3-yl)-benzamide;
4-methyl-3-(morpholinosulfonyl)-N-(2,6,6-trimethylbicyclo-[3.1.1]heptan-3-yl)-benzamide;
N-(3,3-dimethylbutan-2-yl)-4-methyl-3-(morpholinosulfonyl)-benzamide;
N-(4-hydroxy-3,3-dimethylbutan-2-yl)-4-methyl-3-(morpholinosulfonyl)-benzamide;
N,N-diisopropyl-4-methyl-3-(morpholinosulfonyl)-benzamide;
4-ethyl-3-(morpholine-4-sulfonyl)-N-(1,3,3-trimethylbicylo[2.2.1]hept-2-yl)-benzamide;
4-isopropyl-3-(morpholine-4-sulfonyl)-N-(1,3,3-trimethyl-bicylo[2.2.1]hept-2-yl)-benzamide;
4-propyl-3-(morpholine-4-sulfonyl)-N-(1,3,3-trimethylbicylo[2.2.1]hept-2-yl)-benzamide;
4-(3-methoxypropyl)-3-(morpholine-4-sulfonyl)-N-(1,3,3-trimethylbicyclo-[2.2.1]hept-2-yl)-benzamide;
5-methyl-3-(morpholine-4-sulfonyl)-N-(1,3,3-trimethylbicyclo[2.2.1]-hept-2-yl)-benzamide;
4,6-dimethyl-3-(morpholine-4-sulfonyl)-N-(1,3,3-trimethylbicyclo-[2.2.1]hept-2-yl)-benzamide;
3-(N,N-dimethylsulfamoyl-4-bromo-N-(1,3,3-trimethylbicyclo-[2.2.1]-hept-2-yl)-benzamide;
4-bromo-3-(N-methylsulfamoyl)-N-(1,3,3-trimethylbicyclo-[2.2.1]-hept-2-yl)-benzamide;
4-bromo-3-(N-phenylsulfamoyl)-N-(1,3,3-trimethylbicyclo-[2.2.1]-hept-2-yl)-benzamide;
4-bromo-3-(morpholinosulfonyl)-N-(1,3,3-trimethylbicyclo-[2.2.1]-heptan-2-yl)-benzamide;
4-bromo-3-(3-fluoropiperidin-1-ylsulfonyl)-N-(1,3,3-trimethylbicyclo-[2.2.1]heptan-2-yl)-benzamide;
4-bromo-3-(pyrrolidin-1-ylsulfonyl)-N-(1,3,3-trimethylbicyclo-[2.2.1]-heptan-2-yl)-benzamide;
4-bromo-3-(3,5-dimethylpiperidin-1-ylsulfonyl)-N-(1,3,3-trimethylbicyclo-[2.2.1]heptan-2-yl)-benzamide;
4-bromo-3-(2,6-dimethylmorpholinosulfonyl)-N-(1,3,3-trimethylbicyclo-[2.2.1]heptan-2-yl)-benzamide;
ethyl 1-(2-bromo-5-(1,3,3-trimethylbicyclo-[2.2.1]heptan-2-yl-carbamoyl)-phenylsulfonyl)-piperidine-3-carboxylate;
4-bromo-N-((6,6-dimethylbicyclo-[3.1.1]-heptan-2-yl)methyl)-3-(N-(((1R,3S,5S)-6,6-dimethylbicyclo[3.1.1]heptan-3-yl)methyl)sulfamoyl)-benzamide;
4-bromo-3-(morpholine-4-sulfonyl)-N-(2,2-dimethylbutan-2-yl)-benzamide;
4-bromo-3-(pyrrolidine-1-sulfonyl)-N-(2,2-dimethylbutan-2-yl)-benzamide;
4-bromo-3-(N,N-dimethylsulfamoyl-N-(2,2-dimethylbutan-2-yl)-benzamide;
2-chloro-4-fluoro-5-(morpholinosulfonyl)-N-(1,3,3-trimethylbicyclo-[2.2.1]heptan-2-yl)-benzamide;
N-(1-adamantan-1-ylethyl)-5-(morpholinosulfonyl)-2-chloro-4-fluorobenzamide;
N-benzyl-5-(N-benzyl-N-methylsulfamoyl)-2-chloro-4-fluoro-N-methylbenzamide; and
a pharmaceutically acceptable salt thereof.

In yet another aspect, the invention is directed to methods of binding cannabinoid receptors, preferably CB1 and/or CB2 receptors, in a patient in need thereof, comprising the step of administering to said patient an effective amount of a compound of the invention including, for example, a compound of formulas I, Ia, II, III, IV, V, and/or VI.

In some preferred embodiments of the present invention, the cannabinoid receptors are CB1 and/or CB2 cannabinoid receptors. In certain more preferred embodiments, the compound selectively binds the CB2 cannabinoid receptors relative to the CB1 receptors. In certain preferred embodiments, the cannabinoid receptors are located in the central nervous system. In other preferred embodiments, the cannabinoid receptors are located peripherally to the central nervous system. In some other preferred embodiments, the compound exhibits activity toward the cannabinoid receptors. In certain preferred embodiments, compound binding agonizes the activity of the cannabinoid receptors. In other preferred embodiments, compound binding antagonizes the activity of the cannabinoid receptors.

In certain preferred aspects, the methods comprise the step of administering to said patient an effective amount of a compound of formula I:

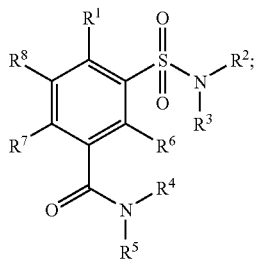

wherein:
  $R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
  $R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
  $R^4$ is H or alkyl;
  $R^5$ is:

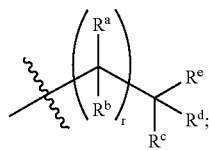

each $R^a$, $R^b$, $R^c$, $R^d$, and $R^e$ is independently H or alkyl; or $R^d$ and $R^e$ taken together with the carbon atom to which they are attached form a carbocyclic ring;
  $R^6$, $R^7$, and $R^8$ are each independently H, F, Cl, Br, or alkyl;
  $R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;
  $R^{10}$ is H, alkyl, or aryl;
  each $R^{11}$ is independently H or alkyl;
  r is 0, 1, 2, or 3; and
  s is 1, 2, 3, or 4;
  provided that:
    at least two of $R^c$, $R^d$, and $R^e$ are other than H; and
    when $R^1$, $R^6$, $R^7$, and $R^8$ are each H, then $R^d$ and $R^e$ taken together form a bicycloalkyl or tricycloalkyl ring;
  or a pharmaceutically acceptable salt thereof.

In other preferred aspects, the methods comprise the step of administering to said patient an effective amount of a compound of formula Ia:

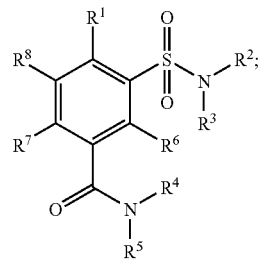

wherein:
  $R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
  $R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
  $R^4$ is H or alkyl;
  $R^5$ is:

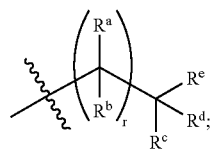

each $R^a$, $R^b$, $R^c$, $R^d$, and $R^e$ is independently H or alkyl; or $R^d$ and $R^e$ taken together with the carbon atom to which they are attached form a carbocyclic ring;
  $R^6$, $R^7$, and $R^8$ are each independently H, F, Cl, Br, or alkyl;
  $R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;
  $R^{10}$ is H, alkyl, or aryl;
  each $R^{11}$ is independently H or alkyl;
  r is 0, 1, 2, or 3; and
  s is 1, 2, 3, or 4;
  provided that:
    (1) when $R^d$ and $R^e$ taken together with the carbon atom to which they are attached form a monocyclic carbocyclic ring, then $R^c$ is alkyl or the monocyclic carbocyclic ring is an alkylcycloalkyl ring; and
    (2) at least two of $R^c$, $R^d$, and $R^e$ are other than H;
  or a pharmaceutically acceptable salt thereof.

In certain more preferred embodiments, the compound of formula Ia which is administered is other than:

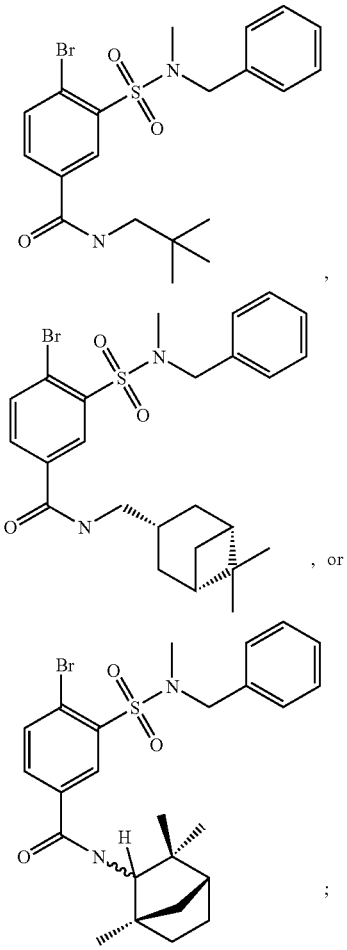

In other more preferred embodiments the compound of formula Ia which is administered it selected from the group consisting of:

4-bromo-N-(2,2-dimethyl-propyl)-3-(piperidine-1-sulfonyl)-benzamide;
4-chloro-3-(piperidine-1-sulfonyl)-N-(1,3,3-trimethyl-bicyclo[2.2.1]hept-2-yl)-benzamide;
3-(N-benzyl-N-methylsulfamoyl)-4-bromo-N-(2,2-dimethylpropyl)-benzamide;
4-bromo-N-(6,6-dimethyl-bicyclo[3.1.1]hept-2-yl-methyl)-3-(piperidine-1-sulfonyl)-benzamide;
3-(N-benzyl-N-methylsulfamoyl)-4-bromo-N-(6,6-dimethyl-bicyclo[3.1.1]hept-2-yl-methyl)-benzamide;
3-(N-benzyl-N-methylsulfamoyl)-4-bromo-N-isobutyl-benzamide;
4-bromo-3-(piperidine-1-sulfonyl)-N-(1,3,3-tri-methylbicyclo[2.2.1]hept-2-yl)-benzamide;
4-isopropyl-3-(piperidine-1-sulfonyl)-N-(1,3,3-trimethyl-bicyclo[2.2.1]-hept-2-yl)-benzamide;
3-(piperidine-1-sulfonyl)-N,S-(1,3,3-trimethyl-bicyclo[2.2.1]hept-2-yl)-benzamide;
3-(piperidine-1-sulfonyl)-N,R-(1,3,3-trimethylbicyclo[2.2.1]hept-2-yl)-benzamide;
3-(N-benzyl-N-methylsulfamoyl)-4-bromo-N-(1,3,3-trimethyl-bicyclo[2.2.1]hept-2-yl)-benzamide;
4-[2-methyl-5-(1,3,3-trimethyl-bicyclo[2.2.1]hept-2-yl-carbamoyl)-benzenesulfonyl]-piperazine-1-carboxylic acid tert-butyl ester;
4-methyl-3-(morpholine-4-sulfonyl)-N,S-(1,3,3-trimethyl-bicyclo[2.2.1]-hept-2-yl)-benzamide;
4-methyl-3-(morpholine-4-sulfonyl)-N,R-(1,3,3-trimethyl-bicyclo[2.2.1]-hept-2-yl)-benzamide;
2-(piperidine-1-sulfonyl)-biphenyl-4-carboxylic acid (1,3,3-trimethyl-bicyclo[2.2.1]hept-2-yl)-amide;
{4-[2-methyl-5-(1,3,3-trimethyl-bicyclo[2.2.1]hept-2-yl-carbamoyl)-benzene-sulfonyl]-piperazin-1-yl}-acetic acid methyl ester;
4-[2-methyl-5-(1,3,3-trimethyl-bicyclo[2.2.1]hept-2-yl-carbamoyl)-benzenesulfonyl]-piperazine-1-carboxylic acid ethylamide;
4-chloro-N-(2,2-dimethylpropyl)-3-(piperidine-1-sulfonyl)-benzamide;
N-(2,2-dimethyl-propyl)-4-methyl-3-(piperidine-1-sulfonyl)-benzamide;
4-bromo-N-(2,2-dimethylpropyl)-3-(pyrrolidine-1-sulfonyl)-benzamide;
4-methyl-3-(piperidine-1-sulfonyl)-N-(1,3,3-trimethyl-bicyclo[2.2.1]hept-2-yl)-benzamide;
3-(a-Acetyl-piperazine-1-sulfonyl)-4-bromo-N-(1,3,3-trimethyl-bicyclo[2.2.1]-hept-2-yl)-benzamide;
4-methyl-3-(piperazine-1-sulfonyl)-N-(1,3,3-trimethylbicyclo[2.2.1]hept-2-yl)-benzamide;
3-(4-methanesulfonyl-piperazine-1-sulfonyl)-4-methyl-N-(1,3,3-tri-methyl-bicyclo[2.2.1]-hept-2-yl)-benzamide; and
a pharmaceutically acceptable salt thereof.

In other embodiments, the invention is directed to methods of binding cannabinoid receptors in a patient in need thereof, comprising the step of administering to the patient in need thereof, an effective amount of a compound of formula III:

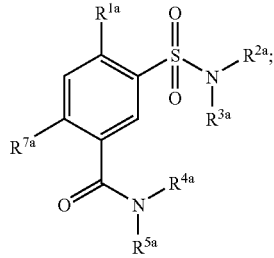

wherein:
$R^{1a}$ is F, Cl or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl or Br;
or a pharmaceutically acceptable salt thereof.

In other embodiments, the invention is directed to methods of binding cannabinoid receptors in a patient in need thereof, comprising the step of administering to the patient in need thereof, an effective amount of a compound of formula VI:

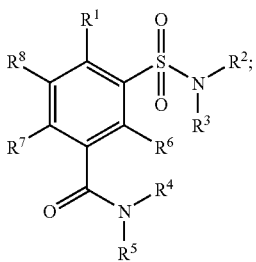

wherein:
R¹ is H, alkyl, cycloalkyl, cycloalkylalkyl, aryl, aralkyl, heterocycloalkyl, heterocycloalkylalkyl, heteroaryl, heteroaralkyl, F, Cl, or Br;
R² and R³ are each independently H, alkyl, cycloalkyl, cycloalkylalkyl, aryl, aralkyl, heterocycloalkyl, heterocycloalkylalkyl, heteroaryl, or heteroaralkyl, provided that at least one of R² and R³ is other than H; or R² and R³ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R⁹)—, —N(R¹⁰)—C(=O)—, or —C(=O)—N(R¹⁰)—;
R⁴ is H or alkyl;
R⁵ is:

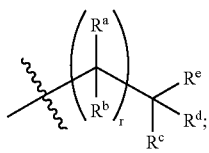

each R$^a$, R$^b$, R$^c$, R$^d$, and R$^e$ is independently H or alkyl; or R$^d$ and R$^e$ taken together with the carbon atom to which they are attached form a carbocyclic ring; or R$^c$, R$^d$, and R$^e$, taken together with the carbon atom to which they are attached, form a bicycloalkyl or tricycloalkyl ring;
R⁶, R⁷, and R⁸ are each independently H, F, Cl, Br, or alkyl;
R⁹ is H, alkyl, aryl, —C(=O)—R¹¹, —C(=O)—OR¹¹, —[C(R¹¹)(R¹¹)]$_s$—C(=O)—OR¹¹, —SO₂R¹¹, or —C(=O)N(R¹¹)R¹¹;
R¹⁰ is H, alkyl, or aryl;
each R¹¹ is independently H or alkyl;
r is 0, 1, 2, or 3; and
s is 1, 2, 3, or 4;
provided that:
 (1) when R$^d$ and R$^e$ taken together with the carbon atom to which they are attached form a monocyclic carbocyclic ring, then R$^c$ is alkyl or the monocyclic carbocyclic ring is an alkylcycloalkyl ring; and
 (2) at least two of R$^c$, R$^d$, and R$^e$ are other than H;
or a pharmaceutically acceptable salt thereof.
In some preferred embodiments of methods for binding cannabinoid receptors, the formula VI compounds are selected from the group consisting of:
N-adamantan-2-yl-4-methyl-3-(morpholine-4-sulfonyl)-benzamide;
N-(1-adamantan-1-ylethyl)-4-methyl-3-(morpholine-4-sulfonyl)-benzamide;
4-methyl-3-(morpholine-4-sulfonyl)-N-(1,7,7-trimethylbicyclo[2.2.1]-hept-2-yl)-benzamide;
N-bicyclo-[2.2.1]hept-2-yl-4-methyl-3-(morpholine-4-sulfonyl)-benzamide;
N-[1-(3-hydroxy-adamantan-1-yl)-ethyl]-4-methyl-3-(morpholine-4-sulfonyl)-benzamide;
N-(2,2-dimethylpropyl)-4-methyl-3-(morpholine-4-sulfonyl)-benzamide;
4-methyl-3-(morpholine-4-sulfonyl)-N-(1-morpholin-4-ylbutan-2-yl)-benzamide;
4-methyl-3-(1,3-dihydroisoindole-2-sulfonyl)-N-(1,3,3-trimethylbicyclo-[2.2.1]-hept-2-yl)-benzamide;
N-bicyclo-[2.2.1]hept-2-yl-3-(1,3-dihydroisoindole-2-sulfonyl)-4-methylbenzamide;
3-(1,3-dihydroisoindole-2-sulfonyl)-4-methyl-N-(1,7,7-trimethylbicyclo-[2.2.1]hept-2-yl)-benzamide;
3-(1,3-dihydroisoindole-2-sulfonyl)-N-(2,2-dimethylpropyl)-4-methylbenzamide;
3-(1,3-dihydroisoindole-2-sulfonyl)-N-[1-(3-hydroxyadamantan-1-yl)-ethyl]-4-methylbenzamide;
3-(1,3-dihydroisoindole-2-sulfonyl)-4-methyl-N-(1-morpholin-4-ylbutan-2-yl)-benzamide;
N-adamantan-2-yl-3-(3,4-dihydro-2H-quinoline-1-sulfonyl)-4,5-dimethylbenzamide;
N-(1-adamantan-1-ylethyl)-3-(3,4-dihydro-2H-quinoline-1-sulfonyl)-4,5-dimethylbenzamide;
3-(3,4-dihydroquinolin-1 (2H)-ylsulfonyl)-4,5-dimethyl-N-(1,3,3-trimethylbicyclo-[2.2.1]-heptan-2-yl)-benzamide;
N-adamantan-2-yl-3,4-dimethyl-5-(octahydroquinoline-1-sulfonyl)-benzamide;
N-(1-adamantan-1-ylethyl)-3,4-dimethyl-5-(octahydroquinoline-1-sulfonyl)-benzamide;
3,4-dimethyl-5-(octahydroquinolin-1 (2H)-ylsulfonyl)-N-(1,3,3-trimethylbicyclo-[2.2.1]heptan-2-yl)benzamide;
N-adamantan-2-yl-3-(2,6-dimethylmorpholine-4-sulfonyl)-4-methylbenzamide;
N-(1-adamantan-1-ylethyl)-3-(2,6-dimethylmorpholine-4-sulfonyl)-4-methylbenzamide;
3-(2,6-dimethylmorpholinosulfonyl)-4-methyl-N-(1,3,3-trimethylbicylo-[2.2.1]heptan-2-yl)-benzamide;
N-adamantan-2-yl-3-(2,6-dimethylmorpholine-4-sulfonyl)-4,5-dimethylbenzamide;
N-(1-adamantan-1-ylethyl)-3-(2,6-dimethylmorpholine-4-sulfonyl)-4,5-dimethylbenzamide;
3-(2,6-dimethylmorpholinosulfonyl)-4,5-dimethyl-N-(1,3,3-trimethylbicyclo-[2.2.1]heptan-2-yl)-benzamide;
N-adamantan-2-yl-5-(N-benzyl-N-methylsulfamoyl)-2-chloro-4-fluoro-benzamide;
N-(1-adamantan-1-ylethyl)-5-(N-benzyl-N-methylsulfamoyl)-2-chloro-4-fluorobenzamide;
5-(N-benzyl-N-methylsulfamoyl)-2-chloro-4-fluoro-N-(1,3,3-trimethylbicyclo[2.2.1]-heptan-2-yl)benzamide;
3,4-dimethyl-5-(morpholinosulfonyl)-N-(1,3,3-trimethylbicyclo-[2.2.1]heptan-2-yl)-benzamide;
N-((6,6-dimethylbicyclo-[3.1.1]-heptan-2-yl)methyl)-3,4-dimethyl-5-(morpholinosulfonyl)-benzamide;
N-(1-adamantan-1-ylethyl)-5-(morpholinosulfonyl)-4,5-dimethylbenzamide;
3-(N-benzyl-N-methyl-sulfamoyl)-4,5-dimethyl-N-(1,3,3-trimethylbicyclo-[2.2.1]-heptan-2-yl)benzamide;
3-(N-benzyl-N-methyl-sulfamoyl)-N-((6,6-dimethylbicyclo-[3.1.1]-heptan-2-yl)methyl)-4,5-dimethylbenzamide;
N-(1-adamantan-1-ylethyl)-5-(N-benzyl-N-methyl-sulfamoyl)-4,5-dimethylbenzamide;

1-(2,3-dimethyl-5-(1,3,3-trimethylbicyclo-[2.2.1]heptan-2-ylcarbamoyl)-phenylsulfonyl)-N,N -diethylpiperidine-3-carboxamide;
3-(azetidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)benzamide;
3-(4-hydroxypiperidin-1-ylsulfonyl)-4-methyl-N-(1,3,3-trimethylbicyclo-[2.2.1]-heptan-2-yl)-benzamide;
N,N-diethyl-1-(2-methyl-5-(1,3,3-trimethylbicylo-[2.2.1]heptan-2-ylcarbamoyl)-phenylsulfonyl) -piperidine-3-carboxamide;
3-(N-(2-methoxyethyl)-N-methylsulfamoyl)-4-methyl-N-(1,3,3-trimethylbicyclo-[2.2.1]heptan-2-yl)-benzamide;
N,N-diethyl-1-(2-methyl-5-(1,3,3-trimethylbicyclo-[2.2.1]heptan-2-ylcarbamoyl)-phenylsulfonyl)-pyrrolidine-3-carboxamide;
N-(1-adamantan-1-ylmethyl)-5-(morpholinosulfonyl)-2-chloro-4-fluorobenzamide;
4-methyl-3-(morpholinosulfonyl)-N(3,3,5-trimethylcyclohexyl)-benzamide;
4-methyl-3-(morpholinosulfonyl)-N-(2,6,6-trimethylbicyclo-[3.1.1]-heptan-3-yl)-benzamide;
4-methyl-3-(morpholinosulfonyl)-N-(2,6,6-trimethylbicyclo-[3.1.1]heptan-3-yl)-benzamide;
N-(3,3-dimethylbutan-2-yl)-4-methyl-3-(morpholinosulfonyl)-benzamide;
N-(4-hydroxy-3,3-dimethylbutan-2-yl)-4-methyl-3-(morpholinosulfonyl)-benzamide;
N,N-diisopropyl-4-methyl-3-(morpholinosulfonyl)-benzamide;
4-ethyl-3-(morpholine-4-sulfonyl)-N-(1,3,3-trimethylbicylo[2.2.1]hept-2-yl)-benzamide;
4-isopropyl-3-(morpholine-4-sulfonyl)-N-(1,3,3-trimethylbicylo[2.2.1]hept-2-yl)-benzamide;
4-propyl-3-(morpholine-4-sulfonyl)-N-(1,3,3-trimethylbicylo[2.2.1]hept-2-yl)-benzamide;
4-(3-methoxypropyl)-3-(morpholine-4-sulfonyl)-N-(1,3,3-trimethylbicyclo-[2.2.1]hept-2-yl)-benzamide;
5-methyl-3-(morpholine-4-sulfonyl)-N-(1,3,3-trimethylbicyclo[2.2.1]-hept-2-yl)-benzamide;
4,6-dimethyl-3-(morpholine-4-sulfonyl)-N-(1,3,3-trimethylbicyclo-[2.2.1]hept-2-yl)-benzamide;
3-(N,N-dimethylsulfamoyl-4-bromo-N-(1,3,3-trimethylbicyclo-[2.2.1]-hept-2-yl)-benzamide;
4-bromo-3-(N-methylsulfamoyl)-N-(1,3,3-trimethylbicyclo-[2.2.1]-hept-2-yl)-benzamide;
4-bromo-3-(N-phenylsulfamoyl)-N-(1,3,3-trimethylbicyclo-[2.2.1]-hept-2-yl)-benzamide;
4-bromo-3-(morpholinosulfonyl)-N-(1,3,3-trimethylbicyclo-[2.2.1]-heptan-2-yl)-benzamide;
4-bromo-3-(3-fluoropiperidin-1-ylsulfonyl)-N-(1,3,3-trimethylbicyclo-[2.2.1]heptan-2-yl)-benzamide;
4-bromo-3-(pyrrolidin-1-ylsulfonyl)-N-(1,3,3-trimethylbicyclo-[2.2.1]-heptan-2-yl)-benzamide;
4-bromo-3-(3,5-dimethylpiperidin-1-ylsulfonyl)-N-(1,3,3-trimethylbicyclo-[2.2.1]heptan-2-yl)-benzamide;
4-bromo-3-(2,6-dimethylmorpholinosulfonyl)-N-(1,3,3-trimethylbicyclo-[2.2.1]heptan-2-yl)-benzamide;
ethyl 1-(2-bromo-5-(1,3,3-trimethylbicyclo-[2.2.1]heptan-2-yl-carbamoyl)-phenylsulfonyl)-piperidine-3-carboxylate;
4-bromo-N-((6,6-dimethylbicyclo-[3.1.1]-heptan-2-yl)methyl)-3-(N-(((1R,3S,5S)-6,6-dimethylbicyclo[3.1.1]heptan-3-yl)methyl)sulfamoyl)-benzamide;
4-bromo-3-(morpholine-4-sulfonyl)-N-(2,2-dimethylbutan-2-yl)-benzamide;
4-bromo-3-(pyrrolidine-1-sulfonyl)-N-(2,2-dimethylbutan-2-yl)-benzamide;
4-bromo-3-(N,N-dimethylsulfamoyl-N-(2,2-dimethylbutan-2-yl)-benzamide;
2-chloro-4-fluoro-5-(morpholinosulfonyl)-N-(1,3,3-trimethylbicyclo-[2.2.1]heptan-2-yl)-benzamide;
N-(1-adamantan-1-ylethyl)-5-(morpholinosulfonyl)-2-chloro-4-fluorobenzamide; and
a pharmaceutically acceptable salt thereof.

In certain embodiments, the present invention is directed to methods of treating an ischemic condition comprising the step of administering to the patient in need thereof, an effective amount of a compound of formula I, I', Ia, II, III, IV, V, or VI. In certain preferred embodiments the ischemic condition is renal ischemia, cerebral stroke, cerebral ischemia, or a combination thereof. In other preferred embodiments, the compound of formula I, I', Ia, II, III, IV, V, or VI is other than:

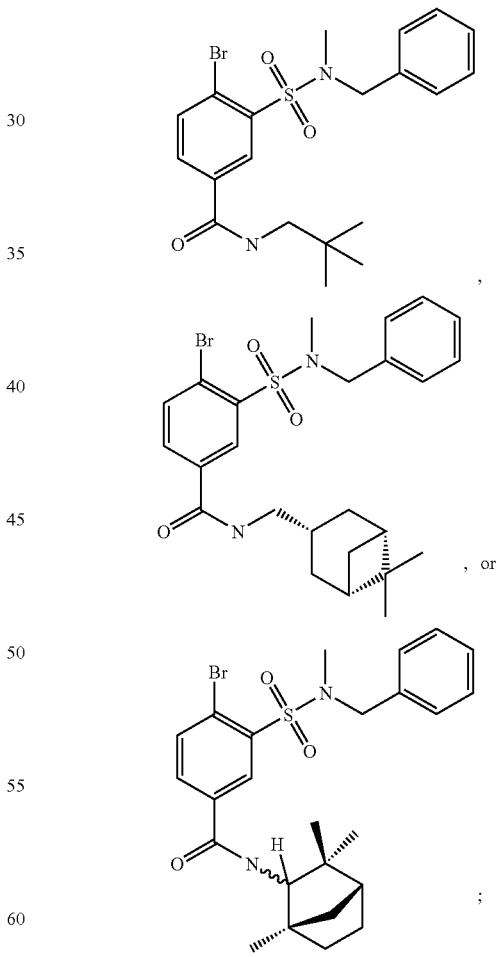

In certain embodiments, the present invention is directed to methods of treating a gastrointestinal disorder, comprising the step of administering to the patient in need thereof, an effective amount of a compound of formula I:

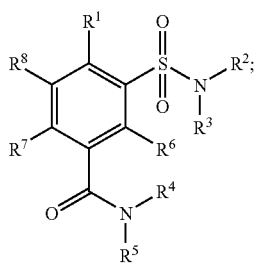

I wherein:
R¹ is H, alkyl, cycloalkyl, cycloalkylalkyl, aryl, aralkyl, heterocycloalkyl, heterocycloalkylalkyl, heteroaryl, heteroaralkyl, F, Cl, or Br;
R² and R³ are each independently H, alkyl, cycloalkyl, cycloalkylalkyl, aryl, aralkyl, heterocycloalkyl, heterocycloalkylalkyl, heteroaryl, or heteroaralkyl, provided that at least one of R² and R³ is other than H; or R² and R³ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R⁹)—, —N(R¹⁰)—C(=O)—, or —C(=O)—N(R¹⁰)—;
R⁴ is H or alkyl;
R⁵ is:

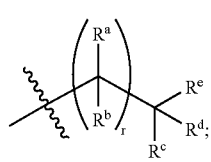

each Rᵃ, Rᵇ, Rᶜ, Rᵈ, and Rᵉ is independently H or alkyl; or Rᵈ and Rᵉ taken together with the carbon atom to which they are attached form a carbocyclic ring;
R⁶, R⁷, and R⁸ are each independently H, F, Cl, Br, or alkyl;
R⁹ is H, alkyl, aryl, —C(=O)—R¹¹, —C(=O)—OR¹¹, —[C(R¹¹)(R¹¹)]ₛ—C(=O)—OR¹¹, —SO₂R¹¹, or —C(=O)N(R¹¹)R¹¹;
R¹⁰ is H, alkyl, or aryl;
each R¹¹ is independently H or alkyl;
r is 0, 1, 2, or 3; and
s is 1, 2, 3, or 4;
provided that:
at least two of Rᶜ, Rᵈ, and Rᵉ are other than H;
when R¹, R⁶, R⁷, and R⁸ are each H, then Rᵈ and Rᵉ taken together form a bicycloalkyl or tricycloalkyl ring; and
the compound of formula I is not:

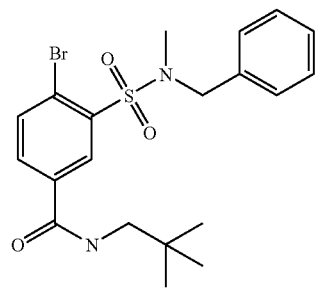

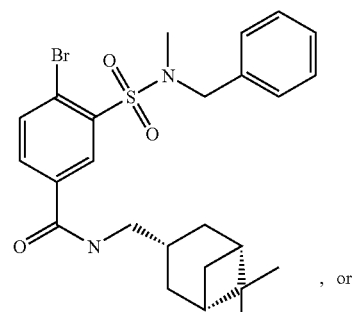

, or

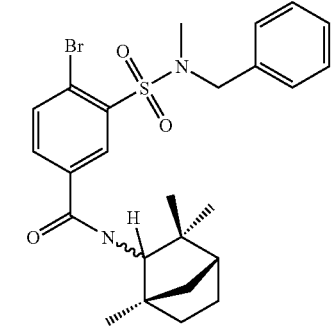

;

or a pharmaceutically acceptable salt thereof.

In certain embodiments, the present invention is directed to methods of treating a gastrointestinal disorder, comprising the step of administering to the patient in need thereof, an effective amount of a compound of formula III:

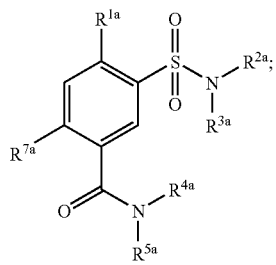

III wherein:
R¹ᵃ is F, Cl or Br;
R²ᵃ is methyl;

$R^{3a}$ is benzyl; or $R^{2a}$ and $R^{3a}$ when taken together with the nitrogen atom to which they are attached, form a morpholine, piperidine or pyrrolidine ring;

$R^{4a}$ is H or methyl;

$R^{5a}$ is benzyl, 3-methoxybenzyl, or pyrid-3-yl methyl; and $R^{7a}$ is H, F, Cl or Br;

or a pharmaceutically acceptable salt thereof.

In certain preferred embodiments, the gastrointestinal disorders which may be treated with the present compounds and methods include, for example, nausea, vomiting, loss of appetite, cachexia, diarrhoea, inflammatory bowel disease, or irritable bowel syndrome.

In some embodiments, the present invention is directed to methods of treating inflammation, comprising the step of administering to the patient in need thereof, an effective amount of a compound of formula I:

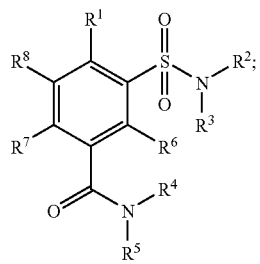

wherein:

$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

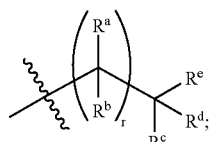

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4; provided that:

at least two of $R^c$, $R^d$, and $R^e$ are other than H;

when $R^1$, $R^6$, $R^7$, and $R^8$ are each H, then $R^d$ and $R^e$ taken together form a bicycloalkyl or tricycloalkyl ring; and the compound of formula I is not:

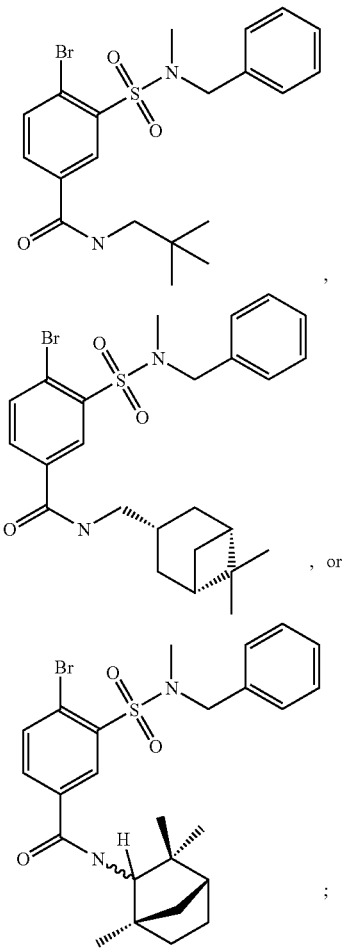

or a pharmaceutically acceptable salt thereof.

In some embodiments, the present invention is directed to methods of treating inflammation, comprising the step of administering to the patient in need thereof, an effective amount of a compound of formula III:

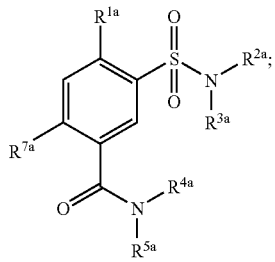

wherein:

$R^{1a}$ is F, Cl or Br;

$R^{2a}$ is methyl;

$R^{3a}$ is benzyl; or $R^{2a}$ and $R^{3a}$ when taken together with the nitrogen atom to which they are attached, form a morpholine, piperidine or pyrrolidine ring;

$R^{4a}$ is H or methyl;

$R^{5a}$ is benzyl, 3-methoxybenzyl, or pyrid-3-yl methyl; and $R^{7a}$ is H, F, Cl or Br;

or a pharmaceutically acceptable salt thereof.

In certain embodiments, the present invention is directed to methods of treating auto immune diseases, comprising the step of administering to the patient in need thereof, an effective amount of a compound of formula I:

wherein:
  $R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
  $R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
  $R^4$ is H or alkyl;
  $R^5$ is:

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^1$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:
  at least two of $R^c$, $R^d$, and $R^e$ are other than H;

when $R^1$, $R^6$, $R^7$, and $R^8$ are each H, then $R^d$ and $R^e$ taken together form a bicycloalkyl or tricycloalkyl ring; and the compound of formula I is not:

or a pharmaceutically acceptable salt thereof.

In certain embodiments, the present invention is directed to methods of treating auto immune diseases, comprising the step of administering to the patient in need thereof, an effective amount of a compound of formula III:

wherein:
  $R^{1a}$ is F, Cl or Br;
  $R^{2a}$ is methyl;

$R^{3a}$ is benzyl; or $R^{2a}$ and $R^{3a}$ when taken together with the nitrogen atom to which they are attached, form a morpholine, piperidine or pyrrolidine ring;

$R^{4a}$ is H or methyl;

$R^{5a}$ is benzyl, 3-methoxybenzyl, or pyrid-3-yl methyl; and $R^{7a}$ is H, F, Cl or Br;

or a pharmaceutically acceptable salt thereof.

In some preferred embodiments, the autoimmune disease is multiple sclerosis, rheumatoid arthritis, psoriasis, Crohn's disease, systemic lupus erythematosus, myasthenia gravis, diabetes mellitus type I, cancer, glaucoma, osteoporosis, renal ischemia, cerebral stroke, cerebral ischemia, inflammatory bowel disease or irritable bowel syndrome, or nephritis.

In some embodiments, the present invention is directed to methods of inhibiting mechanical hyperalgesia associated with nerve injury, comprising the step of administering to the patient in need thereof, an effective amount of a compound of formula I:

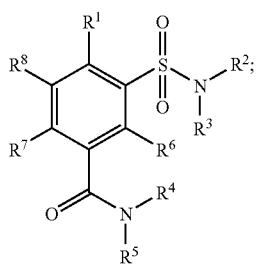

I wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

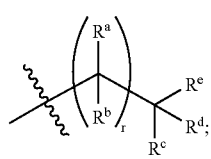

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

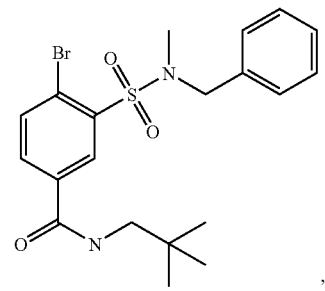

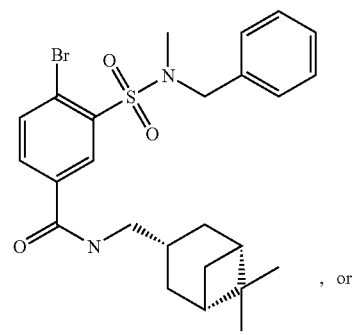

, or

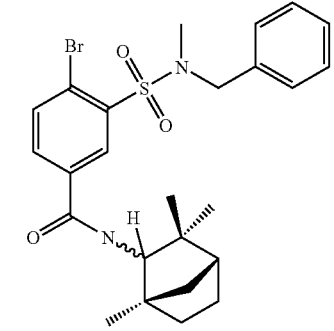

;

or a pharmaceutically acceptable salt thereof.

In some embodiments, the present invention is directed to methods of inhibiting mechanical hyperalgesia associated with nerve injury, comprising the step of administering to the patient in need thereof, an effective amount of a compound of formula III:

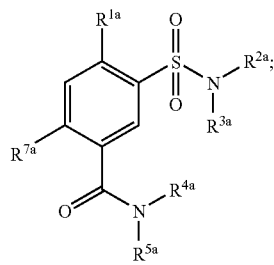

wherein:

R$^{1a}$ is F, Cl or Br;

R$^{2a}$ is methyl;

R$^{3a}$ is benzyl; or R$^{2a}$ and R$^{3a}$ when taken together with the nitrogen atom to which they are attached, form a morpholine, piperidine or pyrrolidine ring;

R$^{4a}$ is H or methyl;

R$^{5a}$ is benzyl, 3-methoxybenzyl, or pyrid-3-yl methyl; and

R$^{7a}$ is H, F, Cl or Br;

or a pharmaceutically acceptable salt thereof.

In some embodiments, the present invention is directed to methods of treating an immune related disorder, comprising the step of administering to the patient in need thereof, an effective amount of a compound of formula I:

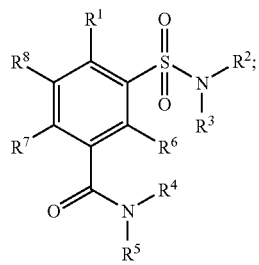

wherein:

R$^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;

R$^4$ is H or alkyl;

R$^5$ is:

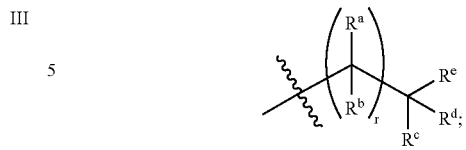

each R$^a$, R$^b$, R$^c$, R$^d$, and R$^e$ is independently H or alkyl; or R$^d$ and R$^e$ taken together with the carbon atom to which they are attached form a carbocyclic ring;

R$^6$, R$^7$, and R$^8$ are each independently H, F, Cl, Br, or alkyl;

R$^9$ is H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;

R$^{10}$ is H, alkyl, or aryl;

each R$^{11}$ is independently H or alkyl;

r is 0, 1, 2, or 3; and s is 1, 2, 3, or 4;

provided that:

at least two of R$^c$, R$^d$, and R$^e$ are other than H;

when R$^1$, R$^6$, R$^7$, and R$^8$ are each H, then R$^d$ and R$^e$ taken together form a bicycloalkyl or tricycloalkyl ring; and the compound of formula I is not:

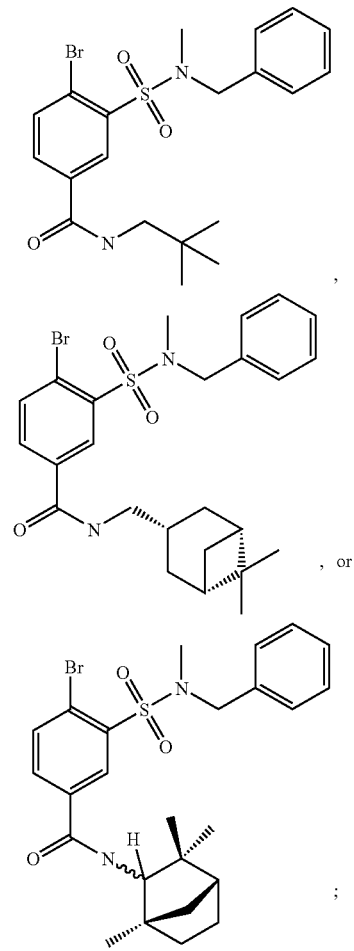

or a pharmaceutically acceptable salt thereof.

In some embodiments, the present invention is directed to methods of treating an immune related disorder, comprising the step of administering to the patient in need thereof, an effective amount of a compound of formula III:

III wherein:
- $R^{1a}$ is F, Cl or Br;
- $R^{2a}$ is methyl;
- $R^{3a}$ is benzyl; or $R^{2a}$ and $R^{3a}$ when taken together with the nitrogen atom to which they are attached, form a morpholine, piperidine or pyrrolidine ring;
- $R^{4a}$ is H or methyl;
- $R^{5a}$ is benzyl, 3-methoxybenzyl, or pyrid-3-yl methyl; and
- $R^{7a}$ is H, F, Cl or Br;

or a pharmaceutically acceptable salt thereof.

In certain preferred embodiments, the immune related disorder is asthma, chronic pulmonary obstructive disorder, emphysema, bronchitis, allergy, tissue rejection in organ transplants, celiac disease, or Sjögren's syndrome.

In certain embodiments, the present invention is directed to methods of treating pain, comprising the step of administering to the patient in need thereof, an effective amount of a compound of formula I:

I wherein:
- $R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

- $R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
- $R^4$ is H or alkyl;
- $R^5$ is:

each $R^a$, $R^b$, $R^c$, $R^d$, and $R^e$ is independently H or alkyl; or $R^d$ and $R^e$ taken together with the carbon atom to which they are attached form a carbocyclic ring;
- $R^6$, $R^7$, and $R^8$ are each independently H, F, Cl, Br, or alkyl;
- $R^9$ is H, alkyl, aryl, —C(=O)—$R^{11}$, —C(=O)—$OR^{11}$, —[C($R^{11}$)($R^{11}$)]$_s$—C(=O)—$OR^{11}$, —SO$_2R^{11}$, or —C(=O)N($R^{11}$)$R^{11}$;
- $R^{10}$ is H, alkyl, or aryl;
- each $R^{11}$ is independently H or alkyl;
- r is 0, 1, 2, or 3; and
- s is 1, 2, 3, or 4;

provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

-continued

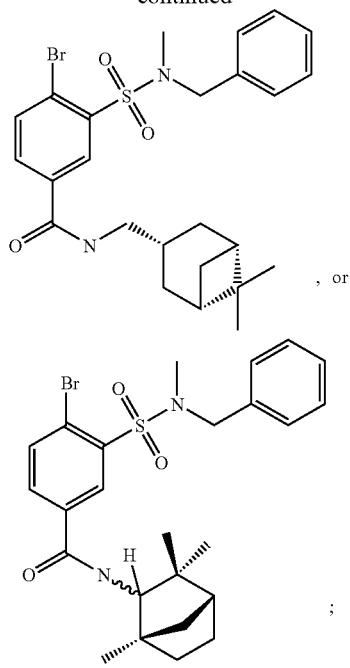

or a pharmaceutically acceptable salt thereof.

In certain embodiments, the present invention is directed to methods of treating pain, comprising the step of administering to the patient in need thereof, an effective amount of a compound of formula III:

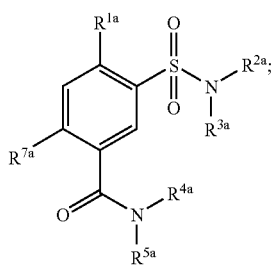

wherein:
$R^{1a}$ is F, Cl or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl or Br;
or a pharmaceutically acceptable salt thereof.

In embodiments involving the treatment or prevention of pain, the pain may be inflammatory pain, neuropathic pain, visceral pain, surgical pain, including pain which occurs during surgery or pain which occurs after surgery (i.e., postsurgical pain), or cancer related pain. In certain more preferred embodiments, the present pain ameliorating methods may further comprise the administration to the patient of at least one opioid in the form of combination products and/or combination therapy. Suitable opioids include, for example, alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil or tramadol, and mixtures thereof. In embodiments involving the treatment or prevention of neuropathic pain, the present methods may further comprise administering to the patient codeine, carbamazepine, gabapentin, lamotrigine, phenyloin, amitryptiline, an NMDA receptor antagonist, an ion channel antagonist, or a nicotinic receptor agonist, or a mixture thereof, in the form of combination products and/or combination therapy.

In some preferred embodiments, the methods for treating pain may further comprise the administration to the patient of at least one cannabinoid.

In some embodiments, the present invention is directed to methods of treating hypertension, comprising the step of administering to the patient in need thereof, an effective amount of a compound of formula I:

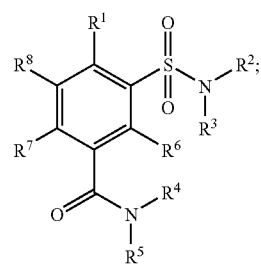

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

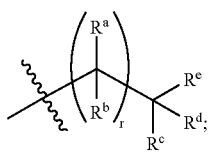

each $R^a$, $R^b$, $R^c$, $R^d$, and $R^e$ is independently H or alkyl; or $R^d$ and $R^e$ taken together with the carbon atom to which they are attached form a carbocyclic ring;
$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:

at least two of $R^c$, $R^d$, and $R^e$ are other than H;

when $R^1$, $R^6$, $R^7$, and $R^8$ are each H, then $R^d$ and $R^e$ taken together form a bicycloalkyl or tricycloalkyl ring; and the compound of formula I is not:

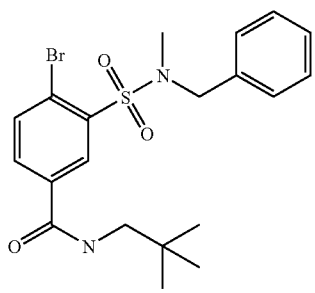

,

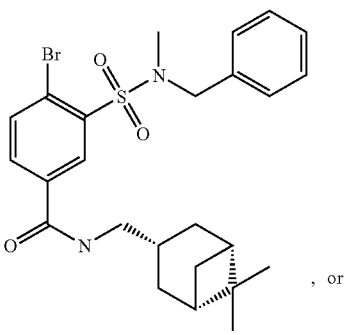

, or

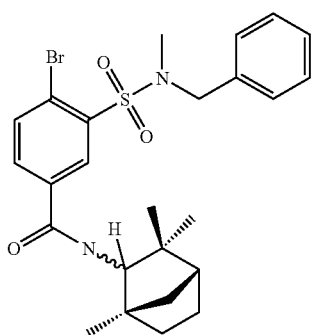

;

or a pharmaceutically acceptable salt thereof.

In some embodiments, the present invention is directed to methods of treating hypertension, comprising the step of administering to the patient in need thereof, an effective amount of a compound of formula III:

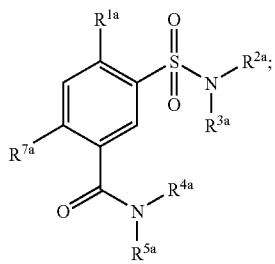

III wherein:

$R^{1a}$ is F, Cl or Br;

$R^{2a}$ is methyl;

$R^{3a}$ is benzyl; or $R^{2a}$ and $R^{3a}$ when taken together with the nitrogen atom to which they are attached, form a morpholine, piperidine or pyrrolidine ring;

$R^{4a}$ is H or methyl;

$R^{5a}$ is benzyl, 3-methoxybenzyl, or pyrid-3-yl methyl; and $R^{7a}$ is H, F, Cl or Br;

or a pharmaceutically acceptable salt thereof.

In other embodiments, the present invention is directed to methods of providing cardioprotection against ischemic and reperfusion effects, comprising the step of administering to the patient in need thereof, an effective amount of a compound of formula I:

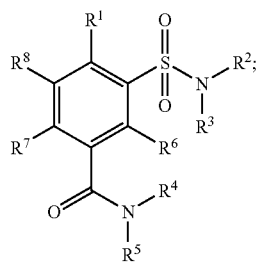

I wherein:

$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

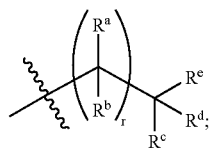

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:

at least two of $R^c$, $R^d$, and $R^e$ are other than H;

when $R^1$, $R^6$, $R^7$, and $R^8$ are each H, then $R^d$ and $R^e$ taken together form a bicycloalkyl or tricycloalkyl ring; and the compound of formula I is not:

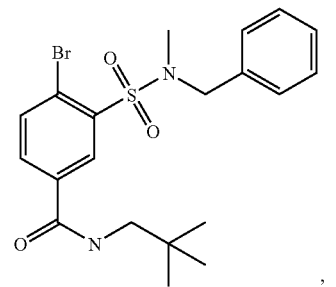

,

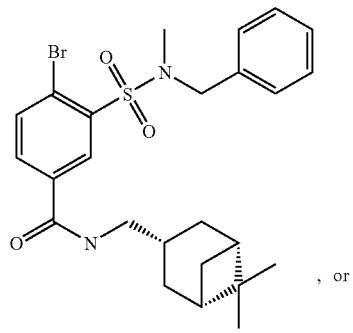

, or

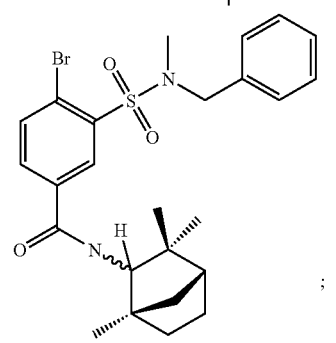

;

or a pharmaceutically acceptable salt thereof.

In other embodiments, the present invention is directed to methods of providing cardioprotection against ischemic and reperfusion effects, comprising the step of administering to the patient in need thereof, an effective amount of a compound of formula III:

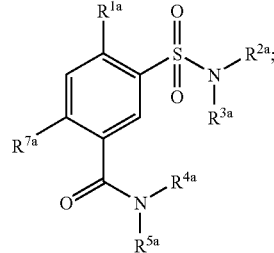

III wherein:

$R^{1a}$ is F, Cl or Br;

$R^{2a}$ is methyl;

$R^{3a}$ is benzyl; or $R^{2a}$ and $R^{3a}$ when taken together with the nitrogen atom to which they are attached, form a morpholine, piperidine or pyrrolidine ring;

$R^{4a}$ is H or methyl;

$R^{5a}$ is benzyl, 3-methoxybenzyl, or pyrid-3-yl methyl; and $R^{7a}$ is H, F, Cl or Br;

or a pharmaceutically acceptable salt thereof.

In certain preferred embodiments, the ischemic or reperfusion effect is arrhythmia or hypertension.

In some embodiments, the present invention is directed to methods of treating neurodegenerative diseases, comprising the step of administering to the patient in need thereof, an effective amount of a compound of formula I:

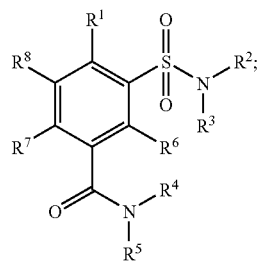

I wherein:

$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;
$R^5$ is:

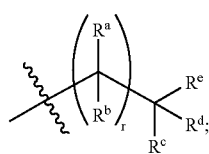

each $R^a$, $R^b$, $R^c$, $R^d$, and $R^e$ is independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2$$R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:
at least two of $R^c$, $R^d$, and $R^e$ are other than H;
when $R^1$, $R^6$, $R^7$, and $R^8$ are each H, then $R^d$ and $R^e$ taken together form a bicycloalkyl or tricycloalkyl ring; and
the compound of formula I is not:

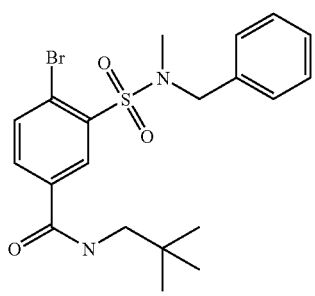

,

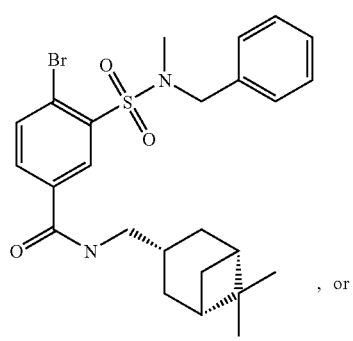

, or

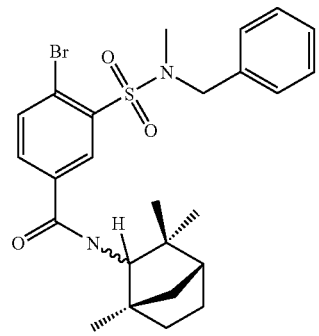

or a pharmaceutically acceptable salt thereof.

In some embodiments, the present invention is directed to methods of treating neurodegenerative diseases, comprising the step of administering to the patient in need thereof, an effective amount of a compound of formula III:

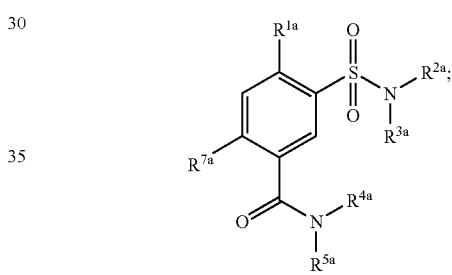

III wherein:
$R^{1a}$ is F, Cl or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl or Br;
or a pharmaceutically acceptable salt thereof.

In some preferred embodiments, the neurodegenerative disease is Parkinson's disease, Alzheimer's disease, Huntington's disease, or amyotrophic lateral sclerosis. In certain more preferred embodiments, these methods may further comprise the administration to the patient of deprenyl, amantadine, levodopa, or carbidopa, in the form of combination products and/or combination therapy.

In other embodiments, the present invention is directed to methods of treating neurological disorders, comprising the step of administering to the patient in need thereof, an effective amount of a compound of formula I:

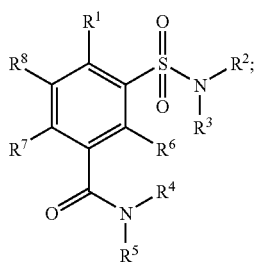

I wherein:
R$^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;

R$^4$ is H or alkyl;

R$^5$ is:

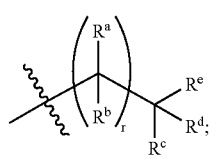

each R$^a$, R$^b$, R$^c$, R$^d$, and R$^e$ is independently H or alkyl; or R$^d$ and R$^e$ taken together with the carbon atom to which they are attached form a carbocyclic ring;

R$^6$, R$^7$, and R$^8$ are each independently H, F, Cl, Br, or alkyl;

R$^9$ is H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;

R$^{10}$ is H, alkyl, or aryl;

each R$^{11}$ is independently H or alkyl;

r is 0, 1, 2, or 3; and s is 1, 2, 3, or 4;

provided that:
at least two of R$^c$, R$^d$, and R$^e$ are other than H;
when R$^1$, R$^6$, R$^7$, and R$^8$ are each H, then R$^d$ and R$^e$ taken together form a bicycloalkyl or tricycloalkyl ring; and
the compound of formula I is not:

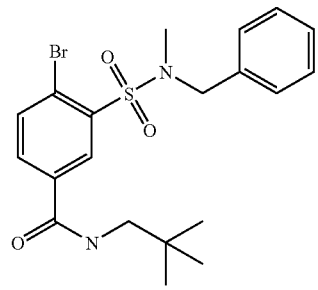

,

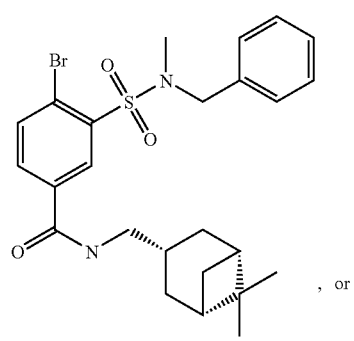

, or

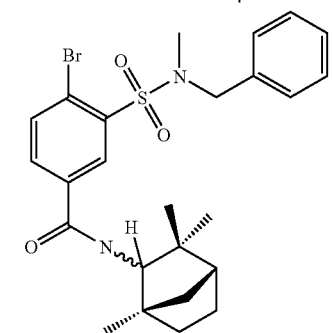

;

or a pharmaceutically acceptable salt thereof.

In other embodiments, the present invention is directed to methods of treating neurological disorders, comprising the step of administering to the patient in need thereof, an effective amount of a compound of formula III:

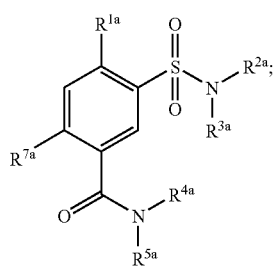

III wherein:
R$^{1a}$ is F, Cl or Br;
R$^{2a}$ is methyl;

R$^{3a}$ is benzyl; or R$^{2a}$ and R$^{3a}$ when taken together with the nitrogen atom to which they are attached, form a morpholine, piperidine or pyrrolidine ring;

R$^{4a}$ is H or methyl;

R$^{5a}$ is benzyl, 3-methoxybenzyl, or pyrid-3-yl methyl; and

R$^{7a}$ is H, F, Cl or Br;

or a pharmaceutically acceptable salt thereof.

In certain preferred embodiments, the neurological disorder is stroke, migraine, or cluster headache.

In other embodiments, the present invention is directed to methods of inducing apoptosis in malignant cells, comprising the step of contacting said cells with an effective amount of a compound of formula I:

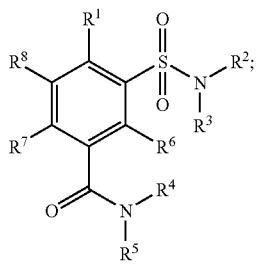

wherein:
R$^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;

R$^4$ is H or alkyl;

R$^5$ is:

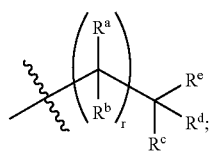

each R$^a$, R$^b$, R$^c$, R$^d$, and R$^e$ is independently H or alkyl; or R$^d$ and R$^e$ taken together with the carbon atom to which they are attached form a carbocyclic ring;

R$^6$, R$^7$, and R$^8$ are each independently H, F, Cl, Br, or alkyl;

R$^9$ is H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;

R$^{10}$ is H, alkyl, or aryl;

each R$^{11}$ is independently H or alkyl;

r is 0, 1, 2, or 3; and s is 1, 2, 3, or 4;

provided that:
at least two of R$^c$, R$^d$, and R$^e$ are other than H;

when R$^1$, R$^6$, R$^7$, and R$^8$ are each H, then R$^d$ and R$^e$ taken together form a bicycloalkyl or tricycloalkyl ring; and the compound of formula I is not:

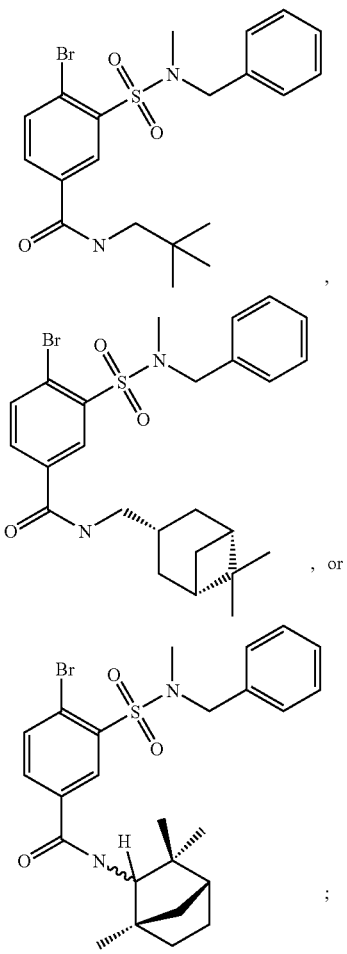

or a pharmaceutically acceptable salt thereof.

In other embodiments, the present invention is directed to methods of inducing apoptosis in malignant cells, comprising the step of administering to the patient in need thereof, an effective amount of a compound of formula III:

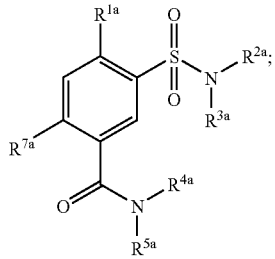

wherein:
R$^{1a}$ is F, Cl or Br;
R$^{2a}$ is methyl;

R³ᵃ is benzyl; or R²ᵃ and R³ᵃ when taken together with the nitrogen atom to which they are attached, form a morpholine, piperidine or pyrrolidine ring;

R⁴ᵃ is H or methyl;

R⁵ᵃ is benzyl, 3-methoxybenzyl, or pyrid-3-yl methyl; and

R⁷ᵃ is H, F, Cl or Br;

or a pharmaceutically acceptable salt thereof.

In some preferred embodiments, the apoptosis occurs in vitro. In other preferred embodiments, the apoptosis occurs in vivo.

In certain embodiments, the invention is directed to methods of treating gastrointestinal disorder, comprising the step of:
administering to a patient in need thereof, a composition comprising an effective amount of a compound of the invention, preferably a compound of formula I, I', Ia, II, III, IV, V, and/or VI, a pharmaceutically acceptable salt thereof. In certain preferred embodiments, the gastrointestinal disorder is nausea, vomiting, loss of appetite, cachexia, diarrhea, inflammatory bowel disease, irritable bowel syndrome or a combination thereof.

In certain embodiments, the invention is directed to methods of treating inflammation, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof.

In certain embodiments, the invention is directed to methods of treating an auto-immune disease, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof. In certain preferred embodiments, the auto-immune disease is multiple sclerosis, rheumatoid arthritis, psoriasis, Crohn's disease, systemic lupus erythematosus, myasthenia gravis, diabetes mellitus type I, osteoporosis, or a combination thereof.

In certain embodiments, the invention is directed to methods of treating an ischemic condition, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof. In certain preferred embodiments, the ischemic condition is renal ischemia, cerebral stroke, cerebral ischemia, or a combination thereof.

In certain embodiments, the invention is directed to methods of treating an immune-related disorder, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof. In certain preferred embodiments, the immune-related disorder is asthma, chronic pulmonary obstructive disorder, emphysema, bronchitis, allergy, tissue rejection in organ transplants, celiac disease, Sjögren's syndrome, or a combination thereof.

In certain embodiments, the invention is directed to methods of treating pain, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof. In certain preferred embodiments, the pain is inflammatory pain, neuropathic pain, visceral pain, surgical pain, post-surgical pain, cancer related pain or a combination thereof. In other preferred embodiments, the method further comprises administering to said patient codeine, carbamazepine, gabapentin, lamotrigine, phenyloin, amitryptiline, an NMDA receptor antagonist, an ion channel antagonist, a nicotinic receptor agonist, or a mixture thereof.

In certain embodiments, the invention is directed to methods of treating hypertension, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof.

In certain embodiments, the invention is directed to methods of treating a neurodegenerative disease, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof. In certain preferred embodiments, the neurodegenerative disease is Parkinson's disease, Alzheimer's disease, Huntington's disease, amyotrophic lateral sclerosis, or combination thereof. In certain other preferred embodiments, the method further comprises administering to said patient deprenyl, amantadine, levodopa, or carbidopa.

In certain embodiments, the invention is directed to methods of treating a neurological disorder, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof. In certain preferred embodiments, neurological disorder is stroke, migraine, cluster headache, or a combination thereof.

In certain embodiments, the invention is directed to methods for providing cardioprotection against ischemic or reperfusion effects, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof. In certain preferred embodiments, the ischemic or reperfusion effect is arrhythmia or hypertension.

In certain embodiments, the invention is directed to methods for inhibiting mechanical hyperalgesia associated with nerve injury, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof.

In certain embodiments, the invention is directed to methods for inducing apoptosis in malignant cells, comprising the step of:
administering to a patient in need thereof, a composition comprising an effective amount of a compound of the invention, preferably a compound of formula I, I', Ia, II, III, IV, V, and/or VI, or a pharmaceutically acceptable salt thereof. In certain preferred embodiments, the apoptosis occurs in vitro. In certain other preferred embodiments, the apoptosis occurs in vivo In certain embodiments, the invention is directed to methods for modulating appetite, comprising the step of:
  administering to a patient in need thereof, a composition comprising an effective amount of a compound of the invention, preferably a compound of formula I, I', Ia, II, III, IV, V, and/or VI, or a pharmaceutically acceptable salt thereof.

Methods of Preparation

Materials: All chemicals were reagent grade and unless otherwise specified purchased from Sigma-Aldrich and used without further purification. All reactions, unless otherwise noted, are carried out at atmospheric pressure, room temperature, and in the presence of an air atmosphere. LC-MS data were obtained using a Thermo-Finnigan Surveyor HPLC and a Thermo-Finnigan AQA MS using positive or negative electrospray ionization. Program (positive) Solvent A: 10 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes. Program (negative) 1 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes.

Abbreviations Used In These Examples
PyBrop bromo-tris-pyrrolidino-phosphonium hexafluorophosphate
DIEA diisopropyl ethyl amine
DCM dichloromethane
FMP resin 4-Formyl-3-methoxyphenoxy resin
TFA trifluoroacetic acid
EE ethyl acetate
TBTU O-benzotriazol-1-yl-N,N',N'-tetramethyluronium tetrafluoroborate
DCE dichloroethane
DME dimethoxyethane Employing the methodology herein described or cited, sulfamoyl benzamide compounds of Formula I, I', Ia, II, III, IV, V, or VI can be readily prepared. The invention is further described in the following examples. The actual examples, herein provided, are for illustrative purposes only, and are not to be construed as limiting the appended claims. They provide a series of sulfamoyl benzamide derivatives (1-103) of I, I', Ia, II, III, IV, V, or VI, prepared according to Schemes 1-5, shown below in Examples 1-10.

Commercially available benzoic acids Ip were converted to sulfonyl chlorides 2 by heating in neat chlorosulfonic acid to 80-120° C. for 12-24 h (Scheme 1, general method A). The sulfonyl chloride IIp was reacted with 3 equivalents of the appropriate amine A in ethylacetate to yield sulfonamide acids IIIp (Scheme 2, general method B). Resin bound amines S (prepared according to general method C) were coupled to sulfonamide acids IIIp with PyBrop followed by TFA cleavage from resin to obtain compounds 1 and 3-16 (Scheme 3, general method D and E). Sulfonamides IIIp were reacted in solution with a second amine B and a suitable coupling reagent (e.g. TBTU or DCC/HOBt, general methods F and G respectively) to afford sulfamoyl benzamides 2, 17-27, 33-74, 81-84 and 86-103. To obtain 75-80 sulfonamide acids IIIp were converted to the acid chlorides VIp and then coupled to amines B (Scheme 4, general methods F-I). Compound 28 was prepared through a standard Suzuki coupling of 17 with phenylboronic acid. Compounds 29-32 were obtained from 25 through TFA-deprotection (29), followed by reaction with bromoacetic acid methyl ester (30), ethylisocyanate (31) or methyl sulfonyl chloride (32) respectively. A Sonogashira coupling of 91 with 3-methoxyprop-1-yne followed by hydrogenation yielded 85 (Scheme 5).

Replacement of the bromo-substituent in VIIp by a trifluoromethyl group is accomplished through treatment with chlorodifluoroacetic acid methyl ester, copper iodide and potassium fluoride (Duan, J. et al. *Journal of Fluorine Chemistry* 1993, 61(3), 279-84). Palladium-catalyzed cyanation of VIIp promoted by low-level tributyltin chloride yields the cyano analogs (Yang, C. and Williams, J. M. *Organic Letters* 2004, 6(17), 2837-2840).

Scheme 1:

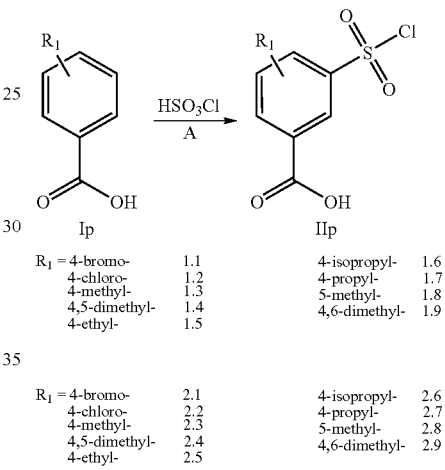

| $R_1$ = 4-bromo- | 1.1 | 4-isopropyl- | 1.6 |
| 4-chloro- | 1.2 | 4-propyl- | 1.7 |
| 4-methyl- | 1.3 | 5-methyl- | 1.8 |
| 4,5-dimethyl- | 1.4 | 4,6-dimethyl- | 1.9 |
| 4-ethyl- | 1.5 | | |

| $R_1$ = 4-bromo- | 2.1 | 4-isopropyl- | 2.6 |
| 4-chloro- | 2.2 | 4-propyl- | 2.7 |
| 4-methyl- | 2.3 | 5-methyl- | 2.8 |
| 4,5-dimethyl- | 2.4 | 4,6-dimethyl- | 2.9 |
| 4-ethyl- | 2.5 | | | commercially available: 4-F,6-Cl- 2.10  H- 2.11

Scheme 2:

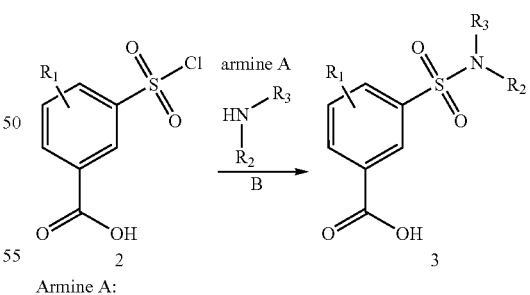

Armine A:

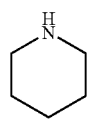

a1

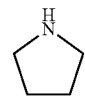

a2

-continued
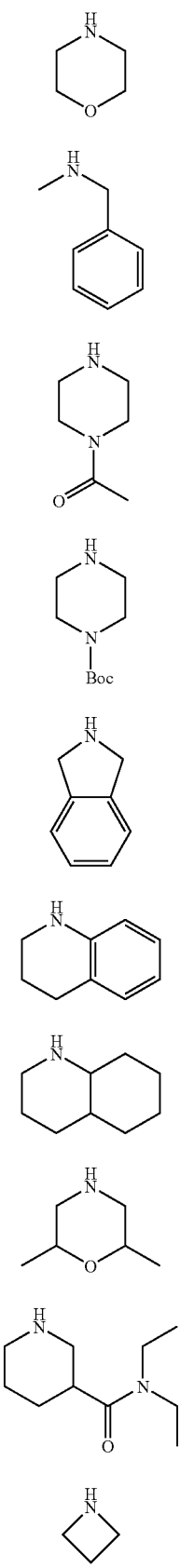
a3
a4
a5
a6
a7
a8
a9
a10
a11
a12
-continued
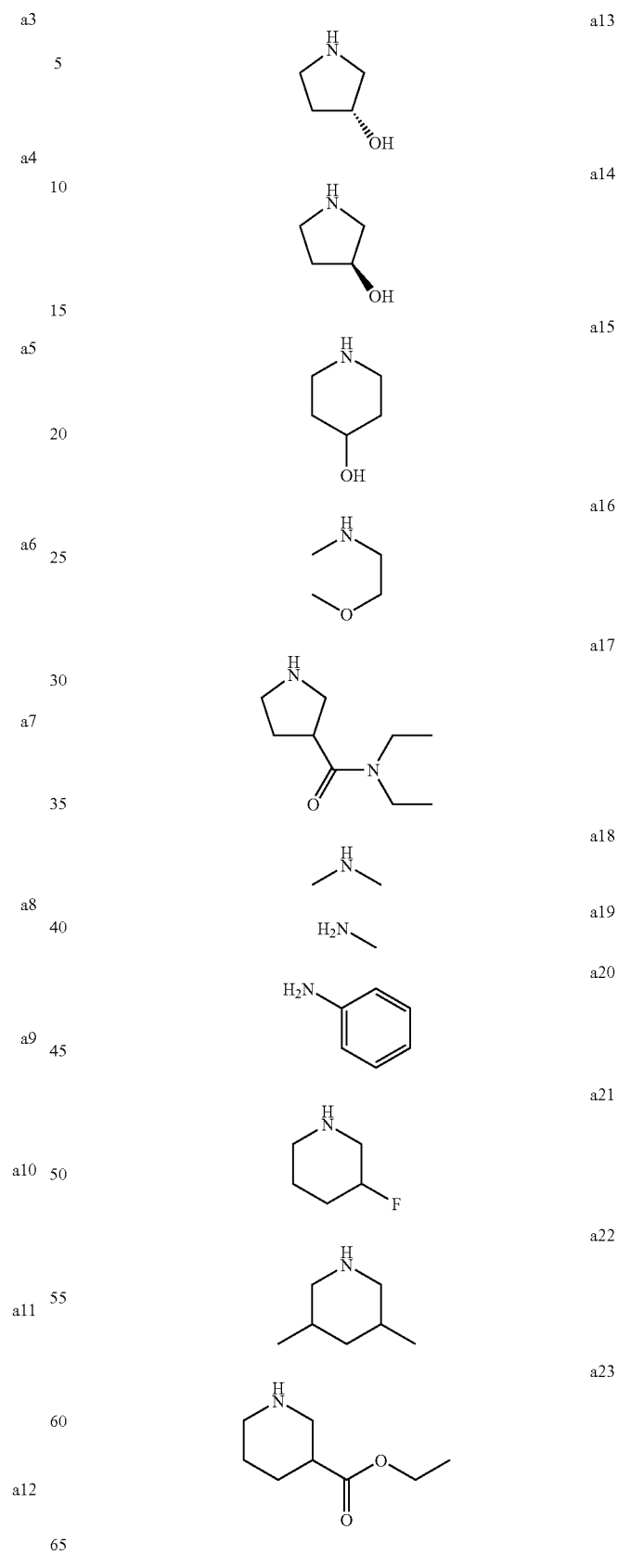
a13
a14
a15
a16
a17
a18
a19
a20
a21
a22
a23

-continued
a24
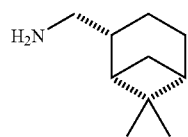
Scheme 3:
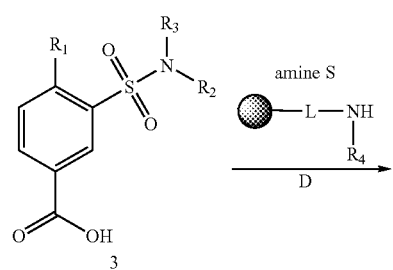
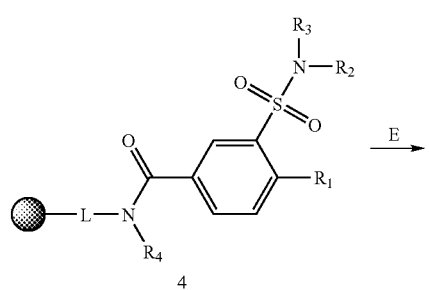
5
compounds 1, 3-16
Amine S:
s1
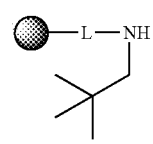
s2
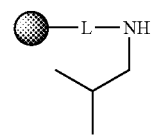
s3
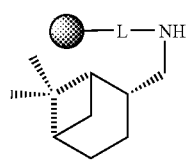
-continued
s4
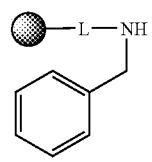
s5
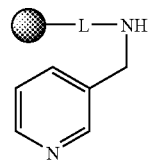
s6
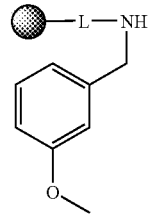
Scheme 4:
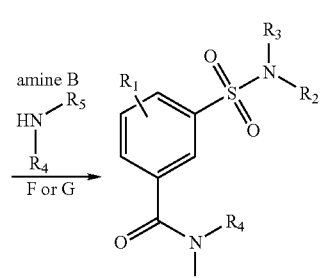
compounds 2, 17-84, 86-103
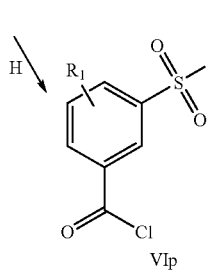
VIp
b1
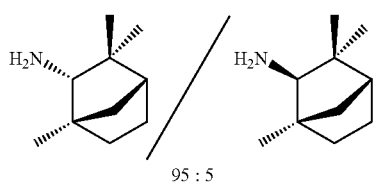
95 : 5

-continued
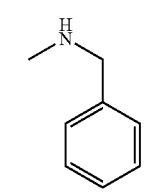  a4
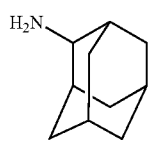  b2
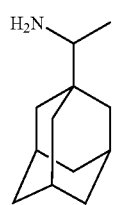  b3
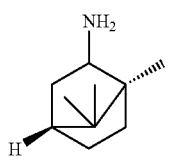  b4
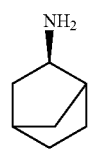  b5
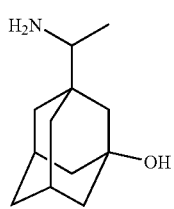  b6
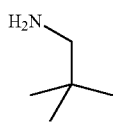  b7
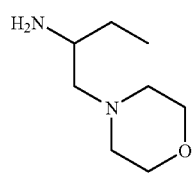  b8
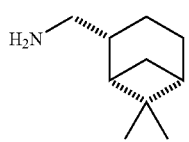  a24
-continued
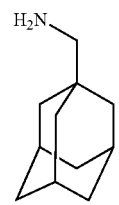  b10
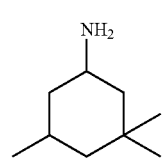  b11
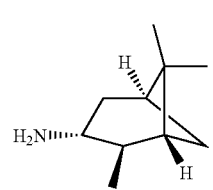  b12
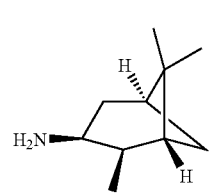  b13
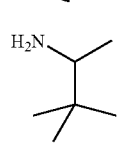  b14
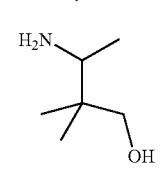  b15
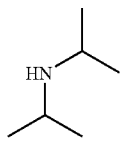  b16
Scheme 5:
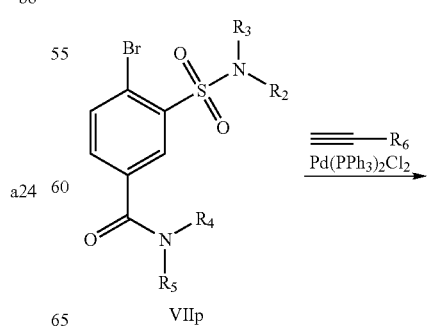

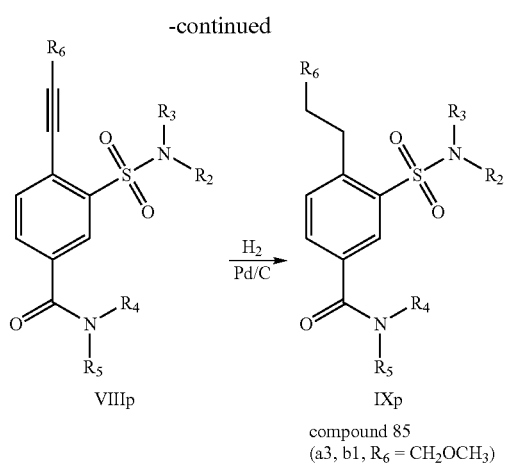

VIIIp compound 85
(a3, b1, R$_6$ = CH$_2$OCH$_3$)

General Methods

A. Preparation of sulfonyl chlorides (IIp):

Benzoic acid Ip (8 mmol) was dissolved in 10 mL HSO$_3$Cl and heated to 80-120° C. for 12-24 hours. The mixture was cooled to room temperature and carefully poured on ice. A white precipitate formed. It was collected, dried and used crude for the following reactions. See EP0659748 for further details.

B. Preparation of Sulfonamides (IIIp):

Sulfonyl chloride acid IIp (8 mmol) was dissolved in 100 mL of ethyl acetate and amine A (3 equiv., 24 mmol) was added. The mixture was stirred at room temperature for 2 hours, then extracted with 80 mL of 0.5M HCl. The organic layer was washed with H$_2$O and brine and the solvent evaporated. Product IIIp was used crude for the following reactions.

C. Preparation of Resin Bound Amines (S):

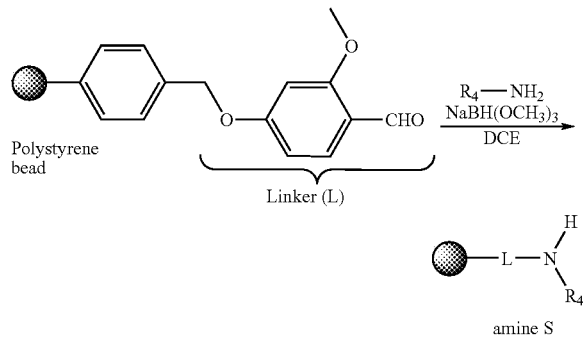

amine S

The resin (1.6 mmol/g, 500 mg, 0.8 mmol) was placed in a vessel, 5 mL dichloroethane added followed by 4 mmol (5 equiv.) of respective amine. The mixture was shaken for 2 hours at room temperature, then the reducing agent, triacetoxyborohydride (4 mmol, 5 equiv., 848 mg) was added and shaken overnight. The resin was filtered and washed with dichloromethane, dichloromethane/methanol (1:1), methanol and dichloromethane and used for the amide formation. (Completeness of the reaction was indicated by disappearance of the carbonyl band in the IR spectrum).

D. Preparation of Resin Bound Amides (IVp):

To a solution of sulfonamide benzoic acid IIIp (1.2 mmol) and 2.4 mmol N,N-diisopropylethylamine in dry dichloromethane, resin bound amine S (250 mg, FMP resin from Polymerlabs, loading 1.6 mmol/g) was added, followed by 1.2 mmol of PyBrop. The mixture was shaken at room temperature overnight, then filtered. The resin bound IVp was washed 3 times alternating among dichloromethane, N,N-dimethylformamide, dichloromethane/methanol and dichloromethane.

E. Cleavage from Resin (Vp):

Resin bound IVp was suspended in TFA/dichloromethane (1:1) for 2 hours at room temperature, then filtered, washed once with dichloromethane. The combined filtrates were evaporated. Crude purities of the final compounds Vp prepared were between 52-100%. Further purification was carried out using flash chromatography or preparative HPLC.

F. TBTU-Coupling (Vp):

Sulfonamide benzoic acid IIIp (0.440 mmol), amine B (0.9 mmol), and TBTU (0.66 mmol) were dissolved in dry acetonitrile (10 mL) under an atmosphere of nitrogen. The reaction was cooled to 0° C. in an ice water bath. Next N,N-diisopropylethylamine (0.3 mL, 2 mmol) was added. The reaction was left to stir for 48 hours at room temperature. The acetonitrile was evaporated and ethyl acetate added. The product was extracted with saturated sodium bicarbonate (20 mL), and the organic layer was dried over magnesium sulfate and the solvent evaporated. The product Vp was purified by silica gel chromatography using hexane/ethyl acetate eluents.

G. DCC/HOBt-Coupling (Vp)

These reactions were done in a 96-well plate. The reagents are given per well. Sulfonamide benzoic acid IIIp (4 mg, 0.012 mmol) in 300 µl N,N-dimethylformamide and polystyrene-DCC resin (15 mg, loading ca. 1.27 mmol/g) were combined with HOBt (2 mg, 0.015 mmol) and amine B (0.010 mmol). The reaction was shaken for 24 h, then polystyrene-(polystyrene)-trisamine resin (9 mg, loading ca. 4.36 mmol/g) was added and shaken overnight. The reaction was filtered and the N,N-dimethylformamide evaporated.

H. Preparation of Acid Chlorides (VIp):

Sulfonamide benzoic acid IIIp (11.6 mmol) was dissolved in dichloromethane (35 mL). The reaction was cooled to 0° C. under an atmosphere of nitrogen and thionyl chloride (4.20 mL, 0.0576 mol) was added dropwise. The reaction was allowed to warm to room temperature and was stirred for 3 hours then refluxed for 1 hour. The solvent was evaporated and the crude oil was used in the next reaction.

I. Acid Chloride/Amine Coupling (Vp):

To amine B (1.95 mmol) in dichloromethane (10 mL) was added N,N-diisopropyl-ethylamine (0.68 mL, 3.9 mmol) in dichloromethane (1 mL). The reaction was cooled to 0° C. (to −30° C. for b15) and a solution of acid chloride VIp (1.30 mmol) in dichloromethane (1 mL) was added slowly through a septum. The reaction was stirred overnight at room temperature. The reaction was washed with 1 N HCl, saturated NaHCO$_3$ solution, and brine, dried over MgSO$_4$, filtered and the solvent evaporated to give the crude product Vp. The product was purified by silica gel chromatography using hexane/ethyl acetate eluents.

EXAMPLE 1

Preparation of 4-Bromo-N-(2,2-dimethyl-propyl)-3-(piperidine-1-sulfonyl)-benzamide (1)

4-Bromo-3-chlorosulfonyl-benzoic acid (2.1)

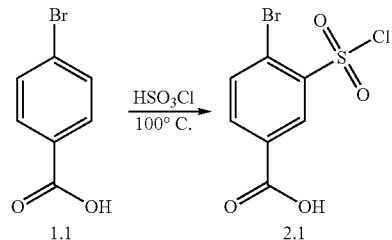

Compound 2.1 was prepared from commercially available 4-bromo benzoic acid 1.1 in 97% yield according to general method A. MS (M−1)=296.

4-Bromo-3-(piperidine-1-sulfonyl)-benzoic acid (3.1)

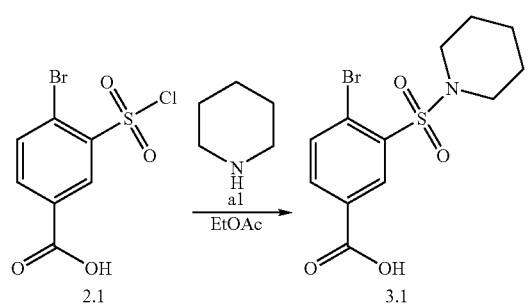

Compound 3.1 was prepared from 4-bromo-3-chlorosulfonyl-benzoic acid 2.1 and piperidine a1 in 88% yield according to general method B. MS (M−1)=346.

4-Bromo-N-(2,2-dimethyl-propyl)-3-(piperidine-1-sulfonyl)-benzamide (1)

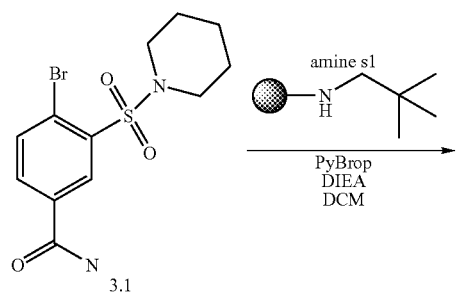

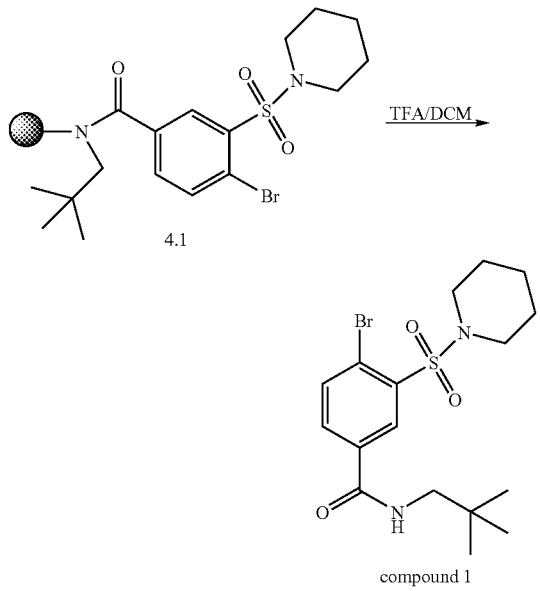

Compound 1 was prepared from 4-bromo-3-(piperidine-1-sulfonyl)-benzoic acid 3.1 and resin bound amine s1 according to general methods D and E. After purification (short SiO$_2$ plug, 20% ethyl acetate/hexane) 90 mg of a clear oil was obtained (56% yield). MS (M−1)=415.

Compounds 3-16 were prepared using general methods A-E analogous to Example 1 utilizing the appropriate combinations of the following synthons identified in TABLE 1.

TABLE 1

| example | Sulfonyl chloride | Amine A | Resin Bound B | LC/MS Purity (purified yield) |
|---|---|---|---|---|
| 3 | 2.2 | a1 | s1 | 72% (64%) |
| 4 | 2.3 | a1 | s1 | 91% (85%) |
| 5 | 2.10 | a3 | s4 | (51%) |
| 6 | 2.1 | a4 | s1 | 99% (50%) |
| 7 | 2.1 | a1 | s3 | 67% (50%) |
| 8 | 2.1 | a4 | s3 | 52% (3%) |
| 9 | 2.1 | a3 | s4 | 100% |
| 10 | 2.1 | a4 | s5 | 95% |
| 11 | 2.1 | a1 | s6 | 98% |
| 12 | 2.1 | a2 | s6 | 98% |
| 13 | 2.1 | a2 | s1 | 100% |
| 14 | 2.1 | a4 | s2 | 95% |
| 15 | 2.1 | a2 | s4 | 99% |
| 16 | 2.1 | a1 | s4 | 99% |

EXAMPLE 2

Preparation of 4-Chloro-3-(piperidine-1-sulfonyl)-N-(1,3,3-trimethyl-bicyclo-[2.2.1]hept-2-yl)benzamide (2)

4-Chloro-3-chlorosulfonyl-benzoic acid (2.2)

Compound 2.2 was prepared from commercially available 4-chloro benzoic acid 1.2 in 92% yield according to general method A. MS (M−1)=252.

4-Chloro-3-(piperidine-1-sulfonyl)-benzoic acid (3.2)

Compound 3.2 was prepared from 4-chloro-3-chlorosulfonyl-benzoic acid 2.2 and piperidine a1 in 89% yield according to general method B. MS (M−1)=302.

4-Chloro-3-(piperidine-1-sulfonyl)-N-(1,3,3-trimethyl-bicyclo[2.2.1]hept-2-yl)-benzamide (2)

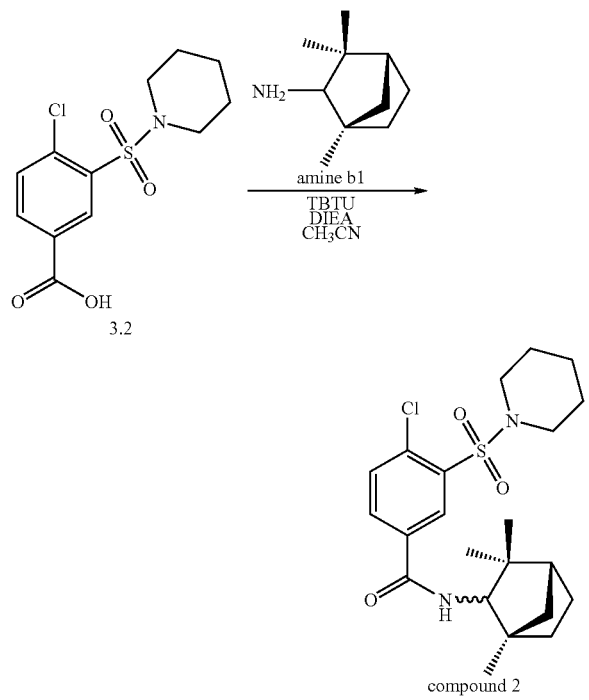

Compound 2 was prepared from 4-chloro-3-(piperidine-1-sulfonyl)-benzoic acid 3.2 and S-fenchyl amine b1 (prepared as reported in FR96/01953, contained about 5% R-isomer) in 41% yield according to general method F. MS (M−1)=438.

Compounds 17-27, 61-74, 81-84 and 86-102 were prepared employing general methods A, B and F analogous to Example 2 utilizing the appropriate combinations of the following synthons as identified in TABLE 2.

TABLE 2

| example | Sulfonyl chloride | Amine 1 | Amine 2 | purified yield |
|---|---|---|---|---|
| 17 | 2.1 | a1 | b1 | 81% |
| 18 | 2.1 | a3 | a4 | 21% |
| 19 | 2.6 | a1 | b1 | 20% |
| 20 | 2.3 | a1 | b1 | 61% |
| 21 | 2.11* | a1 | b1 | 73% |
| 22 | 2.11* | a1 | b1 | 3% |
| 23 | 2.1 | a4 | b1 | 3% |
| 24 | 2.1 | a5 | b1 | 8% |
| 25 | 2.3 | a6 | b1 | 72% |
| 26 | 2.3 | a3 | b1 | 74% |
| 27 | 2.1 | a3 | b1 | 3% |
| 61 | 2.4 | a3 | b1 | 9% |
| 62 | 2.4 | a3 | a24 | 34% |
| 63 | 2.4 | a3 | b3 | 48% |
| 64 | 2.4 | a4 | b1 | 28% |
| 65 | 2.4 | a4 | a24 | 17% |
| 66 | 2.4 | a4 | b3 | 54% |
| 67 | 2.4 | a11 | b1 | 37% |
| 68 | 2.3 | a12 | b1 | 20% |
| 69 | 2.3 | a13 | b1 | 10% |
| 70 | 2.3 | a14 | b1 | 26% |
| 71 | 2.3 | a15 | b1 | 12% |
| 72 | 2.3 | a11 | b1 | 5% |
| 73 | 2.3 | a16 | b1 | 28% |
| 74 | 2.3 | a17 | b1 | 69% |
| 81 | 2.3 | a3 | b16 | 48% |
| 82 | 2.5 | a3 | b1 | 37% |
| 83 | 2.6 | a3 | b1 | 10% |
| 84 | 2.7 | a3 | b1 | 8% |
| 86 | 2.8 | a3 | b1 | 33% |
| 87 | 2.9 | a3 | b1 | 26% |
| 88 | 2.1 | a18 | b1 | 33% |
| 89 | 2.1 | a19 | b1 | 12% |
| 90 | 2.1 | a20 | b1 | 10% |
| 91 | 2.1 | a3 | b1 | 31% |
| 92 | 2.1 | a21 | b1 | 60% |
| 93 | 2.1 | a2 | b1 | 60% |
| 94 | 2.1 | a22 | b1 | 6% |
| 95 | 2.1 | a10 | b1 | 21% |
| 96 | 2.1 | a23 | b1 | 7% |
| 97 | 2.1 | a24 | a24 | 6% |
| 98 | 2.1 | a3 | b14 | 52% |
| 99 | 2.1 | a2 | b14 | 98% |
| 100 | 2.1 | a18 | b14 | 56% |
| 101 | 2.10 | a3 | b1 | 49% |
| 102 | 2.10 | a3 | b3 | 17% |

Pure R-isomers 22 and 27 could be separated from 21 and 26 (S-isomers) by preparative HPLC. (S-fenchyl amine b1 used contained about 5% R-isomer). Note: S and R in this instance specifies the chirality of the amino-bearing carbon atom.

EXAMPLE 3

Preparation of 2-(Piperidine-1-sulfonyl)-biphenyl-4-carboxylic acid (1,3,3-trimethyl-bicyclo-[2.2.1]hept-2-yl)-amide (28)

Compound 28 was prepared from 50 mg 17 under standard Suzuki coupling conditions, using 19 mg of phenyl boronic acid, 138 mg $K_2CO_3$ and tetrakistriphenylphosphine as catalyst in 4 mL dimethoxyethane/$H_2O$ (3:1). The mixture was stirred overnight at 80° C. After aqueous work-up the product was isolated by preparative HPLC chromatography and 13 mg of a light yellow solid was obtained (78% yield). MS (M−1)=479.

EXAMPLE 4

Preparation of 4-Methyl-3-(piperazine-1-sulfonyl)-N-(1,3,3-trimethyl-bicyclo-[2.2.1]hept-2-yl)-benzamide (29)

Compound 29 was prepared from 2.85 g 25 by stirring in 100 mL dichloromethane/TFA (1:1) for 2 hours at room temperature. The solvent was evaporated and 2.90 g of 29 as TFA salt was obtained. (quantitative yield). MS (M−1)=418.

EXAMPLE 5

Preparation of {4-[2-Methyl-5-(1,3,3-trimethyl-bicyclo-[2.2.1]hept-2-ylcarbamoyl)-benzene-sulfonyl]-piperazin-1-yl}-acetic acid methyl ester (30)

Compound 30 was prepared from 117 mg 29 by stirring in 5 mL dry dichloromethane adding 100 μl N,N-diisopropylethylamine and 25 μl bromoacetic acid methylester overnight at room temperature. After aqueous work-up the product 30 was isolated by SiO₂ chromatography (5-20% ethylacetate/hexane) and 23 mg of an off white solid was obtained (21% yield). MS (M+1)=492.

EXAMPLE 6

Preparation of 4-[2-Methyl-5-(1,3,3-trimethyl-bicyclo-[2.2.1]hept-2ylcarbamoyl)-benzenesulfonyl]-piperazine-1-carboxylic acid ethyl amide(31)

Compound 31 was prepared from 117 mg 29 by stirring in 5 mL dry dichloromethane adding 100 μl N,N-diisopropylethylamine and 31 μl ethyl isocyanate overnight at room temperature. After aqueous work-up the product was isolated by SiO₂ chromatography (5-20% ethyl acetate/hexane) and 105 mg of an off white solid was obtained (97% yield). MS (M+1)=491.

EXAMPLE 7

Preparation of 3-(4-Methanesulfonyl-piperazine-1-sulfonyl)-4-methyl-N-(1,3,3-tri-methyl-bicyclo-[2,2,1]-hept-2-yl)-benzamide (32)

Compounds 32 was prepared from 117 mg 29 by stirring in 5 mL dry dichloromethane adding 100 μl N,N-diisopropylethylamine and 20 μl methyl sulfonyl chloride overnight at room temperature. After aqueous work-up the product was isolated by preparative HPLC chromatography and 48 mg of an off white solid was obtained (44% yield). MS (M−1)=496.

EXAMPLE 8

Preparation of N-Adamantan-2-yl-4-methyl-3-(morpholine-4-sulfonyl)-benzamide (33)

Compound 33 was prepared from commercially available 4-methyl benzoic acid 1.3, morpholine a3 and adamantan-2-yl amine b2 employing general methods A, B and G, in 54% purity by LC/MS. MS (M+1)=419.

Compounds 34-60 and 103 were prepared employing general methods A, B and G analogous to Example 8 utilizing the appropriate combinations of the following synthons as identified in TABLE 3.

TABLE 3

| example | Sulfonyl chloride | Amine 1 | Amine 2 | LC/MS purity |
|---|---|---|---|---|
| 34 | 2.3 | a3 | b3 | 99% |
| 35 | 2.3 | a3 | b4 | 92% |
| 36 | 2.3 | a3 | b5 | 90% |
| 37 | 2.3 | a3 | b6 | 95% |
| 38 | 2.3 | a3 | b7 | 99% |
| 39 | 2.3 | a3 | b8 | 88% |
| 40 | 2.3 | a7 | b1 | 99% |
| 41 | 2.3 | a7 | b5 | 98% |
| 42 | 2.3 | a7 | b4 | 99% |
| 43 | 2.3 | a7 | b7 | 99% |
| 44 | 2.3 | a7 | b6 | 99% |
| 45 | 2.3 | a7 | b8 | 99% |
| 46 | 2.4 | a8 | b2 | 90% |
| 47 | 2.4 | a8 | b3 | 89% |
| 48 | 2.4 | a8 | b1 | 89% |
| 49 | 2.4 | a9 | b2 | 90% |
| 50 | 2.4 | a9 | b3 | 70% |
| 51 | 2.4 | a9 | b1 | 93% |
| 52 | 2.3 | a10 | b2 | 99% |
| 53 | 2.3 | a10 | b3 | 99% |
| 54 | 2.3 | a10 | b1 | 99% |
| 55 | 2.4 | a10 | b2 | 92% |
| 56 | 2.4 | a10 | b3 | 99% |
| 57 | 2.4 | a10 | b1 | 97% |
| 58 | 2.10 | a4 | b2 | 97% |
| 59 | 2.10 | a4 | b3 | 97% |
| 60 | 2.10 | a4 | b1 | 90% |
| 103 | 2.10 | a4 | a4 | 93% |

EXAMPLE 9

Preparation of N-(1-Adamantan-1-yl-methyl)-3-(morpholino-sulfamoyl)-4-methyl-benzamide (75)

Compound 75 was prepared from commercially available 4-methyl benzoic acid 1.3, morpholine a3 and adamantan-1-yl methylamine b10 employing general methods A, B, H and I, in 61% yield. MS(M+1)=433.

Compounds 76-80 were prepared employing general methods A, B, H and I analogous to Example 9 utilizing the appropriate combinations of the following synthons as identified in TABLE 4.

TABLE 4

| example | Sulfonyl chloride | Amine 1 | Amine 2 | purified yield |
|---|---|---|---|---|
| 76 | 2.1 | a3 | b11 | 68% |
| 77 | 2.1 | a3 | b12 | 84% |
| 78 | 2.1 | a3 | b13 | 74% |
| 79 | 2.1 | a3 | b14 | 61% |
| 80 | 2.1 | a3 | b15 | 84% |

EXAMPLE 10

Preparation of 4-(3-Methoxy-propyl)-3-(morpholine-4-sulfonyl)-N-((1S,4R)-1,3,3-trimethyl-bicyclo[2.2.1]hept-2-yl)-benzamide (85)

4-(3-methoxyprop-1-ynyl)-3-(morpholinosulfonyl)-N-((1S,4R)-1,3,3-trimethylbicyclo[2.2.1]heptan-2-yl)benzamide (6.1)

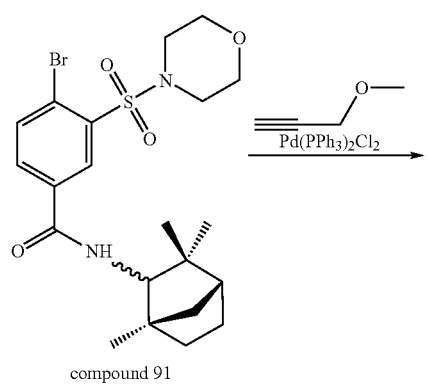

compound 91

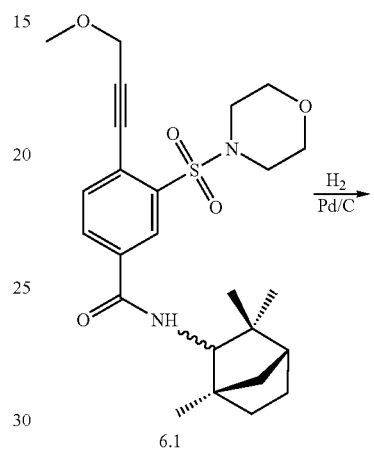

6.1

4-(3-Methoxy-propyl)-3-(morpholine-4-sulfonyl)-N-((1S,4R)-1,3,3-trimethyl-bicyclo[2.2.1]hept-2-yl)-benzamide (85)

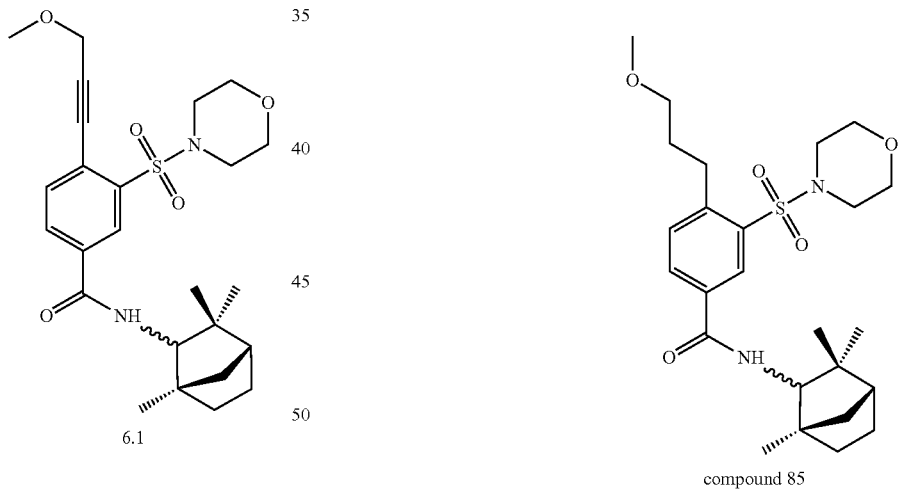

6.1 compound 85

A solution of 4-bromo-3-(morpholinosulfonyl)-N-((1S,4R)-1,3,3-trimethylbicyclo-[2.2.1]heptan-2-yl)benzamide 91 (400 mg, 0.8 mmol), bis(triphenylphosphine)-palladium (II) chloride (30 mg, 0.04 mmol), triphenylphosphine (39.7 mg, 0.151 mmol), copper(I) iodide (9 mg, 0.04 mmol), N-ethylethanamine (1.18 mL, 11.4 mmol) in N,N-dimethylformamide (1 mL) was degassed with nitrogen and sonicated. The reaction mixture was heated in the microwave at 125° C. for 25 minutes. The reaction mixture was poured into saturated ammonium chloride solution and extracted with ethyl acetate. The organic layer was washed with brine, dried over Na$_2$SO$_4$, filtered and evaporated. The residue was purified by silica gel chromatography using hexane/ethyl acetate (0-50%) to give the product 6.1 as a yellow oil (240 mg, 60% yield).

To a solution of 4-(3-methoxy-prop-1-ynyl)-3-(morpholine-4-sulfonyl)-N-((1S,4R)-1,3,3-trimethyl-bicyclo[2.2.1]hept-2-yl)-benzamide 6.1 (220 mg, 0.46 mmol) in ethanol (20 mL) under nitrogen was added palladium on carbon (10 mg, 0.08 mmol). The reaction mixture was stirred under a hydrogen atmosphere for 2 hours then filtered through celite washing with ethanol. The solvent was evaporated and the residue was purified by silica gel chromatography using hexane/ethyl acetate (0-50%) to give the product 85 as a white solid (120 mg, 54% yield).

TABLE 5

Examples 1–103 claimed in the present application

| Example | Name | Structure | M + 1 |
|---|---|---|---|
| 1 | 4-Bromo-N-(2,2-dimethyl-propyl)-3-(piperidine-1-sulfonyl)-benzamide | 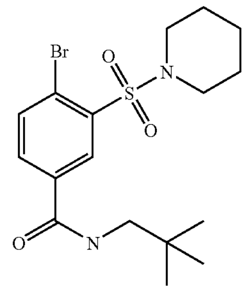 | 417 |
| 2 | 4-Chloro-3-(piperidine-1-sulfonyl)-N-(1,3,3-trimethyl-bicyclo-[2.2.1]-hept-2-yl)-benzamide | 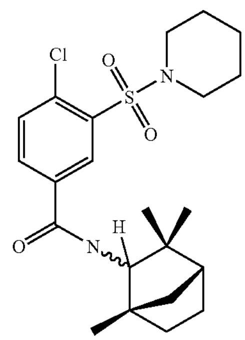 | 439 |
| 3 | 4-Chloro-N-(2,2-dimethyl-propyl)-3-(piperidine-1-sulfonyl)-benzamide | 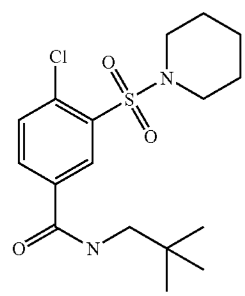 | 373 |
| 4 | N-(2,2-Dimethyl-propyl)-4-methyl-3-(piperidine-1-sulfonyl)-benzamide | 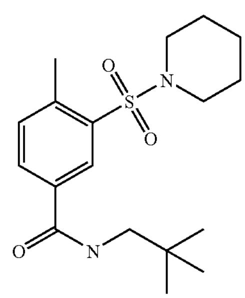 | 353 |
| 5 | N-Benzyl-2-chloro-4-fluoro-5-(morpholine-4-sulfonyl)-benzamide | 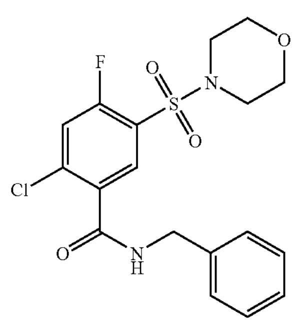 | 413 |

TABLE 5-continued

Examples 1–103 claimed in the present application

| Example | Name | Structure | M + 1 |
|---------|------|-----------|-------|
| 6 | 3-(Benzyl-methyl-sulfamoyl)-4-bromo-N-(2,2-dimethyl-propyl)-benzamide | 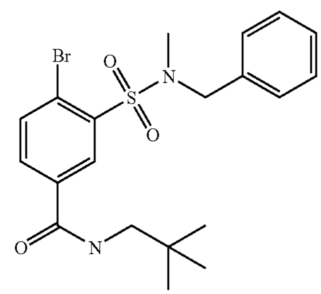 | 453 |
| 7 | 4-Bromo-N-(6,6-dimethyl-bicyclo-[3.1.1]hept-2-yl-methyl)-3-(piperidine-1-sulfonyl)-benzamide | 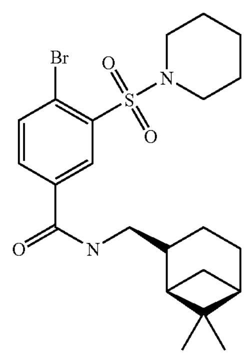 | 483 |
| 8 | 3-(Benzyl-methyl-sulfamoyl)-4-bromo-N-(6,6-dimethyl-bicyclo-[3.1.1]hept-2-yl-methyl)-benzamide | 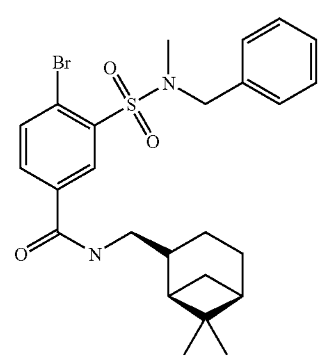 | 519 |
| 9 | N-Benzyl-4-bromo-3-(morpholine-4-sulfonyl)-benzamide | 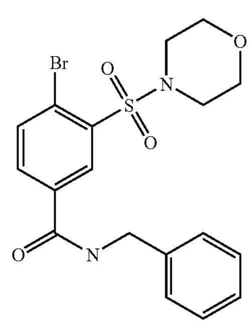 | 439 |

TABLE 5-continued

Examples 1–103 claimed in the present application

| Example | Name | Structure | M + 1 |
|---|---|---|---|
| 10 | 3-(Benzyl-methyl-sulfamoyl)-4-bromo-N-pyridin-3-yl-methyl-benzamide | 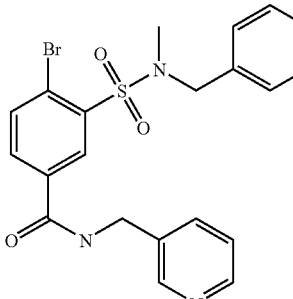 | 474 |
| 11 | 4-Bromo-N-(3-methoxybenzyl)-3-(piperidine-1-sulfonyl)-benzamide | 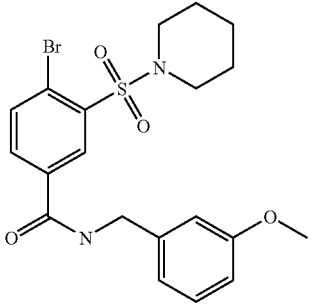 | 467 |
| 12 | 4-Bromo-N-(3-methoxybenzyl)-3-(pyrrolidine-1-sulfonyl)-benzamide | 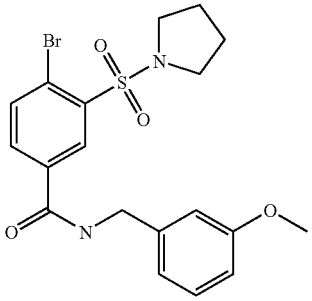 | 453 |
| 13 | 4-Bromo-N-(2,2-dimethylpropyl)-3-(pyrrolidine-1-sulfonyl)-benzamide | 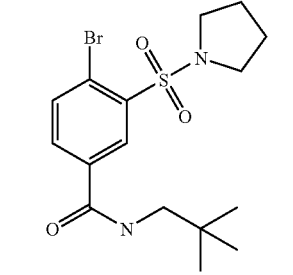 | 403 |
| 14 | 3-(Benzyl-methyl-sulfamoyl)-4-bromo-N-isobutyl-benzamide | 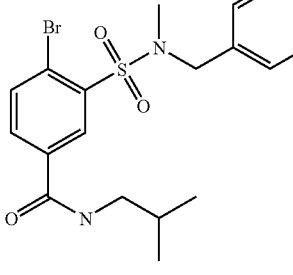 | 439 |

TABLE 5-continued

Examples 1–103 claimed in the present application

| Example | Name | Structure | M + 1 |
|---|---|---|---|
| 15 | N-Benzyl-4-bromo-3-(pyrrolidine-1-sulfonyl)-benzamide | 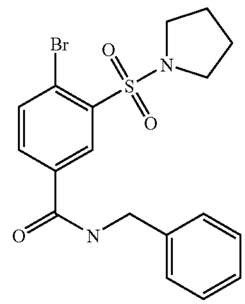 | 423 |
| 16 | N-Benzyl-4-bromo-3-(piperidine-1-sulfonyl)-benzamide | 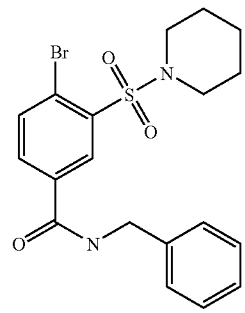 | 437 |
| 17 | 4-Bromo-3-(piperidine-1-sulfonyl)-N-(1,3,3-trimethylbicyclo[2.2.1]hept-2-yl)-benzamide | 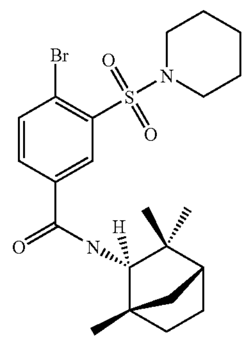 | 483 |
| 18 | N-Benzyl-4-bromo-N-methyl-3-(morpholine-4-sulfonyl)-benzamide | 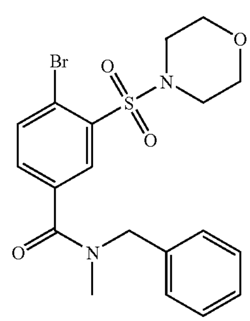 | 453 |

TABLE 5-continued

Examples 1–103 claimed in the present application

| Example | Name | Structure | M + 1 |
|---|---|---|---|
| 19 | 4-Isopropyl-3-(piperidine-1-sulfonyl)-N-(1,3,3-trimethyl-bicyclo-[2.2.1]-hept-2-yl)-benzamide | 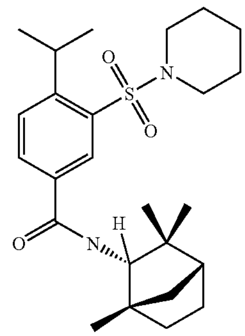 | 447 |
| 20 | 4-Methyl-3-(piperidine-1-sulfonyl)-N-(1,3,3-trimethyl-bicyclo-[2.2.1]hept-2-yl)-benzamide | 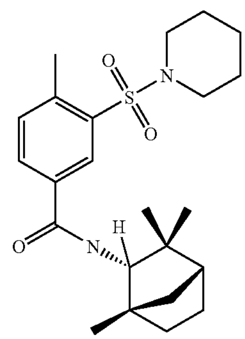 | 419 |
| 21 | 3-(piperidin-1-ylsulfonyl)-N-((1S,2S,4R)-1,3,3-trimethylbicyclo[2.2.1]heptan-2-yl)benzamide | 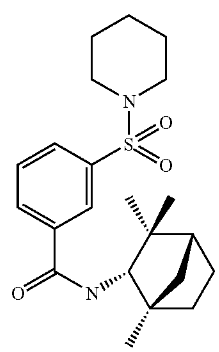 | 405 |
| 22 | 3-(piperidin-1-ylsulfonyl)-N-((1S,2R,4R)-1,3,3-trimethylbicyclo[2.2.1]heptan-2-yl)benzamide | 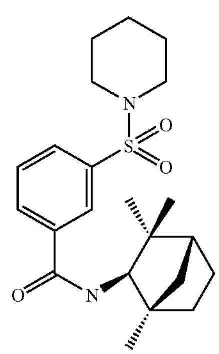 | 405 |

TABLE 5-continued

Examples 1–103 claimed in the present application

| Example | Name | Structure | M + 1 |
|---|---|---|---|
| 23 | 3-(Benzyl-methyl-sulfamoyl)-4-bromo-N-(1,3,3-trimethyl-bicyclo[2.2.1]hept-2-yl)-benzamide | 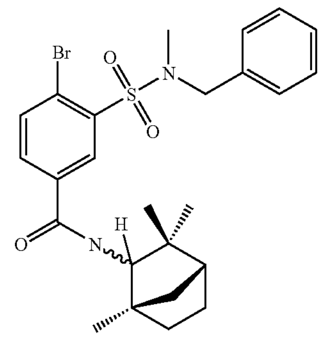 | 519 |
| 24 | 3-(4-Acetyl-piperazine-1-sulfonyl)-4-bromo-N-(1,3,3-trimethyl-bicyclo[2.2.1]-hept-2-yl)-benzamide | 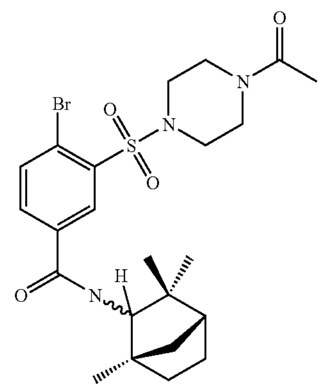 | 526 |
| 25 | 4-[2-Methyl-5-(1,3,3-trimethyl-bicyclo-[2.2.1]hept-2-yl-carbamoyl)-benzenesulfonyl]-piperazine-1-carboxylic acid tert-butyl ester | 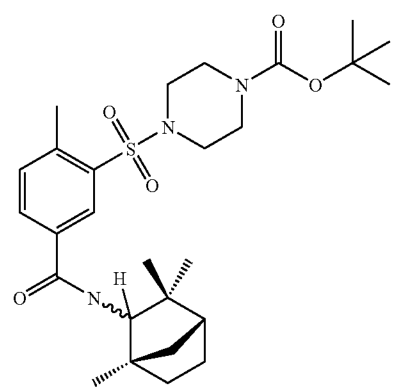 | 520 |
| 26 | 4-Methyl-3-(morpholine-4-sulfonyl)-N,S-(1,3,3-trimethyl-bicyclo[2.2.1]-hept-2-yl)-benzamide | 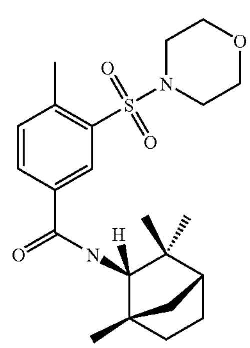 | 421 |

TABLE 5-continued

Examples 1–103 claimed in the present application

| Example | Name | Structure | M + 1 |
|---|---|---|---|
| 27 | 4-Methyl-3-(morpholine-4-sulfonyl)-N,R-(1,3,3-trimethyl-bicyclo[2.2.1]-hept-2-yl)-benzamide | 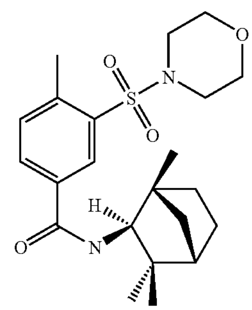 | 421 |
| 28 | 2-(Piperidine-1-sulfonyl)-biphenyl-4-carboxylic acid (1,3,3-trimethyl-bicyclo-[2.2.1]hept-2-yl)-amide | 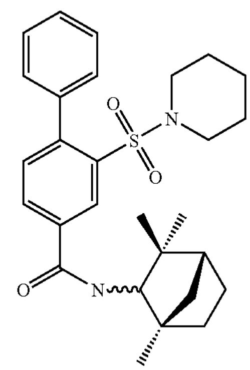 | 481 |
| 29 | 4-Methyl-3-(piperazine-1-sulfonyl)-N-(1,3,3-trimethyl-bicyclo-[2.2.1]hept-2-yl)-benzamide | 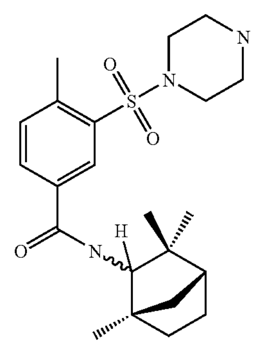 | 420 |
| 30 | {4-[2-Methyl-5-(1,3,3-trimethyl-bicyclo-[2.2.1]hept-2-yl-carbamoyl)-benzene-sulfonyl]-piperazin-1-yl}-acetic acid methyl ester | 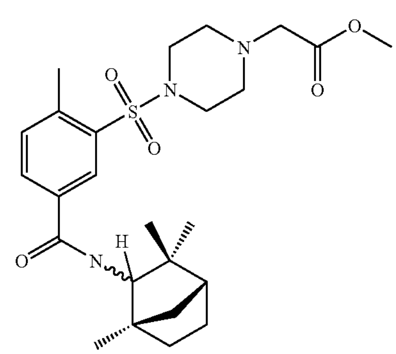 | 492 |

TABLE 5-continued

Examples 1–103 claimed in the present application

| Example | Name | Structure | M + 1 |
|---|---|---|---|
| 31 | 4-[2-Methyl-5-(1,3,3-tri-methyl-bicyclo-[2.2.1]hept-2yl-carbamoyl)-benzene-sulfonyl]-piperazine-1-carboxylic acid ethylamide | 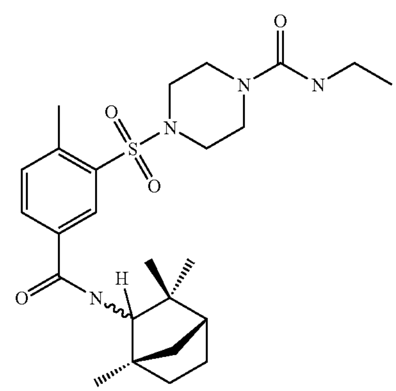 | 491 |
| 32 | 3-(4-Methanesulfonyl-piperazine-1-sulfonyl)-4-methyl-N-(1,3,3-tri-methyl-bicyclo-[2.2.1]-hept-2-yl)-benzamide | 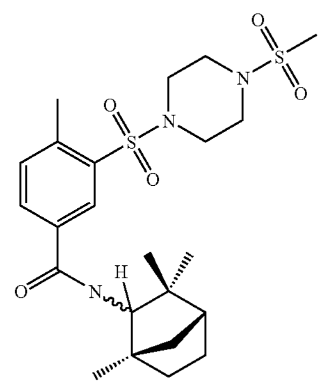 | 498 |
| 33 | N-Adamantan-2-yl-4-methyl-3-(morpholine-4-sulfonyl)-benzamide | 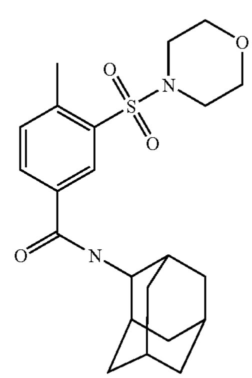 | 419 |

TABLE 5-continued

Examples 1–103 claimed in the present application

| Example | Name | Structure | M + 1 |
|---------|------|-----------|-------|
| 34 | N-(1-Adamantan-1-yl-ethyl)-4-methyl-3-(morpholine-4-sulfonyl)-benzamide | 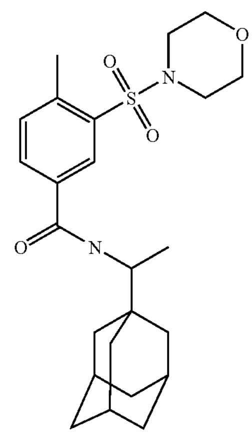 | 447 |
| 35 | 4-Methyl-3-(morpholine-4-sulfonyl)-N-((1S,4R)-1,7,7-trimethyl-bicyclo[2.2.1]-hept-2-yl)-benzamide | 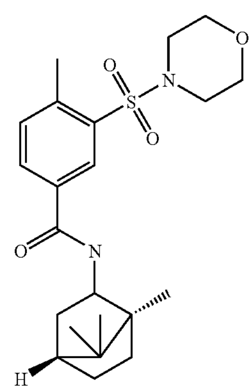 | 421 |
| 36 | N-(R)-Bicyclo[2.2.1]hept-2-yl-4-methyl-3-(morpholine-4-sulfonyl)-benzamide | 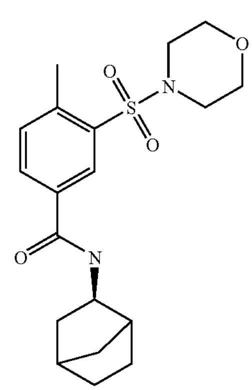 | 379 |

TABLE 5-continued

Examples 1–103 claimed in the present application

| Example | Name | Structure | M + 1 |
|---|---|---|---|
| 37 | N-[1-(3-Hydroxy-adamantan-1-yl)-ethyl]-4-methyl-3-(morpholine-4-sulfonyl)-benzamide | 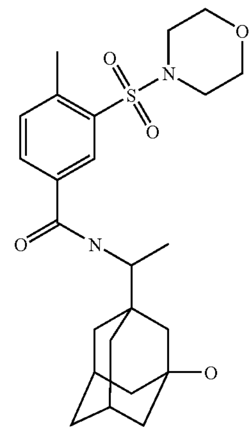 | 463 |
| 38 | N-(2,2-Dimethyl-propyl)-4-methyl-3-(morpholine-4-sulfonyl)-benzamide | 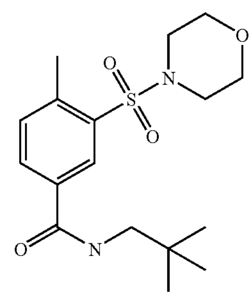 | 355 |
| 39 | 4-Methyl-3-(morpholine-4-sulfonyl)-N-(1-morpholin-4-yl-methyl-propyl)-benzamide | 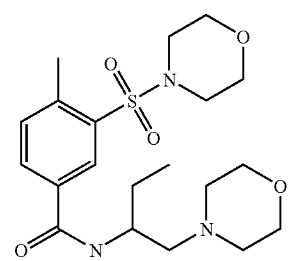 | 426 |
| 40 | 4-Methyl-3-(1,3-dihydro-isoindole-2-sulfonyl)-N,S-(1,3,3-trimethyl-bicyclo-[2.2.1]-hept-2-yl)benzamide | 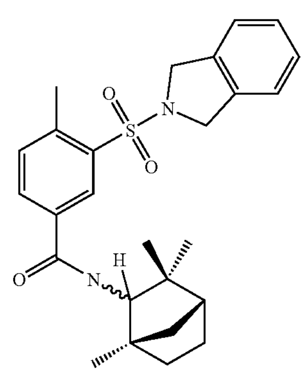 | 453 |

TABLE 5-continued

Examples 1–103 claimed in the present application

| Example | Name | Structure | M + 1 |
|---|---|---|---|
| 41 | N-(R)-Bicyclo[2.2.1]hept-2-yl-3-(1,3-di-hydro-isoindole-2-sul-fonyl)-4-methyl-benzamide | 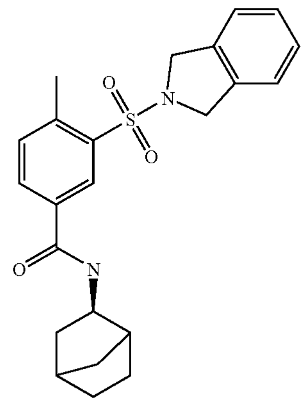 | 411 |
| 42 | 3-(1,3-Dihydro-isoindole-2-sul-fonyl)-4-methyl-N-((1S,4R)-1,7,7-trimethyl-bicyclo[2.2.1]hept-2-yl)-benzamide | 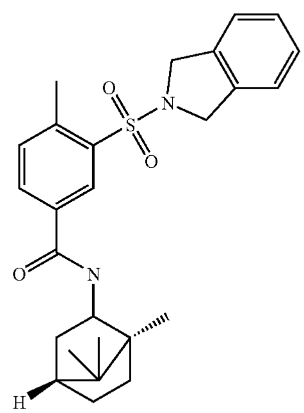 | 453 |
| 43 | 3-(1,3-Dihydro-isoindole-2-sul-fonyl)-N-(2,2-dimethyl-propyl)-4-methyl-benzamide | 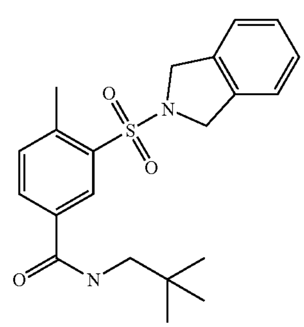 | 387 |

TABLE 5-continued

Examples 1–103 claimed in the present application

| Example | Name | Structure | M + 1 |
|---|---|---|---|
| 44 | 3-(1,3-Dihydro-isoindole-2-sulfonyl)-N-[1-(3-hydroxy-adamantan-1-yl)-ethyl]-4-methyl-benzamide | 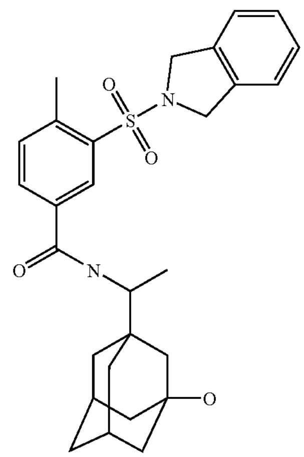 | 495 |
| 45 | 3-(1,3-Dihydro-isoindole-2-sulfonyl)-4-methyl-N-(1-morpholin-4-ylmethyl-propyl)-benzamide | 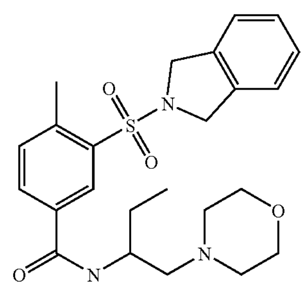 | 458 |
| 46 | N-Adamantan-2-yl-3-(3,4-dihydro-2H-quinoline-1-sulfonyl)-4,5-dimethyl-benzamide | 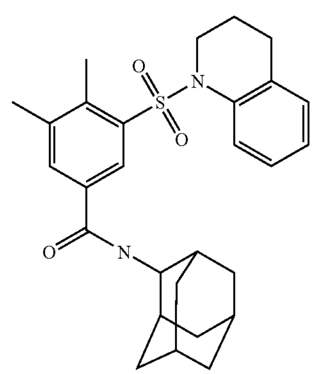 | 479 |
| 47 | N-(1-Adamantan-1-yl-ethyl)-3-(3,4-dihydro-2H-quinoline-1-sulfonyl)-4,5-dimethyl-benzamide | 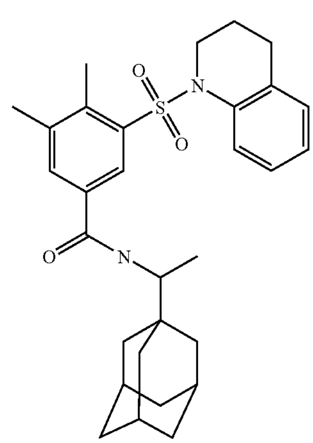 | 507 |

TABLE 5-continued

Examples 1–103 claimed in the present application

| Example | Name | Structure | M + 1 |
|---|---|---|---|
| 48 | 3-(3,4-dihydroquinolin-1(2H)-yl-sulfonyl)-4,5-dimethyl-N-((1S,4R)-1,3,3-trimethylbicyclo[2.2.1]-heptan-2-yl)benzamide | 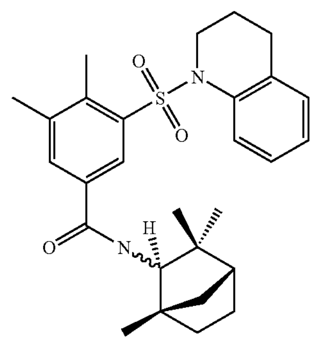 | 481 |
| 49 | N-Adamantan-2-yl-3,4-dimethyl-5-(octahydro-quinoline-1-sulfonyl)-benzamide | 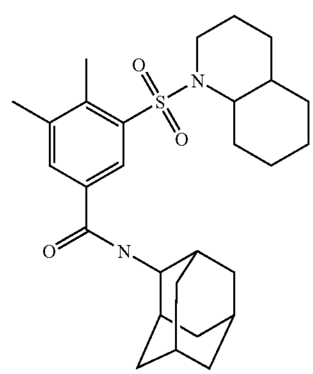 | 485 |
| 50 | N-(1-Adamantan-1-yl-ethyl)-3,4-dimethyl-5-(octahydro-quinoline-1-sulfonyl)-benzamide | 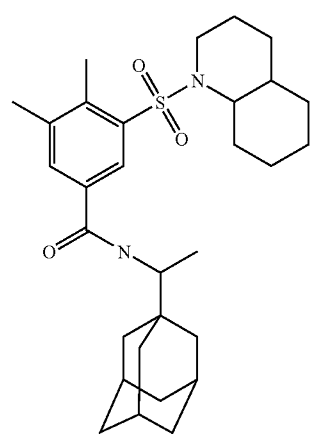 | 513 |
| 51 | 3,4-dimethyl-5-(octahydroquinolin-1(2H)-yl-sulfonyl)-N-((1S,4R)-1,3,3-trimethylbicyclo-[2.2.1]heptan-2-yl)benzamide | 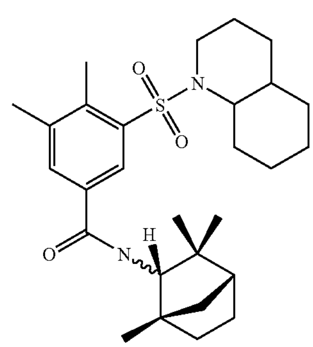 | 487 |

TABLE 5-continued

Examples 1–103 claimed in the present application

| Example | Name | Structure | M + 1 |
|---------|------|-----------|-------|
| 52 | N-Adamantan-2-yl-3-(2,6-di-methyl-morpholine-4-sulfonyl)-4-methyl-benzamide | 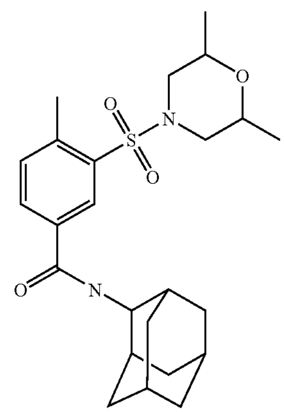 | 447 |
| 53 | N-(1-Adamantan-1-yl-ethyl)-3-(2,6-dimethyl-morpholine-4-sulfonyl)-4-methyl-benzamide | 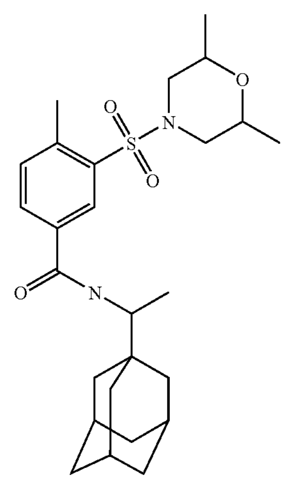 | 475 |
| 54 | 3-(2,6-dimethylmorpholino-sulfonyl)-4-methyl-N-((1S,4R)-1,3,3-trimethyl-bicyclo[2.2.1]heptan-2-yl)benzamide | 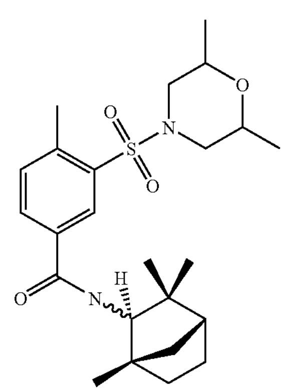 | 449 |

TABLE 5-continued

Examples 1–103 claimed in the present application

| Example | Name | Structure | M + 1 |
|---------|------|-----------|-------|
| 55 | N-Adamantan-2-yl-3-(2,6-dimethyl-morpholine-4-sulfonyl)-4,5-dimethyl-benzamide | 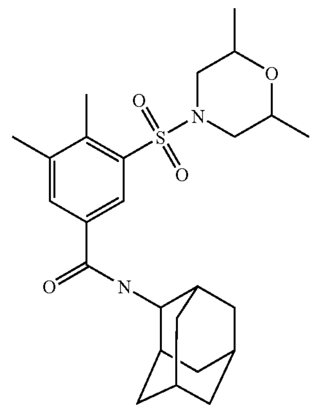 | 461 |
| 56 | N-(1-Adamantan-1-yl-ethyl)-3-(2,6-dimethyl-morpholine-4-sulfonyl)-4,5-dimethyl-benzamide | 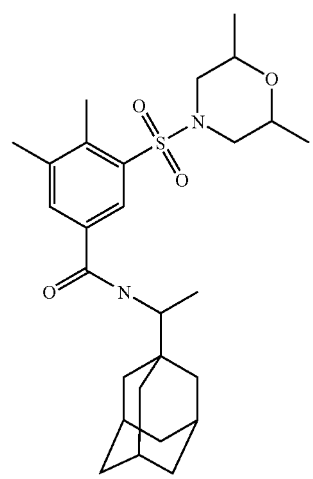 | 489 |
| 57 | 3-(2,6-dimethylmorpholino-sulfonyl)-4,5-dimethyl-N-((1S,4R)-1,3,3-trimethyl-bicyclo-[2.2.1]heptan-2-yl)benzamide | 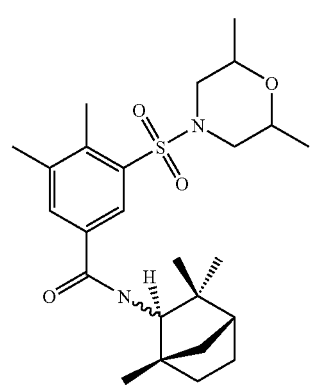 | 463 |

TABLE 5-continued

Examples 1–103 claimed in the present application

| Example | Name | Structure | M + 1 |
|---|---|---|---|
| 58 | N-Adamantan-2-yl-5-(benzyl-methyl-sulfamoyl)-2-chloro-4-fluoro-benzamide | 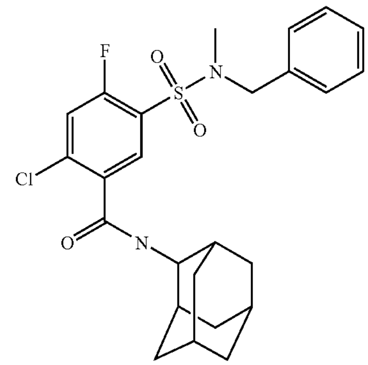 | 492 |
| 59 | N-(1-Adamantan-1-yl-ethyl)-5-(benzyl-methyl-sulfamoyl)-2-chloro-4-fluoro-benzamide | 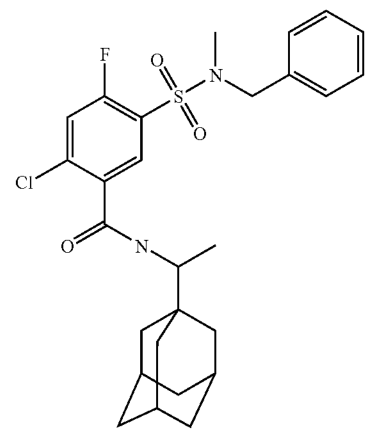 | 520 |
| 60 | 5-(N-benzyl-N-methyl-sulfamoyl)-2-chloro-4-fluoro-N-((1S,4R)-1,3,3-trimethylbicyclo[2.2.1]-heptan-2-yl)benzamide | 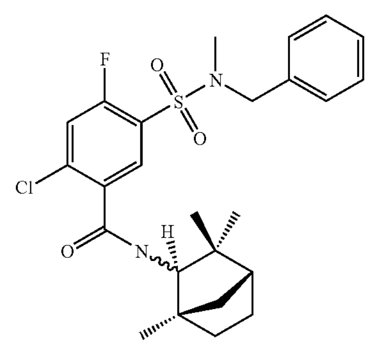 | 494 |
| 61 | 3,4-dimethyl-5-(morpholinosulfonyl)-N-((1S,4R)-1,3,3-trimethylbicyclo-[2.2.1]heptan-2-yl)benzamide | 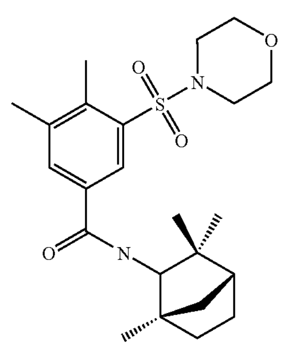 | 435 |

TABLE 5-continued

Examples 1–103 claimed in the present application

| Example | Name | Structure | M + 1 |
|---------|------|-----------|-------|
| 62 | N-(((1S,2R,5S)-6,6-dimethylbicyclo[3.1.1]-heptan-2-yl)methyl)-3,4-dimethyl-5-(morpholinosulfonyl)benzamide | 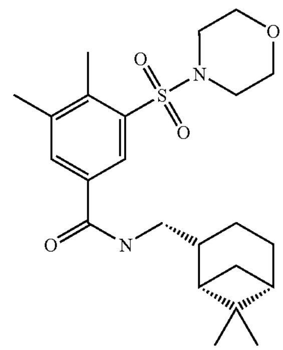 | 435 |
| 63 | N-(1-Adamantan-1-yl-ethyl)-5-(morpholinosulfamoyl)-4,5-dimethyl-benzamide | 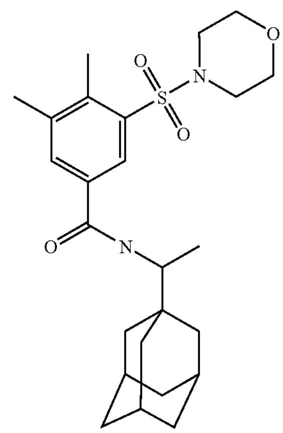 | 461 |
| 64 | 3-(N-benzyl-N-methyl-sulfamoyl)-4,5-dimethyl-N-((1S,4R)-1,3,3-trimethylbicyclo[2.2.1]-heptan-2-yl)benzamide | 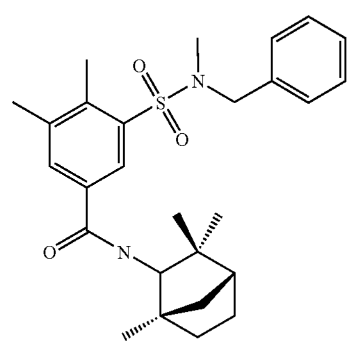 | 469 |
| 65 | 3-(N-benzyl-N-methylsulfamoyl)-N-(((1S,2R,5S)-6,6-dimethylbicyclo[3.1.1]-heptan-2-yl)methyl)-4,5-dimethylbenzamide | 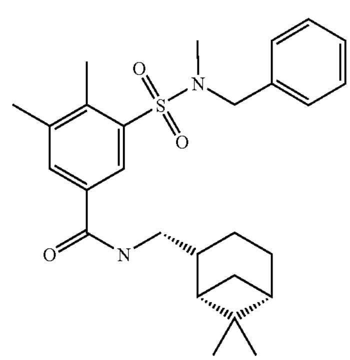 | 469 |

TABLE 5-continued

Examples 1–103 claimed in the present application

| Example | Name | Structure | M + 1 |
|---------|------|-----------|-------|
| 66 | N-(1-Adamantan-1-yl-ethyl)-5-(benzyl-methyl-sulfamoyl)-4,5-dimethyl-benzamide | 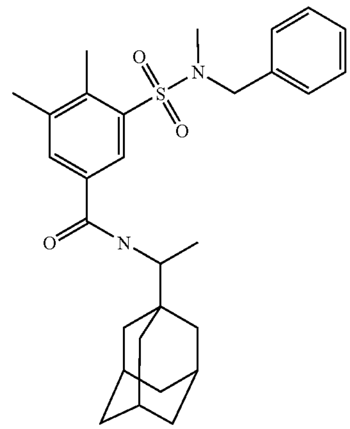 | 511 |
| 67 | 1-(2,3-dimethyl-5-(((1S,4R)-1,3,3-tri-methylbicyclo-[2.2.1]heptan-2-ylcarbamoyl)phenyl-sulfonyl)-N,N-di-ethylpiperidine-3-carboxamide | 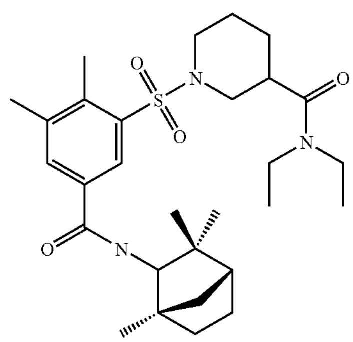 | 532 |
| 68 | 3-(azetidin-1-ylsulfonyl)-4-methyl-N-((1S,4R)-1,3,3-tri-methylbicyclo[2.2.1]-heptan-2-yl)benzamide | 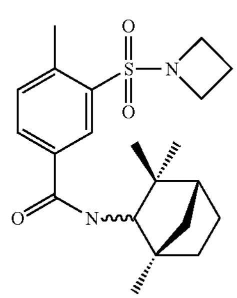 | 391 |
| 69 | 3-((S)-3-hydroxypyrrolidin-1-yl-sulfonyl)-4-methyl-N-((1S,4R)-1,3,3-tri-methylbicyclo[2.2.1]heptan-2-yl)benzamide | 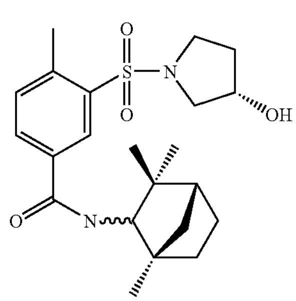 | 421 |

TABLE 5-continued

Examples 1–103 claimed in the present application

| Example | Name | Structure | M + 1 |
|---------|------|-----------|-------|
| 70 | 3-((R)-3-hydroxypyrrolidin-1-yl-sulfonyl)-4-methyl-N-((1S,4R)-1,3,3-tri-methylbicyclo[2.2.1]-heptan-2-yl)benzamide | 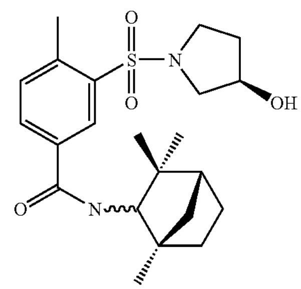 | 421 |
| 71 | 3-(4-hydroxypiperidin-1-yl-sulfonyl)-4-methyl-N-((1S,4R)-1,3,3-tri-methylbicyclo[2.2.1]-heptan-2-yl)benzamide | 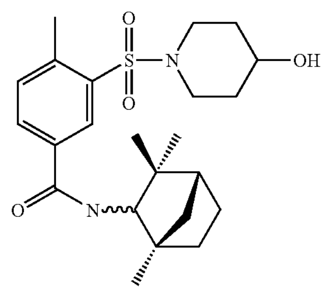 | 435 |
| 72 | N,N-diethyl-1-(2-methyl-5-((1S,4R)-1,3,3-tri-methyl-bicyclo[2.2.1]heptan-2-yl-carbamoyl)-phenyl-sulfonyl)-piperidine-3-carboxamide | 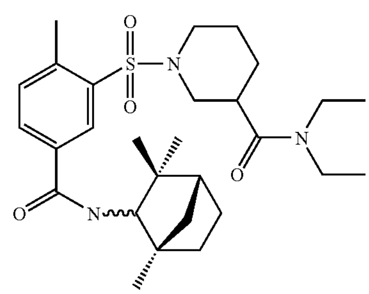 | 518 |
| 73 | 3-(N-(2-methoxyethyl)-N-methylsulfamoyl)-4-methyl-N-((1S,4R)-1,3,3-tri-methyl-bicyclo[2.2.1]heptan-2-yl)-benzamide | 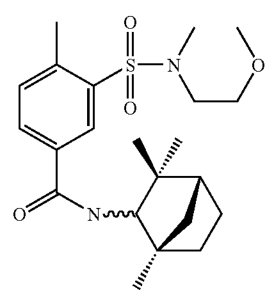 | 423 |
| 74 | N,N-diethyl-1-(2-methyl-5-((1S,4R)-1,3,3-tri-methyl-bicyclo[2.2.1]heptan-2-ylcarbamoyl)phenyl-sulfonyl)pyrrolidine-3-carboxamide | 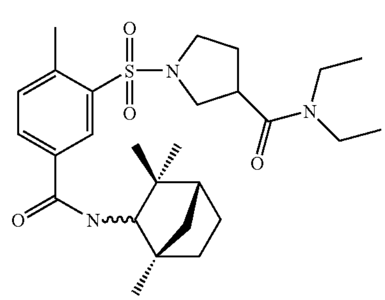 | 504 |

TABLE 5-continued

Examples 1–103 claimed in the present application

| Example | Name | Structure | M + 1 |
|---------|------|-----------|-------|
| 75 | N-(1-Adamantan-1-yl-methyl)-3-(morpholino-sulfamoyl)-4-methyl-benzamide | 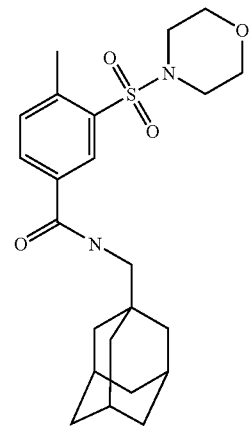 | 433 |
| 76 | 4-methyl-3-(morpholino-sulfonyl)-N(3,3,5trimethyl-cyclohexyl)benzamide | 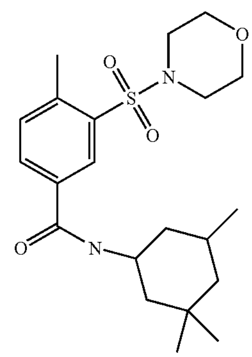 | 409 |
| 77 | 4-methyl-3-(morpholino-sulfonyl)-N-((1R,2R,3R,5S)-2,6,6-tri-methylbicyclo-[3.1.1]-heptan-3-yl)benzamide | 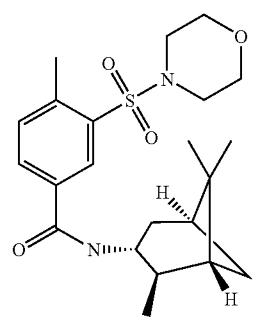 | 421 |
| 78 | 4-methyl-3-(morpholino-sulfonyl)-N-((1S,2S,3S,5R)-2,6,6-tri-methylbicyclo-[3.1.1]heptan-3-yl)benzamide | 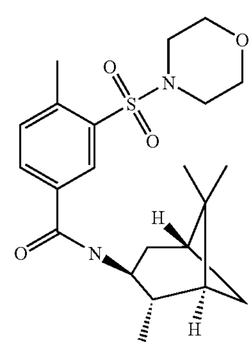 | 421 |

TABLE 5-continued

Examples 1–103 claimed in the present application

| Example | Name | Structure | M + 1 |
|---|---|---|---|
| 79 | N-(3,3-dimethylbutan-2-yl)-4-methyl-3-(morpholinosulfonyl)benzamide | 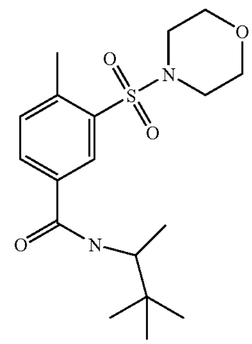 | 369 |
| 80 | N-(4-hydroxy-3,3-dimethylbutan-2-yl)-4-methyl-3-(morpholinosulfonyl)benzamide | 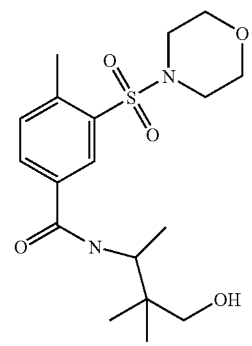 | 371 |
| 81 | N,N-diisopropyl-4-methyl-3-(morpholinosulfonyl)-benzamide | 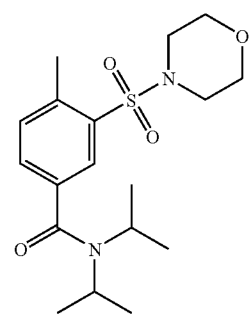 | 369 |
| 82 | 4-Ethyl-3-(morpholine-4-sulphonyl)-N,S-(1,3,3-trimethyl-bicyclo[2.2.1]-hept-2-yl)-benzamide | 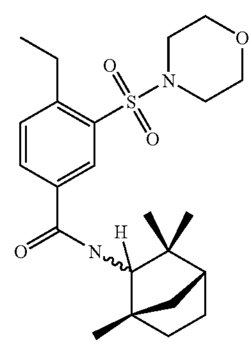 | 432 |

TABLE 5-continued

Examples 1–103 claimed in the present application

| Example | Name | Structure | M + 1 |
|---|---|---|---|
| 83 | 4-Isopropyl-3-(morpholine-4-sulfonyl)-N,S-(1,3,3-trimethyl-bicyclo[2.2.1]-hept-2-yl)-benzamide | 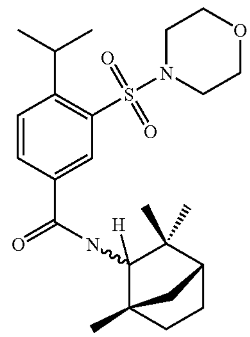 | 449 |
| 84 | 4-Propyl-3-(morpholine-4-sulfonyl)-N,S-(1,3,3-trimethyl-bicyclo[2.2.1]-hept-2-yl)-benzamide | 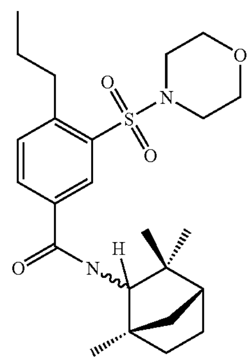 | 449 |
| 85 | 4-(3-Methoxy-propyl)-3-(morpholine-4-sulfonyl)-N-((1S,4R)-1,3,3-trimethyl-bicyclo[2.2.1]hept-2-yl)-benzamide | 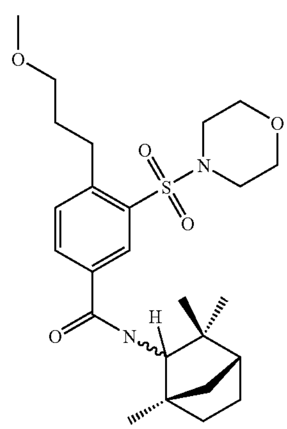 | 479 |
| 86 | 5-Methyl-3-(morpholine-4-sulfonyl)-N-((1S,4R)-1,3,3-trimethyl-bicyclo[2.2.1]-hept-2-yl)-benzamide | 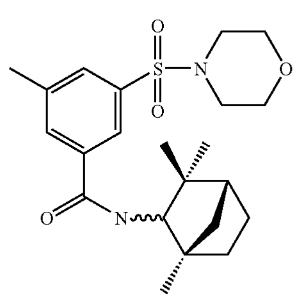 | 421 |

TABLE 5-continued

Examples 1–103 claimed in the present application

| Example | Name | Structure | M + 1 |
|---|---|---|---|
| 87 | 4,6-Dimethyl-3-(morpholine-4-sulfonyl)-N-((1S,4R)-1,3,3-trimethyl-bicyclo-[2.2.1]hept-2-yl)-benzamide | 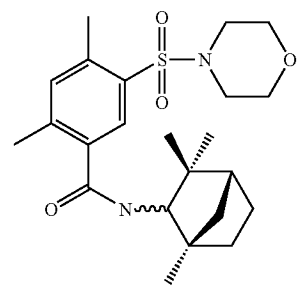 | 435 |
| 88 | 3-Dimethylsulfamoyl-4-bromo-N-((1S,4R)-1,3,3-trimethyl-bicyclo[2.2.1]-hept-2-yl)-benzamide | 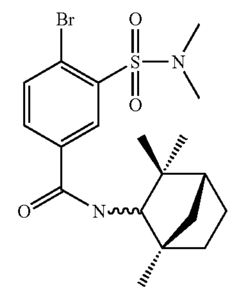 | 444 |
| 89 | 4-Bromo-3-methylsulfamoyl-N-((1S,4R)-1,3,3-trimethyl-bicyclo[2,2,1]-hept-2-yl)-benzamide | 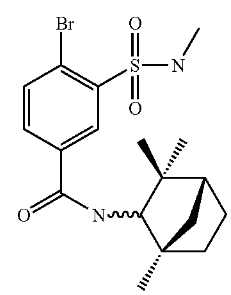 | 430 |
| 90 | 4-Bromo-N-phenyl-sulfamoyl-N-((1S,4R)-1,3,3-trimethyl-bicyclo[2,2,1]-hept-2-yl)-benzamide | 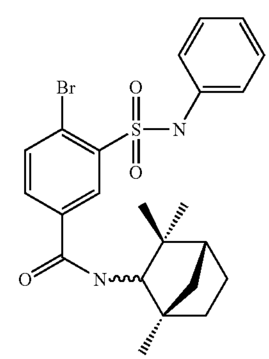 | 492 |
| 91 | 4-bromo-3-(morpholinosulfonyl)-N-((1S,4R)-1,3,3-trimethylbicyclo[2.2.1]-heptan-2-yl)benzamide | 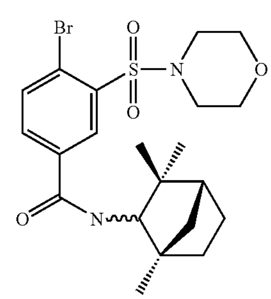 | 486 |

TABLE 5-continued

Examples 1–103 claimed in the present application

| Example | Name | Structure | M + 1 |
|---------|------|-----------|-------|
| 92 | 4-bromo-3-(3-fluoro-piperidin-1-ylsulfonyl)-N-((1S,4R)-1,3,3-trimethyl-bicyclo[2.2.1]heptan-2-yl)benzamide | 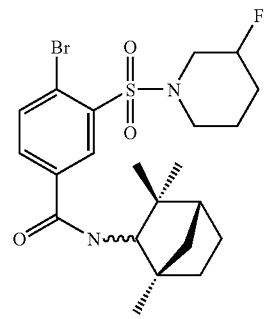 | 502 |
| 93 | 4-bromo-3-(pyrrolidin-1-yl-sulfonyl)-N-((1S,4R)-1,3,3-tri-methyl-bicyclo-[2.2.1]-heptan-2-yl)benzamide | 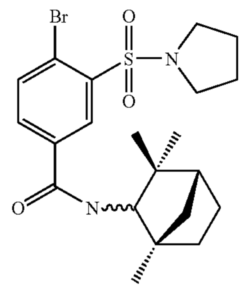 | 470 |
| 94 | 4-bromo-3-(3,5-dimethyl-piperidin-1-ylsulfonyl)-N-((1S,4R)-1,3,3-tri-methyl-bicyclo[2.2.1]heptan-2-yl)benzamide | 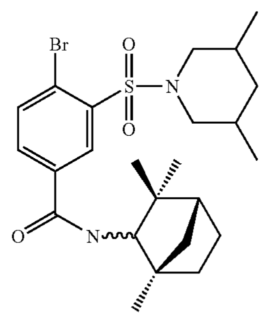 | 512 |
| 95 | 4-bromo-3-(2,6-dimethyl-morpholinosulfonyl)-N-((1S,4R)-1,3,3-trimethyl-bicyclo[2.2.1]heptan-2-yl)benzamide | 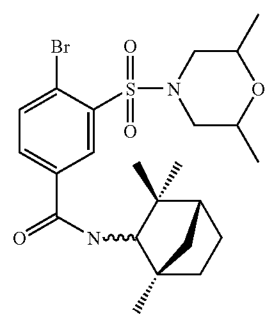 | 514 |
| 96 | ethyl 1-(2-bromo-5-((1S,4R)-1,3,3-trimethyl-bicyclo[2.2.1]heptan-2-yl-carbamoyl)phenyl-sulfonyl)-piperidine-3-carboxylate | 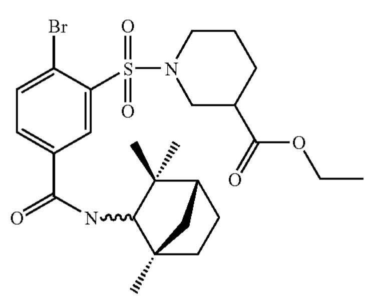 | 556 |

TABLE 5-continued

Examples 1–103 claimed in the present application

| Example | Name | Structure | M + 1 |
|---------|------|-----------|-------|
| 97 | 4-bromo-N-(((1S,2R,5S)-6,6-dimethylbicyclo-[3.1.1]-heptan-2-yl)methyl)-3-(N-(((1R,3S,5S)-6,6-dimethyl-bicyclo[3.1.1]heptan-3-yl)methyl)sulfamoyl)benzamide | 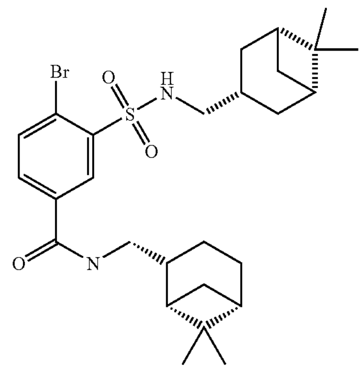 | 552 |
| 98 | 4-Bromo-3-(morpholine-4-sulfonyl)-N-(3,3-dimethylbutan-2-yl)-benzamide | 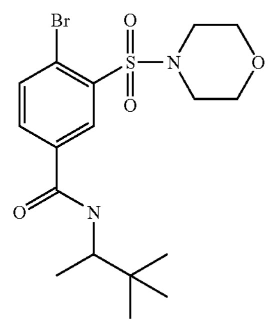 | 434 |
| 99 | 4-Bromo-3-(pyrrolidine-1-sulfonyl)-N-(3,3-dimethylbutan-2-yl)-benzamide | 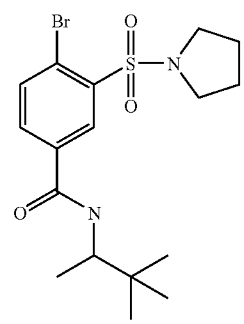 | 418 |
| 100 | 4-Bromo-3-dimethyl-sulfamoyl-N-(3,3-dimethylbutan-2-yl)-benzamide | 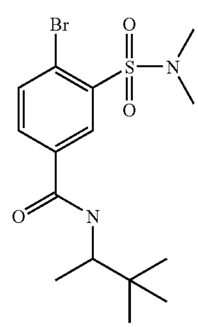 | 392 |

TABLE 5-continued

Examples 1–103 claimed in the present application

| Example | Name | Structure | M + 1 |
|---|---|---|---|
| 101 | 2-chloro-4-fluoro-5-(morpholinosulfonyl)-N-((1S,4R)-1,3,3-trimethyl-bicyclo[2.2.1]heptan-2-yl)benzamide | 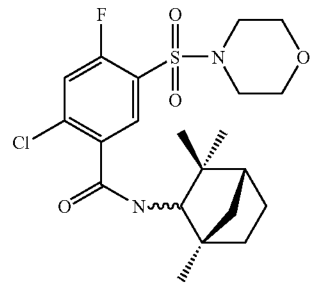 | 459 |
| 102 | N-(1-Adamantan-1-yl-ethyl)-5-(morpholino-sulfamoyl)-2-chloro-4-fluoro-benzamide | 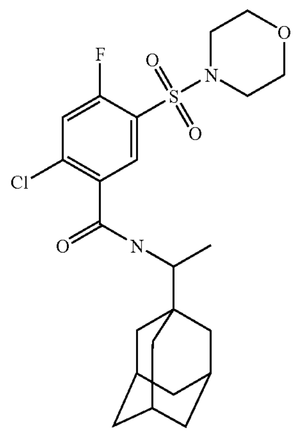 | 486 |
| 103 | N-benzyl-5-(N-benzyl-N-methyl-sulfamoyl)-2-chloro-4-fluoro-N-methyl-benzamide | 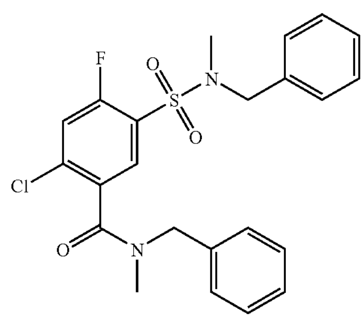 | 461 |

Biological Assays

In Vitro Methods $K_i$ values in receptor binding experiments were determined by Cheng-Prusoff correction of $IC_{50}$ values derived from automated nonlinear regression analysis of sigmoidal titration curves using a three-parameter modification (slope set to 1.0) of the four-parameter equation described in Cheng, Y.-C. and W. H. Prusoff, *Biochem. Pharmacol.* 22:3099-3108 (1973) and DeLean et al., *Am. J. Physiol.* 235:E97-E102 (1978).

$EC_{50}$ values in functional assays were also derived from automated nonlinear regression analysis of sigmoidal titration curves using the three-parameter modification of the four-parameter equation.

Preparation of Membranes for hCB1 and hCB2 Receptor Binding and Receptor-Mediated Stimulation of [$^{35}$S]GTPγS Binding Chinese hamster ovary cells (CHO-K1), stably transfected with either hCB1 or hCB2, were washed two times with cold PBS, scraped from 500 cm² tissue culture plates, and pelleted by centrifugation at 1000×g for 10 min. The supernatant was discarded and the pellet was resuspended in Tris assay buffer (50 mM Tris HCl, pH 7.8, containing 1.0 mM EGTA, 5.0 mM $MgCl_2$, 10 mg/mL leupeptin, 10 mg/mL pepstatin A, 200 mg/mL bacitracin, and 0.5 mg/mL aprotinin), homogenized with a Polytron homogenizer (Brinkmann) at a setting of 1 for 20 sec and centrifuged at 38,000×g for 20 min at 4° C. The pellet was resuspended in Tris assay buffer and aliquots of 1 mg protein/mL were stored at −80° C. for further use.

Preparation of Rat Cerebellar Membranes for Cannabinoid Receptor-Mediated Stimulation of [$^{35}$S]GTPγS Binding Rat cerebella were excised and placed into homogenization buffer (50 mM Tris HCl, pH 7.4, containing 3 mM $MgCl_2$ and 1 mM EGTA) and homogenized for 20 sec using a Polytron homogenizer at a setting of 1 and centrifuged at 4° C. for 10 min at 48,000×g. The supernatant was removed and the pellet was resuspended in homogenization buffer and centrifuged at 4° C. for 10 min at 48,000×g. The supernatant was removed and the pellets were resuspended in 50 mM Tris HCl, pH 7.4, containing 3 mM $MgCl_2$ and 0.2 mM EGTA and stored as aliquots of 1 mg protein/mL at −80° C. for further use.

Inhibition of Cb Receptor Binding by Test Compounds

Binding assays were performed by incubating 0.2-0.6 nM (34,000-100,000 dpm) [$^3$H]CP55940 with membranes prepared from cells expressing cloned human CB1 or CB2 receptors in buffer A (50 mM Tris HCl, pH 7.0, 5.0 mM $MgCl_2$, 1.0 mM EGTA and 1.0 mg/mL fatty acid free bovine serum albumin). After incubation for 60 min at room temperature for the hCB2 binding assay or 120 min at 30° C. for the hCB1 assay, the assays were filtered through GF/C filters that had been pre-soaked overnight in 0.5% (w/v) PEI and 0.1% BSA in water. The filters were rinsed 6 times with one mL of cold wash buffer (50 mM Tris HCl, pH 7.0, 5.0 mM $MgCl_2$, 1.0 mM EGTA and 0.75 mg/mL fatty acid free bovine serum albumin), 30 µL of MicroScint 20 was added to each filter and the radioactivity on the filters determined by scintillation spectroscopy. Nonspecific binding was determined in the presence of 10 µM WIN55212-2.

Cannabinoid Receptor-Mediated Stimulation of [$^{35}$S]GTPγS Binding hCB1-Mediated stimulation of [$^{35}$S]GTPγS binding was measured in a mixture containing 100-150 pM [$^{35}$S]GTPγS, 150 mM NaCl, 45 mM $MgCl_2$, 3 mM GDP, 0.4 mM DTT, 1 mM EGTA, 1 mg/mL fatty acid free BSA, 25 µg of membrane protein and agonist in a total volume of 250 µL of buffer A in 96 well Basic Flashplates (Perkin Elmer). After incubation at room temperature for 2 hours the plates were centrifuged at 800×g at 4° C. for 5 min and the radioactivity bound to the membranes was determined by scintillation spectrometry using the Topcount (Perkin Elmer).

hCB2-Mediated [$^{35}$S]GTPγS binding was measured in the same way except the assay mixture contained 10 mM GDP and the incubation time was 6 hours. [$^{35}$S]GTPγS binding in rat cerebellar homogenate was determined in a mixture containing 40-60 pM [$^{35}$S]GTPγS, homogenate assay buffer (50 mM Tris-HCl, 3 mM $MgCl_2$, 0.2 mM EGTA), 100 mM NaCl, 10 mM $MgCl_2$, 100 mM GDP, 20 µg homogenate protein/well and agonist in a total volume of 250 µL in 96 well Basic Flashplates (Perkin Elmer). After incubation at 30° C. for 2 hours, the plates were centrifuged at 800×g at 4° C. for 5 min and the radioactivity bound to the membrane was determined by scintillation spectrometry using the Topcount (Perkin Elmer).

In Vitro Results

Compounds 1-32, listed in Table 5, were tested for their affinity toward the human cloned CB1 and CB2 receptors. All ligands tested bound to the human CB1 and/or CB2 receptor with affinity ranging from 0.1-10000 nM. These ligands displayed various degrees of selectivity, CB2 vs. CB1. The functional potency of selected ligands was also evaluated in vitro. These compounds were found to exhibit agonist activity at CB1 and/or CB2 receptors. For example, compound 17 ($K_i$ (CB1)=93 nM, $K_i$ (CB2)=13.1 nM) and compound 26 ($K_i$ (CB1)=121 nM, $K_i$ (CB2)=3.7 nM) were found to possess some in vitro CB1 receptor agonist potency (17: $EC_{50}$=326 nM, 26: $EC_{50}$=2003 nM) and potent in vitro CB2 receptor agonist potency (17: $EC_{50}$=18.2 nM, 26: $EC_{50}$=7.8 nM). Some compounds were also found to exhibit antagonist activity towards the CB2 receptor. Compound 23 ($K_i$ (CB1)>1000 nM, $K_i$ (CB2)=10.3 nM) was found to possess potent in vitro CB2 receptor antagonist potency ($IC_{50}$=13.7 nM).

In Vivo Methods

Neuropathic Pain

Preparation of Animals.

Male Sprague-Dawley rats (120-250 g, Harlan Laboratories, Columbus, Ohio) were housed in pairs and allowed free access to food and water throughout the study. Room temperature and humidity were maintained at 21° C. and 70%, respectively. Nerve injury was produced with tight ligation of the left L5 spinal nerve (Kim, S. H., and J. M. Chung, *Pain,* 50, 355-363 (1992); LaBuda, C. J. and Fuchs, P. N., *Exp Neurol.,* 163, 490-494(2000); LaBuda, C. J. and Fuchs, P. N., *Neurosci Letters,* 290, 137-140(2000); LaBuda, C. J., Donahue, R., Fuchs, P. N., *Pain,* 94, 59-63, (2001)). Briefly, animals were placed in the prone position to access the left L4-L6 spinal nerves. Under magnification, approximately one third of the L6 transverse process was removed. The L5 spinal nerve was identified and carefully dissected free from the adjacent L4 spinal nerve and then tightly ligated using 6-0 silk suture. The wound was treated with an antiseptic solution, the muscle layer was sutured, and the wound was closed with wound clips. Sham-operated surgical controls were prepared in the same manner, but the L5 spinal nerve was not exposed. All housing conditions and experimental procedures were performed in accordance with the ethical guidelines of the IASP and the Adolor Corporation Animal Care and Use Committee.

Behavioral Testing.

Seven to ten animals per group were used for all behavioral assays. After a 7-10 day post-surgical recovery, animals were tested for baseline sensitivity to tactile stimulation of both hindpaws. Allodynic animals were defined as animals having a threshold of less than 7.5 grams of pressure applied to the injured hindpaw. Tactile sensitivity was evaluated using von Frey monofilaments before and after treatment. Animals received a coded injection of physiological saline or test compound (0, 10 or 30 mg/kg, i.p.). Thirty minutes after treatment, tactile sensitivity was evaluated. Five to seven days later, animals were tested using a different compound. Each animal was tested three times with different compounds. All behavioral testing was performed between 9:00 AM and 5:00 PM in a well-illuminated room with white background noise.

Tactile Sensitivity.

Animals were placed in a Plexiglas chamber (20 cm×10.5 cm×40.5 cm) and habituated for 15 minutes. The chamber was positioned on top of a mesh screen so that von Frey monofilaments could be presented to the plantar surfaces of both hindpaws. Measurements of tactile sensitivity for each hindpaw were obtained using the up/down method (Dixon, W. J., *Annu Rev Pharmacol Toxicol* 20, 441-462, 1980) with seven von Frey monofilaments (0.04, 0.07, 0.16, 0.4, 1, 6, and 15 grams). Each trial started with a von Frey force of 0.4 g delivered to the right hindpaw and then the left hindpaw for approximately 1-2 sec each. If there was no withdrawal response, the next higher force was delivered. If there was a response, the next lower force was delivered. This procedure was performed until no response was made at the highest force (15 grams) or until four stimuli were administered following the initial response. The 50% paw withdrawal threshold for each paw was calculated using the following formula: [Xth]log=[vFr]log+ky where [vFr] is the force of the last von Frey filament used, k=0.2249 which is the average interval (in log units) between the von Frey monofilaments, and y is a value that depends upon the pattern of withdrawal responses (Dixon, Id.). If an animal did not respond to the highest von Frey hair (15 g), then the paw was assigned a value of 18.23 g. Testing for tactile sensitivity was performed twice and the mean 50% withdrawal value assigned as the tactile sensitivity for the right and left paws for each animal.

Statistical Analysis.

Tactile sensitivity for both hindpaws before and after treatments were analyzed using one-way analysis of variance (ANOVA) followed by post-hoc comparisons (protected t-test) for group differences. An alpha level of 0.05 was used for all analyses.

TABLE A

Results of Neuropathic Pain Assay with compound 26, WIN and AM1241. Compound 26 reversed L5 SNL-induced tactile allodynia. (n = 7–8/group).

|  | Anti-Allodynia [%] |
| --- | --- |
| Ligation | 0.04 ± 0.06 |
| Vehicle (DMSO) | 0.04 ± 0.05 |
| Compound 26 @ 1 mg/kg | 53.5 ± 14.2 |
| Compound 26 @ 3 mg/kg | 61.7 ± 13.6# |
| Compound 26 @ 6 mg/kg | 61.1 ± 12.6# |
| Compound 26 @ 10 mg/kg | 44.0 ± 16.2 |
| WIN @ 2.5 mg/kg | 75.2 ± 13.8 |
| AM1241 @ 3 mg/kg | 27.5 ± 10.1 |

= $p < 0.05$ compared to vehicle-treated, L5 SNL animals.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound of formula I':

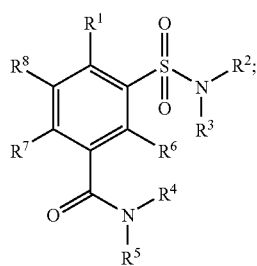

I' wherein:

$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

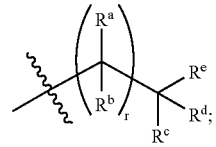

$R^a$, $R^b$, and $R^c$ are each independently H or alkyl;

$R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:

(1) when $R^d$ and $R^e$ taken together with the carbon atom to which they are attached form a monocyclic carbocyclic ring, then $R^c$ is alkyl; and (2) when $R^5$ is:

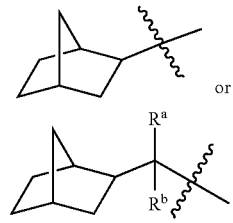

then $R^2$ and $R^3$ are taken together with the nitrogen atom to which they are attached to form a 3- to 8-membered heterocycloalkyl ring;

or a pharmaceutically acceptable salt thereof.

2. A compound according to claim 1, wherein $R^1$ is alkyl, F, Cl, or Br.

3. A compound according to claim 2, wherein $R^1$ is alkyl.

4. A compound according to claim 3, wherein $R^1$ is $C_{1-6}$ alkyl.

5. A compound according to claim 4, wherein $R^1$ is $C_{1-3}$ alkyl.

6. A compound according to claim 2, wherein $R^1$ is F, Cl, or Br.

7. A compound according to claim 6, wherein $R^1$ is Br.

8. A compound according to claim 1, wherein $R^2$ and $R^3$ are each independently alkyl, cycloalkyl, cycloalkylalkyl, aryl, aralkyl, heterocycloalkyl, heterocycloalkylalkyl, heteroaryl, or heteroaralkyl, or taken together with the nitrogen atom to which they are attached, $R^2$ and $R^3$ form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—.

9. A compound according to claim 8, wherein at least one of $R^2$ and $R^3$ is independently cycloalkyl, cycloalkylalkyl, aryl, aralkyl, heterocycloalkyl, heterocycloalkylalkyl, heteroaryl, or heteroaralkyl, or taken together with the nitrogen atom to which they are attached, $R^2$ and $R^3$ form a 3- to 8-membered heterocycloalkyl ring, wherein 1 or 2 of the heterocycloalkyl ring carbon atoms independently are optionally replaced by —O—, —S—, —N($R^9$)—, —N($R^{10}$)—C(=O)—, or —C(=O)—N($R^{10}$)—.

10. A compound according to claim 9, wherein at least one of $R^2$ and $R^3$ is aralkyl.

11. A compound according to claim 10, wherein at least one of $R^2$ and $R^3$ is benzyl.

12. A compound according to claim 8, wherein $R^2$ and $R^3$, taken together with the nitrogen atom to which they are attached, form a 3- to 8-membered heterocycloalkyl ring, wherein one of the heterocycloalkyl ring carbon atoms is optionally replaced by —O—, —S—, —N($R^9$)—, —N($R^{10}$)—C(=O)—, or —C(=O)—N($R^{10}$)—.

13. A compound according to claim 12, wherein $R^2$ and $R^3$, taken together with the nitrogen atom to which they are attached, form a 3- to 8-membered heterocycloalkyl ring, wherein one of the heterocycloalkyl ring carbon atoms is replaced by —O—, —S—, —N($R^9$)—, —N($R^{10}$)—C(=O)—, or —C(=O)—N($R^{10}$)—.

14. A compound according to claim 13, wherein $R^2$ and $R^3$, taken together with the nitrogen atom to which they are attached, form a 3- to 8-membered heterocycloalkyl ring, wherein one of the heterocycloalkyl ring carbon atoms is replaced by —O—, —S—, or —N($R^9$)—.

15. A compound according to claim 1, wherein $R^4$ is H.

16. A compound according to claim 1, wherein r is 0, 1 or 2.

17. A compound according to claim 16, wherein r is 0 or 1.

18. A compound according to claim 17, wherein r is 0.

19. A compound according to claim 1, wherein $R^a$ and $R^b$ are each H.

20. A compound according to claim 19, wherein r is 1.

21. A compound according to claim 1, wherein $R^c$ is H.

22. A compound according to claim 1, wherein $R^c$ is alkyl.

23. A compound according to claim 22, wherein $R^d$ and $R^e$ taken together with the carbon atom to which they are attached form a monocyclic carbocyclic ring.

24. A compound according to claim 1, wherein $R^d$ and $R^e$, taken together with the carbon atom to which they are attached, form a 3- to 12-membered carbocyclic ring, wherein the carbocyclic ring is substituted with 0-5 groups each independently selected from $C_{1-4}$alkyl and $C_{1-4}$alkoxyl.

25. A compound according to claim 24, wherein the carbocyclic ring is bicycloalkyl or tricycloalkyl.

26. A compound according to claim 25, wherein the carbocyclic ring is bicycloalkyl.

27. A compound according to claim 26, wherein the bicycloalkyl ring is substituted with 1-3 $C_{1-4}$alkyl groups.

28. A compound according to claim 1, wherein $R^5$ is:

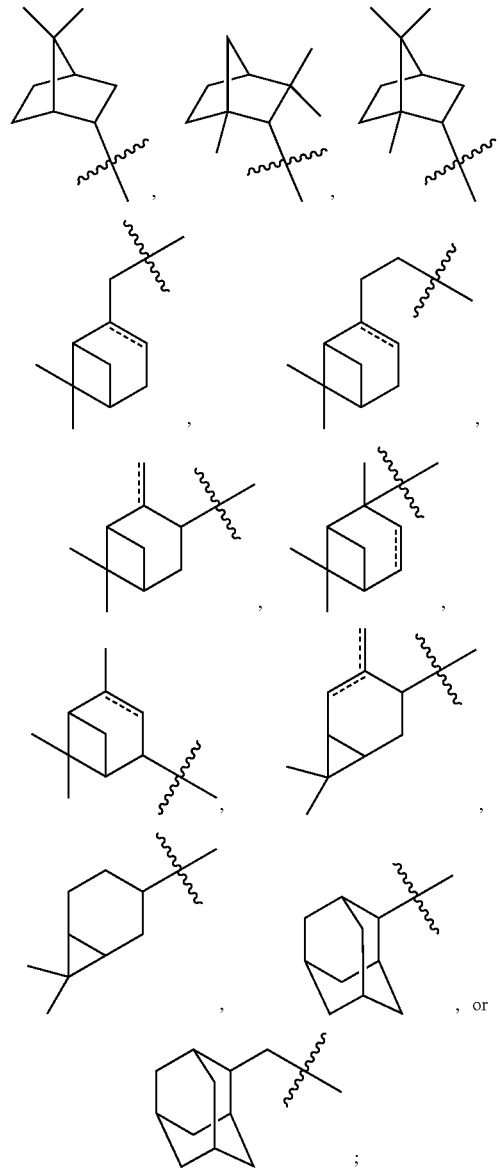

or an enantiomeric or diastereomeric form thereof;

wherein:

======represents a single or double bond between the two bonded carbon atom termini.

29. A compound according to claim 1, wherein $R^6$ and $R^7$ are each independently H, F, Cl, or Br.

30. A compound according to claim 29, wherein $R^6$ and $R^7$ are each H.

31. A compound according to claim 1, wherein when $R^6$, $R^7$, or $R^8$ is alkyl, said alkyl is independently substituted with one or more fluorine atoms.

32. A compound according to claim 31, wherein when $R^6$, $R^7$, or $R^8$ is alkyl, said alkyl is perfluorinated.

33. A compound according to claim 1, wherein $R^8$ is H.

34. A compound according to claim 1 wherein $R^{11}$ is alkyl.

35. A compound according to claim 1 of formula II:

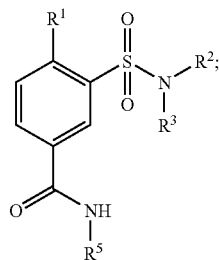

wherein:
R¹ is H, alkyl, aryl, F, Cl, or Br;
R² and R³ are each independently alkyl or aralkyl, or R² and R³, when taken together with the nitrogen atom to which they are attached, form a 5- or 6-membered heterocycloalkyl ring, wherein one of the ring carbon atoms may be optionally replaced by —O— or —N(R⁹)—; and
R⁹ is —C(═O)—O-alkyl, —CH₂—C(═O)—O-alkyl, —SO₂-alkyl, or —C(═O)N(H)-alkyl;
or a pharmaceutically acceptable salt thereof.

36. A compound according to claim 35, wherein:
R² and R³ are each independently alkyl or aralkyl, or R² and R³, when taken together with the nitrogen atom to which they are attached, form a 5- or 6-membered heterocycloalkyl ring, wherein one of the heterocycloalkyl ring carbon atoms is replaced by —O—.

37. A compound according to claim 36, wherein R$^d$ and R$^e$, taken together with the carbon atom to which they are attached form a bicycloalkyl or tricycloalkyl ring.

38. A compound according to claim 37, wherein r is 0 or 1.

39. A compound according to claim 37, wherein R$^a$, R$^b$, and R$^c$ are each H.

40. A compound according to claim 1, wherein the compound is selected from the group consisting of:
  4-chloro-3-(piperidine-1-sulfonyl)-N-(1,3,3-trimethylbicyclo[2.2.1]hept-2-yl)-benzamide;
  4-bromo-N-(6,6-dimethylbicyclo[3.1.1]hept-2-ylmethyl)-3-(piperidine-1-sulfonyl)-benzamide;
  3-(N-benzyl-N-methylsulfamoyl)-4-bromo-N-(6,6-dimethylbicyclo[3.1.1]hept-2-yl-methyl)-benzamide;
  4-bromo-3-(piperidine-1-sulfonyl)-N-(1,3,3-trimethylbicyclo[2.2.1]hept-2-yl)-benzamide;
  4-isopropyl-3-(piperidine-1-sulfonyl)-N-(1,3,3-trimethyl-bicyclo[2.2.1]-hept-2-yl)-benzamide;
  3-(piperidine-1-sulfonyl)-N,S-(1,3,3-trimethylbicyclo[2.2.1]hept-2-yl)-benzamide;
  3-(piperidine-1-sulfonyl)-N,R-(1,3,3-trimethylbicyclo[2.2.1]hept-2-yl)-benzamide;
  3-(N-benzyl-N-methylsulfamoyl)-4-bromo-N-(1,3,3-trimethylbicyclo[2.2.1]hept-2-yl)-benzamide;
  4-[2-methyl-5-(1,3,3-trimethylbicyclo[2.2.1]hept-2-ylcarbamoyl)-benzenesulfonyl]-piperazine-1-carboxylic acid tert-butyl ester;
  4-methyl-3-(morpholine-4-sulfonyl)-N,S-(1,3,3-trimethylbicyclo[2.2.1]-hept-2-yl)-benzamide;
  4-methyl-3-(morpholine-4-sulfonyl)-N,R-(1,3,3-trimethylbicyclo[2.2.1]-hept-2-yl)-benzamide;
  2-(piperidine-1-sulfonyl)-biphenyl-4-carboxylic acid (1,3,3-trimethylbicyclo[2.2.1]hept-2-yl)-amide;
  {4-[2-methyl-5-(1,3,3-trimethyl-bicyclo[2.2.1]hept-2-yl-carbamoyl)-benzene-sulfonyl]-piperazin-1-yl}-acetic acid methyl ester;
  4-[2-methyl-5-(1,3,3-trimethylbicyclo[2.2.1]hept-2ylcarbamoyl)-benzenesulfonyl]-piperazine-1-carboxylic acid ethylamide;
  4-methyl-3-(piperidine-1-sulfonyl)-N-(1,3,3-trimethyl-bicyclo[2.2.1]hept-2-yl)-benzamide;
  3-(4-acetyl-piperazine-1-sulfonyl)-4-bromo-N-(1,3,3-trimethylbicyclo[2.2.1]-hept-2-yl)-benzamide;
  3-(4-methanesulfonyl-piperazine-1-sulfonyl)-4-methyl-N-(1,3,3-trimethylbicyclo[2.2.1]-hept-2-yl)-benzamide;
  4-methyl-3-(piperazine-1-sulfonyl)-N-(1,3,3-trimethylbicyclo-[2.2.1]hept-2-yl)-benzamide; and
  a pharmaceutically acceptable salt thereof.

41. A compound according to claim 1, wherein the compound is selected from the group consisting of:
  4-chloro-3-(piperidine-1-sulfonyl)-N-(1,3,3-trimethylbicyclo[2.2.1]hept-2-yl)-benzamide;
  4-bromo-N-(6,6-dimethylbicyclo[3.1.1]hept-2-ylmethyl)-3-(piperidine-1-sulfonyl)-benzamide;
  3-(N-benzyl-N-methylsulfamoyl)-4-bromo-N-(6,6-dimethylbicyclo[3.1.1]hept-2-yl-methyl)-benzamide;
  4-bromo-3-(piperidine-1-sulfonyl)-N-(1,3,3-trimethylbicyclo[2.2.1]hept-2-yl)-benzamide;
  4-isopropyl-3-(piperidine-1-sulfonyl)-N-(1,3,3-trimethyl-bicyclo[2.2.1]-hept-2-yl)-benzamide;
  3-(piperidine-1-sulfonyl)-N,S-(1,3,3-trimethylbicyclo[2.2.1]hept-2-yl)-benzamide;
  3-(piperidine-1-sulfonyl)-N,R-(1,3,3-trimethylbicyclo[2.2.1]hept-2-yl)-benzamide;
  3-(N-benzyl-N-methylsulfamoyl)-4-bromo-N-(1,3,3-trimethylbicyclo[2.2.1]hept-2-yl)-benzamide;
  4-[2-methyl-5-(1,3,3-trimethylbicyclo[2.2.1]hept-2-yl-carbamoyl)-benzenesulfonyl]-piperazine-1-carboxylic acid tert-butyl ester;
  4-methyl-3-(morpholine-4-sulfonyl)-N,S-(1,3,3-trimethylbicyclo[2.2.1]-hept-2-yl)-benzamide;
  4-methyl-3-(morpholine-4-sulfonyl)-N,R-(1,3,3-trimethylbicyclo[2.2.1]-hept-2-yl)-benzamide;
  2-(piperidine-1-sulfonyl)-biphenyl-4-carboxylic acid (1,3,3-trimethylbicyclo[2.2.1]hept-2-yl)-amide;
  {4-[2-methyl-5-(1,3,3-trimethylbicyclo[2.2.1]hept-2-yl-carbamoyl)-benzene-sulfonyl]-piperazin-1-yl}-acetic acid methyl ester;
  4-[2-methyl-5-(1,3,3-trimethylbicyclo[2.2.1]hept-2ylcarbamoyl)-benzenesulfonyl]-piperazine-1-carboxylic acid ethylamide;
  3-(4-methanesulfonyl-piperazine-1-sulfonyl)-4-methyl-N-(1,3,3-trimethylbicyclo[2.2.1]-hept-2-yl)-benzamide; and
  a pharmaceutically acceptable salt thereof.

42. A compound selected from the group consisting of:
  4-bromo-N-(2,2-dimethylpropyl)-3-(piperidine-1-sulfonyl)-benzamide;
  3-(N-benzyl-N-methylsulfamoyl)-4-bromo-N-(2,2-dimethylpropyl)-benzamide;
  3-(N-benzyl-N-methylsulfamoyl)-4-bromo-N-isobutyl-benzamide;
  4-chloro-N-(2,2-dimethylpropyl)-3-(piperidine-1-sulfonyl)-benzamide;
  N-(2,2-dimethylpropyl)-4-methyl-3-(piperidine-1-sulfonyl)-benzamide;
  4-bromo-N-(2,2-dimethylpropyl)-3-(pyrrolidine-1-sulfonyl)-benzamide; and
  a pharmaceutically acceptable salt thereof.

43. A compound according to claim 1, wherein the compound is selected from the group consisting of:
- 4-chloro-3-(piperidine-1-sulfonyl)-N-(1,3,3-trimethylbicyclo[2.2.1]hept-2-yl)-benzamide;
- 3-(benzyl-methyl-sulfamoyl)-4-bromo-N-(6,6-dimethyl-bicyclo[3.1.1]hept-2-yl-methyl)-benzamide;
- 4-bromo-3-(piperidine-1-sulfonyl)-N-(1,3,3-trimethylbicyclo[2.2.1]hept-2-yl)-benzamide;
- 4-isopropyl-3-(piperidine-1-sulfonyl)-N-(1,3,3-trimethyl-bicyclo[2.2.1]-hept-2-yl)-benzamide;
- 4-methyl-3-(piperidine-1-sulfonyl)-N,R-(1,3,3-trimethyl-bicyclo[2.2.1]-hept-2-yl)-benzamide;
- 3-(piperidine-1-sulfonyl)-N-(1,3,3-trimethylbicyclo[2.2.1]hept-2-yl)-benzamide;
- 3-(benzyl-methyl-sulfamoyl)-4-bromo-N-(1,3,3-trimethylbicyclo[2.2.1]hept-2-yl)-benzamide;
- 4-methyl-3-(morpholine-4-sulfonyl)-N,S-(1,3,3-trimethylbicyclo[2.2.1]-hept-2-yl)-benzamide;
- 4-methyl-3-(morpholine-4-sulfonyl)-N,R-(1,3,3-trimethylbicyclo[2.2.1]-hept-2-yl)-benzamide;
- 2-(piperidine-1-sulfonyl)-biphenyl-4-carboxylic acid (1,3,3-trimethylbicyclo[2.2.1]hept-2-yl)-amide; and
- a pharmaceutically acceptable salt thereof.

44. A compound according to claim 1, wherein the compound is selected from the group consisting of:
- 4-chloro-3-(piperidine-1-sulfonyl)-N-(1,3,3-trimethylbicyclo[2.2.1]hept-2-yl)-benzamide;
- 3-(benzyl-methyl-sulfamoyl)-4-bromo-N-(6,6-dimethyl-bicyclo[3.1.1]hept-2-yl-methyl)-benzamide;
- 4-bromo-3-(piperidine-1-sulfonyl)-N-(1,3,3-trimethylbicyclo[2.2.1]hept-2-yl)-benzamide;
- 3-(benzyl-methyl-sulfamoyl)-4-bromo-N-(1,3,3-trimethylbicyclo[2.2.1]hept-2-yl)-benzamide;
- 4-methyl-3-(morpholine-4-sulfonyl)-N,S-(1,3,3-trimethylbicyclo[2.2.1]-hept-2-yl)-benzamide; and
- a pharmaceutically acceptable salt thereof.

45. A compound of formula III:

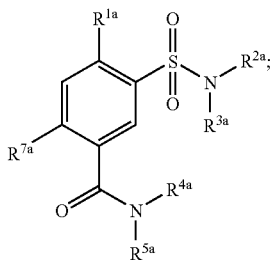

wherein:
$R^{1a}$ is F or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H or chloro;
provided that:
the compound of formula III is other than N-benzyl-4-bromo-3-(morpholine-4-sulfonyl)-benzamide, N-benzyl-4-bromo-3-(piperidine-1-sulfonyl)-benzamide, N-benzyl-4-fluoro-N-methyl-3-(piperidine-1-sulfonyl)-benzamide, or N-benzyl-4-fluoro-N-methyl-3-(morpholine-4-sulfonyl)-benzamide;
or a pharmaceutically acceptable salt thereof.

46. A compound according to claim 45, wherein the compound is selected from the group consisting of:
- N-benzyl-2-chloro-4-fluoro-5-(morpholine-4-sulfonyl)-benzamide;
- 3-(N-benzyl-N-methylsulfamoyl)-4-bromo-N-pyridin-3-yl-methyl-benzamide;
- 4-bromo-N-(3-methoxybenzyl)-3-(piperidine-1-sulfonyl)-benzamide;
- 4-bromo-N-(3-methoxybenzyl)-3-(pyrrolidine-1-sulfonyl)-benzamide;
- N-benzyl-4-bromo-3-(pyrrolidine-1-sulfonyl)-benzamide;
- N-benzyl-4-bromo-N-methyl-3-(morpholine-4-sulfonyl)-benzamide; and
- a pharmaceutically acceptable salt thereof.

47. A compound according to claim 46, wherein the compound is N-benzyl-2-chloro-4-fluoro-5-(morpholine-4-sulfonyl)-benzamide.

48. A compound according to claim 45, wherein the compound is N-benzyl-5-(N-benzyl-N-methylsulfamoyl)-2-chloro-4-fluoro-N-methylbenzamide.

49. A pharmaceutical composition, comprising:
a pharmaceutically acceptable carrier; and a compound of formula Ia:

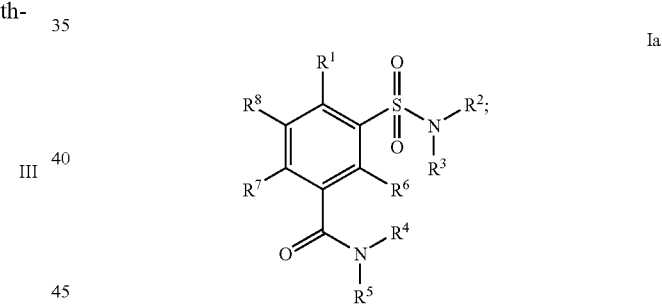

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(═O)—, or —C(═O)—N($R^{10}$)—;
$R^4$ is H or alkyl;
$R^5$ is:

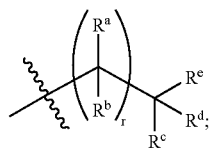

each $R^a$, $R^b$, $R^c$, $R^d$, and $R^e$ are each independently H or alkyl; or $R^d$ and $R^e$ taken together with the carbon atom to which they are attached form a carbocyclic ring;

$R^6$, $R^7$, and $R^8$ are each independently H, F, Cl, Br, or alkyl;

$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;

$R^{10}$ is H, alkyl, or aryl;

each $R^{11}$ is independently H or alkyl;

r is 0, 1, 2, or 3; and s is 1, 2, 3, or 4;

provided that:

(1) when $R^d$ and $R^e$ taken together with the carbon atom to which they are attached form a monocyclic carbocyclic ring, then $R^c$ is alkyl or the monocyclic carbocyclic ring is an alkylcycloalkyl ring;

(2) at least two of $R^c$, $R^d$, and $R^e$ are other than H; and (3) when $R^1$ is methyl or bromo, $R^2$, $R^4$, $R^6$, $R^7$, and $R^8$ are each H, and $R^3$ is methyl, then $R^5$ is other than but-2-yl, pent-2-yl, hex-2-yl, hept-2-yl, 1,1,1-dimethyleth-1-yl, 1-dimethylprop-1-yl, 1,1-dimethylbut-1-yl, or 1,1-dimethylpent-1-yl;

or a pharmaceutically acceptable salt thereof.

50. A pharmaceutical composition according to claim 49, wherein when $R^d$ and $R^e$ are taken together with the carbon atom to which they are attached to form a monocyclic carbocyclic ring, then $R^c$ is alkyl.

51. A pharmaceutical composition according to claim 49, wherein the compound of formula Ia is selected from the group consisting of:

4-bromo-N-(2,2-dimethyl-propyl)-3-(piperidine-1-sulfonyl)-benzamide;
4-chloro-3-(piperidine-1-sulfonyl)-N-(1,3,3-trimethyl-bicyclo[2.2.1]hept-2-yl)-benzamide;
3-(N-benzyl-N-methylsulfamoyl)-4-bromo-N-(2,2-dimethylpropyl)-benzamide;
4-bromo-N-(6,6-dimethyl-bicyclo[3.1.1]hept-2-yl-methyl)-3-(piperidine-1-sulfonyl)-benzamide;
3-(N-benzyl-N-methylsulfamoyl)-4-bromo-N-(6,6-dimethyl-bicyclo[3.1.1]hept-2-yl-methyl)-benzamide;
3-(N-benzyl-N-methylsulfamoyl)-4-bromo-N-isobutylbenzamide;
4-bromo-3-(piperidine-1-sulfonyl)-N-(1,3,3-tri-methylbicyclo[2.2.1]hept-2-yl)-benzamide;
4-isopropyl-3-(piperidine-1-sulfonyl)-N-(1,3,3-trimethyl-bicyclo[2.2.1]-hept-2-yl)-benzamide;
3-(piperidine-1-sulfonyl)-N,S-(1,3,3-trimethyl-bicyclo[2.2.1]hept-2-yl)-benzamide;
3-(piperidine-1-sulfonyl)-N,R-(1,3,3-trimethylbicyclo[2.2.1]hept-2-yl)-benzamide;
3-(N-benzyl-N-methylsulfamoyl)-4-bromo-N-(1,3,3-tri-methyl-bicyclo[2.2.1]hept-2-yl)-benzamide;
4-[2-methyl-5-(1,3,3-trimethyl-bicyclo[2.2.1]hept-2-yl-carbamoyl)-benzenesulfonyl]-piperazine-1-carboxylic acid tert-butyl ester;
4-methyl-3-(morpholine-4-sulfonyl)-N,S-(1,3,3-trimethyl-bicyclo[2.2.1]-hept-2-yl)-benzamide;
4-methyl-3-(morpholine-4-sulfonyl)-N,R-(1,3,3-trimethyl-bicyclo[2.2.1]-hept-2-yl)-benzamide;
2-(piperidine-1-sulfonyl)-biphenyl-4-carboxylic acid (1,3,3-trimethyl-bicyclo[2.2.1]hept-2-yl)-amide;
{4-[2-methyl-5-(1,3,3-trimethyl-bicyclo[2.2.1]hept-2-yl-carbamoyl)-benzene-sulfonyl]-piperazin-1-yl}-acetic acid methyl ester;
4-[2-methyl-5-(1,3,3-trimethyl-bicyclo[2.2.1]hept-2yl-carbamoyl)-benzenesulfonyl]-piperazine-1-carboxylic acid ethylamide;
4-chloro-N-(2,2-dimethylpropyl)-3-(piperidine-1-sulfonyl)-benzamide;
N-(2,2-dimethyl-propyl)-4-methyl-3-(piperidine-1-sulfonyl)-benzamide;
4-bromo-N-(2,2-dimethylpropyl)-3-(pyrrolidine-1-sulfonyl)-benzamide;
4-methyl-3-(piperidine-1-sulfonyl)-N-(1,3,3-trimethyl-bicyclo[2.2.1]hept-2-yl)-benzamide;
3-(4-acetyl-piperazine-1-sulfonyl)-4-bromo-N-(1,3,3-trimethyl-bicyclo[2.2.1]-hept-2-yl)-benzamide;
4-methyl-3-(piperazine-1-sulfonyl)-N-(1,3,3-trimethylbicyclo[2.2.1]hept-2-yl)-benzamide;
3-(4-methanesulfonyl-piperazine-1-sulfonyl)-4-methyl-N-(1,3,3-tri-methyl-bicyclo[2.2.1]-hept-2-yl)-benzamide; and
a pharmaceutically acceptable salt thereof.

52. A pharmaceutical composition according to claim 49, further comprising at least one cannabinoid.

53. A pharmaceutical composition according to claim 52, wherein the cannabinoid is $\Delta^9$-tetrahydrocannabinol or cannabidiol.

54. A pharmaceutical composition according to claim 49, further comprising at least one opioid.

55. A pharmaceutical composition according to claim 54, wherein said opioid is selected from the group consisting of alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil and tramadol, and mixtures thereof.

56. A pharmaceutical composition according to claim 49, further comprising at least one analgesic.

57. A pharmaceutical composition according to claim 56, wherein the analgesic is a COX2 inhibitor, aspirin, acetaminophen, ibuprophen, or naproxen, or a mixture thereof.

58. A pharmaceutical composition according to claim 49, further comprising at least one agent selected from the group consisting of an anti-seizure agent, an anti-depressant, an NMDA receptor antagonist, an ion channel antagonist, a nicotinic receptor agonist, and an anti-Parkinson's agent.

59. A pharmaceutical composition according to claim 58 wherein said anti-seizure agent is carbamazepine, gabapentin, lamotrigine, or phenyloin, or a mixture thereof.

60. A pharmaceutical composition according to claim 58 wherein said anti-depressant is amitryptiline.

61. A pharmaceutical composition according to claim 58, wherein said anti-Parkinson's agent is deprenyl, amantadine, levodopa, or carbidopa, or a mixture thereof.

62. A pharmaceutical composition, comprising:
a pharmaceutically acceptable carrier; and a compound of formula III:

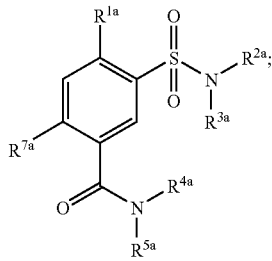

wherein:
$R^{1a}$ is F, Cl or Br;
$R^{2a}$ is methyl;
$R^{3a}$ is benzyl; or $R^{2a}$ and $R^{3a}$ when taken together with the nitrogen atom to which they are attached, form a morpholine, piperidine or pyrrolidine ring;
$R^{4a}$ is H or methyl;
$R^{5a}$ is benzyl, 3-methoxybenzyl, or pyrid-3-yl methyl; and
$R^{7a}$ is H, F, Cl or Br;
or a pharmaceutically acceptable salt thereof.

63. A pharmaceutical composition according to claim 62, wherein the compound of formula III is selected from the group consisting of:
N-benzyl-4-bromo-3-(morpholine-4-sulfonyl)-benzamide;
N-benzyl-2-chloro-4-fluoro-5-(morpholine-4-sulfonyl)-benzamide;
3-(N-benzyl-N-methylsulfamoyl)-4-bromo-N-pyridin-3-yl-methylbenzamide;
4-bromo-N-(3-methoxybenzyl)-3-(piperidine-1-sulfonyl)-benzamide;
4-bromo-N-(3-methoxybenzyl)-3-(pyrrolidine-1-sulfonyl)-benzamide;
N-benzyl-4-bromo-3-(pyrrolidine-1-sulfonyl)-benzamide;
N-benzyl-4-bromo-3-(piperidine-1-sulfonyl)-benzamide,
N-benzyl-4-bromo-N-methyl-3-(morpholine-4-sulfonyl)-benzamide; and
a pharmaceutically acceptable salt thereof.

64. A pharmaceutical composition according to claim 62, further comprising at least one cannabinoid.

65. A pharmaceutical composition according to claim 64, wherein the cannabinoid is $\Delta^9$-tetrahydrocannabinol or cannabidiol.

66. A pharmaceutical composition according to claim 62, further comprising at least one opioid.

67. A pharmaceutical composition according to claim 66, wherein said opioid is selected from the group consisting of alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil and tramadol, and mixtures thereof.

68. A pharmaceutical composition according to claim 62, further comprising at least one analgesic.

69. A pharmaceutical composition according to claim 68, wherein the analgesic is a COX2 inhibitor, aspirin, acetaminophen, ibuprophen, or naproxen, or a mixture thereof.

70. A pharmaceutical composition according to claim 62, further comprising at least one agent selected from the group consisting of an anti-seizure agent, an anti-depressant, an NMDA receptor antagonist, an ion channel antagonist, a nicotinic receptor agonist, and an anti-Parkinson's agent.

71. A pharmaceutical composition according to claim 70 wherein said anti-seizure agent is carbamazepine, gabapentin, lamotrigine, or phenyloin, or a mixture thereof.

72. A pharmaceutical composition according to claim 70 wherein said anti-depressant is amitryptiline.

73. A pharmaceutical composition according to claim 72, wherein said antiParkinson's agent is deprenyl, amantadine, levodopa, or carbidopa, or a mixture thereof.

74. A compound of formula IV:

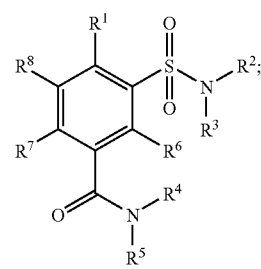

wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;
$R^4$ is H or alkyl;
$R^5$ is:

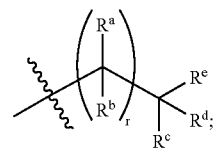

each $R^a$, $R^b$, and $R^c$, is independently H or alkyl;
$R^d$ and $R^e$ taken together with the carbon atom to which they are attached form a carbocyclic ring; or $R^c$, $R^d$, and $R^e$, taken together with the carbon atom to which they are attached, form a bicycloalkyl or tricycloalkyl ring;
$R^6$, $R^7$, and $R^8$ are each independently H, F, Cl, Br, or alkyl;
$R^9$ is H, alkyl, aryl, —C(=O)—$R^{11}$, —C(=O)—$OR^{11}$, —[C($R^{11}$)($R^{11}$)]$_s$—C(=O)—$OR^{11}$, —$SO_2R^{11}$, or —C(=O)N($R^{11}$)$R^{11}$;

$R^{10}$ is H, alkyl, or aryl;
each $R^{11}$ is independently H or alkyl;
r is 0, 1, 2, or 3; and
s is 1, 2, 3, or 4;
provided that:
(1) when $R^d$ and $R^e$ taken together with the carbon atom to which they are attached form a monocyclic carbocyclic ring, then $R^c$ is alkyl;
(2) when $R^5$ is:

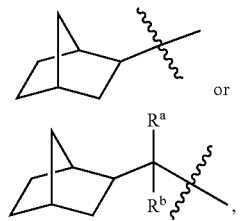

then $R^2$ and $R^3$ are taken together with the nitrogen atom to which they are attached to form a 3- to 8-membered heterocycloalkyl ring;
(3) when $R^1$ is H or Cl, $R^2$ and $R^3$ are each independently cyclohexyl, 1,5-dimethyl-2-phenyl-1,2-dihydro-pyrazol-3-on-4-yl, or substituted or unsubstituted alkyl, substituted or unsubstituted benzyl, or substituted or unsubstituted phenyl, or $R^2$ and $R^3$ taken together with the nitrogen atom to which they are attached form a 3- to 8-membered heterocycloalkyl ring, wherein 1 of the heterocycloalkyl ring carbon atoms may be optionally replaced by —O— or —N($R^9$)—, $R^6$, $R^8$, and $R^b$ are H, and $R^7$ is H or chloro, then $R^5$ is other than 1-adamantyl, adamant-1-ylmethyl, or adamant-1-yleth-1-yl; and
(4) the compound of formula IV is other than N-(2-adamantan-1-yl-ethyl)-2,4-dichloro-5-dimethylsulfamoyl-benzamide, N-(2-adamantan-1-yl-ethyl)-3-(morpholine-4-sulfonyl)-benzamide, N-adamantan-1-yl-4-methyl-3-(piperidine-1-sulfonyl)-benzamide, N-(1-adamantan-1-yl-ethyl)-4-methyl-3-(piperidine-1-sulfonyl)-benzamide, N-adamantan-1-ylmethyl-3-(ethyl-phenyl-sulfamoyl)-4-methyl-benzamide, N-adamantan-1-yl-4-bromo-3-(morpholine-4-sulfonyl)-benzamide, N-(1-adamantan-1-yl-ethyl)-4-fluoro-3-(morpholine-4-sulfonyl)-benzamide, 2,4-dichloro-N-(3,5-dimethyl-adamantan-1-yl)-5-dimethylsulfamoyl-benzamide, or N-cycloheptyl-4-methyl-3-(morpholinosulfonyl)benzamide;
or a pharmaceutically acceptable salt thereof.

75. A compound according to claim 74, wherein $R^1$ is alkyl, F, Cl, or Br.

76. A compound according to claim 75, wherein $R^1$ is alkyl.

77. A compound according to claim 76, wherein $R^1$ is $C_{1-6}$ alkyl.

78. A compound according to claim 77, wherein $R^1$ is $C_{1-3}$ alkyl.

79. A compound according to claim 75, wherein $R^1$ is F or Br.

80. A compound according to claim 79, wherein $R^1$ is Br.

81. A compound according to claim 74, wherein $R^2$ and $R^3$ are each independently alkyl, cycloalkyl, cycloalkylalkyl, aryl, aralkyl, heterocycloalkyl, heterocycloalkylalkyl, heteroaryl, or heteroaralkyl, or taken together with the nitrogen atom to which they are attached, $R^2$ and $R^3$ form a 3- to 8-membered heterocycloalkyl ring, wherein 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—.

82. A compound according to claim 81, wherein at least one of $R^2$ and $R^3$ is independently cycloalkyl, cycloalkylalkyl, aryl, aralkyl, heterocycloalkyl, heterocycloalkylalkyl, heteroaryl, or heteroaralkyl, or taken together with the nitrogen atom to which they are attached, $R^2$ and $R^3$ form a 3- to 8-membered heterocycloalkyl ring, wherein 1 or 2 of the heterocycloalkyl ring carbon atoms independently are optionally replaced by —O—, —S—, —N($R^9$)—, —N($R^{10}$)—C(=O)—, or —C(=O)—N($R^{10}$)—.

83. A compound according to claim 81, wherein at least one of $R^2$ and $R^3$ is aralkyl.

84. A compound according to claim 82, wherein at least one of $R^2$ and $R^3$ is benzyl.

85. A compound according to claim 81, wherein $R^2$ and $R^3$, taken together with the nitrogen atom to which they are attached, form a 3- to 8-membered heterocycloalkyl ring, wherein one of the heterocycloalkyl ring carbon atoms is optionally replaced by —O— or —N($R^9$)—.

86. A compound according to claim 84, wherein $R^2$ and $R^3$, taken together with the nitrogen atom to which they are attached, form a 3- to 8-membered heterocycloalkyl ring, wherein one of the heterocycloalkyl ring carbon atoms is replaced by —O— or —N($R^9$)—.

87. A compound according to claim 81, wherein $R^2$ and $R^3$, taken together with the nitrogen atom to which they are attached, form a 3- to 8-membered heterocycloalkyl ring, wherein one of the heterocycloalkyl ring carbon atoms is replaced by —O—, —S—, or —N($R^9$)—.

88. A compound according to claim 87, wherein $R^2$ and $R^3$, taken together with the nitrogen atom to which they are attached, form a 3- to 8-membered heterocycloalkyl ring which is optionally substituted with at least one substituent selected from the group consisting of alkyl, alkoxyl, halo, N,N-dialkylaminocarbonyl, alkoxycarbonyl, and hydroxyl.

89. A compound according to claim 88, wherein $R^2$ and $R^3$, taken together with the nitrogen atom to which they are attached, form morpholin-4-yl, pyrrolidin-1-yl, 1,3-dihydroisoindol-2-yl, 3,4-dihydro-2H-quinolin-1-yl, octahydroquinolin-1-yl, 2,6-dimethylmorpholin-1-yl, 3,5-dimethylpiperidin-1-yl, 2-methylpiperidin-1-yl, 4-hydroxypiperidin-1-yl, 3-N,N-diethylaminocarbonylpiperidin-1-yl, 3-fluoropiperidin-1-yl, 3-hydroxypyrrolidin-1-yl, 3-ethoxycarbonylpiperidin-1-yl, or 3-N,N-diethylaminocarbonylpyrrolidin-1-yl.

90. A compound according to claim 74, wherein $R^4$ is H.

91. A compound according to claim 74, wherein r is 0, 1 or 2.

92. A compound according to claim 91, wherein r is 0 or 1.

93. A compound according to claim 92, wherein r is 0.

94. A compound according to claim 74, wherein $R^a$ is H and $R^b$ is H or alkyl.

95. A compound according to claim 94, wherein r is 1.

96. A compound according to claim 74, wherein $R^c$ is H.

97. A compound according to claim 74, wherein $R^c$ is alkyl.

98. A compound according to claim 74, wherein $R^d$ and $R^e$ are each alkyl.

99. A compound according to claim 74, wherein $R^d$ and $R^e$, taken together with the carbon atom to which they are attached, form a 3- to 12-membered carbocyclic ring, wherein the carbocyclic ring is substituted with 0-5 groups each independently selected from $C_{1-4}$ alkyl, hydroxyl, and $C_{1-4}$ alkoxyl.

100. A compound according to claim 99, wherein the carbocyclic ring is bicycloalkyl or tricycloalkyl.

101. A compound according to claim 100, wherein the carbocyclic ring is bicycloalkyl.

102. A compound according to claim 101, wherein the bicycloalkyl ring is substituted with 1-3 alkyl groups, each selected independently.

103. A compound according to claim 74, wherein $R^5$ is:

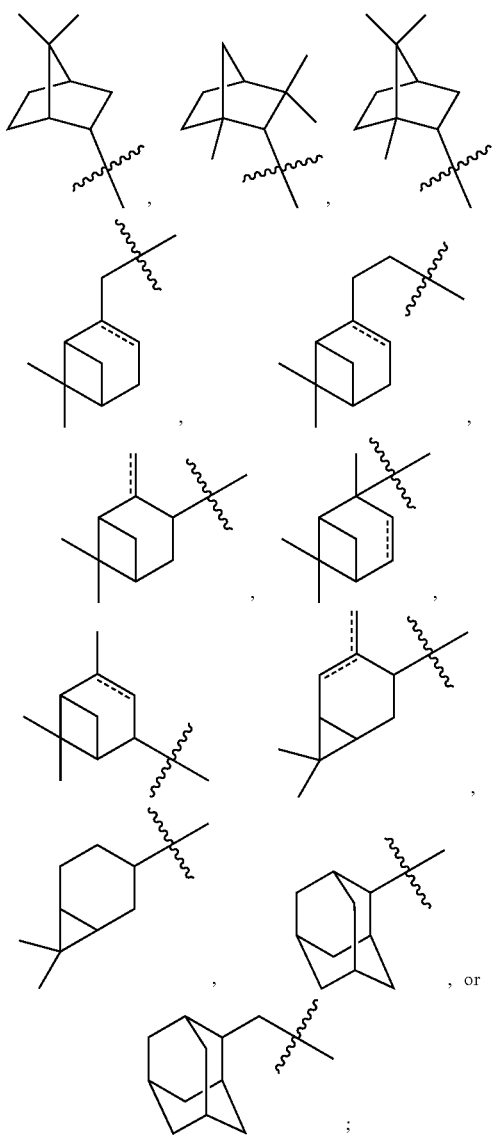

or an enantiomeric or diastereomeric form thereof;
wherein:
====== represents a single or double bond between the two bonded carbon atom termini.

104. A compound according to claim 74, wherein $R^c$, $R^d$, and $R^e$, taken together with the carbon atom to which they are attached, form a bicycloalkyl or tricycloalkyl ring.

105. A compound according to claim 104, wherein the bicycloalkyl or tricycloalkyl ring is substituted with 1-3 groups selected independently from alkyl, alkoxyl, or hydroxyl.

106. A compound according to claim 74, wherein $R^6$ and $R^7$ are each independently H, F, Cl, or Br.

107. A compound according to claim 104, wherein $R^6$ and $R^7$ are each H.

108. A compound according to claim 74, wherein $R^8$ is H.

109. A compound according to claim 74 of formula V:

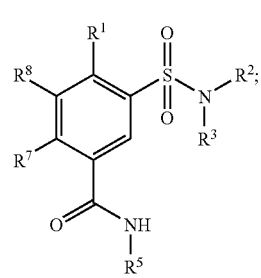

V wherein:
$R^1$ is H, alkyl, F, or Br;
$R^2$ and $R^3$ are each independently alkyl or aralkyl, or $R^2$ and $R^3$, when taken together with the nitrogen atom to which they are attached, form a 5- or 6-membered heterocycloalkyl ring, wherein one of the ring carbon atoms may be optionally replaced by —O— or —N($R^9$)—;
$R^7$ is H, Cl, or alkyl;
$R^8$ is H or alkyl; and
$R^9$ is H, alkyl, —C(=O)—O-alkyl, —CH$_2$—C(=O)—O-alkyl, —SO$_2$-alkyl, or —C(=O)N(H)-alkyl.

110. A compound according to claim 109, wherein:
$R^2$ and $R^3$ are each independently alkyl or aralkyl, or $R^2$ and $R^3$, when taken together with the nitrogen atom to which they are attached, form a 5- or 6-membered heterocycloalkyl ring, wherein one of the heterocycloalkyl ring carbon atoms is replaced by —O—; and $R^d$ and $R^e$, taken together with the carbon atom to which they are attached form a carbocyclic ring.

111. A compound according to claim 110, wherein $R^d$ and $R^e$, taken together with the carbon atom to which they are attached form a bicycloalkyl or tricycloalkyl ring.

112. A compound according to claim 109, wherein:
$R^2$ and $R^3$ are each independently alkyl or aralkyl, or $R^2$ and $R^3$, when taken together with the nitrogen atom to which they are attached, form a 5- or 6-membered heterocycloalkyl ring, wherein one of the heterocycloalkyl ring carbon atoms is replaced by —O—; and $R^c$, $R^d$, and $R^e$, taken together with the carbon atom to which they are attached, form a bicycloalkyl or tricycloalkyl ring.

113. A compound according to claim 112, wherein the bicycloalkyl or tricycloalkyl ring is substituted with 1-3 groups selected independently from alkyl, alkoxyl, or hydroxyl.

114. A compound according to claim 111, wherein r is 0 or 1.

115. A compound according to claim 111, wherein $R^a$, $R^b$, and $R^c$ are each H.

116. A compound according to claim 74, selected from the group consisting of:

N-adamantan-2-yl-4-methyl-3-(morpholine-4-sulfonyl)-benzamide;
N-(1-adamantan-1-ylethyl)-4-methyl-3-(morpholine-4-sulfonyl)-benzamide;
4-methyl-3-(morpholine-4-sulfonyl)-N-(1,7,7-trimethyl-bicyclo[2.2.1]-hept-2-yl)-benzamide;
N-bicyclo-[2.2.1]hept-2-yl-4-methyl-3-(morpholine-4-sulfonyl)-benzamide;
N-[1-(3-hydroxy-adamantan-1-yl)-ethyl]-4-methyl-3-(morpholine-4-sulfonyl)-benzamide;
4-methyl-3-(1,3-dihydroisoindole-2-sulfonyl)-N-(1,3,3-trimethylbicyclo-[2.2.1]-hept-2-yl)-benzamide;
N-bicyclo-[2.2.1]hept-2-yl-3-(1,3-dihydroisoindole-2-sulfonyl)-4-methylbenzamide;
3-(1,3-dihydroisoindole-2-sulfonyl)-4-methyl-N-(1,7,7-trimethylbicyclo-[2.2.1]hept-2-yl)-benzamide;
3-(1,3-dihydroisoindole-2-sulfonyl)-N-[1-(3-hydroxy-adamantan-1-yl)-ethyl]-4-methylbenzamide;
N-adamantan-2-yl-3-(3,4-dihydro-2H-quinoline-1-sulfonyl)-4,5-dimethylbenzamide;
N-(1-adamantan-1-ylethyl)-3-(3,4-dihydro-2H-quinoline-1-sulfonyl)-4,5-dimethylbenzamide;
3-(3,4-dihydroquinolin-1 (2H)-ylsulfonyl)-4,5-dimethyl-N-(1,3,3-trimethylbicyclo-[2.2.1]-heptan-2-yl)-benzamide;
N-adamantan-2-yl-3,4-dimethyl-5-(octahydroquinoline-1-sulfonyl)-benzamide;
N-(1-adamantan-1-ylethyl)-3,4-dimethyl-5-(octahydro-quinoline-1-sulfonyl)-benzamide;
3,4-dimethyl-5-(octahydroquinolin-1(2H)-ylsulfonyl)-N-(1,3,3-trimethylbicyclo-[2.2.1]heptan-2-yl)benzamide;
N-adamantan-2-yl-3-(2,6-dimethylmorpholine-4-sulfonyl)-4-methylbenzamide;
N-(1-adamantan-1-ylethyl)-3-(2,6-dimethylmorpholine-4-sulfonyl)-4-methylbenzamide;
3-(2,6-dimethylmorpholinosulfonyl)-4-methyl-N-(1,3,3-trimethylbicylo-[2.2.1]heptan-2-yl)-benzamide;
N-adamantan-2-yl-3-(2,6-dimethylmorpholine-4-sulfonyl)-4,5-dimethylbenzamide;
N-(1-adamantan-1-ylethyl)-3-(2,6-dimethylmorpholine-4-sulfonyl)-4,5-dimethylbenzamide;
3-(2,6-dimethylmorpholinosulfonyl)-4,5-dimethyl-N-(1,3,3-trimethylbicyclo-[2.2.1]heptan-2-yl)-benzamide;
N-adamantan-2-yl-5-(N-benzyl-N-methylsulfamoyl)-2-chloro-4-fluoro-benzamide;
N-(1-adamantan-1-ylethyl)-5-(N-benzyl-N-methylsulfamoyl)-2-chloro-4-fluorobenzamide;
5-(N-benzyl-N-methylsulfamoyl)-2-chloro-4-fluoro-N-(1,3,3-trimethylbicyclo[2.2.1]-heptan-2-yl)benzamide;
3,4-dimethyl-5-(morpholinosulfonyl)-N-(1,3,3-trimethyl-bicyclo-[2.2.1]heptan-2-yl)-benzamide;
N-((6,6-dimethylbicyclo-[3.1.1]-heptan-2-yl)methyl)-3,4-dimethyl-5-(morpholinosulfonyl)-benzamide;
N-(1-adamantan-1-ylethyl)-5-(morpholinosulfonyl)-4,5-dimethylbenzamide;
3-(N-benzyl-N-methyl-sulfamoyl)-4,5-dimethyl-N-(1,3,3-trimethylbicyclo-[2.2.1]-heptan-2-yl)benzamide;
3-(N-benzyl-N-methyl-sulfamoyl)-N-((6,6-dimethylbicyclo-[3.1.1]-heptan-2-yl)methyl)-4,5-dimethylbenzamide;
N-(1-adamantan-1-ylethyl)-5-(N-benzyl-N-methyl-sulfamoyl)-4,5-dimethylbenzamide;
1-(2,3-dimethyl-5-(1,3,3-trimethylbicyclo-[2.2.1]heptan-2-ylcarbamoyl)-phenylsulfonyl)-N,N-diethylpiperidine-3-carboxamide;
3-(azetidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)-benzamide;
3-(4-hydroxypiperidin-1-ylsulfonyl)-4-methyl-N-(1,3,3-trimethylbicyclo-[2.2.1]-heptan-2-yl)-benzamide;
N,N-diethyl-1-(2-methyl-5-(1,3,3-trimethylbicylo-[2.2.1]heptan-2-ylcarbamoyl)-phenylsulfonyl)-piperidine-3-carboxamide;
3-(N-(2-methoxyethyl)-N-methylsulfamoyl)-4-methyl-N-(1,3,3-trimethylbicyclo-[2.2.1]heptan-2-yl)-benzamide;
N,N-diethyl-1-(2-methyl-5-(1,3,3-trimethylbicyclo-[2.2.1]heptan-2-ylcarbamoyl)-phenylsulfonyl)-pyrrolidine-3-carboxamide;
N-(1-adamantan-1-ylmethyl)-5-(morpholinosulfonyl)-2-chloro-4-fluorobenzamide;
4-methyl-3-(morpholinosulfonyl)-N-(2,6,6-trimethylbicyclo-[3.1.1]-heptan-3-yl)-benzamide;
4-ethyl-3-(morpholine-4-sulfonyl)-N-(1,3,3-trimethylbicyclo[2.2.1]hept-2-yl)-benzamide;
4-isopropyl-3-(morpholine-4-sulfonyl)-N-(1,3,3-trimethylbicylo[2.2.1]hept-2-yl)-benzamide;
4-propyl-3-(morpholine-4-sulfonyl)-N-(1,3,3-trimethylbicyclo[2.2.1]hept-2-yl)-benzamide;
4-(3-methoxypropyl)-3-(morpholine-4-sulfonyl)-N-(1,3,3-trimethylbicyclo-[2.2.1]hept-2-yl)-benzamide;
5-methyl-3-(morpholine-4-sulfonyl)-N-(1,3,3-trimethylbicyclo[2.2.1]-hept-2-yl)-benzamide;
4,6-dimethyl-3-(morpholine-4-sulfonyl)-N-(1,3,3-trimethylbicyclo-[2.2.1]hept-2-yl)-benzamide;
3-(N,N-dimethylsulfamoyl-4-bromo-N-(1,3,3-trimethylbicyclo-[2.2.1]-hept-2-yl)-benzamide;
4-bromo-3-(N-methylsulfamoyl)-N-(1,3,3-trimethylbicyclo-[2.2.1]-hept-2-yl)-benzamide;
4-bromo-3-(N-phenylsulfamoyl)-N-(1,3,3-trimethylbicyclo-[2.2.1]-hept-2-yl)-benzamide;
4-bromo-3-(morpholinosulfonyl)-N-(1,3,3-trimethylbicyclo-[2.2.1]-heptan-2-yl)-benzamide;
4-bromo-3-(3-fluoropiperidin-1-ylsulfonyl)-N-(1,3,3-trimethylbicyclo-[2.2.1]heptan-2-yl)-benzamide;
4-bromo-3-(pyrrolidin-1-ylsulfonyl)-N-(1,3,3-trimethylbicyclo-[2.2.1]-heptan-2-yl)-benzamide;
4-bromo-3-(3,5-dimethylpiperidin-1-ylsulfonyl)-N-(1,3,3-trimethylbicyclo-[2.2.1]-heptan-2-yl)-benzamide;
4-bromo-3-(2,6-dimethylmorpholinosulfonyl)-N-(1,3,3-trimethylbicyclo-[2.2.1]heptan-2-yl)-benzamide;
ethyl 1-(2-bromo-5-(1,3,3-trimethylbicyclo-[2.2.1]heptan-2-yl-carbamoyl)-phenylsulfonyl)-piperidine-3-carboxylate;
4-bromo-N-(((6,6-dimethylbicyclo-[3.1.1]-heptan-2-yl)methyl)-3-(N-((6,6-dimethylbicyclo[3.1.1]heptan-3-yl)methyl)sulfamoyl)-benzamide;
2-chloro-4-fluoro-5-(morpholinosulfonyl)-N-(1,3,3-trimethylbicyclo-[2.2.1]heptan-2-yl)-benzamide;
N-(1-adamantan-1-ylethyl)-5-(morpholinosulfonyl)-2-chloro-4-fluorobenzamide; and
a pharmaceutically acceptable salt thereof.

117. A compound selected from the group consisting of:
N-(2,2-dimethylpropyl)-4-methyl-3-(morpholine-4-sulfonyl)-benzamide;
4-methyl-3-(morpholine-4-sulfonyl)-N-(1-morpholin-4-ylbutan-2-yl)-benzamide;
3-(1,3-dihydroisoindole-2-sulfonyl)-N-(2,2-dimethylpropyl)-4-methylbenzamide;
3-(1,3-dihydroisoindole-2-sulfonyl)-4-methyl-N-(1-morpholin-4-ylbutan-2-yl)-benzamide;
4-methyl-3-(morpholinosulfonyl)-N(3,3,5-trimethylcyclohexyl)-benzamide;

N-(3,3-dimethylbutan-2-yl)-4-methyl-3-(morpholinosulfonyl)-benzamide;
N-(4-hydroxy-3,3-dimethylbutan-2-yl)-4-methyl-3-(morpholinosulfonyl)-benzamide;
N,N-diisopropyl-4-methyl-3-(morpholinosulfonyl)-benzamide;
4-bromo-3-(morpholine-4-sulfonyl)-N-(3,3-dimethylbutan-2-yl)-benzamide;
4-bromo-3-(pyrrolidine-1-sulfonyl)-N-(3,3-dimethylbutan-2-yl)-benzamide;
4-bromo-3-(N,N-dimethylsulfamoyl-N-(3,3-dimethylbutan-2-yl)-benzamide;
4-(3-methoxyprop-1-ynyl)-3-(morpholinosulfonyl)-N-(1,3,3-trimethylbicyclo[2.2.1]heptan-2-yl)benzamide
4-(3-methoxyprop-1-ynyl)-3-(morpholinosulfonyl)-N-((1S,4R)-1,3,3-trimethylbicyclo[2.2.1]heptan-2-yl)benzamide; and
a pharmaceutically acceptable salt thereof.

118. A compound according to claim 74, selected from the group consisting of:
N-adamantan-2-yl-4-methyl-3-(morpholine-4-sulfonyl)-benzamide;
N-(1-adamantan-1-ylethyl)-4-methyl-3-(morpholine-4-sulfonyl)-benzamide;
4-methyl-3-(morpholine-4-sulfonyl)-N-((1S,4R)-1,7,7-trimethylbicyclo[2.2.1]-hept-2-yl)-benzamide;
N-(R)-bicyclo-[2.2.1]hept-2-yl-4-methyl-3-(morpholine-4-sulfonyl)-benzamide;
N-[1-(3-hydroxy-adamantan-1-yl)-ethyl]-4-methyl-3-(morpholine-4-sulfonyl)-benzamide;
4-methyl-3-(1,3-dihydroisoindole-2-sulfonyl)-N,S-(1,3,3-trimethylbicyclo-[2.2.1]-hept-2-yl)-benzamide;
N-(R)-bicyclo-[2.2.1]hept-2-yl-3-(1,3-dihydroisoindole-2-sulfonyl)-4-methylbenzamide;
3-(1,3-dihydroisoindole-2-sulfonyl)-4-methyl-N-((1S,4R)-1,7,7-trimethylbicyclo-[2.2.1]hept-2-yl)-benzamide;
3-(1,3-dihydroisoindole-2-sulfonyl)-N-[1-(3-hydroxy-adamantan-1-yl)-ethyl]-4-methylbenzamide;
N-adamantan-2-yl-3-(3,4-dihydro-2H-quinoline-1-sulfonyl)-4,5-dimethylbenzamide;
N-(1-adamantan-1-ylethyl)-3-(3,4-dihydro-2H-quinoline-1-sulfonyl)-4,5-dimethylbenzamide;
3-(3,4-dihydroquinolin-1(2H)-ylsulfonyl)-4,5-dimethyl-N-((1S,4R)-1,3,3-trimethylbicyclo-[2.2.1]-heptan-2-yl)-benzamide;
N-adamantan-2-yl-3,4-dimethyl-5-(octahydroquinoline-1-sulfonyl)-benzamide;
N-(1-adamantan-1-ylethyl)-3,4-dimethyl-5-(octahydroquinoline-1-sulfonyl)-benzamide;
3,4-dimethyl-5-(octahydroquinolin-1(2H)-ylsulfonyl)-N-((1S,4R)-1,3,3-trimethylbicyclo[2.2.1]heptan-2-yl)benzamide;
N-adamantan-2-yl-3-(2,6-dimethylmorpholine-4-sulfonyl)-4-methylbenzamide;
N-(1-adamantan-1-ylethyl)-3-(2,6-dimethylmorpholine-4-sulfonyl)-4-methylbenzamide;
3-(2,6-dimethylmorpholinosulfonyl)-4-methyl-N-((1S,4R)-1,3,3-trimethylbicylo-[2.2.1]heptan-2-yl)-benzamide;
N-adamantan-2-yl-3-(2,6-dimethylmorpholine-4-sulfonyl)-4,5-dimethylbenzamide;
N-(1-adamantan-1-ylethyl)-3-(2,6-dimethylmorpholine-4-sulfonyl)-4,5-dimethylbenzamide;
3-(2,6-dimethylmorpholinosulfonyl)-4,5-dimethyl-N-((1S,4R)-1,3,3-trimethylbicyclo-[2.2.1]heptan-2-yl)-benzamide;
N-adamantan-2-yl-5-(N-benzyl-N-methylsulfamoyl)-2-chloro-4-fluoro-benzamide;
N-(1-adamantan-1-ylethyl)-5-(N-benzyl-N-methylsulfamoyl)-2-chloro-4-fluorobenzamide;
5-(N-benzyl-N-methylsulfamoyl)-2-chloro-4-fluoro-N-((1S,4R)-1,3,3-trimethylbicyclo[2.2.1]-heptan-2-yl)benzamide;
3,4-dimethyl-5-(morpholinosulfonyl)-N-((1S,4R)-1,3,3-trimethylbicyclo-[2.2.1]heptan-2-yl)-benzamide;
N-(((1S,2R,5S)-6,6-dimethylbicyclo-[3.1.1]-heptan-2-yl)methyl)-3,4-dimethyl-5-(morpholinosulfonyl)-benzamide;
N-(1-adamantan-1-ylethyl)-5-(morpholinosulfonyl)-4,5-dimethylbenzamide;
3-(N-benzyl-N-methyl-sulfamoyl)-4,5-dimethyl-N-((1S,4R)-1,3,3-trimethylbicyclo-[2.2.1]-heptan-2-yl)benzamide;
3-(N-benzyl-N-methyl-sulfamoyl)-N-(((1S,2R,5S)-6,6-dimethylbicyclo-[3.1.1]-heptan-2-yl)methyl)-4,5-dimethylbenzamide;
N-(1-adamantan-1-ylethyl)-5-(N-benzyl-N-methyl-sulfamoyl)-4,5-dimethylbenzamide;
1-(2,3-dimethyl-5-((1S,4R)-1,3,3-trimethylbicyclo-[2.2.1]heptan-2-ylcarbamoyl)-phenylsulfonyl)-N,N-diethypiperdine-3-carboxamide;
3-(azetidin-1-ylsulfonyl)-4-methyl-N-((1S,4R)-1,3,3-trimethylbicyclo-[2.2.1]-heptan-2-yl)-benzamide;
3-((S)-3-hydroxypyrrolidin-1-ylsulfonyl)-4-methyl-N-((1S,4R)-1,3,3-trimethylbicyclo-[2.2.1]-heptan-2-yl)-benzamide;
3-((R)-3-hydroxypyrrolidin-1-ylsulfonyl)-4-methyl-N-((1S,4R)-1,3,3-trimethylbicyclo-[2.2.1]-heptan-2-yl)benzamide;
3-(4-hydroxypiperidin-1-ylsulfonyl)-4-methyl-N-((1S,4R)-1,3,3-trimethylbicyclo-[2.2.1]-heptan-2-yl)-benzamide;
N,N-diethyl-1-(2-methyl-5-((1S,4R)-1,3,3-trimethylbicyclo-[2.2.1]heptan-2-ylcarbamoyl)-phenylsulfonyl)-piperidine-3-carboxamide;
3-(N-(2-methoxyethyl)-N-methylsulfamoyl)-4-methyl-N-((1S,4R)-1,3,3-trimethylbicyclo-[2.2.1]heptan-2-yl)-benzamide;
N,N-diethyl-1-(2-methyl-5-((1S,4R)-1,3,3-trimethylbicyclo-[2.2.1]heptan-2-ylcarbamoyl)-phenylsulfonyl)-pyrrolidine-3-carboxamide;
N-(1-adamantan-1-ylmethyl)-5-(morpholinosulfonyl)-2-chloro-4-fluorobenzamide;
4-methyl-3-(morpholinosulfonyl)-N-((1R,2R,3R,5S)-2,6,6-trimethylbicyclo-[3.1.1]-heptan-3-yl)-benzamide;
4-methyl-3-(morpholinosulfonyl)-N-((1S,2S,3S,5R)-2,6,6-trimethylbicyclo-[3.1.1]heptan-3-yl)-benzamide;
4-ethyl-3-(morpholine-4-sulfonyl)-N-((1S,4R)-1,3,3-trimethylbicylo[2.2.1]hept-2-yl)-benzamide;
4-isopropyl-3-(morpholine-4-sulfonyl)-N-((1S,4R)-1,3,3-trimethylbicylo[2.2.1]hept-2-yl)-benzamide;
4-propyl-3-(morpholine-4-sulfonyl)-N-((1S,4R)-1,3,3-trimethylbicylo[2.2.1]hept-2-yl)-benzamide;
4-(3-methoxypropyl)-3-(morpholine-4-sulfonyl)-N-((1S,4R)-1,3,3-trimethylbicyclo-[2.2.1]hept-2-yl)-benzamide;
5-methyl-3-(morpholine-4-sulfonyl)-N-((1S,4R)-1,3,3-trimethylbicyclo[2.2.1]-hept-2-yl)-benzamide;
4,6-dimethyl-3-(morpholine-4-sulfonyl)-N-((1S,4R)-1,3,3-trimethylbicyclo-[2.2.1]hept-2-yl)-benzamide;
3-(N,N-dimethylsulfamoyl-4-bromo-N-((1S,4R)-1,3,3-trimethylbicyclo-[2.2.1]-hept-2-yl)-benzamide;

4-bromo-3-(N-methylsulfamoyl)-N-((1S,4R)-1,3,3-trimethylbicyclo-[2.2.1]-hept-2-yl)-benzamide;
4-bromo-3-(N-phenylsulfamoyl)-N-((1S,4R)-1,3,3-trimethylbicyclo-[2.2.1]-hept-2-yl)-benzamide;
4-bromo-3-(morpholinosulfonyl)-N-((1S,4R)-1,3,3-trimethylbicyclo-[2.2.1]-heptan-2-yl)-benzami
4-bromo-3-(3-fluoropiperidin-1-ylsulfonyl)-N-((1S,4R)-1,3,3-trimethylbicyclo-[2.2.1]heptan-2-yl)-benzamide;
4-bromo-3-(pyrrolidin-1-ylsulfonyl)-N-((1S,4R)-1,3,3-trimethylbicyclo-[2.2.1]-heptan-2-yl)-benzamide;
4-bromo-3-(3,5-dimethylpiperidin-1-ylsulfonyl)-N-((1S,4R)-1,3,3-trimethylbicyclo-[2.2.1]heptan-2-yl)-benzamide;
4-bromo-3-(2,6-dimethylmorpholinosulfonyl)-N-((1S,4R)-1,3,3-trimethylbicyclo-[2.2.1]heptan-2-yl)-benzamide;
ethyl 1-(2-bromo-5-((1S,4R)-1,3,3-trimethylbicyclo-[2.2.1]heptan-2-yl-carbamoyl)-phenylsulfonyl)-piperidine-3-carboxylate;
4-bromo-N-(((1S,2R,5S)-6,6-dimethylbicyclo-[3.1.1]-heptan-2-yl)methyl)-3-(N-(((1R,3S,5S)-6,6-dimethylbicyclo[3.1.1]heptan-3-yl)methyl)sulfamoyl)-benzamide;
2-chloro-4-fluoro-5-(morpholinosulfonyl)-N-((1S,4R)-1,3,3-trimethylbicyclo-[2.2.1]heptan-2-yl)-benzamide;
N-(1-adamantan-1-ylethyl)-5-(morpholinosulfonyl)-2-chloro-4-fluorobenzamide; and
a pharmaceutically acceptable salt thereof.

119. A compound according to claim 116, selected from the group consisting of:
3,4-dimethyl-5-(morpholinosulfonyl)-N-(1,3,3-trimethylbicyclo-[2.2.1]heptan-2-yl)-benzamide;
3-(azetidin-1-ylsulfonyl)-4-methyl-N-(1,3,3-trimethylbicyclo-[2.2.1]-heptan-2-yl)-benzamide;
3-(3-hydroxypyrrolidin-1-ylsulfonyl)-4-methyl-N-(1,3,3-trimethylbicyclo-[2.2.1]-heptan-2-yl)-benzamide;
4-(3-methoxypropyl)-3-(morpholine-4-sulfonyl)-N-(1,3,3-trimethylbicyclo-[2.2.1]hept-2-yl)-benzamide;
5-methyl-3-(morpholine-4-sulfonyl)-N-(1,3,3-trimethylbicyclo[2.2.1]-hept-2-yl)-benzamide;
N-(1-adamantan-1-yl-ethyl)-4-methyl-3-(morpholine-4-sulfonyl)-benzamide;
4-methyl-3-(morpholine-4-sulfonyl)-N-(1,7,7-trimethylbicyclo-[2.2.1]-hept-2-yl)-benzamide;
N-((6,6-dimethylbicyclo-[3.1.1]-heptan-2-yl)methyl)-3,4-dimethyl-5-(morpholino-sulfonyl)-benzamide;
4-propyl-3-(morpholine-4-sulfonyl)-N-(1,3,3-trimethylbicyclo-[2.2.1]-hept-2-yl)-benzamide;
4-bromo-3-(3-fluoropiperidin-1-ylsulfonyl)-N-(1,3,3-trimethylbicyclo-[2.2.1]-heptan-2-yl)-benzamide; and
a pharmaceutically acceptable salt thereof.

120. A compound according to claim 118, selected from the group consisting of:
3,4-dimethyl-5-(morpholinosulfonyl)-N-((1S,4R)-1,3,3-trimethylbicyclo-[2.2.1]heptan-2-yl)-benzamide;
3-(azetidin-1-ylsulfonyl)-4-methyl-N-((1S,4R)-1,3,3-trimethylbicyclo-[2.2.1]-heptan-2-yl)-benzamide;
3-((S)-3-hydroxypyrrolidin-1-ylsulfonyl)-4-methyl-N-((1S,4R)-1,3,3-trimethylbicyclo-[2.2.1]-heptan-2-yl)-benzamide;
4-(3-methoxypropyl)-3-(morpholine-4-sulfonyl)-N-((1S,4R)-1,3,3-trimethylbicyclo-[2.2.1]hept-2-yl)-benzamide;
5-methyl-3-(morpholine-4-sulfonyl)-N-((1S,4R)-1,3,3-trimethylbicyclo[2.2.1]-hept-2-yl) -benzamide;
N-(1-adamantan-1-yl-ethyl)-4-methyl-3-(morpholine-4-sulfonyl)-benzamide;
4-methyl-3-(morpholine-4-sulfonyl)-N-((1S,4R)-1,7,7-trimethylbicyclo-[2.2.1]-hept-2-yl)-benzamide;
N-(((1S,2R,5S)-6,6-dimethylbicyclo-[3.1.1]-heptan-2-yl)methyl)-3,4-dimethyl-5-(morpholino-sulfonyl)-benzamide;
4-propyl-3-(morpholine-4-sulfonyl)-N,S-(1,3,3-trimethylbicyclo-[2.2.1]-hept-2-yl)-benzamide;
4-bromo-3-(3-fluoropiperidin-1-ylsulfonyl)-N-((1S,4R)-1,3,3-trimethylbicyclo-[2.2.1]-heptan-2-yl)-benzamide; and
a pharmaceutically acceptable salt thereof.

121. A compound according to claim 119, selected from the group consisting of:
3,4-dimethyl-5-(morpholinosulfonyl)-N-(1,3,3-trimethylbicyclo-[2.2.1]heptan-2-yl)-benzamide;
3-(3-hydroxypyrrolidin-1-ylsulfonyl)-4-methyl-N-(1,3,3-trimethylbicyclo-[2.2.1]-heptan-2-yl)-benzamide;
N-(1-adamantan-1-yl-ethyl)-4-methyl-3-(morpholine-4-sulfonyl)-benzamide;
4-methyl-3-(morpholine-4-sulfonyl)-N-(1,7,7-trimethylbicyclo-[2.2.1]-hept-2-yl)-benzamide;
4-(3-methoxypropyl)-3-(morpholine-4-sulfonyl)-N-(1,3,3-trimethylbicyclo-[2.2.1]hept-2-yl)-benzamide; and
a pharmaceutically acceptable salt thereof.

122. A compound according to claim 120, selected from the group consisting of:
3,4-dimethyl-5-(morpholinosulfonyl)-N-((1S,4R)-1,3,3-trimethylbicyclo-[2.2.1]heptan-2-yl)-benzamide;
3-((S)-3-hydroxypyrrolidin-1-ylsulfonyl)-4-methyl-N-((1S,4R)-1,3,3-trimethylbicyclo-[2.2.1]-heptan-2-yl)-benzamide;
N-(1-adamantan-1-yl-ethyl)-4-methyl-3-(morpholine-4-sulfonyl)-benzamide;
4-methyl-3-(morpholine-4-sulfonyl)-N-((1S,4R)-1,7,7-trimethylbicyclo-[2.2.1]-hept-2-yl)-benzamide;
4-(3-methoxypropyl)-3-(morpholine-4-sulfonyl)-N-((1S,4R)-1,3,3-trimethylbicyclo-[2.2.1]hept-2-yl)-benzamide; and
a pharmaceutically acceptable salt thereof.

123. A pharmaceutical composition, comprising:
a pharmaceutically acceptable carrier; and a compound of formula VI:

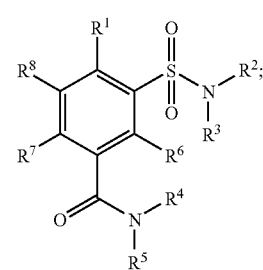

VI wherein:
$R^1$ is H, alkyl, cycloalkyl, cycloalkylalkyl, aryl, aralkyl, heterocycloalkyl, heterocycloalkylalkyl, heteroaryl, heteroaralkyl, F, Cl, or Br;
$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$ when taken together with the nitrogen atom to which they are attached, form a 3- to 8-membered heterocycloalkyl ring, wherein 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;

R$^4$ is H or alkyl;

R$^5$ is:

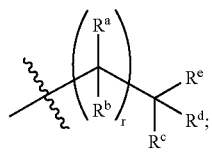

each R$^a$, R$^b$, R$^c$, R$^d$, and R$^e$ is independently H or alkyl; or R$^d$ and R$^1$ taken together with the carbon atom to which they are attached form a carbocyclic ring; or R$^c$, R$^d$, and R$^e$, taken together with the carbon atom to which they are attached, form a bicycloalkyl or tricycloalkyl ring;

R$^6$, R$^7$, and R$^8$ are each independently H, F, Cl, Br, or alkyl;

R$^9$ is H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;

R$^{10}$ is H, alkyl, or aryl;

each R$^{11}$ is independently H or alkyl;

r is 0, 1, 2, or 3; and s is 1, 2, 3, or 4;

provided that:
(1) when R$^d$ and R$^e$ taken together with the carbon atom to which they are attached form a monocyclic carbocyclic ring, then R$^c$ is alkyl or the monocyclic carbocyclic ring is an alkylcycloalkyl ring;
(2) at least two of R$^c$, R$^d$, and R$^e$ are other than H; and
(3) when R$^1$ is methyl or bromo, R$^2$, R$^4$, R$^6$, R$^7$, and R$^8$ are each H, and R$^3$ is methyl, then R$^5$ is other than but-2-yl, pent-2-yl, hex-2-yl, hept-2-yl, 1,1,1-dimethyleth-1-yl, 1-dimethylprop-1-yl, 1,1-dimethylbut-1-yl, or 1,1-dimethylpent-1-yl;

or a pharmaceutically acceptable salt thereof.

124. A pharmaceutical composition according to claim 123, wherein when R$^d$ and R$^e$ are taken together with the carbon atom to which they are attached to form a monocyclic carbocyclic ring, then R$^c$ is alkyl.

125. A pharmaceutical composition according to claim 123, wherein the compound of formula VI is selected from the group consisting of:

N-adamantan-2-yl-4-methyl-3-(morpholine-4-sulfonyl)-benzamide;

N-(1-adamantan-1-ylethyl)-4-methyl-3-(morpholine-4-sulfonyl)-benzamide;

4-methyl-3-(morpholine-4-sulfonyl)-N-(1,7,7-trimethyl-bicyclo[2.2.1]-hept-2-yl)-benzamide;

N-bicyclo-[2.2.1]hept-2-yl-4-methyl-3-(morpholine-4-sulfonyl)-benzamide;

N-[1-(3-hydroxy-adamantan-1-yl)-ethyl]-4-methyl-3-(morpholine-4-sulfonyl)-benzamide;

N-(2,2-dimethylpropyl)-4-methyl-3-(morpholine-4-sulfonyl)-benzamide;

4-methyl-3-(morpholine-4-sulfonyl)-N-(1-morpholin-4-ylbutan-2-yl)-benzamide;

4-methyl-3-(1,3-dihydroisoindole-2-sulfonyl)-N-(1,3,3-trimethylbicyclo-[2.2.1]-hept-2-yl)-benzamide;

N-bicyclo-[2.2.1]hept-2-yl-3-(1,3-dihydroisoindole-2-sulfonyl)-4-methylbenzamide;

3-(1,3-dihydroisoindole-2-sulfonyl)-4-methyl-N-(1,7,7-trimethylbicyclo-[2.2.1]hept-2-yl)-benzamide;

3-(1,3-dihydroisoindole-2-sulfonyl)-N-(2,2-dimethylpropyl)-4-methylbenzamide;

3-(1,3-dihydroisoindole-2-sulfonyl)-N-[1-(3-hydroxy-adamantan-1-yl)-ethyl]-4-methylbenzamide;

3-(1,3-dihydroisoindole-2-sulfonyl)-4-methyl-N-(1-morpholin-4-ylbutan-2-yl)-benzamide;

N-adamantan-2-yl-3-(3,4-dihydro-2H-quinoline-1-sulfonyl)-4,5-dimethylbenzamide;

N-(1-adamantan-1-ylethyl)-3-(3,4-dihydro-2H-quinoline-1-sulfonyl)-4,5-dimethylbenzamide;

3-(3,4-dihydroquinolin-1(2H)-ylsulfonyl)-4,5-dimethyl-N-(1,3,3-trimethylbicyclo-[2.2.1]-heptan-2-yl)-benzamide;

N-adamantan-2-yl-3,4-dimethyl-5-(octahydroquinoline-1-sulfonyl)-benzamide;

N-(1-adamantan-1-ylethyl)-3,4-dimethyl-5-(octahydroquinoline-1-sulfonyl)-benzamide;

3,4-dimethyl-5-(octahydroquinolin-1(2H)-ylsulfonyl)-N-(1,3,3-trimethylbicyclo-[2.2.1]heptan-2-yl)benzamide;

N-adamantan-2-yl-3-(2,6-dimethylmorpholine-4-sulfonyl)-4-methylbenzamide;

N-(1-adamantan-1-ylethyl)-3-(2,6-dimethylmorpholine-4-sulfonyl)-4-methylbenzamide;

3-(2,6-dimethylmorpholinosulfonyl)-4-methyl-N-(1,3,3-trimethylbicylo-[2.2.1]heptan-2-yl)-benzamide;

N-adamantan-2-yl-3-(2,6-dimethylmorpholine-4-sulfonyl)-4,5-dimethylbenzamide;

N-(1-adamantan-1-ylethyl)-3-(2,6-dimethylmorpholine-4-sulfonyl)-4,5-dimethylbenzamide;

3-(2,6-dimethylmorpholinosulfonyl)-4,5-dimethyl-N-(1,3,3-trimethylbicyclo-[2.2.1]heptan-2-yl)-benzamide;

N-adamantan-2-yl-5-(N-benzyl-N-methylsulfamoyl)-2-chloro-4-fluoro-benzamide;

N-(1-adamantan-1-ylethyl)-5-(N-benzyl-N-methylsulfamoyl)-2-chloro-4-fluorobenzamide;

5-(N-benzyl-N-methylsulfamoyl)-2-chloro-4-fluoro-N-(1,3,3-trimethylbicyclo[2.2.1]-heptan-2-yl)benzamide;

3,4-dimethyl-5-(morpholinosulfonyl)-N-(1,3,3-trimethyl-bicyclo-[2.2.1]heptan-2-yl)-benzamide;

N-((6,6-dimethylbicyclo-[3.1.1]-heptan-2-yl)methyl)-3,4-dimethyl-5-(morpholinosulfonyl)-benzamide;

N-(1-adamantan-1-ylethyl)-5-(morpholinosulfonyl)-4,5-dimethylbenzamide;

3-(N-benzyl-N-methyl-sulfamoyl)-4,5-dimethyl-N-(1,3,3-trimethylbicyclo-[2.2.1]-heptan-2-yl)benzamide;

3-(N-benzyl-N-methyl-sulfamoyl)-N-((6,6-dimethylbicyclo-[3.1.1]-heptan-2-yl)methyl)-4,5-dimethylbenzamide;

N-(1-adamantan-1-ylethyl)-5-(N-benzyl-N-methyl-sulfamoyl)-4,5-dimethylbenzamide;

1-(2,3-dimethyl-5-(1,3,3-trimethylbicyclo-[2.2.1]heptan-2-ylcarbamoyl)-phenylsulfonyl)-N,N-diethylp 3-carboxamide;

3-(azetidin-1-ylsulfonyl)-4-methyl-N-(1,3,3-trimethylbicyclo-[2.2.1]-heptan-2-yl)-benzamide;

3-(3-hydroxypyrrolidin-1-ylsulfonyl)-4-methyl-N-(1,3,3-trimethylbicyclo-[2.2.1]-heptan-2-yl)-benzamide;

3-(3-hydroxypyrrolidin-1-ylsulfonyl)-4-methyl-N-(1,3,3-trimethylbicyclo-[2.2.1]-heptan-2-yl)benzamide;

3-(4-hydroxypiperidin-1-ylsulfonyl)-4-methyl-N-(1,3,3-trimethylbicyclo-[2.2.1]-heptan-2-yl)-benzamide;

N,N-diethyl-1-(2-methyl-5-(1,3,3-trimethylbicylo-[2.2.1]
heptan-2-ylcarbamoyl)-phenylsulfonyl)-piperidine-3-
carboxamide;
3-(N-(2-methoxyethyl)-N-methylsulfamoyl)-4-methyl-
N-(1,3,3-trimethylbicyclo-[2.2.1]heptan-2-yl)-benza-
mide;
N,N-diethyl-1-(2-methyl-5-(1,3,3-trimethylbicyclo-
[2.2.1]heptan-2-ylcarbamoyl)-phenylsulfonyl)-pyrroli-
din-3-carboxamide;
N-(1-adamantan-1-ylmethyl)-5-(morpholinosulfonyl)-2-
chloro-4-fluorobenzamide;
4-methyl-3-(morpholinosulfonyl)-N(3,3,5-trimethylcy-
clohexyl)-benzamide;
4-methyl-3-(morpholinosulfonyl)-N-(2,6,6-trimethylbi-
cyclo-[3.1.1]-heptan-3-yl)-benzamide;
4-methyl-3-(morpholinosulfonyl)-N-(2,6,6-trimethylbi-
cyclo-[3.1.1]heptan-3-yl)-benzamide;
N-(3,3-dimethylbutan-2-yl)-4-methyl-3-(morpholinosul-
fonyl)-benzamide;
N-(4-hydroxy-3,3-dimethylbutan-2-yl)-4-methyl-3-(mor-
pholinosulfonyl)-benzamide;
N,N-diisopropyl-4-methyl-3-(morpholinosulfonyl)-ben-
zamide;
4-ethyl-3-(morpholine-4-sulfonyl)-N-(1,3,3-trimethylbi-
cylo[2.2.1]hept-2-yl)-benzamide;
4-isopropyl-3-(morpholine-4-sulfonyl)-N-(1,3,3-trimeth-
ylbicylo[2.2.1]hept-2-yl)-benzamide;
4-propyl-3-(morpholine-4-sulfonyl)-N-(1,3,3-trimethyl-
bicylo[2.2.1]hept-2-yl)-benzamide;
4-(3-methoxypropyl)-3-(morpholine-4-sulfonyl)-N-(1,3,
3-trimethylbicyclo-[2.2.1]hept-2-yl)-benzamide;
5-methyl-3-(morpholine-4-sulfonyl)-N-(1,3,3-trimethyl-
bicyclo[2.2.1]-hept-2-yl)-benzamide;
4,6-dimethyl-3-(morpholine-4-sulfonyl)-N-(1,3,3-trim-
ethylbicyclo-[2.2.1]hept-2-yl)-benzamide;
3-(N,N-dimethylsulfamoyl-4-bromo-N-(1,3,3-trimethyl-
bicyclo-[2.2.1]-hept-2-yl)-benzamide;
4-bromo-3-(N-methylsulfamoyl)-N-(1,3,3-trimethylbicy-
clo-[2.2.1]-hept-2-yl)-benzamide;
4-bromo-3-(N-phenylsulfamoyl)-N-(1,3,3-trimethylbicy-
clo-[2.2.1]-hept-2-yl)-benzamide;
4-bromo-3-(morpholinosulfonyl)-N-(1,3,3-trimethylbicy-
clo-[2.2.1]-heptan-2-yl)-benzamide;
4-bromo-3-(3-fluoropiperidin-1-ylsulfonyl)-N-(1,3,3-tri-
methylbicyclo-[2.2.1]heptan-2-yl)-benzamide;
4-bromo-3-(pyrrolidin-1-ylsulfonyl)-N-(1,3,3-trimethyl-
bicyclo-[2.2.1]-heptan-2-yl)-benzamide;
4-bromo-3-(3,5-dimethylpiperidin-1-ylsulfonyl)-N-(1,3,
3-trimethylbicyclo-[2.2.1]heptan-2-yl)-benzamide;
4-bromo-3-(2,6-dimethylmorpholinosulfonyl)-N-(1,3,3-
trimethylbicyclo-[2.2.1]heptan-2-yl)-benzamide;
ethyl 1-(2-bromo-5-(1,3,3-trimethylbicyclo-[2.2.1]hep-
tan-2-yl-carbamoyl)-phenylsulfonyl)-piperidine-3-car-
boxylate;
4-bromo-N-((6,6-dimethylbicyclo-[3.1.1]-heptan-2-yl)
methyl)-3-(N-(((1R,3S,5S)-6,6-dimethylbicyclo[3.1.1]
heptan-3-yl)methyl)sulfamoyl)-benzamide;
4-bromo-3-(morpholine-4-sulfonyl)-N-(3,3-dimethylbu-
tan-2-yl)-benzamide;
4-bromo-3-(pyrrolidine-1-sulfonyl)-N-(3,3-dimethylbu-
tan-2-yl)-benzamide;
4-bromo-3-(N,N-dimethylsulfamoyl-N-(3,3-dimethylbu-
tan-2-yl)-benzamide;
2-chloro-4-fluoro-5-(morpholinosulfonyl)-N-(1,3,3-trim-
ethylbicyclo-[2.2.1]heptan-2-yl)-benzamide;
N-(1-adamantan-1-ylethyl)-5-(morpholinosulfonyl)-2-
chloro-4-fluorobenzamide; and
a pharmaceutically acceptable salt thereof.

126. A pharmaceutical composition according to claim 125, further comprising at least one cannabinoid.

127. A pharmaceutical composition according to claim 126, wherein the cannabinoid is $\Delta^9$-tetrahydrocannabinol or cannabidiol.

128. A pharmaceutical composition according to claim 125, further comprising at least one opioid.

129. A pharmaceutical composition according to claim 128, wherein said opioid is selected from the group consisting of alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil and tramadol, and mixtures thereof.

130. A pharmaceutical composition according to claim 128, further comprising at least one analgesic.

131. A pharmaceutical composition according to claim 130,
wherein the analgesic is a COX2 inhibitor, aspirin, acetaminophen, ibuprophen, or naproxen, or a mixture thereof.

132. A pharmaceutical composition according to claim 125, further comprising at least one agent selected from the group consisting of an anti-seizure agent, an anti-depressant, an NMDA receptor antagonist, an ion channel antagonist, a nicotinic receptor agonist, and an anti-Parkinson's agent.

133. A pharmaceutical composition according to claim 132 wherein said anti-seizure agent is carbamazepine, gabapentin, lamotrigine, or phenyloin, or a mixture thereof.

134. A pharmaceutical composition according to claim 132 wherein said anti-depressant is amitryptiline.

135. A pharmaceutical composition according to claim 132, wherein said anti-Parkinson's agent is deprenyl, amantadine, levodopa, or carbidopa, or a mixture thereof.

* * * * *